United States Patent
Hinks et al.

(10) Patent No.: US 6,239,175 B1
(45) Date of Patent: *May 29, 2001

(54) CARBAMOYLOXY DERIVATIVES OF MUTILINE AND THEIR USE AS ANTIBACTERIALS

(75) Inventors: Jeremy David Hinks, Horsham; Andrew Kenneth Takle; Eric Hunt, both of Great Dunmow, all of (GB)

(73) Assignee: Smithkline Beecham p.l.c., Great West Road (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/467,695

(22) Filed: Dec. 21, 1999

Related U.S. Application Data

(62) Division of application No. 09/101,210, filed as application No. PCT/EP96/05874 on Dec. 4, 1996, now Pat. No. 6,020,368.

(30) Foreign Application Priority Data

Jan. 3, 1996 (GB) .................................. 9600048
Aug. 2, 1996 (GB) .................................. 9616305

(51) Int. Cl.[7] .......................... A01N 47/10; C07C 261/00
(52) U.S. Cl. ...................... 514/480; 514/23; 514/231.2; 514/252; 514/277; 514/305; 514/315; 514/340; 514/359; 514/363; 514/364; 514/378; 514/381; 514/383; 514/396; 514/461; 514/650; 544/224; 544/242; 546/1; 546/184; 546/340; 560/157; 560/162; 560/115; 560/148; 560/160; 560/480
(58) Field of Search ................................... 514/23, 231.2, 514/252, 277, 305, 315, 340, 359, 363, 364, 378, 381, 383, 396, 461, 480, 650; 544/59, 224, 242; 546/1, 184, 340, 341; 548/146; 549/29; 558/14; 560/12, 13, 20, 29, 32, 115, 148, 160, 162, 157

(56) References Cited

U.S. PATENT DOCUMENTS 6,020,368 * 2/2000 Hinks et al. ......................... 514/480

OTHER PUBLICATIONS

Egger et al., Journal of Antibiotics, 29(9), pp. 923–927 (1976).

* cited by examiner

*Primary Examiner*—Gary Geist
*Assistant Examiner*—T. Victor Oh
(74) *Attorney, Agent, or Firm*—Edward R. Gimmi; William T. King; Charles M. Kinzig

(57) ABSTRACT

Derivatives of mutiline of formula (1A) and pharmaceutically acceptable salts and derivatives thereof, in which $R^1$ is ethyl or vinyl, Y is a carbamoyloxy group, in which the N-atom is unsubstituted, or mono- or di-substituted, are useful in the treatment of bacterial infections.

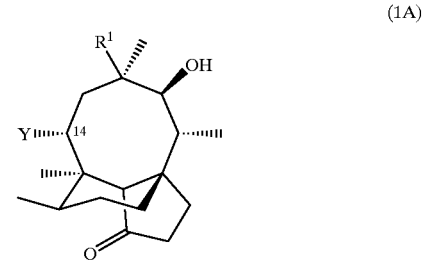

(1A)

4 Claims, No Drawings

CARBAMOYLOXY DERIVATIVES OF MUTILINE AND THEIR USE AS ANTIBACTERIALS

This application is a division of application Ser. No. 09/101,210 filed Dec. 4, 1998, now U.S. Pat. No. 6,020,368, granted Feb. 1, 2000, which is a 371 of PCT/EP96/05874, filed Dec. 19, 1996.

The present invention relates to novel compounds, to processes for their preparation, to pharmaceutical compositions containing them and to their use in medical therapy, particularly antibacterial therapy.

Pleuromutilin, the compound of formula (1), is a naturally occurring antibiotic which has antimycoplasmal activity and modest antibacterial activity. It has been shown that the antimicrobial activity can be improved by replacing the glycolic ester moiety at position 14 by an R—X—CH$_2$CO$_2$— group, where R is an aliphatic or aromatic moiety and X is O, S, or Nr' (H Egger and H Reinshagen, *J Antibiotics*, 1976, 29, 923). Tiamulin, the compound of formula (2), which is used as a veterinary antibiotic, is a derivative of this type (G Hogenauer in *Antibiotics*, Vol. V, part 1, ed. F E Hahn, Springer-Verlag, 1979, p. 344).

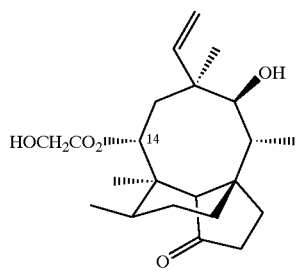

(1)

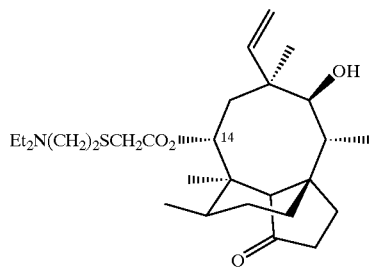

(2)

In this application, the non-conventional numbering system which is generally used in the literature (G Hogenauer, loc. cit.) is used.

We have found that pleuromutilin analogues containing a 14-O-carbamoyl group, also have improved antimicrobial properties.

Accordingly, in its broadest aspect, the present invention proyldes a 14-O-carbamoyl derivative of mutilin or 19,20-dihydromutilin, in which the N-atom of the carbamoyl group is unsubstituted, mono- or di-substituted.

More specifically, this invention proyldes a compound of general formula (3)

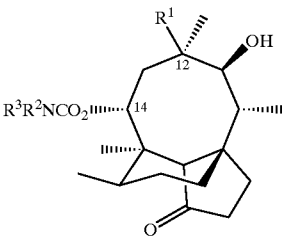

(3)

in which:

$R^1$ is vinyl or ethyl;

$R^2$ and $R^3$ are the same or different groups selected from hydrogen;
  a straight or branch chained, saturated or unsaturated, optionally substituted, $C_1$ to $C_6$ hydrocarbon group;
  a saturated or unsaturated, optionally substituted, $C_3$ to $C_8$ cyclic hydrocarbon group;
  an optionally substituted heterocyclic group;
  an optionally substituted aryl group;
  or together form an optionally substituted cyclic group of 3 to 8 ring atoms, optionally containing one additional heteroatom selected from N, O and S, and optionally fused to a hydrocarbon ring, a heterocyclic group or an aromatic group; or $R^2$ is one of the above monovalent groups and $R^3$ is a group selected from $SO_2R^4$, $COR^5$, $OR^5$ and $NR^6R^7$ where
  $R^4$ is selected from a straight or branch chained, saturated or unsaturated, optionally substituted, $C_1$ to $C_6$ hydrocarbon group; a saturated or unsaturated, optionally substituted, $C_3$ to $C_8$ cyclic hydrocarbon group; an optionally substituted heterocyclic group; an optionally substituted aryl group; an optionally substituted $C_1$ to $C_6$ alkyl amino group; and an optionally substituted aryl amino group;
  $R^5$ is selected from hydrogen; a straight or branch chained, saturated or unsaturated, optionally substituted, $C_1$ to $C_6$ hydrocarbon group; a saturated or unsaturated, optionally substituted, $C_3$ to $C_8$ cyclic hydrocarbon group; an optionally substituted heterocyclic group; and an optionally substituted aryl group;
  $R^6$ and $R^7$ are the same or different groups selected from hydrogen; a straight or branch chained, saturated or unsaturated, optionally substituted, $C_1$ to $C_6$ hydrocarbon group; a saturated or unsaturated, optionally substituted, $C_3$ to $C_8$ cyclic hydrocarbon group; an optionally substituted heterocyclic group, and an optionally substituted aryl group; or together form an optionally substituted cyclic group of 3 to 8 ring atoms, optionally containing one additional heteroatom selected from N, O and S, and optionally fused to a hydrocarbon ring, a heterocyclic group or an aromatic group.

Suitable $C_1$ to $C_6$ hydrocarbon groups include straight and branched chain alkyl groups having from 1 to 6 carbon atoms, for instance methyl, ethyl, n-propyl and iso-propyl, preferably methyl.

Suitable $C_3$ to $C_8$ cyclic hydrocarbon groups include cyclopropyl, cyclopentyl and cyclohexyl.

Suitable optional substituents for the $(C_{1-6})$alkyl groups and the $(C_{3-8})$cycloalkyl groups include, for example, halogen, hydroxy, $(C_{1-6})$alkoxy, aryloxy, carboxy and salt thereof, $(C_{1-6})$alkoxycarbonyl, carbamoyl, mono- or di($C_{1-6}$)alkylcarbamoyl, sulphamoyl, mono- and di($C_{1-6}$) alkylsulphamoyl, amino, mono- and di($C_{1-6}$)alkylamino, $(C_{1-6})$acylamino, ureido, $(C_{1-6})$alkoxycarbonylamino, aryl, heterocyclyl, oxo, hydroxyimino, acyl, $(C_{1-6})$alkylthio, arylthio, $(C_{1-6})$alkane-sulphinyl, arylsulphinyl, $(C_{1-6})$ alkanesulphonyl, arylsulphonyl.

When used herein, the term "aryl" includes phenyl and naphthyl. Suitably an aryl group, including phenyl and naphthyl, may be optionally substituted by up to five, preferably up to three substituents. Suitable substituents include halogen, $(C_{1-6})$alkyl, aryl($C_{1-4}$)alkyl, $(C_{1-6})$alkoxy, $(C_{1-6})$alkoxy($C_{1-6}$)alkyl, halo($C_{1-6}$)alkyl, hydroxy, nitro, amino, mono- and di-N-$(C_{1-6})$alkylamino, acylamino, acyloxy, carboxy, carboxy salts, carboxy esters, carbamoyl, mono- and di-N-$(C_{1-6})$alkylcarbamoyl, $(C_{1-6})$ alkoxycarbonyl, aryloxycarbonyl, ureido, guanidino, sulphonylamino, aminosulphonyl, $(C_{1-6})$alkylthio, $(C_{1-6})$ alkyl sulphinyl $(C_{1-6})$alkylsulphonyl, heterocyclyl and heterocyclyl $(C_{1-4})$alkyl. In addition, two adjacent ring carbon atoms may be linked by a $(C_{3-5})$alkylene chain, to form a carbocyclic ring.

When used herein, the term "heteroaryl" includes aromatic single and fused rings containing up to four heteroatoms in each ring, each of which is selected from oxygen, nitrogen and sulphur, which rings may be unsubstituted or substituted by, for example, up to three substituents. Each heteroaryl ring suitably has 5 or 6 ring atoms. A fused heteroaryl ring may include carbocyclic rings and need include only one heteroaryl ring.

When used herein the terms "heterocyclyl" and "heterocyclic" suitably include, unless otherwise defined, aromatic and non-aromatic, single and fused, rings suitably containing up to four heteroatoms in each ring, each of which is selected from oxygen, nitrogen and sulphur, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring.

Preferably a substituent for a heteroaryl or a heterocyclyl group is selected from halogen, $(C_{1-6})$alkyl, aryl($C_{1-4}$)alkyl, $(C_{1-6})$alkoxy, $(C_{1-6})$alkoxy($C_{1-6}$)alkyl, halo($C_{1-6}$)alkyl, hydroxy, amino, mono- and di-N-$(C_{1-6})$alkyl-amino, acylamino, carboxy salts, carboxy esters, carbamoyl, mono- and di-N-$(C_{1-6})$alkylcarbonyl, aryloxycarbonyl, $(C_{1-6})$ alkoxycarbonyl$(C_{1-6})$alkyl, aryl, oxy groups, ureido, guanidino, sulphonylamino, aminosulphonyl, $(C_{1-6})$ alkylthio, $(C_{1-6})$alkylsulphinyl, $(C_{1-6})$alkylsulphonyl, heterocyclyl and heterocyclyl($C_{1-4}$)alkyl.

Particularly suitable values for $R^2$ and $R^3$ are hydrogen, hydroxy, methoxy, phenyl, methyl, iso-propyl, phenylsulphonyl, methoxyphenyl, nitrophenyl, trichloroacetyl, benzyl, hydroxyiminobenzyl, benzylaminosulfonyl, dichloropyridinyl, hydroxyethyl, 2-phenylethyl, 1-(R)-phenyl-2-hydroxyethyl, 2-(methoxycarbonyl)ethyl, 2-carboxyethyl, dimethylamino, dimethylaminopropyl, methanesulphonylamino, methanesulphonyl, benzoylamino, benzoyl optionally substituted by trifluoromethyl, carboxy, methoxy, hydroxy, acetoxy, amino or nitro, furoyl, nicotinoyl, isonicotinoyl, acetyl, phenylacetyl, and phenoxy. Particularly suitable values for cyclic groups $R^2R^3N$ are indolino and morpholino.

In a further aspect the present invention proyldes a method for preparing compounds of the invention, which comprises reacting a compound of formula (4) where X is hydrogen or a hydroxyl protecting group, such as an acyl group, or a compound of formula (5) with an appropriately substituted carbamate-forming reagent.

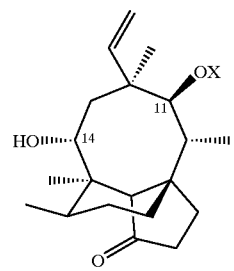

(4)

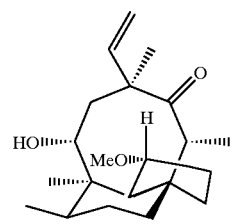

(5)

General methods for preparing carbamates are described, for example, by A F Hegarty in *Comprehensive Organic Chemistry*, Vol. 2, ed. I O Sutherland, Pergamon Press, 1979, p. 1083. Typical procedures are reaction with an isocyanate or a carbamoyl chloride, or reaction with phosgene or a phosgene equivalent followed by reaction with an amine.

More particularly, in one aspect the present invention proyldes a process for the preparation of a compound of formula (3) which comprises reacting a compound of formula (4) in which X is hydrogen or a hydroxyl protecting group, with (a) a compound $R^2$ NCO,
(b) a compound $R^2R^3$NCOCl, or
(c) phosgene or a chloroformate or a carbonate followed by a compound $R^2R^3$NH, where $R^2$ and $R^3$ are as defined above and are protected where appropriate, and where necessary deprotecting the group X to generate a hydroxyl group at position 11, deprotecting a protected group $R^2$ or $R^3$, converting one group $R^2$ or $R^3$ to another group $R^2$ or $R^3$, or hydrogenating the vinyl group at position 12 to form an ethyl group.

Although in principle it may be possible to prepare compounds of formula (3) by reaction at the 14-hydroxyl in the known compound mutilin (X=H in formula (4)), in practice it is desirable to use an intermediate in which the 11-hydroxyl is protected.

Suitable compounds as formula (4) are
11-O-acyl mutilin derivatives, e.g. mutilin 11-acetate (X=Ac in formula (4)) (A J Birch, C W Holzapfel, R W Richards, *Tetrahedron* (Suppl.), 1966, 8, Part II, 359). After formation of the 14-O-carbamoyl derivative, the 11-O-acyl group may be removed by selective hydrolysis (e.g. using NaOH in MeOH);

In another aspect, the present invention provides a process for the preparation of a compound of formula (3) which comprises reacting a compound of formula (5), with (a) a compound $R^2$NCO,
(b) a compound $R^2R^3$NCOCl, or
(c) phosgene or a chloroformate or a carbonate followed by a compound $R^2R^3$NH, where $R^2$ and $R^3$ are as defined above and are protected where appropriate, treating the product with acid, deprotecting a protected group $R^2$ or $R^3$, converting one group $R^2$ or $R^3$ to another group $R^2$ or $R^3$, or hydrogenating the vinyl group at position 12 to form an ethyl group.

Formula (5) is (3R)-3-deoxo-11-deoxy-3-methoxy-11-oxo-4-epi-mutilin (H Berner, G Schulz and H Schneider, *Tetrahedron*, 1980, 36, 1807). After formation of the 14-carbamate, the intermediate may be converted into (3) by treatment with conc. HCl or Lukas reagent (conc. HCl saturated with $ZnCl_2$) in dioxane.

For preparation of 19,20-dihydro analogues (compounds of formula (3) in which $R^1$=Et), before or after the carbamoylation, of a compound of formula (4) or (5), a vinyl group $R^1$ can be reduced by hydrogenation over a palladium catalyst (e.g. 10% Palladium-on-carbon) in a solvent such as ethyl acetate, ethanol, dioxane, or tetrahydrofuran.

The formation of the carbamate at position 14 may be carried out as follows:

(1) Reaction of the 14-hydroxyl with an isocyanate ($R^2N=C=O$) in an inert solvent (e.g. $CH_2Cl_2$, $CHCl_3$, terrahydrofuran, diethyl ether, dioxane), optionally in the presence of an organic or inorganic base (e.g. N,N-di-iso-propylethylamine, $K_2CO_3$). This will give an $R^2NHCO_2$— group at position 14. Methods for preparing isocyanate are described, for example, by J March in "Advanced Organic Chemistry", 4th ed., 1992, Wiley, N.Y., p. 1290.

(2) Reaction of the 14-hydroxyl with an N,N-disubstituted carbamoyl chloride ($R^2R^3NCOCl$) in the presence of a hindered tertiary base (e.g. 2,6-lutidine, N,N-di-iso-propylethylamine) in an inert solvent (e.g. $CH_2Cl_2$, $CHCl_3$, tetrahydrofuran, diethyl ether, dioxane). This will give an $R^2R^3NCO_2$— group at position 14. Methods for preparing carbomoyl chlorides are described, for example, by A F Hegarry, loc. cit, p. 1088.

(3) Reaction of the 14-hydroxyl with phosgene or an equivalent reagent [e.g. trichloromethyl chloroformate, bis(trichloromethyl) carbonate] in the presence of an organic base (e.g. pyridine, 2,6-lutidine, N,N-di-iso-propylethylamine), and reaction of the resulting 14-chloroformate with a primary or secondary amine ($R^2NH_2$ or $R^2R^3NH$).

Suitable hydroxy, carboxy and amino protecting groups are those well known in the art and which may be removed under conventional conditions and without disrupting the remainder of the molecule. A comprehensive discussion of the ways in which hydroxy, carboxy and amino groups may be protected and methods for cleaving the resulting protected derivatives is given in for example "Protective Groups in Organic Chemistry" (T. W. Greene, Wiley-Interscience, New York, 2nd edition, 1991). Particularly suitable hydroxy protecting groups include, for example, triorganosilyl groups such as, for instance, trialkylsilyl and also organocarbonyl and organooxycarbonyl groups such as, for instance, acetyl, allyloxycarbonyl, 4-methoxybenzyloxycarbonyl and 4-nitrobenzyloxycarbonyl. Particularly suitable carboxy protecting groups include alkyl and aryl groups, for instance methyl, ethyl and phenyl. Particularly suitable amino protecting groups include alkoxycarbonyl, 4-methoxybenzyloxycarbonyl and 4-nitrobenzyloxycarbonyl.

In cases where the intermediate of formula (4) (such as X=acetyl) is used, a base-labile protecting group may conveniently be removed at the same time as the group X is deprotected. In cases when the intermediate of formula (5) is used, an acid-labile protecting group may conveniently be removed at the same time as the compound (5) is converted into the compound (3).

Intermediate compounds formed in the processes of this invention, for example, the 14-chloroformate derivative and the 14-O-carbamoyl derivatives of the compound of formula (5), are when novel also part of the invention.

The compounds of this invention may be in crystalline or non-crystalline form, and, if crystalline, may optionally be hydrated or solvated. When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be present in the crystalline product. This invention includes within its scope stoichiometric hydrates as well as compounds containing variable amounts of water that may be produced by processes such as lyophilisation.

The compounds according to the invention are suitably proylded in substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

The present invention also includes pharmaceutically acceptable salts and derivatives of the compounds of the invention. Salt formation may be possible when one of the substituents carries an acidic or basic group. Salts may be prepared by salt exchange in conventional manner.

The compounds of the present invention and their pharmaceutically acceptable salts or derivatives have antimicrobial properties and are useful for the treatment of microbial infections in animals, especially mammals, including humans, in particular humans and domesticated animals (including farm animals). The compounds may be used for the treatment of infections caused by, for example, Gram-positive and Gram-negative bacteria and mycoplasmas, including, for example, *Staphylococcus aureus, Enterococcus faecalis, Streptococcus pyogenes, Streptococcus agalactiae, Streptococcus pneumoniae*, Haemophilus sp., Neisseria sp., Legionella sp., *Mycoplasma pneumoniae*, and *Mycoplasma gallisepticum.*

The present invention proyldes a pharmaceutical composition comprising a compound of formula (3) or a pharmaceutically acceptable salt or derivative thereof together with a pharmaceutically acceptable carrier or excipient.

The present invention also proyldes a method of treating microbial infections in animals, especially in humans and in domesticated mammals, which comprises administering a compound of formula (3) or a pharmaceutically acceptable salt or derivative thereof, or a composition according to the invention, to a patient in need thereof.

The invention further proyldes the use of a compound of the invention or a pharmaceutically acceptable salt or derivative thereof in the preparation of a medicament composition for use in the treatment of microbial infections.

The compounds and compositions according to the invention may be formulated for administration in any convenient way for use in human or veterinary medicine, by analogy with other antibiotics.

The compounds and compositions according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitn monooleate or acacia: non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, car drops, nose drops, nasal sprays, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilised before being filled into a suitable vial or ampoule, which is then sealed. Advantageously, conventional additives including, for example, local anaesthetics, preservatives, and buffering agents can be dissolved in the vehicle. In order to enhance the stability of the solution, the composition may be frozen after being filled into the vial, and the water removed under vacuum; the resulting dry lyophilized powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

A compound or composition according to the invention may suitably be administered to the patient in an antimicrobially effective amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.0 to 50 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferable from 50 to 500 mg, of a compound according to the invention.

The following Examples illustrate the present invention.

EXAMPLE 1

Mutilin 14-(N-phenylcarbamate)
Step 1. (3R)-3-Deoxo-11-deoxy-3-methoxy-11-oxo-4-epi-mutilin 14-(N-phenyl-carbamate)

(3R)-3-Deoxo-11-deoxy-3-methoxy-11-oxo-4-epi-mutilin (H Berner, G Schulz and H Schneider, *Tetrahedron*, 1980, 36, 1807) (170 mg) in dry $CH_2Cl_2$ (3 ml) was treated with phenyl isocyanate (0.12 ml) and N,N-di-isopropylethylamine (1 drop) and the solution was kept at room temperature, with exclusion of moisture, for 7 days. The solution was diluted with ethyl acetate (50 ml) and was washed with dil. HCl (20 ml), water (20 ml), and saturated $NaHCO_3$ solution (20 ml). The solution was dried ($Na_2SO_4$) and the solvent was removed by evaporation under reduced pressure to yield a colourless oil. The oil was chromatographed on silica gel, using 1:4 ethyl acetate-hexane, to give (3R)-3-deoxo-11-deoxy-3-methoxy-11-oxo-4-epi-mutilin 14-(N-phenylcarbamate) as a colourless gum (190 mg); $v_{max}$ ($CHCl_3$) 3435, 1724, 1695, 1603, and 1523 $cm^{-1}$.

Step 2. Mutilin 14-(N-phenylcarbamate)

(3R)-3-deoxo-11-deoxy-3-methoxy-11-oxo-4-epi-mutilin 14-(N-phenyl-carbamate) (160 mg) in dioxane (3 ml) was treated with a saturated solution of zinc chloride in conc. HCl (1.2 ml) and the solution was stirred at room temperature for 3.5 hours. The mixture was diluted with ethyl acetate (50 ml) and the solution was washed with saturated NaCl solution (20 ml) and saturated $NaHCO_3$ solution (20 ml). The solution was dried ($Na_2SO_4$) and the solvent was removed by evaporation under reduced pressure to yield a colourless oil. The oil was chromatographed on silica gel, using 1:3 ethyl acetate-hexane, to give mutilin 14-(N-phenylcarbamate) as a colourless gum (145 mg); crystallisation from $CH_2Cl_2$— hexane gave colourless prisms (130 mg), m.p. 211–212° C.; $\lambda_{max}$ (EtOH) 236 nm ($\epsilon$ 19000); $v_{max}$ ($CHCl_3$) 3630, 3562, 3435, 1726, 1602, and 1523 $cm^{-1}$; MS(EI) m/z 439 ($M^+$).

EXAMPLE 2

Mutilin 14-(N-methylcarbamate)
Step 1. (3R)-3-Deoxo-11-deoxy-3-methoxy-11-oxo-4-epi-mutilin 14-(N-methylcarbamate)

(3R)-3-Deoxo-11-deoxy-3-methoxy-11-oxo-4-epi-mutilin (335 mg, 1.0 mmol) was reacted with methyl isocyanate (0.12 ml, 2.0 mmol) and N,N-di-isopropyl-ethylamine (1 drop) in dichloromethane (5 ml), as for Example 1 Step 1, to afford the title compound (145 mg, 37%); $v_{max}$ ($CH_2Cl_2$) 3459, 1711, and 1516 $cm^{-1}$; $^1H$ NMR ($CDCl_3$) 6.79 (1H, dd, J 17.5, 10.5 Hz) 5.65 (1H, d, J 9.9 Hz) 5.31 (1H, d, J 10.9 Hz) 5.01 (1H, d, 17.6 Hz) 4.55 (1H, br)

3.46 (1H, m) 3.23 (3H, s) 2.95 (1H, q, J 6.4 Hz) 2.83 (3H,br d, J 4.8 Hz) 2.40 (1H, dd, J 15.3, 9.8 Hz) 2.20 (1H, m) 2.02 (2H, m) 1.65 (3H,m) 1.47 (1H, m) 1.30–1.07 (4H, m) 1.20 (6H, s) 0.99 (3H, d, J 6.4 Hz) 0.85 (3H, br d, J 6.9 Hz); MS(EI) m/z 391 (M$^+$).

Step 2. Mutilin 14-(N-methylcarbamate)

The product of Step 1 (135 mg, 0.34 mmol) in dioxane (2 ml) was treated with a saturated solution of zinc chloride in conc. HCl (0.5 ml), as for Example 1 Step 2, to afford the title compound (89 mg, 69%); $v_{max}$ (CH$_2$Cl$_2$) 3460, 1732, and 1714 cm$^{-1}$; $^1$H NMR (CDCl$_3$) 6.61 (1H, dd, J 17.4, 11.0 Hz) 5.64 (1H, d, J 8.4 Hz) 5.37 (1H, br d, J 11.0 Hz) 5.21 (1H, dd, J 17.4, 1.6 Hz) 4.47 (1H, br) 3.34 (1H, dd, J 11.0, 6.7 Hz) 2.78 (3H, br d, J 4.8 Hz) 2.37 (1H, quintet, J 6.8 Hz) 2.21 (4H, m) 2.02 (2H, m) 1.70 (4H, m) 1.42 (6H, m) 1.23 (3H, s) 0.86 (3H, d, J 7.0 Hz) 0.76 (3H, d, J 6 Hz); MS (EI) m/z 377 (M$^+$).

EXAMPLE 3

Mutilin 14-(N-iso-propylcarbamnate)

Step 1. (3R)-3-Deoxo-11-deoxy-3-methoxy-11-oxo-4-epi-mutilin 14-(N-iso-propylcarbamate)

(3R)-3-Deoxo-11-deoxy-3-methoxy-11-oxo-4-epi-mutilin (335 mg, 10 mmol) was reacted with isopropyl isocyanate (0.2 ml, 2.0 mmol) and N,N-di-iso-propyl-ethylarnine (1 drop) in dichioromethane (5 ml), as for Example 1 Step 1, to afford the title compound (367 mg, 87%); $v_{max}$ (CH$_2$Cl$_2$) 3435, 1700 cm$^{-1}$; $^1$H NMR (CDCl$_3$) 6.77 (1H, dd, J 17.5, 10.6 Hz) 5.64 (1H, d, J 9.8 Hz) 5.30 (1H, d, J 10.6 Hz) 5.00 (1H, d, J 17.5 Hz) 4.44 (1H, d, J 7.8 Hz) 3.83 (1H, m) 3.45 (1H, m) 3.22 (3H, s) 2.94 (1H, q, J 6.4 Hz) 2.39 (1H, dd, 15.1, 9.9 Hz) 2.18 (1H, m) 2.00 (2H, m) 1.65 (4H, m) 1.46 (1H, m) 1.29–1.05 (5H, m) 0.98 (3H, d, J 6.4 Hz) 0.84 (3H, d, J 6.8 Hz); MS(EI) m/z 419 (M$^+$).

Step 2. Mutilin 14-(N-iso-propylcarbamate)

The product of Step 1 (324 mg, 0.77 mmol) in dioxane (10 ml) was treated with a saturated solution of zinc chloride in conc. HCl (2 ml), as for Example 1 Step 2, to afford the title compound (102 mg, 33%); $v_{max}$(CH$_2$Cl$_2$) 3436, 1733, 1710, 1505 cm$^{-1}$; $^1$H NMR (CDCl$_3$) 6.60 (1 H, dd, J 17.4, 11.0 Hz) 5.64 (1H, d, J 8.4 Hz) 5.36 (1H, dd, J 11.0, 1.6 Hz) 5.20 (1H, dd, J 17.5, 1.6 Hz) 4.36 (1H, br) 3.79 (1H, m) 3.34 (1H, dd, J 11.0, 6.6 Hz) 2.38 (1H, m) 2.21 (2H, m) 2.02 (2H, m) 1.81–1.59 (4H, m) 1.49–1.26 (7H, m) 1.14 (10H, m) 0.86 (3H, d, J 7.1 Hz) 0.76 (3H, br d, J 5.8 Hz); MS(NH$_3$ DCI) m/z 406 (MH$^+$).

EXAMPLE 4

Mutilin 14-(N-phenylsulphonylcarbamate)

Step 1. (3R)-3-Deoxo-11-deoxy-3-methoxy-11-oxo-4-epi-mutilin 14-(N-phenylsulphonylcarbamate)

(3R)-3-Deoxo-11-deoxy-3-methoxy-11-oxo-4-epi-mutilin (335 mg, 1.0 mmol) was reacted with benzene-sulphonylisocyanate (0.27 ml, 2.0 mmol) and N,N-di-iso-propylethylamine (1 drop) in dichloromethane (5 ml), as for Example 1 Step 1, to afford the title compound (365 mg, 71%); $v_{max}$(CH$_2$Cl$_2$) 3361, 1745, 1698 1450 1354 cm$^{-1}$; $^1$H NMR (CDCl$_3$) 8.05 (2H, d, J 7.1 Hz) 7.68 (1H, t, J 7.3 Hz) 7.57 (2H, m) 6.42 (1H, dd, J 17.5, 10.7 Hz) 5.67 (1H, d, J 10.0 Hz) 5.25 (1H, d, J 10.7 Hz) 4.96 (1H, d, J 17.5 Hz) 3.37 (1H, ddd, J 11.1, 8.3, 5.1 Hz) 3.21 (3H, s) 2.77 (1H, q, J 6.4 Hz) 2.32 (1H, dd, J 15.3, 10.0 Hz) 2.16 (1H, m) 1.99 (2H, m) 1.67 (1H, d, J 11.3 Hz) 1.48–1.02 (7H, m) 1.15 (3H, s) 1.10 (3H, s) 0.95 (3H, d, J 6.4 Hz) 0.62 (3H, d, J 6.9 Hz); MS(EI) m/z 517 (M$^+$), Found: 517.2504, C$_{22}$H$_{39}$NO$_6$S requires 517.2498.

Step 2. Mutilin 14-(N-phenylsulphonylcarbamate)

The product of Step 1 (340 mg, 0.66 mmol) in dioxane (5 ml) was treated with a saturated solution of zinc chloride in conc. HCl (1 ml), as for Example 1 Step 2, to afford the title compound (291 mg, 88%); mp 125–7° C.; $v_{max}$ (CH$_2$Cl$_2$) 3364, 1736, 1450, 1420, 1353 cm$^{-1}$; $^1$H NMR (CDCl$_3$) 8.00 (2H, d, J 7.4 Hz) 7.65 (1H, t, J 7.4 Hz) 7.54 (2H, t, J 7.5 Hz) 6.26 (1H, dd, J 17.4, 11.0 Hz) 5.61 (1H, d, J 8.4 Hz) 5.23 (1H, dd, J 11.0, 1.3 Hz) 5.07 (1H, dd, J 17.5, 1.3 Hz) 3.18 (1H, dd, J 10.1, 6.7 Hz) 2.19 (3H, m) 1.95 (2H, m) 1.75–1.23 (8H, m) 1.33 (3H, s) 1.08 (1H, m) 1.07 (3H, s) 0.85 (3H, d, J 7.0 Hz) 0.51 (3H, d, J 6.7 Hz); MS(EI) m/z 503 (M$^+$), Found: 503.2348, C$_{27}$H$_{37}$NO$_6$S requires 503.2342.

EXAMPLE 5

Mutilin 14-(N-4-methoxyphenylcarbamate)

Step 1. (3R)-3-Deoxo-11-deoxy-3-methoxy-11-oxo-4-epi-mutilin 14-(N-4-methoxyphenylcarbamate)

(3R)-3-Deoxo-11-deoxy-3-methoxy-11-oxo-4-epi-mutilin (1.0 g, 2.97 mmol) in dry CH$_2$Cl$_2$ (10 ml) was treated with 4-methoxyphenyl isocyanate (0.77 ml, 5.95 mmol) and N,N-di-iso-propylethylamine (5 drops) and the solution was kept at room temperature, with exclusion of moisture, for 8 days. The solution was diluted with CH$_2$Cl$_2$ and washed with water followed by brine. The solution was dried (MgSO$_4$) and the solvent removed by evaporation under reduced pressure. The residue was triturated with ethyl acetate/hexane and the resulting solid was removed by filtration before reducing the mother liquors to low volume under reduced pressure. Purification was accomplished by chromatography on silica gel eluting with 1:4 ethyl acetate-hexane. The title compound was isolated as a foam (1.37 g, 95%); $v_{max}$ (CH$_2$Cl$_2$) 3428, 2932, 1722, 1697, and 1597 cm$^{-1}$; $^1$H NMR (CDCl$_3$) 0.89 (3H, d, J 6.1 Hz), 0.99 (3H, d, J 6.4 Hz), 1.20 (6H, s) superimposed on 1.07–1.29 (5H, m), 1.34–1.37 (1H, m), 1.70 (1H, d, J 15.3 Hz), 1.73 (1H, d, J 11.3 Hz), 1.94–2.05 (2H, m), 2.15–2.24 (1H, m), 2.46 (1H, dd, J 15.2, 10.0 Hz), 2.96 (1H, q, J 6.4 Hz), 3.23 (3H, s), 3.47 (1H, m), 3.80 (3H, s), 5.01 (1H, d, J 17.4 Hz), 5.31 (1H, d, J 10.7 Hz), 5.77 (1H, d, J 9.9 Hz), 6.43 (1H, broad s), 6.75 (1H, dd, J 17.5, 10.6 Hz), 6.86 (2H, d, J 8.9 Hz), 7.31 (2H, broad d); MS (ESI –ve ion) m/z 482 ((M–H)$^-$).

Step 2. Mutilin 14-(N-4-methoxyphenylcarbamate)

(3R)-3-deoxy-11-deoxy-3-methoxy-11-oxo-4-epi-mutilin 14-(N4-methoxyphenylcarbamate) (483 mg, 1 mmol) in dioxane (5 ml) was treated with a saturated solution of zinc chloride in conc. HCl (1 ml) as described in Example 1 Step 2. The title compound was isolated as a crystalline solid (400 mg, 86%); m.p. (CH$_2$Cl$_2$/hexane) 192–194° C.; $v_{max}$ (CH$_2$Cl$_2$) 3625, 3563, 2937, 1725, 1597, and 1519 cm$^{-1}$; $^1$H NMR (CDCl$_3$) 0.79 (3H, broad d), 0.87 (3H, d, J 7.0 Hz), 1.18 (6H, s), 1.14–1.82 (13H, m), 2.04–2.26 (3H, m), 2.37 (1H, quint, J 6.9 Hz), 3.36 (1H, dd, J 10.9, 6.7 Hz), 3.78 (3H, s), 4.81 (1H, dd, J 17.4, 1.6 Hz), 5.36 (1H, dd, J 10.9, 1.4 Hz), 5.73 (1H, d, J 8.3 Hz), 6.39 (1H, broad s), 6.59 (1H, dd, J 17.4, 10.9 Hz), 6.85 (2H, d, J 8.9 Hz), 7.26 (2H, broad d); MS (EI) m/z 469 (M$^+$). C$_{28}$H$_{39}$NO$_5$ requires 469.2828, Found: 469.2830.

EXAMPLE 6

Mutilin 14-(N-4-nitrophenylcarbamate)

Step 1. (3R)-3-Deoxo-11-deoxy-3-methoxy-11-oxo-4-epi-mutilin 14-(N-4-nitrophenylcarbamate)

(3R)-3-Deoxo-11-deoxy-3-methoxy-11-oxo-4-epi-mutilin (1.0 g, 2.97 mmol) and 4-nitrophenyl isocyanate (731 mg, 4.5 mmol) and N,N-di-iso-propylethylamine (5 drops) were dissolved in dry CH$_2$Cl$_2$ (10 ml), as described in Example 5 Step 1, to give the title compound (702 mg); $v_{max}$ (CH$_2$Cl$_2$) 3415, 2981, 1733, 1698, and 1599 cm$^{-1}$; $^1$H NMR (CDCl$_3$) 0.87 (3H, d, J 6.9 Hz), 1.01 (3H, d, J 6.4 Hz), 1.21 (3H,s) and 1.26 (3H,s) superimposed on 1.10–1.90 (6H, m), 1.68 (1H, d, J 15.4 Hz), 1.75 (1H, d, J 11.5 Hz), 1.94–2.06 (2H, m), 2.16–2.25 (1H, m), 2.51 (1H, dd, J 15.2, 10.1 Hz), 2.94 (1H, q, J 6.3 Hz), 3.23 (3H, s), 3.47–3.49 (1H, m), 5.04 (1H, d, J 17.5 Hz), 5.32 (1H, d, J 10.7 Hz), 5.82 (1H, d, J 9.9 Hz), 6.70 (1H, dd, J 17.5, 10.6 Hz), 6.93 (1H, broad s), 7.61 (2H, d, J 9.1 Hz), 8.22 (2H, d, J 9.1 Hz); MS ($NH_3DCI$) m/z 499 (MH$^+$), m/z 516 (MNH$_4{}^+$).

Step 2. Mutilin 14-(N-4-nitrophenylcarbamate)

(3R)-3-deoxo-11-deoxy-3-methoxy-11-oxo-4-epi-mutilin 14-(N-4-nitrophenylcarbamate) (203 mg, 0.41 mmol) in dioxane (5 ml) was treated with a saturated solution of zinc chloride in conc. HCl (0.5 ml) as described in Example 1 Step 2. The title compound was isolated as a crystalline solid (163 mg, 82%); m.p. ($CH_2Cl_2$/hexane) 208–210° C.; $v_{max}$ ($CH_2Cl_2$) 3562, 3314, 2939, 1733, 1598, and 1536 cm$^{-1}$; $^1$H NMR (CDCl$_3$) 0.78 (3H, d, J 6.5 Hz), 0.92 (3H, d, J 7.0 Hz), 1.20 (3H, s) and 1.46 (3H, s) both superimposed on 1.20–1.84 (10H, m), 2.09–2.28 (3H, m), 2.39 (1H, quint, J 7.0 Hz), 3.38 (1H, dd, J 10.7, 6.6 Hz), 5.23 (1H, dd, J 17.5, 1.4 Hz), 5.39 (1H, dd, J 10.9, 1.4 Hz), 5.80 (1H, d, J 9.3 Hz), 6.56 (1H, dd, J 17.4, 10.9 Hz), 6.88 (1H, broad s), 7.56 (2H, d, J 9.2 Hz), 8.20 (2H, d, J 9.2 Hz); MS (EI) m/z 484 (M$^+$). $C_{27}H_{36}N_2O_6$ requires 484.2573, Found: 484.2571.

EXAMPLE 7

Mutilin 14-carbamate

Step 1. (3R)-3-Deoxo-11-deoxy-3-methoxy-11-oxo-4-epi-mutilin 14-(N-trichloroacetylcarbamate)

(3R)-3-Deoxo-11-deoxy-3-methoxy-11-oxo-4-epi-mutilin (1.0 g, 2.97 mmol) and trichloroacetyl isocyanate (0.389 ml, 3.3 mmol) and N,N-di-iso-propylethylamine (5 drops) were dissolved in dry $CH_2Cl_2$ (10 ml), as described in Example 5 Step 1, to give the title compound (1.80 g, quant.); $v_{max}$ ($CH_2Cl_2$) 3510, 3396, 1737, 1698, and 1583 cm$^{-1}$; $^1$H NMR (d$_6$-acetone) 0.85–0.91 (3H, m), 1.02 (3H, d, J 6.4 Hz), 1.11–1.79 (14H, m), 1.90–2.23 (3H, m), 2.42–2.63 (1H, m), 3.01 (1H, q, J 6.4 Hz), 3.18–3.27 (5H, m), 3.50–3.59 (1H, m), 4.04–4.18 (2H, m), 4.99 (1H, d, J 17.6 Hz), 5.30 (1H, d, J 10.8 Hz), 5.83–5.87 (1H, m), 6.82–6.99 (m), 7.16–7,23 (m), 7.88–7.91(m) (total 4H); MS ($NH_3DCI$) m/z 521 (MH$^+$), m/z 539 (MNH$_4{}^+$).

Step 2. Mutilin 14-(N-trichloroacetylcarbamate)

(3R)-3-Deoxo-11-deoxy-3-methoxy-11-oxo-4-epi-mutilin 14-(N-trichloroacetylcarbamate) (1.8 g, 2.97 mmol) in dioxane (10 ml) was treated with a saturated solution of zinc chloride in conc. HCl (2.0 ml) as described in Example 1 Step 2. The title compound was isolated as a solid (901 mg, 60%); $v_{max}$ ($CH_2Cl_2$) 3406, 1803, and 1736 cm$^{-1}$; $^1$H NMR (d$_6$-acetone) 0.89 (3H, d, J 6.8 Hz), 1.01 (3H, d, J 6.4 Hz), 1.11–2.22 (17H, m), 2.55 (1H, dd, J 15.4, 10.1 Hz), 2.91–2.96 (1H, m), 3.19 (3H, s), 3.45–3.55 (1H, m), 5.00 (1H, d, J 17.6 Hz), 5.31 (1H, d, J 10.7 Hz), 5.88 (1H, d, J 10.0 Hz), 6.74 (1H, dd, J 17.5, 10.7 Hz), 10.59 (1H broad s); MS (ESI –ve ion) m/z 506 ((M–H)$^-$).

Step 3. Mutilin 14-carbamate

Mutilin 14-(N-trichloroacetylcarbamate) (300 mg) was dissolved in $CH_2Cl_2$ (2 ml) and methanol (2 ml) before treating with potassium carbonate (122 mg, 0.9 mmol). The reaction was stirred at room temperature for 4 hours before diluting with $CH_2Cl_2$. The organic phase was washed with water (twice) followed by saturated sodium chloride solution, and the solvent removed under reduced pressure. Trituration of the residue gave the title compound as a white solid (179 mg, 85%); $v_{max}$ ($CH_2Cl_2$) 3538, 3421, 1725, and 1582 cm$^{-1}$; $^1$H NMR (CDCl$_3$) 0.79 (3H, d, J 6.4 Hz), 0.86 (3H, d, J 7.0 Hz), 1.17 (3H, s), 1.39 (3H, s) superimposed on 1.38–1.79 (10H, m), 2.02–2.25 (1H, d, J 8.6 Hz), 2.09 (1H, broad s), 2.17–2.31 (2H,m), 2.36 (1H, quint, J 6.9 Hz), 3.35 (1H, broad t), 4.52 (2H, broad s), 5.21 (1H, dd, J 17.4, 1.5 Hz), 5.36 (1H, dd, J 11.0, 1.5 Hz), 5.62 (1H, d, J 8.5 Hz) 6.57 (1H, dd, J 17.4, 10.9 Hz); MS ($NH_3DCI$) m/z 364 (MH$^+$), m/z 381 (MNH$_4{}^+$).

EXAMPLE 8

Mutilin 14-(N-benzylcarbamate)

Step 1. (3R)-3-Deoxo-11-deoxy-3-methoxy-11-oxo-4-epi-mutilin 14-(N-benzylcarbamate)

(3R)-3-Deoxo-11-deoxy-3-methoxy-11-oxo-4-epi-mudlin (336 mg, 1.0 mmol) was dissolved in dry $CH_2Cl_2$ (5 ml) and treated with benzyl isocyanaee (0.16 ml, 1.30 mmol) and N,N-di-iso-propylethylamine (5 drops) and the reaction was carried out as described in Example 5, Step 1. The title compound was isolated as a white foam (432 mg, 95%); $v_{max}$ ($CH_2Cl_2$) 3444, 2930, 1711, 1698, and 1456 cm$^{-1}$; $^1$H NMR (CDCl$_3$) 0.87 (3H, d, J 6.8 Hz), 0.98 (3H, d, J 6.4 Hz), 1.18 (3H, s) and 1.19 (3H, s) both superimposed on 1.02–1.54 (6H, m), 1.67 (1H, d, J 15.2 Hz), 1.70 (1H, d, J 11.3 Hz), 1.93–2.04 (2H, m), 2.15–2.23 (1H, m), 2.42 (1H, dd, J 15.1, 10.0 Hz), 2.95 (1H, q, J 6.4 Hz), 3.22 (3H, s), 3.42–3.51 (1H, m), 4.32 (1H, dd, J 14.9, 5.5 Hz), 4.52 (1H, dd, J 14.9, 6.4 Hz), 4.95 (1H, broad s), 5.01 (1H, d, J 17.6 Hz), 5.32 (1H, d, J 10.7 Hz), 5.69 (1H, d, J 9.8 Hz), 6.79 (1H, dd, J 17.5, 10.6 Hz), 7.26–7.37 (5H, m).

Step 2. Mutilin 14-(N-benzylcarbamate)

(3R)-3-Deoxo-11-deoxy-3-methoxy-11-oxo-4-epi-mutilin 14-(N-benzylcarbamate) (400 mg, 0.85 mmol) in dioxane (5 ml) was treated with a saturated solution of zinc chloride in conc. HCl (1.0 ml) as described in Example 1 Step 2. The title compound was isolated as a foam (329 mg, 82%); $v_{max}$ ($CH_2Cl_2$) 3626, 3563, 2934, 1718, 1581, and 1510 cm$^{-1}$; $^1$H NMR (CDCl$_3$) 0.77 (3H, d, J 5.9 Hz), 0.86 (3H, d, J 7.0 Hz), 1.17 (3H, s) and 1.39 (1H, s) superimposed on 1.08–1.80 (8H, m), 1.99–2.07 (3H, m), 2.17–2.24 (2H, m), 2.39 (1H, quint, J 6.9 Hz), 3.35 (1H, dd, J 10.8, 6.7 Hz), 4.31 (1H, dd, J 5.9 Hz), 4.41 (1H, dd, J 16.0, 6.2 Hz), 4.90 (1H, broad t), 5.20 (1H, d, J 17.3 Hz), 5.36 (1H, d, J 10.9 Hz), 5.69 (1H, d, J 8.4 Hz), 6.61 (1H, dd, J 17.4, 11.0 Hz), 7.24–7.43 (5H, m); MS (EI) m/z 391 (M$^+$); MS ($NH_3DCI$) m/z 392 (MH$^+$).

EXAMPLE 9

Mutilin 14-[N-(Benzylaminosulfonyl)carbamate]

Step 1. (3R)-3-Deoxo-11-deoxy-3-methoxy-11-oxo-4-epi-mutilin 14-[N-(chlorosulfonyl)carbamate]

(3R)-3-Deoxo-11-deoxy-3-methoxy-11-oxo-4-epi-mutilin (1.0 g, 2.97 mmol) was dissolved in dry $CH_2Cl_2$ (5 ml) and treated with chlorosulfonyl isocyanate (0.284 ml, 3.30 mmol) and the reaction was carried out as described in Example 5, Step 1. The title compound was isolated as a white foam (1.03 g, 75%); $v_{max}$ ($CH_2Cl_2$) 3331, 2929, 1765, 1698, and 1441 cm$^{-1}$; $^1$H NMR (CDCl$_3$) 0.93 (3H, d, J 6.9 Hz), 1.02 (3H, d, J 6.4 Hz), 1.20 (3H, s) and 1.26 (3H, s) and 1.82 (1H, d, J 15.2 Hz) all superimposed on 1.22–2.26 (5H, m), 2.60 (1H, dd, J 15.4, 10.2 Hz), 2.95 (1H, q, J 6.4 Hz), 2.97 (3H, s), 3.46–3.55 (1H, m), 5.02 (1H, d, J 17.5 Hz), 5.33 (1H, d, J 10.7 Hz), 5.88 (1H, d, J 10.1 Hz), 6.68 (1H, dd, J 17.5, 10.7 Hz).

Step 2. (3R)-3-Deoxo-11-deoxy-3-methoxy-11-oxo-4-epi-mutilin 14-[N-(benzylaminosulfonyl)carbamate]

(3R)-3-Deoxo-11-deoxy-3-methoxy-11-oxo-4epi-mutilin 14-[N-(chlorosulfonyl)carbamate](300 mg, 0.65 mmol) was dissolved in dry dichloromethane under an atmosphere of argon. The solution was treated with benzylamine (0.077 ml, 0.71 mmol) followed by triethylamine (0.1 ml, 0.71 mmol). After 12 hours stirring at room temperature the reaction was diluted with dichloromethane and washed with water and saturated sodium chloride solution. After drying (MgSO$_4$) the crude material was purified by chromatography on silica gel eluting with 1:4 ethyl acetate-hexane. The title compound was isolated as a foam (233 mg, 65%); $v_{max}$ ($CH_2Cl_2$) 3370, 2981, 2930, 1734, 1698, and 1456 cm$^{-1}$; $^1$H NMR (CDCl$_3$) 0.88 (3H, d, J 6.8 Hz), 0.99 (3H, d, J 6.4 Hz), 1.19

(3H, s), 1.21 (3H, s), 1.54 (1H, d, J 15.4 Hz), 1.72 (1H, d, J 11.3 Hz), 1.07–1.74 (6H, m), 1.93–2.02 (2H, m), 2.14–2.23 (1H, m), 2.44 (1H, dd, J 15.2, 10.2 Hz), 2.84 (1H, q, J 6.5 Hz), 3.21 (3H, s), 3.38–3.47 (1H, m), 4.19 (1H, dd, J 13.6, 5.3 Hz), 4.30 (1H, dd, J 13.7, 6.9 Hz), 5.02 (1H, d, J 17.5 Hz), 5.30 (1H, d, J 10.7 Hz), 5.40 (1H, broad t, J ~5.7 Hz) 5.74 (1H, d, J 10.0 Hz), 6.56 (1H, dd, J 17.5, 10.7 Hz), 7.35 (5H, broad s), 7.50 (1H, broad s); MS (NH$_3$DCI) m/z 564 (MNH$_4$$^+$); MS (EI) m/z 546 (M$^+$). C$_{29}$H$_{42}$N$_2$O$_6$S requires 546.2764, Found: 546.2764.

Step 3: Mutilin 14-[N-(Benzylaminosulfonyl)carbamate]

(3R)-3-Deoxo-11-deoxy-3-methoxy-11-oxo-4-epi-mutilin 14-[N-(benzylaminosulfonyl)carbamate] (233 mg, 0.43 mmol) in dioxane (4 ml) was treated with a saturated solution of zinc chloride in conc. HCl (0.5 ml) as described in Example 1 Step 2. The title compound was isolated as a foam (169 mg, 82%); $v_{max}$ (CH$_2$Cl$_2$) 3562, 3372, 2934, and 1734 cm$^{-1}$; $^1$H NMR (CDCl$_3$) 0.79 (3H, d, J 6.8 Hz), 0.88 (3H, d, J 7.0 Hz), 1.20 (3H, s), 1.40 (1H, s), 1.47 (1H, d, J 10.7 Hz), 1.10–1.81 (10H, m), 2.08–2.32 (5H, m), 3.36 (1H, dd, J 10.3, 6.7 Hz), 4.19 (1H, s), 4.20 (1H, s), 5.26 (1H, dd, J 17.3, 1.4 Hz), 5.37 (1H, dd, J 10.9, 1.3 Hz), 5.34–5.39 (1H, m), 5.72 (1H, d, J 8.5 Hz), 6.46 (1H, dd, J 17.4, 11.0 Hz), 7.28–7.37 (5H, m); MS (NH$_3$DCI) m/z 550 (MNH$_4$$^+$).

EXAMPLE 10

Mutilin 14-[N-(2,6-Dichloropyridin-4-yl)carbamate]
Step 1. (3R)-3-Deoxo-11-deoxy-3-methoxy-11-oxo-4-epi-mutilin 14-[N-(2,6-dichloropyridin-4-yl)carbamate]

(3R)-3-Deoxo-11-deoxy-3-methoxy-11-oxo-4-epi-mutilin (336 mg, 1.0 mmol) was dissolved in dry CH$_2$Cl$_2$ (5 ml) and treated with 2,6-dichloropyridine-4-isocyanate (283 mg, 1.5 mmol) and N,N-di-iso-propylethylamine (5 drops) and the reaction was carried out as described in Example 5, Step 1. The title compound was isolated as a white foam (589 mg, quant.); $v_{max}$ (CH$_2$Cl$_2$) 3407, 3295, 2981, 1734, 1698, 1575 and 1502 cm$^{-1}$; $^1$H NMR (CDCl$_3$) 0.83 (3H, d, J 6.9 Hz), 1.01 (3H, d, J 6.4 Hz), 1.20 (3H, s), 1.21 (3H, s), 1.08–1.56 (6H, m) 1.64 (1H, d, J 15.3 Hz), 1.74 (1H, d, J 11.3 Hz), 1.94–2.05 (2H, m), 2.16–2.30 (1H, m), 2.50 (1H, dd, J 12.7, 6.4 Hz), 2.91 (1H, q, J 6.2 Hz), 3.23 (3H, s), 3.41–3.48 (1H, m), 5.04 (1H, d, J 17.5 Hz), 5.36 (1H, d, J 10.7 Hz), 5.80 (1H, d, J 9.9 Hz), 6.65 (1H, dd, J 17.6, 10.7 Hz), 7.07 (1H, broad s), 7.34 (1H, s), 7.44 (1H, s), MS (NH$_3$DCI) m/z 523 (MH$^+$).

Step 2. Mutilin 14-[N-(2,6-Dichloropyridin-4-yl)carbamate]

(3R)-3-Deoxo-11-deoxy-3-methoxy-11-oxo-4-epi-mutilin 14-[N-(2,6-dichloropyridin-4-yl)carbamate](569 mg, 1.0 mmol) in dioxane (5 ml) was treated with a saturated solution of zinc chloride in conc. HCl (1.5 ml) as described in Example 1 Step 2. The title compound was isolated as a foam which was crystallised from ethyl acetate/hexane(266 mg, 52%), m.p. (EtOAc/hexane) 237° C.; $v_{max}$ (CH$_2$Cl$_2$) 3404, 2926, 1739, 1719, 1579, and 1507 cm$^{-1}$; $^1$H NMR (CDCl$_3$) 0.61 (3H, d, J 6.2 Hz), 0.77 (3H, d, J 7.0 Hz), 0.96–1.08 (4H, m), 0.96–1.08 (10H, m), 1.90–2.27 (6H, m), 3.20–3.26 (2H, m), 5.07 (1H, dd, J 17.4, 1.4 Hz), 5.22 (1H, dd, J 10.9, 1.3 Hz), 5.58 (1H, d, J 8.3 Hz), 6.34 (1H, dd, J 17.4, 11.0 Hz), 7.34 (2H, s); MS (EI) m/z 508 (M$^+$); MS (NH$_3$DCI) m/z 509 (MH$^+$).

EXAMPLE 11

Mutilin-14-(N,N-Dimethylcarbamate)
Step 1. (3R)-3-Deoxo-11-deoxy-3-methoxy-11-oxo-4-epi-mutilin 14-(N,N-dimethylcarbamate)

(3R)-3-Deoxo-11-deoxy-3-methoxy-11-oxo-4-epi-mutilin (336 mg, 1.0 mmol) was dissolved in pyridine (10 ml) before treating with N,N-dimethylcarbamoyl chloride (0.12 ml, 1.3 mmol). The reaction was warmed to reflux under an atmosphere of argon. Further portions of N,N-dimethylcarbamoyl chloride (0.12 ml, 1.3 mmol) were added to the reaction at 5 daily intervals during its duration. After 14 days at reflux the reaction was allowed to cool and then partitioned between ethyl acetate and 1.0M HCl. The organic phase was separated and washed with water followed by saturated sodium chloride solution. After drying (MgSO$_4$) the crude material was purified by chromatography on silica gel, loading in PhCH$_3$ and eluting with 1:9 ethyl acetate-hexane. The title compound was isolated as a white solid (158 mg, 40%); $v_{max}$ (CH$_2$Cl$_2$) 2931, 1693, and 1456 cm$^{-1}$; $^1$H NMR (CDCl$_3$) 0.87 (3H, d, J 6.7 Hz), 0.98 (3H, d, J 6.4 Hz), 1.20 (3H, s) and 1.26 (3H, s) both superimposed on 1.07–1.74 (6H, m), 1.99–2.04 (2H, m), 2.16–2.24 (1H, m), 2.82 and 2.92 (3H, s+s), 2.92 (1H, m), 3.21 and 3.23 (3H, s+s), 3.46–3.56 (1H, m), 4.28 and 4.76 (ABq, J 15.2 Hz) with 4.32 and 4.76 (ABq, J 15.7 Hz) (total 2H), 5.01 (1H, d, J 17.6 Hz), 5.32 (1H, d, J 10.2 Hz), 5.72 (1H, d, J 9.9 Hz), 6.79–6.90 (1H,m), 7.22–7.31 (5H, m).

Step 2. Mutilin-14-(N,N-dimethylcarbamate)

(3R)-3-Deoxo-11-deoxy-3-methoxy-11-oxo-4-epi-mutilin 14-(N,N-dimethylcarbamate) (158 mg, 0.40 mmol) in dioxane (3 ml) was treated with a saturated solution of zinc chloride in conc. HCl (0.5 ml) as described in Example 1 Step 2. The title compound was isolated as a solid (74 mg, 49%); $v_{max}$ (CH$_2$Cl$_2$) 3564, 2933, 1734, 1692, and 1454 cm$^{-1}$; $^1$H NMR (CDCl$_3$) 0.73 (3H, d, J 6.4 Hz), 0.84 (3H, d, J 7.1 Hz), 1.16 (3H, s) and 1.36 (1H, d, J 16.0 Hz) and 1.45 (3H, s) all superimposed on 1.08–1.80 (5H, m), 2.00–2.10 (2H, m), 2.18–2.26 (2H, m), 2.37 (1H, quint., J 6.9 Hz), 2.86 (3H, s), 2.90 (3H, s), 3.34 (1H, dd, J 11.3, 6.6 Hz), 5.20 (1H, dd, J 17.4, 1.7 Hz), 5.36 (1H, dd, J 11.0, 1.6 Hz), 5.67 (1H, d, J 8.4 Hz), 6.65 (1H, dd, J 17.4, 11.0 Hz); MS (EI) m/z 391 (M$^+$); MS (NH$_3$DCI) m/z 392 (MH$^+$).

EXAMPLE 12

14-O-(Indolinylcarbonyl)mutilin
Step 1. (3R)-3-Deoxo-11-deoxy-3-methoxy-11-oxo-4-epi-mutilin 14-chloroformate
Method 1

(3R)-3-Deoxo-11-deoxy-3-methoxy-11-oxo-4-epi-mutilin (1.0 g, 2.97 mmol) was dissolve in dry tetrahydrofuran (10 ml) under an atmosphere of argon. The reaction was cooled to 0° C. and treated with trichloromethylchloroformate (0.215 ml, 1.48 mmol) followed by triethylamine (0.495 ml, 3.56 mmol). The heterogeneous mixture was stirred at room temperature for 2 hours and then treated with further trichloromethylchloroformate (0.215 ml, 1.48 mmol) and triethylamine (0.495 ml, 3.56 mmol). After a further two hours more trichloromethylchloroformate (0.108 ml, 0.74 mmol) and triethylamine (0.250 ml, 1.78 mmol) were added. The reaction was diluted with tetrahydrofuran (30 ml) and toluene (10 ml). After washing with saturated sodium chloride the organic phase was separated and dried (MgSO$_4$). Removal of solvent gave a yellow oil which crystallised on standing (1.42 g, quant). Purification of a portion of this solid (286 mg) was accomplished by chromatography on silica gel, loading and eluting with 1:19 ethyl acetate-hexane. The title compound was isolate as a white crystalline solid (145 mg, 62%); $v_{max}$ (CH$_2$Cl$_2$) 1765, 1732, 1699, and 1458 cm$^{-1}$; $^1$H NMR (d$_6$-acetone) 0.94 (3H, d, J 6.8 Hz), 1.00 (3H, d, J 6.4 Hz), {1.21 (3H, s) 1.27 (3H, s), 1.78 (1H, d, J 11.3 Hz), 1.91 (1H, d, J 15.7 Hz)} all superimposed on 1.11–2.26 (9H, m), 2.63 (1H, dd, J 15.6, 10.3 Hz), 2.82 (1H, q, obscured by HOD), 3.14 (3H, s), 3.49–3.53 (1H, m), 5.02 (1H, d, J 17.6 Hz), 5.35 (1H, d, J 10.7 Hz), 5.83 (1H, d, J 10.2 Hz), 6.52 (1H, dd, J 17.6, 10.7 Hz).

Method 2

(3R)-3-Deoxo-11-deoxy-3-methoxy-11-oxo-4-epi-mutilin (1.0 g, 2.97 mmol) was dissolved in toluene under an atmosphere of argon. The solution was cooled to 0° C. and treated with phosgene (2.82 ml of 12.5% w/w solution in toluene, 3.56 mmol) followed by pyridine (0.24 ml, 2.97 mmol). The heterogeneous reaction mixture was stirred at room temperature. After 2 and 12 hour intervals the same quantities of phosgene and pyridine were added. The reaction mixture was then diluted with toluene (40 ml) and washed with saturated sodium chloride solution adding just enough water to completely dissolve all the solid in the aqueous phase. After drying ($MgSO_4$) the material was purified by chromatography on silica gel to give the title compound as a crystalline solid (926 mg, 78%).

Step 2. (3R)-3-Deoxo-11-deoxy-3-methoxy-11-oxo-14-O-(indolinylcarbonyl)-4-epi-mutilin (3R)-3-Deoxo-11-deoxy-3-methoxy-11-oxo-)-4-epi-mutilin 14-chloroformate (300 mg, 0.75 mmol) was dissolved in dry $CH_2Cl_2$ whilst under an atmosphere of argon. The solution was treated with indoline (268 mg, 2.2 mmol) and the reaction stirred at room temperature for 15 minutes. The mixture was diluted with $CH_2Cl_2$ and washed sequentially with 1.0M HCl followed by water and saturated sodium chloride solution. The organic phase was dried ($MgSO_4$) and the solvents removed by evaporation under reduced pressure. Purification was achieved by chromatography on silica gel loading and eluting with 1:9 ethyl acetate-hexane. The title compound was isolated as a foam (308 mg, 86%); $v_{max}$ ($CH_2Cl_2$) 2930, 1731, 1696, and 1602 $cm^{-1}$; $^1$H NMR ($d_6$-acetone) 0.85–0.91 (3H, m), 1.02 (3H, d, J 6.4 Hz), 1.11–1.79 (14H, m), 1.90–2.23 (3H, m), 2.63 (1H, m), 3.01 (1H, q, J 6.4 Hz), 3.18–3.27 (5H, m), 3.50–3.59 (1H, m), 4.04–4.18 (2H, m), 4.99 (1H, d, J 17.6 Hz), 5.30 (1H, d, J 10.8 Hz), 5.83–5.87 (1H, m), 6.82–6.99 (m), 7.16–7,23 (m), 7.88–7.91 (m) (total 4H); MS (EI) m/z 479 ($M^+$), ($NH_3DCI$) m/z 480 ($MH^+$).

Step 3: 14-O-(Indolinylcarbonyl)mutilin (3R)-3-Deoxo-11-deoxy-3-methoxy-11-oxo-14-O-(indolinylcarbonyl)-4-epi-mutilin (260 mg, 0.54 mmol) in dioxane (5 ml) was treated with a saturated solution of zinc chloride in conc. HCl (0.5 ml) as described in Example 1 Step 2. The title compound was isolated as a solid which was crystallised from $CH_2Cl_2$— hexane(195 mg, 77%); $v_{max}$ ($CH_2Cl_2$) 3627, 3563, 2934, 1734, 1697, 1602, 1487, and 1407 $cm^{-1}$; $^1$H NMR ($CDCl_3$) 0.76 (3H, m), 0.89 (3H, d, J 7.1 Hz), 1.06–1.83 (16H, m), 2.14–2.29 (4H, m), 2.44 (1H, quint, J 6.9 Hz), 3.12 (2H, t, J 8.6 Hz), 3.38 (1H, m), 3.94–4.04 (1H, m), 5.22 (1H, dd, J 17.5, 1.5 Hz), 5.38 (1H, dd, J 11.0, 1.5 Hz), 5.72–5.86 (1H, m), 6.58–6.64 (1H, m), 6.92–6.98 (m), 7.19–7.22 (m), 7.89–7.92(m) (total 4H); MS (EI) m/z 465 ($M^+$). $C_{29}H_{39}NO_4$ requires 465.2879, Found: 465.2885.

EXAMPLE 13

Mutilin 14-[N-(2-Hydroxyethyl)carbamate]

Step 1. (3R)-3-Deoxo-11-deoxy-3-methoxy-11-oxo-4-epi-mutilin 14-[N-(2-hydroxyethyl)carbamate]

(3R)-3-Deoxo-11-deoxy-3-methoxy-11-oxo-)-4-epi-mutilin 14-chloroformate (300 mg, 0.75 mmol) (prepared as described in Example 12, Step 1, Method 2) was dissolved in dry dichloromethane (5 ml) and treated with ethanolamine (0.137 ml, 2.25 mmol) and reacted as described in Example, Step 1. The title compound was isolated as a foam (323 mg, quant.); $v_{max}$ ($CH_2Cl_2$) 3616, 3446, 2931, 1699, and 1513 $cm^{-1}$; $^1$H NMR ($CDCl_3$) 0.85 (3H, d, J 6.9 Hz), 0.98 (3H, d, J 6.4 Hz), 1.23 (6H, s), 1.61 (1H, d, exchange in $D_2O$) superimposed on 0.95–1.72 (7H, m), 1.93–2.04 (2H, m), 2.14–2.36 (1H, m), 2.41 (1H, dd, J 15.2, 10.1 Hz), 2.93 (1H, q, J 6.4 Hz), 3.22 (3H, s), 3.37–3.48 (3H, m), 3.72 (2H, m, collapses to t in $D_2O$, J 5.0 Hz), 5.00 (1H, d, J 17.6 Hz) superimposed on 5.04 (1H, broad s) 5.29 (1H, d, J 10.8 Hz), 5.69 (1H, d, J 9.9 Hz), 6.73 (1H, dd, J 17.5, 10.6 Hz); MS ($NH_3DCI$) m/z 422 ($MH^+$), m/z 439 ($MNH_4^+$).

Step 2. Mutilin 14-[N-(2-Hydroxyethyl)carbamate]

(3R)-3-Deoxo-11-deoxy-3-methoxy-11-oxo-4-epi-mutilin 14-[N-(2-hydroxyethyl)carbamate] (300 mg, 0.56 mmol) in dioxane (5 ml) was treated with a saturated solution of zinc chloride in conc. HCl (0.5 ml) as described in Example 1 Step 2. The title compound was isolated as a solid which was crystallised from $CH_2Cl_2$/hexane(108 mg, 47%); $v_{max}$ ($CH_2Cl_2$) 3620, 3564, 3446, 2937, 1733, 1712, 1512, and 1455 $cm^{-1}$; $^1$H NMR ($CDCl_3$) 0.76 (3H, d, J 6.4 Hz), 0.86 (3H, d, J 7.0 Hz), 1.08–1.81 (16H, m) {including 1.16 (3H, s), 1.40 (3H, s)}, 2.08 (1H, broad s) superimposed in 1.98–2.13 (1H, m), 2.18–2.24 (2H, m), 2.39 (1H, quint, J 6.9 Hz), 3.31–3.38 (3H, m), 3.68 (2H, m, collapses to t in $D_2O$, J 5.0 Hz), 4.98 (1H, broad t), 5.20 (1H, dd, J 17.5, 1.5 Hz), 5.35 (1H, dd, J 11.3, 1.5 Hz), 5.64 (1H, d, J 8.3 Hz), 6.56 (1H, dd, J 17.4, 11.0 Hz); MS (EI) m/z 484 ($M^+$). $C_{23}H_{37}NO_5$ requires 407.2762, Found: 407.2670.

EXAMPLE 14

Mutilin 14-(N-Methyl-N-benzylcarbamate)

Step 1. (3R)-3-Deoxo-11-deoxy-3-methoxy-11-oxo-4-epi-mutilin 14-(N-methyl-N-benzylcarbamate)

(3R)-3-Deoxo-11-deoxy-3-methoxy-11-oxo-)-4-epi-mutilin 14-chloroformate (300 mg, 0.75 mmol) (prepared as described in Example 12, Step 1, Method 2) was dissolved in dry dichloromethane (5 ml) and treated with N-methyl-benzylamine (0.293 ml, 2.25 mmol) and reacted as described in Example, Step 1. The title compound was isolated as a foam (323 mg, 90%.); $v_{max}$ ($CH_2Cl_2$) 2981, 2929, 1698, and 1454 $cm^{-1}$; $^1$H NMR ($CDCl_3$) 0.87 (3H, d, J 6.7 Hz), 0.98 (3H, d, J 6.4 Hz), 1.20 (3H, s) and 1.26 (3H, s) both superimposed on 1.07–1.74 (12H, m), 1.99–2.04 (2H, m), 2.16–2.24 (1H, m), 2.82 and 2.92 (3H, s+s), 2.92 (1H, m), 3.21 and 3.23 (3H, s+s), 3.46–3.56 (1H, m), 4.28 and 4.76 (ABq, J 15.2 Hz) with 4.32 and 4.76 (ABq, J 15.7 Hz) (total 2H), 5.01 (1H, d, J 17.6 Hz), 5.32 (1H, d, J 10.2 Hz), 5.72 (1H, d, J 9.9 Hz), 6.79–6.90 (1H,m), 7.22–7.31 (5H, m); MS ($NH_3DCI$) m/z 482 ($MH^+$), m/z 499 ($MNH_4^+$); MS (EI) m/z 481 ($M^+$). $C_{30}H_{43}NO_4$ requires 481.3192, Found: 481.3199.

Step 2. Mutilin 14-(N-Methyl-N-benzylcarbamate)

(3R)-3-Deoxo-11-deoxy-3-methoxy-11-oxo-4-epi-mutilin 14-(N-methyl-N-benzylcarbamate) (270 mg, 0.56 mmol) in dioxane (5 ml) was treated with a saturated solution of zinc chloride in conc. HCl (0.5 ml) as described in Example 1 Step 2. The title compound was isolated as a solid (187 mg, 72%); $v_{max}$ ($CH_2Cl_2$) 3656, 3564, 2932, 1734, 1688, and 1453 $cm^{-1}$; $^1$H NMR ($CDCl_3$) 0.76 (3H, d, J 5.9 Hz), 0.86 (3H, d, J 7.0 Hz), 1.41–1.81 (5H, m), 1.97–2.42 (5H, m), 2.78 and 2.89 (3H, s+s), 3.32–3.38 (1H, m), 4.24 and 4.34 (1H, d+d, J 15.8 Hz), 4.61 (1H, d, J 15.3 Hz), 5.32 (1H, d, J 17.5 Hz), 5.38 (1H, d, J 10.8 Hz), 5.75 (1H, d, J 8.3 Hz), 6.56–6.73 (1H, m), 7.20–7.31 (5H, m); MS (EI) m/z 467 ($M^+$); MS ($NH_3DCI$) m/z 468 ($MH^+$).

EXAMPLE 15

14-O-(Morpholinocarbonyl)mutilin

Step 1. (3R)-3-Deoxo-11-deoxy-3-methoxy-11-oxo-14-O-(morpholinocarbonyl)-4-epi-mutilin Morpholine (0.2 ml, 2.29 mmol) was added to a solution of (3R)-3-deoxo-11-deoxy-3-methoxy-11-oxo-4-epi-mutilin 14-chloroformate (300 mg, 0.75 mmol) (Example 12, Step 1, Method 2) in dichloromethane (5 ml) under an atmosphere of argon. After two days the reaction was diluted with dichloromethane and washed with 1M HCl. The organic phase was dried ($MgSO_4$) and the solvent removed to afford the crude product. Chromatography on silica gel afforded the title compound (193 mg, 57%); $v_{max}$ ($CH_2Cl_2$) 1691 $cm^{-1}$, $^1$H NMR ($CDCl_3$) 6.79 (1H, dd, J 17.6, 10.7 Hz), 5.86 (1H, d, J 9.9 Hz), 5.31 (1H, d, J 10.7 Hz), 5.01 (1H, d, J 17.6 Hz), 3.66 (4H, m), 3.49 (5H, m), 3.22 (3H, s), 2.93 (1H, q, J 6.4 Hz), 2.43 (1H, dd, J 15.2, 10.0 Hz), 2.20 (1H, m), 1.99 (2H, m), 1.72 (1H, d, J 11.3 Hz), 1.63 (1H, d, J 15.2 Hz), 1.52–1.20 (5H, m), 1.23 (3H,s), 1.20 (3H, s), 1.09 (1H, m), 0.98 (3H, d, J 6.4 Hz), 0.89 (3H, d, J 6.9 Hz), MS(EI), m/z 447 (M$^+$) Found: 447.2990, $C_{26}H_{41}NO_5$ requires 447.2985.

Step 2. 14-O-(Morpholinocarbonyl)-mutilin

The product of Step 1 (153 mg, 0.34 mmol) in dioxane (5 ml) was treated with a saturated solution of zinc chloride in conc. HCl (1 ml), as for Example 1 Step 2, to afford the title compound (81 mg, 55%); $v_{max}$ ($CH_2Cl_2$) 3563, 1733, and 1689 cm$^{-1}$, $^1$H NMR (CDCl$_3$) 6.62 (1H, dd, J 17.4, 11.0 Hz), 5.70 (1H, d, J 8.4 Hz), 5.37 (1H, dd, J 11.0, 1.6 Hz), 5.21 (1H, dd, J 17.4, 1.6 Hz), 3.62 (4H, m), 3.43 (4H, m), 3.35 (1H, d, J 11.2, 6.6 Hz), 2.36 (1H, quintet, J 7.0 Hz), 2.22 (2H, m), 2.10 (1H, br), 2.04 (1H, m), 1.81–1.57 (4H, m), 1.54–1.34 (4H, m), 1.43 (3H, s), 1.19 (1H, m), 1.17 (3H, s), 0.86 (3H, d, J 7.0 Hz), 0.74 (3H, d, J 6.5 Hz), MS(EI) m/z 433 (M$^+$) Found: 433.2834, $C_{25}H_{39}NO_5$ requires 433.2828.

EXAMPLE 16

Mutilin 14-(N-methyl-N-phenylcarbamate)

Step 1. (3R)-3-Deoxo-11-deoxy-3-methoxy-11-oxo-4-epi-mutilin 14-(N-methyl-N-phenylcarbamate)

N-Methylaniline (0.3 ml, 2.32 mmol) was reacted with (3R)-3-deoxo-11-deoxy-3-methoxy-11-oxo-4-epi-mutilin 14-chloroformate (300 mg, 0.75 mmol) (Example 12, Step 1, Method 2) in dichloromethane (5 ml), as for Example 12 Step 2, to afford the title compound (287 mg, 81%); $v_{max}$ ($CH_2Cl_2$) 1693 cm$^{-1}$; $^1$H NMR (CDCl$_3$) 7.37 (2H, m), 7.24 (3H, m), 6.83 (1H, m), 5.69 (1H, m), 5.30 (1H, d, J 10.7 Hz), 5.00 (1H, d, J 17.5 Hz), 3.45 (1H, m), 3.32 (3H, s), 3.19 (3H, s), 2.92 (1H, m), 2.41 (1H, m), 2.18 (1H, m), 1.99 (2H, m), 1.74–1.58 (3H, m), 1.38–1.02 (11H, m), 0.97 (3H, d, J 6.4 Hz), 0.82 (3H, m); MS(EI) m/z 467 (M$^+$) Found: 467.3040, $C_{29}H_{41}NO_4$ requires 467.3036.

Step 2. Mutilin 14-(N-methyl-N-phenylcarbamate)

The product of Step 1 (270 mg, 0.58 mmol) in dioxane (5 ml) was treated with a saturated solution of zinc chloride in conc. HCl (1 ml), as for Example 1 Step 2, to afford the title compound (172 mg, 66%); $v_{max}$ ($CH_2Cl_2$) 3562, 1734, 1691 cm$^{-1}$; $^1$H NMR (CDCl$_3$) 7.34 (2H, m), 7.20 (3H, m), 6.64 (1H, dd, J 17.3, 11.0 Hz), 5.71 (1H, m), 5.38 (1H, d, J 10.7 Hz), 5.23 (1H, d, J 17.6 Hz), 3.33 (1H, dd, J 11.2, 6.7 Hz), 3.28 (3H, s), 2.38–2.05 (5H, m), 1.78–1.07 (9H, m), 1.58 (3H, s), 1.18 (3H, s), 0.85 (3H, d, J 7.0 Hz), 0.74 (3H, m); MS(EI) m/z 453 (M$^+$) Found: 453.2884, $C_{28}H_{39}NO_4$ requires 453.2879.

EXAMPLE 17

Mutilin 14-[N-(3-dimethylaminopropyl)carbamate]

Step 1. (3R)-3-Deoxo-11-deoxy-3-methoxy-11-oxo-4-epi-mutilin 14-[N-(3-dimethylaminopropyl)carbamate]

3-Dimethylaminopropylamine (0.07 ml, 0.56 mmol) was reacted with (3R)-3-deoxo-11-deoxy-3-methoxy-11-oxo-4-epi-mutilin 14-chloroformate (170 mg, 0.43 mmol) in dichloromethane (3 ml), as for Example 12 Step 2, to afford the title compound (147 mg, 74%); $v_{max}$ ($CH_2Cl_2$) 3447, 1698 cm$^{-1}$, $^1$H NMR (CDCl$_3$) 6.78 (1H, dd, J 17.5, 10.7 Hz), 5.62 (1H, dd, J 9.9 Hz), 5.52 (1H, m), 5.29 (1H, d, J 10.7 Hz), 4.99 (1H, d, J 17.5 Hz), 3.48–3.15 (3H, m), 3.21 (3H, s), 2.94 (1H, q, J 6.4 Hz), 2.42 (1H, m), 2.33 (2H, t, J 6.7 Hz), 2.21 (6H, s), 2.16 (1H, m), 1.98 (2H, m), 1.83 (1H, br), 1.67 (5H, m), 1.47 (1H, m), 1.30–1.05 (3H, m), 1.18 (6H, s), 0.97 (3H, d, J 6.4 Hz), 0.85 (3H, d, J 6.9 Hz), MS(EI) m/z 462 (M$^+$) Found: 462.3457, $C_{27}H_{46}N_2O_4$ requires 462.3458.

Step 2. Mutilin 14-[N-(3-dimethylaminopropyl)carbamate]

The product of Step 1 (141 mg, 0.3 mmol) in dioxane (3 ml) was treated with concentrated HCl (1 ml), and stirred at room temperature for 24 h. The reaction was carefully partitioned between ethyl acetate and saturated sodium hydrogen carbonate and the aqueous phase reextracted with ethyl acetate. The combined organics were dried (MgSO$_4$) and concentrated to afford the title compound (123 mg, 90%); $v_{max}$ ($CH_2Cl_2$) 3447, 1733, 1708 cm$^{-1}$; $^1$H NMR (CDCl$_3$) 6.61 (1H, dd, J 17.4, 11.0 Hz), 5.63 (1H, d, J 8.4 Hz), 5.35 (2H, includes 1H, dd, J 11.0, 1.5 Hz), 5.19 (1H, dd, J 17.4, 1.6 Hz), 3.22 (3H, m), 2.35 (4H, m), 2.19 (6H, s), 2.00 (2H, m), 1.68 (7H, m), 1.42 (7H, m), 1.16 (3H, s), 1.15 (1H, m), 0.85 (3H, d, J 7.0 Hz), 0.76 (3H, d, J 6.0 Hz); MS(EI) m/z 448 (M$^+$) Found: 448.3302, $C_{26}H_{44}N_2O_4$ requires 448.3301.

EXAMPLE 18

Mutilin 14-(N-hydroxycarbamate)

Step 1. (3R)-3-Deoxo-11-deoxy-3-methoxy-11-oxo-4-epi-mutilin 14-(N-hydroxycarbamate)

Hydroxylamine hydrochloride (50 mg, 0.72 mmol) was reacted with (3R)-3-deoxo-11-deoxy-3-methoxy-11-oxo-4-epi-muuilin 14-chloroformate (150 mg, 0.38 mmol) and diisopropylethylamine (0.2 ml, 1.15 mmol) in dichloromethane (3 ml), as for Example 12 Step 2, to afford the title compound (80 mg, 54%); $v_{max}$ ($CH_2Cl_2$) 3534, 1720, 1698 cm$^{-1}$; $^1$H NMR (CDCl$_3$) 7.18 (1H, s), 6.67 (2H includes 1H, dd, J 17.5, 10.6 Hz), 5.73 (1H, d, J 9.9 Hz), 5.29 (1H, d, J 10.7 Hz), 5.02 (1H, d, 17.5 Hz), 3.44 (1H, ddd, J 11.2, 8.0, 5.4 Hz), 3.21 (3H, s), 2.89 (1H, q, J 6.4 Hz), 2.45 (1H, dd, J 15.2, 10.1 Hz), 2.19 (1H, m), 1.99 (2H, m), 1.72 (1H, d, J 11.3 Hz), 1.62 (1H, d, J 15.2 Hz), 1.49 (2H, m), 1.35–1.03 (4H, m), 1.19 (6H, s), 0.99 (3H, d, J 6.4 Hz), 0.84 (3H, d, J 6.9 Hz); MS(3 NOBA sodium) m/z 416 (MNa$^+$).

Step 2. Mutilin 14-(N-hydroxycarbamate)

The product of Step 1 (72 mg, 0.18 mmol) in dioxane (3 ml) was treated with a saturated solution of zinc chloride in conc. HCl (1 ml), as for Example 1 Step 2, to afford the title compound (47 mg, 68%); $v_{max}$ (KBr disc) 3418, 1728 cm$^{-1}$, $^1$H NMR (CDCl$_3$) 9.38 (1H, s), 8.59 (1H, s), 6.24 (1H, dd, J 17.7, 11.1 Hz), 5.46 (1H, d, J 8.0 Hz), 5.11 (1H, dd, J 17.7, 1.8 Hz), 5.04 (1H, dd, J 11.2, 1.9 Hz), 4.46 (1H, d, J 6.1 Hz), 3.40 (1H, m,), 2.36 (1H,br s), 2.09 (4H, m), 1.65 (2H, m), 1.49 (2H, m), 1.33 (3H, s), 1.26 (3H, m), 1.06 (4H, includes 3H, s), 0.81 (3H, d, J 6.8 Hz), 0.67 (3H,br d, J 5.7 Hz); MS(CI) m/z 397 (MNH$_4^+$).

EXAMPLE 19

Mutilin 14-(N-methoxycarbamate)

Step 1. (3R)-3-Deoxo-11-deoxy-3-methoxy-11-oxo-4-epi-mutilin 14-(N-methoxycarbamate)

Methoxylamine hydrochloride (70 mg, 0.84 mmol) was reacted with (3R)-3-deoxo-11-deoxy-3-methoxy-11-oxo-4-epi-mutilin 14-chloroformate (167 mg, 0.42 mmol) and diisopropylethylamine (0.22 ml, 1.26 mmol) in dichloromethane (3 ml), as for Example 12 Step 2, to afford the title compound (164 mg, 96%); $v_{max}$ ($CH_2Cl_2$) 3379, 1742, 1698 cm$^{-1}$, $^1$H NMR (CDCl$_3$) 7.39 (1H, s), 6.70 (1H, dd, J 17.5, 10.7 Hz), 5.73 (1H, d, J 10.0 Hz), 5.29 (1H, d, J 10.7 Hz), 5.00 (1H, d, 17.5 Hz), 3.75 (3H,s), 3.46 (1H, ddd, J 11.2, 4.9, 2.9 Hz), 3.21 (3H, s), 2.90 (1H, q, J 6.4 Hz), 2.46 (1H, dd, J 15.3, 10.1 Hz), 2.19 (1H, m), 2.00 (2H, m), 1.72 (1H, d, J 11.3 Hz), 1.65 (1H, d, J 15.3 Hz), 1.57 (2H, m), 1.36–1.06 (4H, m), 1.21 (3H, s), 1.19 (3H, s), 0.99 (3H, d, J 6.4 Hz), 0.86 (3H, d, J 6.9 Hz); MS(EI) m/z 407 (M$^+$) Found: 407.2670, $C_{23}H_{37}NO_5$ requires 407.2672.

Step 2. Mutilin 14-(N-methoxycarbamate)

The product of Step 1 (144 mg, 0.35 mmol) in dioxane (3 ml) was treated with a saturated solution of zinc chloride in conc. HCl (1 ml), as for Example 1 Step 2, to afford the title compound (98 mg, 70%); $v_{max}$ ($CH_2Cl_2$) 3379, 1735 cm$^{-1}$, $^1$H NMR (CDCl$_3$) 7.28 (1H, s), 6.54 (1H, dd, J 17.4, 11.0 Hz), 5.71 (1H, d, J 8.5 Hz), 5.37 (1H, dd, J 11.0, 1.5 Hz), 5.22 (1H, dd, J 17.4, 1.5 Hz), 3.71 (3H, s), 3.35 (1H, dd, J 10.8, 6.7 Hz), 2.34 (1H, quintet, J 6.9 Hz), 2.23 (2H, m), 2.08 (2H, m), 1.71 (4H, m), 1.46–1.38 (4H, m), 1.42 (3H, s), 1.18 (3H, s), 1.15 (1H, m), 0.88 (3H, d, J 7.1 Hz), 0.78 (3H, d, J 6.6 Hz), MS(CI) m/z 411 (MNH$_4^+$), 394 (MH$^+$).

EXAMPLE 20

Mutilin 14-(N-dimethylaminocarbamate)
Step 1. (3R)-3-Deoxo-11-deoxy-3-methoxy-11-oxo-4-epi-mutilin 14-(N-dimethylaminocarbamate)

1,1-Dimethylhydrazine (0.04 ml, 0.52 mmol) was reacted with (3R)-3-deoxo-11-deoxy-3-methoxy-11-oxo-4-epi-mutilin 14-chloroformate (167 mg, 0.42 mmol) and diisopropylethylamine (0.15 ml, 0.86 mmol) in dichloromethane (3 ml), as for Example 12 Step 2, to afford the title compound (130 mg, 73%); $\nu_{max}$ (CH$_2$Cl$_2$) 3330, 1729, 1696 cm$^{-1}$, $^1$H NMR (CDCl$_3$) 6.78 (1H, dd, J 17.5, 10.7 Hz), 5.66 (1H, d, J 9.9 Hz), 5.54 (1H, br s), 5.26 (1H, d, J 10.7 Hz), 4.98 (1H, d, 17.5 Hz), 3.46 (1H, ddd, J 11.2, 4.7, 2.9 Hz), 3.21 (3H, s), 2.92 (1H, q, J 6.4 Hz), 2.58 (6H,s), 2.40 (1H, dd, J 14.9, 10.2 Hz), 2.18 (1H, m), 1.98 (2H, m), 1.64 (3H, m), 1.53–1.05 (5H, m), 1.18 (6H, s), 0.98 (3H, d, J 6.4 Hz), 0.84 (3H, d, J 6.9 Hz); MS(EI) m/z 420 (M$^+$) Found: 420.2994, C$_{24}$H$_{40}$N$_2$O$_4$ requires 420.2988.

Step 2. Mutilin 14-(N-dimethylaminocarbamate)

The product of Step 1 (114 mg, 0.27 mmol) in dioxane (3 ml) was treated with concentrated HCl (1 ml), as for Example 17 Step 2, to afford the title compound (98 mg, 89%); $\nu_{max}$ (CH$_2$Cl$_2$) 3330, 1732 cm$^{-1}$, $^1$H NMR (CDCl$_3$) 6.60 (1H, dd, J 17.4, 11.0 Hz), 5.65 (1H, d, J 8.4 Hz), 5.41 (1H, br s), 5.34 (1H, dd, J 11.0, 1.5 Hz), 5.19 (1H, dd, J 17.4, 1.5 Hz), 3.34 (1H, dd, J 10.9, 6.6 Hz), 2.55 (6H, s), 2.36 (1H, quintet, J 6.9 Hz), 2.22 (2H, m), 2.03 (2H, m), 1.81–1.59 (4H, m), 1.42 (7H, m), 1.16 (3H, s), 1.12 (1H, m), 0.87 (3H, d, J 7.0 Hz), 0.76 (3H, d, J 6.2 Hz); MS(EI) m/z 406 (M$^+$) Found: 406.2838, C$_{23}$H$_{38}$N$_2$O$_4$ requires 406.2832.

EXAMPLE 21

Mutilin 14-[N-(methanesulphonylamino)carbamate]
Step 1. (3R)-3-Deoxo-11-deoxy-3-methoxy-11-oxo-4-epi-mutilin 14-[N-(methanesulphonylamino)carbamate]

Methanesulphonyl hydrazide (94 mg, 0.85 mmol) was reacted with (3R)-3-deoxo-11-deoxy-3-methoxy-11-oxo-4-epi-mutilin 14-chloroformate (170 mg, 0.43 mmol), diisopropylethylamine (0.19 ml, 1.09 mmol) and 4-dimethylaminopyridine (catalytic amount) in dichloromethane (3 ml), as for Example 12 Step 2, to afford the title compound (179 mg, 89%); $\nu_{max}$ (CH$_2$Cl$_2$) 3372, 1716, 1698 cm$^{-1}$, $^1$H NMR (CDCl$_3$) 6.63 (1H, dd, J 17.5, 10.7 Hz), 5.85 (1H, d, J 10.1 Hz), 5.31 (1H, d, J 10.7 Hz), 5.03 (1H, d, 17.5 Hz), 4.32 (2H, s), 3.47 (1H, ddd, J 11.3, 8.1, 5.3 Hz), 3.33 (3H, s), 3.22 (3H, s), 2.87 (1H, q, J 6.4 Hz), 2.57 (1H, dd, J 15.3, 10.1 Hz), 2.21 (1H, m), 2.00 (2H, m), 1.76 (1H, d, J 11.3 Hz), 1.67 (1H, d, J 15.3 Hz), 1.54–1.05 (6H, m), 1.33 (3H, s), 1.21 (3H, s), 1.00 (3H, d, J 6.4 Hz), 0.87 (3H, d, J 6.9 Hz); MS(EI) m/z 470 (M$^+$).

Step 2. Mutilin 14-[N-(methanesulphonylamino)carbamate]

The product of Step 1 (124 mg, 0.26 mmol) in dioxane (3 ml) was treated with a saturated solution of zinc chloride in conc. HCl (1 ml), as for Example 1 Step 2, to afford the title compound (102 mg, 85%); $\nu_{max}$ (CH$_2$Cl$_2$) 3371, 1733 cm$^{-1}$, $^1$H NMR (CDCl$_3$) 6.48 (1H, dd, J 17.4, 11.0 Hz), 5.81 (1H, d, J 8.6 Hz), 5.37 (1H, dd, J 11.0, 1.4 Hz), 5.23 (1H, dd, J 17.4, 1.4 Hz), 4.28 (2H, s), 3.37 (1H, dd, J 10.6, 6.7 Hz), 3.29 (3H, s), 2.24 (4H, m), 2.12 (1H, br s), 1.81–1.41 (8H, m), 1.59 (3H, s), 1.19 (3H, s), 1.17 (1H, m), 0.89 (3H, d, J 7.0 Hz), 0.77 (3H, d, J 6.8 Hz); MS(CI) m/z 474 (MNH$_4^+$).

EXAMPLE 22

Mutilin 14-(N-methanesulphonylcarbamate)
Step 1. (3R)-3-Deoxo-11-deoxy-3-methoxy-11-oxo-4-epi-mutilin 14-(N-methanesulphonylcarbamate)

Methanesulphonamide (80 mg, 0.84 mmol) in DMF (0.5 ml) was reacted with (3R)-3-deoxo-11-deoxy-3-methoxy-11-oxo-4-epi-mutilin 14-chloroformate (170 mg, 0.43 mmol), diisopropylethylamine (0.19 ml, 1.09 mmol) and 4-dimethylaminopyridine (catalytic amount) in dichloromethane (3 ml), as for Example 12 Step 2, to afford the title compound (191 mg, 98%); $\nu_{max}$ (CH$_2$Cl$_2$) 3364, 1742, 1698 cm$^{-1}$, $^1$H NMR (CDCl$_3$) 6.59 (1H, dd, J 17.5, 10.7 Hz), 5.80 (1H, d, J 10.0 Hz), 5.31 (1H, d, J 10.7 Hz), 5.07 (1H, d, 17.5 Hz), 3.44 (1H, ddd, J 11.2, 8.2, 5.5 Hz), 3.32 (3H, s), 3.22 (3H, s), 2.86 (1H, q, J 6.4 Hz), 2.52 (1H, dd, J 15.4, 10.1 Hz), 2.20 (1H, m), 1.99 (2H, m), 1.74 (1H, d, J 11.3 Hz), 1.66 (1H, d, J 15.4 Hz), 1.55–1.05 (6H, m), 1.23 (3H, s), 1.21 (3H, s), 1.03 (3H, d, J 6.4 Hz), 0.88 (3H, d, J 6.9 Hz); MS(EI) m/z 455 (M$^+$).

Step 2. Mutilin 14-(N-methanesulphonylcarbamate)

The product of Step 1 (144 mg, 0.32 mmol) in dioxane (3 ml) was treated with a saturated solution of zinc chloride in conc. HCl (1 ml), as for Example 1 Step 2, to afford the title compound (113 mg, 81%); $\nu_{max}$ (CH$_2$Cl$_2$) 3366, 1737 cm$^{-1}$, $^1$H NMR (CDCl$_3$) 6.45 (1H, dd, J 17.4, 11.0 Hz), 5.75 (1H, d, J 8.5 Hz), 5.37 (1H, dd, J 11.0, 1.3 Hz), 5.23 (1H, dd, J 17.4, 1.4 Hz), 3.36 (1H, dd, J 10.4, 6.7 Hz), 3.27 (3H, s), 2.24 (4H, m), 2.09 (1H, br s), 1.81–1.40 (8H, m), 1.43 (3H, s), 1.20 (3H, s), 1.19 (1H, m), 0.89 (3H, d, J 7.0 Hz), 0.78 (3H, d, J 6.8 Hz); MS(CI) m/z 459 (MNH$_4^+$).

EXAMPLE 23

Mutilin 14-(N-benzoylaminocarbamate)
Step 1. (3R)-3-Deoxo-11-deoxy-3-methoxy-11-oxo-4-epi-mutilin 14-(N-benzoylaminocarbamate)

Benzoic hydrazide (90 mg, 0.66 mmol) was reacted with (3R)-3-deoxo-11-deoxy-3-methoxy-11-oxo-4-epi-mutilin 14-chloroformate (130 mg, 0.33 mmol), diisopropylethylamine (0.17 ml, 0.98 mmol) in dichloromethane (3 ml), as for Example ? Step 1, to afford the title compound (163 mg, 100%); $\nu_{max}$ (CH$_2$Cl$_2$) 3403, 1729, 1696 cm$^{-1}$, $^1$H NMR (CDCl$_3$) 8.12 (1H, br), 7.82 (2H, d, J 7.3 Hz), 7.56 (1H, t, J 7.3 Hz), 7.45 (2H, t, J 7.4 Hz), 6.84 (1H, br), 6.68 (1H, dd, J 17.5, 10.7 Hz), 5.73 (1H, d, J 9.9 Hz), 5.26 (1H, d, J 10.7 Hz), 5.00 (1H, d, 17.5 Hz), 3.44 (1H, m), 3.22 (3H, s), 2.89 (1H, q, J 6.4 Hz), 2.47 (1H, dd, J 15.2, 10.0 Hz), 2.19 (1H, m), 2.01 (2H, m), 1.75–1.20 (13H, m), 1.12 (1H, m), 0.98 (3H, d, J 6.4 Hz), 0.94 (3H, br d, J 6.5 Hz); MS(EI) m/z 496 (M$^+$).

Step 2. Mutilin 14-(N-benzoylaminocarbamate)

The product of Step 1 (153 mg, 0.31 mmol) in dioxane (3 ml) was treated with a saturated solution of zinc chloride in conc. HCl (1 ml), as for Example 1 Step 2, to afford the title compound (110 mg, 67%); $\nu_{max}$ (CH$_2$Cl$_2$) 3405, 1734, 1691 cm$^{-1}$, $^1$H NMR (CDCl$_3$) 8.14 (1H, br), 7.79 (2H, d, J 7.2 Hz), 7.54 (1H, t, J 7.3 Hz), 7.43 (2H, t, J 7.4 Hz), 6.80 (1H, br), 6.52 (1H, dd, J 17.4, 11.1 Hz), 5.69 (1H, d, J 8.5 Hz), 5.34 (1H, dd, J 11.3 Hz), 5.23 (1H, dd, J 17.4 Hz), 3.36 (1H, dd, J 10.7, 6.5 Hz), 2.27 (3H, m), 2.07 (2H, m), 1.80–1.43 (8H, m), 1.61 (3H, s), 1.19 (3H, s), 1.18 (1H, m), 0.87 (6H, d, J 6.9 Hz); MS(EI) m/z 482 (M$^+$).

EXAMPLE 24

Mutilin 14-(N-benzoylcarbamate)
Step 1. (3R)-3-Deoxo-11-deoxy-3-methoxy-11-oxo-4-epi-mutilin 14-(N-benzoylcarbamate)

(3R)-3-Deoxo-11-deoxy-3-methoxy-11-oxo-4-epi-mutilin (335 mg, 1.0 mmol) was reacted with benzoyl isocyanate (0.25 ml, 2.0 mmol) in dichloromethane (5 ml), as for Example 1 Step 1, to afford the title compound (478 mg, 99%); $v_{max}$ (CH$_2$Cl$_2$) 3423, 1777, 1714 1698 cm$^{-1}$, $^1$H NMR (CDCl$_3$) 7.99 (1H, br s), 7.83 (2H, d, J 7.0 Hz), 7.61 (1H, t, J 7.3 Hz), 7.50 (2H, m), 6.73 (1H, dd, J 17.4, 10.6 Hz), 5.85 (1H, d, J 9.9 Hz), 5.30 (1H, d, J 10.7 Hz), 5.02 (1H, d, 17.5 Hz), 3.47 (1H, ddd, J 11.2, 8.3, 5.3 Hz), 3.23 (3H, s), 2.91 (1H, q, J 6.4 Hz), 2.54 (1H, dd, J 15.3, 10.1 Hz), 2.21 (1H, m), 2.01 (2H, m), 1.75 (1H, d, J 11.2 Hz), 1.73 (1H, d, J 15.3 Hz), 1.62–1.08 (6H, m), 1.32 (3H, s), 1.21 (3H, s), 1.01 (3H, d, J 6.4 Hz), 0.91 (3H, d, J 6.9 Hz); MS(EI) m/z 481 (M$^+$) Found: 481.2823, C$_{29}$H$_{39}$NO$_5$ requires 481.2828.

Step 2. Mutilin 14-(N-benzoylcarbamate)

The product of Step 1 (370 mg, 0.77 mmol) in dioxane (3 ml) was treated with a saturated solution of zinc chloride in conc. HCl (1 ml), as for Example 1 Step 2, to afford the title compound (208 mg, 58%); $v_{max}$ (CH$_2$Cl$_2$) 3429, 1779, 1733 cm$^{-1}$, $^1$H NMR (CDCl$_3$) 7.96 (1H, s), 7.80 (2H, d, J 7.1 Hz), 7.59 (1H, t, J 7.3 Hz), 7.48 (2H, t, J 7.4 Hz), 6.56 (1H, dd, J 17.4, 11.0 Hz), 5.84 (1H, d, J 8.5 Hz), 5.38 (1H, dd, J 11.0, 1.5 Hz), 5.24 (1H, dd, J 17.4, 1.5 Hz), 3.77 (1H, dd, J 10.9, 6.6 Hz), 2.35 (1H, quintet, J 7.0 Hz), 2.19 (4H, m), 1.82–1.30 (8H, m), 1.52 (3H, s), 1.20 (3H, s), 1.13 (1H, m), 0.89 (3H, d, J 7.0 Hz), 0.81 (3H, d, J=6.6 Hz); MS(CI) m/z 485 (MNH$_4^+$).

EXAMPLE 25

Antibacterial Activity

The following Table illustrates the antibacterial activities of representative 14-carbamate derivatives, in comparison with tiamulin. Activities are given as minimum inhibitory concentrations (10$^{-6}$ g/ml), and were determined using a standard broth dilution method in microtitre.

| Organism | tiamulin | mutilin 14-carbamate (Example 7) | mutilin 14-(N-hydroxy) carbamate (Example 18) | mutilin 14-(N-benzoyl) carbamate (Example 24) |
|---|---|---|---|---|
| B.f. | 1 | 0.25 | 1 | <0.06 |
| E.c. | 16 | 2 | 0.5 | 0.5 |
| H.i. | 2 | 2 | 1 | 2 |
| M.c. | <0.06 | <0.06 | <0.06 | <0.06 |
| E.f. | >64 | 4 | >64 | >64 |
| S.a. | 0.25 | 0.5 | 0.5 | 0.125 |
| S.e. | 0.125 | 0.125 | 0.5 | <0.06 |
| S.ag. | <0.06 | 0.5 | 0.25 | <0.06 |
| S.pn. | <0.06 | 0.5 | 1 | <0.06 |
| S.p. | <0.06 | 0.25 | 1 | <0.06 |

B.f. = *Bacteroides fragilis* B70; E.c. = *Escherichia coli* DC2; H.i. = *Haemophilus influenzae* Q1;
M.c. = *Moraxella catarrhalis* 1502; E.f. = *Enterococcus faecalis* 1; S.a. = *Staphylococcus aureus* Oxford;
S.e. = *Staphylococcus epidermidis* PHLN 20; S.ag. = *Streptococcus agalactiae* Hester;
S.pn. = *Streptococcus pneumaniae* 1761; S.p. = *Streptococcus pyogenes* CN 10.

EXAMPLE 26

Mutilin 14-[N-(2-phenylethyl)carbamate]
Step 1. (3R)-3-Deoxo-11-deoxy-3-methoxy-11-oxo-4-epi-mutilin 14-[N-(2-phenylethyl)carbamate]

Phenethylamine (0.16 ml, 1.29 mmol) was reacted with (3R)-3-deoxo-11-deoxy-3-methoxy-11-oxo-4-epi-mutilin 14-chloroformate (170 mg, 0.43 mmol) in dichloromethane (5 ml), as described in Example 12, Step 2, to afford the title compound (200 mg, 97%); $v_{max}$ (CH$_2$Cl$_2$) 2902, 2254, 1794, 1703, 1644, and 1465 cm$^{-1}$; $^1$H NMR (CDCl$_3$) 0.84 (3H, d, J 6.9 Hz), 0.97 (3H, d, J 6.4 Hz), 1.05–2.27 (12H, m) including 1.14 (3H, s) and 1.18 (3H, s), 2.38 (1H, dd, J 15.3, 10.0 Hz), 2.82 (1H, dd, J 13.2, 6.9 Hz), 2.94 (1H, q, J 6.4 Hz), 3.21 (3H, s), 3.37–3.61 (3H, m), 4.65 (1H, broad t), 5.00 (1H, d, J 17.5 Hz), 5.31 (1H, d, J 10.6 Hz), 5.64 (1H, d, J 9.8 Hz), 6.75 (1H, dd, J 17.8, 10.7 Hz), 7.18–7.34 (5H, m); MS (NH$_3$DCI) m/z 482 (MH$^+$).

Step 2. Mutilin 14-[N-(2-phenylethyl)carbamate]

The product of Step 1 (200 mg, 0.42 mmol) in dioxane (5 ml) was treated with a saturated solution of zinc chloride in conc. HCl (0.5 ml), as for Example 1, Step 2, to afford the title compound (75 mg, 39%); $v_{max}$ (CH$_2$Cl$_2$) 3445, 1733, 1712, and 1635 cm$^{-1}$; $^1$H NMR (CDCl$_3$) 0.75 (3H, broad s), 0.86 (3H, d, J 7.0 Hz), 1.0–2.23 (18H, m) including 1.16 (3H, s) and 1.35 (3H, s), 2.37 (1H, quint., J 6.6 Hz), 2.77 (1H, q, J 6.5 Hz), 3.30–3.51 (3H, m), 4.11 (2H, q, J 7.2 Hz), 4.66 (1H, broad s), 5.21 (1H, dd, J 17.3, 1.2 Hz), 5.35 (1H, d, J 10.8 Hz), 5.64 (1H, d, J 8.3 Hz), 6.58 (1H, dd, J 17.4, 10.9 Hz), 7.14–7.31 (5H, m); MS(EI) m/z 467 (M$^+$), MS (NH$_3$DCI) m/z 468 (MH$^+$).

EXAMPLE 27

Mutilin 14-[N-(1-(R)-phenyl-2-hydroxy) ethylcarbamate]

Step 1. (3R)-3-Deoxo-11-deoxy-3-methoxyv-11-oxo-4-epi-mutilin 14-[N-(1-(R)-phenyl-2-hydroxy)ethylcarbamate]

(R)-2-Phenylglycinol (177 mg, 1.29 mmol) was reacted with (3R)-3-deoxo-11-deoxy-3-methoxy-11-oxo-4-epi-mutilin 14-chloroformate (170 mg, 0.43 mmol) in dichloromethane (5 ml), as described in Example 12, Step 2, to afford the title compound (220 mg, quant.); $v_{max}$ (CH$_2$Cl$_2$) 3600, 3433, 2931, 1698, and 1503 cm$^{-1}$, $^1$H NMR (CDCl$_3$) 0.82 (3H, d, J 6.6 Hz), 0.95 (3H, d, J 6.4 Hz), 0.98–2.22 (18H, m), 2.43 (1H, dd, J 15.3, 10.0 Hz), 2.87 (1H, q, J 6.5 Hz), 3.23 (3H, s), 3.46 (1H, s), 3.89 (2H, m), 4.13 (2H, dd, J 14.3, 7.1 Hz), 4.87 (1H, broad s), 4.99 (1H, d, J 17.5 Hz), 5.27 (1H, d, J 7.3 Hz), 5.64 (1H, d, J 9.9 Hz), 6.66 (1H, dd, J 17.4, 10.6 Hz), 7.27–7.37 (5H, m).

Step 2. Mutilin 14-[N-(1-(R)-phenyl-2-hydroxy) ethylcarbamate]

The product of Step 1 (212 mg, 0.42 mmol) in dioxane (5 ml) was treated with a saturated solution of zinc chloride in conc. HCl (0.5 ml), as for Example 1 Step 2, to afford the title compound (81 mg, 39%); $v_{max}$ (CH$_2$Cl$_2$) 3565, 3433, 2961, 1732, 1713, and 1503 cm$^{-1}$; $^1$H NMR (CDCl$_3$) 0.73 (3H, broad d), 0.84 (3H, d, J 7.0 Hz), 0.97–1.76 (18H, m), 1.93–2.30 (3H, m), 2.32 (1H, quint., J 6.6 Hz), 3.25–3.40 (1H, m), 3.70–3.95 (2H, m), 4.75–4.87 (1H, broad s), 5.15–5.35 (3H, m), 5.62 (1H, d, J 8.3 Hz), 7.27–7.37 (5H,m); MS(EI) m/z 483 (M$^+$), (NH$_3$DCI) m/z 484 (MH$^+$).

EXAMPLE 28

Mutilin 14-[N-2-(methoxycarbonyl)ethylcarbamate]
Step 1. (3R)-3-Deoxo-11-deoxy-3-methoxy-11-oxo-4-epi-mutilin 14-[N-2-(methoxycarbonyl)ethylcarbamate]

β-Alanine methyl ester hydrochloride (120 mg, 0.86 mmol) was reacted with (3R)-3-deoxo-11-deoxy-3-methoxy-11-oxo-4-epi-mutilin 14-chloroformate (170 mg, 0.43 mmol) and N,N-diisopropylethylamine (0.150 ml, 0.86 mmol) in dichloromethane (5 ml), as described in Example 12, Step 2, to afford the title compound (185 mg, 93%); $v_{max}$ (CH$_2$Cl$_2$) 3446, 2930, 1733, 1709, 1509, and 1456 cm$^{-1}$; $^1$H NMR (CDCl$_3$) 0.81 (3H, d, J 6.9 Hz), 0.97 (3H, d, J 6.4 Hz), 1.04–1.71 (14H, m), 1.92–2.04 (2H, m), 2.13–2.22 (1H, m), 2.39 (1H, dd, J 15.2, 10.0 Hz), 2.55 (2H, t, J 5.7 Hz), 2.92 (1H, q, J 6.4 Hz), 3.21 (3H, s), 3.41–3.54 (3H, m), 3.69 (3H, s), 4.99 (1H, d, J 17.6 Hz), 5.13 (1H, t, J 6.0 Hz), 5.28 (1H, d, J 10.7 Hz), 5.63 (1H, d, J 9.9 Hz), 6.74 (1H, d, J 17.5, 10.7 Hz); MS (NH$_3$DCI) m/z 464 (MH$^+$), m/z 481 (MNH$_4^+$)

Step 2. Mutilin 14-[N-2-(methoxycarbonyl)ethylcarbamate]

The product of Step 1 (200 mg, 0.42 mmol) in dioxane (5 ml) was treated with a saturated solution of zinc chloride in conc. HCl (0.5 ml) and the reaction stirred at room temperature overnight. The solution was poured into ethyl acetate and saturated sodium chloride solution. The aqueous phase was reextracted with ethyl acetate and the combined organic phases were washed with saturated sodium hydrogen carbonate solution (twice). The organic phase was finally washed with saturated sodium chloride solution and dried (MgSO$_4$). Purification was accomplished by chromatography on silica gel, loading in dichloromethane and eluting with mixtures of ethyl acetate in hexane. The title compound was isolated as a foam (21 mg, 12%); $v_{max}$ (CH$_2$Cl$_2$) 3564, 3446, 1734, 1713, and 1509 cm$^{-1}$; $^1$H NMR (CDCl$_3$) 0.71 (3H, broad d, J 6.0 Hz), 0.85 (3H, d, J 7.0 Hz), 1.07–1.79 (15H, m) including 1.13 (3H, s) and 1.37 (3H, s), 1.96–2.23 (4H, m), 2.35 (1H, quint, J 6.9 Hz), 2.52 (2H, t, J 5.9 Hz), 3.30–3.50 (3H, m), 3.67 (3H, s), 5.06 (1H, broad t), 5.26 (1H, dd, J 17.5, 1.5 Hz), 5.34 (1H, dd, J 11.0, 1.5 Hz), 5.62 (1H, d, J 8.4 Hz), 6.56 (1H, dd, J 17.4, 11.0 Hz); MS(EI) m/z 449 (M$^+$), (NH$_3$DCI) m/z 450 (MH$^+$).

EXAMPLE 29

Mutilin 14-[N-2-carboxyethylcarbamate]
Step 1. Mutilin 14-[N-2-carboxyethylcarbamate]
The sodium hydrogen carbonate solutions from Example 28, Step 2, were acidified with hydrchloric acid (5M) and the resulting solution extracted with ethyl acetate (twice). After washing the organic phase with saturated sodium chloride solution it was dried (MgSO$_4$) and the solvent removed by evaporation in vacuo to give the title compound as a white solid (43 mg, 24%); $v_{max}$ (CH$_2$Cl$_2$) 3446, 2961, 1730, 1714, and 1509 cm$^{-1}$; $^1$H NMR (CDCl$_3$) 0.72 (3H, broad d, J 5.7 Hz), 0.86 (3H, d, J 7.0 Hz), 0.97–1.79 (15H, m), 1.96–2.23 (5H, m), 2.55–2.60 (2H, m), 3.34–3.46 (3H, m), 5.07–5.38 (3H, m), 5.61–5.68 (1H, m), 6.50–6.52 (1H, m); MS(EI) m/z 435 (M$^+$); MS (NH$_3$DCI) m/z 436 (MH$^+$), m/z 453 (MNH$_4^+$).

EXAMPLE 30

Mutilin 14-[N-(hydroxyiminobenzyl)carbamate]
Step 1. (3R)-3-Deoxo-11-deoxy-3-methoxy-11-oxo-4-epi-mutilin 14-[N-(hydroxyiminobenzyl)carbamate]
Benzamidoxime (129 mg, 0.94 mmol) was reacted with (3R)-3-deoxo-11-deoxy-3-methoxy-11-oxo-4-epi-mutilin 14-chloroformate (170 mg, 0.43 mmol) in dichloromethane (3 ml), as described in Example 12, Step 2, to afford the title compound (180 mg, 84%); $v_{max}$ (CH$_2$Cl$_2$) 3519, 3414, 2930, 1759, 1697, 1640, 1586, and 1457 cm$^{-1}$; $^1$H NMR (CDCl$_3$) 0.93 (3H, d, J 6.9 Hz), 1.00 (3H, d, J 6.4 Hz), 1.07–1.60 (13H, m) including, 1.20 (3H, s) and 1.30 (3H, s), 1.74 (1H, d, J 11.2 Hz), 1.77 (1H, d, J 15.3 Hz), 1.94–2.04 (2H, m), 2.15–2.24 (1H, m), 2.52 (1H, dd, J 15.2, 10.2 Hz), 2.88 (1H, q, J 6.4 Hz), 3.23 (3H, s), 3.43–3.54 (1H, m), 4.99 (1H, d, J 17.4 Hz), 5.09 (1H, broad s), 5.27 (1H, d, J 10.8 Hz), 5.70 (1H, d, J 10.0 Hz), 6.75 (1H, dd, J 17.5, 10.7 Hz), 7.38–7.52 (3H, m), 7.69–7.73 (2H, m); MS (NH$_3$DCI) m/z 497 (MH$^+$).
Step 2. Mutilin 14-[N-(hydroxyiminobenzyl)carbamate]
The product of Step 1 (160 mg, 0.33 mmol) in dioxane (4 ml) was treated with a saturated solution of zinc chloride in conc. HCl (0.8 ml), as for Example 1, Step 2, to afford the title compound (114 mg, 72%); $v_{max}$ (CH$_2$Cl$_2$) 3520, 3414, 2932, 1761, 1733, 1710, 1640, and 1587 cm$^{-1}$; $^1$H NMR (CDCl$_3$) 0.84 (3H, d, J 6.7 Hz), 0.88 (3H, d, J 7.1 Hz), 0.99–1.82 (16H, m) including 1.19 (3H, s) and 1.50 (3H, s), 2.08–2.34 (4H, m) including 2.32 (1H, quint., J 6.8 Hz), 3.36 (1H, dd, J 10.5, 6.6 Hz), 5.06 (2H, broad s), 5.23 (1H, dd, J 17.3, 1.5 Hz), 5.37 (1H, dd, J 11.2, 1.4 Hz), 5.69 (1H, d, J 8.6 Hz), 6.57 (1H, dd, J 17.3. 11.0 Hz), 7.26–7.51 (3H, m), 7.67–7.71 (2H, m); MS (NH$_3$DCI) m/z 483 (MH$^+$).

EXAMPLE 31

Mutilin 14-[N-(4-methoxybenzoyl)carbamate]
Step 1. 4-Methoxybenzoylisocyanate
Silver cyanate (689 mg, 4.6 mmol) was suspended in dry dichloromethane (5 ml) under an atmosphere of argon. A solution of 4-methoxybenzoylchloride (682 mg, 4.0 mmol) in dichloromethane (5 ml) was added and the heterogeneous mixture stirred at reflux under subdued light according to the method of Arcus et. al. (*J. Chem. Soc.* 1954, 4018). After one hour the reaction was allowed to cool and filtered through Kieselguhr. The solution was used immediately in the next reaction. $v_{max}$ (CH$_2$Cl$_2$) 2246 cm$^{-1}$.
Step 2. (3R)-3-Deoxo-11-deoxy-3-methoxy-11-oxo-4-epi-mutilin 14-[N-(4-methoxybenzoyl)carbamate]
The solution from step 1 was cooled to 0° C. and treated with (3R)-3-deoxo-11-deoxy-3-methoxy-11-oxo-4-epi-mutilin (335 mg, 1.0 mmol) and the reaction stirred for 1 hour. The mixture was diluted with dichloromethane and washed with 1.0M hydrochloric acid followed by water and saturated sodium chloride solution. After drying (MgSO$_4$) the crude material was purified by chromatography on silica gel, loading in dichloromethane and eluting with 20% ethyl acetate in hexane. Evaporation of solvents in vacuo gave the title compound (488 mg, 95%); m.p. (CH$_2$Cl$_2$/hexane) 168° C.; $v_{max}$ (CH$_2$Cl$_2$) 3427, 3300, 2931, 1774, 1697, 1605, and 1479 cm$^{-1}$; $^1$H NMR (CDCl$_3$) 0.90 (3H, d, J 6.9 Hz), 1.00 (3H, d, J 6.4 Hz), 1.07–1.56 (12H, m) including 1.20 (3H, s) and 1.32 (3H, s), 1.72 (1H, d, J 15.3 Hz), 1.74 (1H, d, J 11.2 Hz), 1.94–2.04 (2H, m), 2.16–2.24 (1H, m), 2.53 (1H, dd, J 15.2, 10.1 Hz), 2.91 (1H, q, J 6.2 Hz), 3.23 (3H, s), 3.42–3.50 (1H, m), 3.87 (3H, s), 5.00 (1H, d, J 17.5 Hz), 5.29 (1H, d, J 10.7 Hz), 5.84 (1H, d, J 9.9 Hz), 6.73 (1H, dd, J 17.4, 10.6 Hz), 6.97 (2H, d, J 8.9 Hz), 7.81 (2H, d, J 8.9 Hz); MS (EI) m/z 511 (MH$^+$); (NH$_3$DCI) m/z 512 (MH$^+$); (Found: C, 70.38; H, 8.21; N, 2.91. C$_{30}$H$_{41}$NO$_6$ requires C, 70.42; H, 8.08; N, 2.74)
Step 3. Mutilin 14-[N-(4-methoxybenzoyl)carbamate]
The product of Step 2 (440 mg, 0.85 mmol) in dioxane (5 ml) was treated with a saturated solution of zinc chloride in conc. HCl (1 ml), as for Example 1 Step 2, to afford the title compound (140 mg, 33%); m.p. (CH$_2$Cl$_2$/hexane) 108° C. (dec.); $v_{max}$ (CH$_2$Cl$_2$) 3564, 3429, 2961, 1776, 1733, 1710, 1607, and 1479 cm$^{-1}$; $^1$H NMR (CDCl$_3$) 0.81 (3H, d, J 6.6 Hz), 0.88 (3H, d, J 7.0 Hz), 1.10–1.81 (15H, m) including 1.15 (3H, s) and 1.51 (3H, s), 2.12 (1H, bs) superimposed on 2.09–2.26 (2H, m), 2.35 (1H, quint, J 6.9 Hz), 3.36 (1H, dd, J 11.0, 6.6 Hz), 3.86 (3H, s), 5.22 (1H, dd, J 17.3, 1.5 Hz), 5.37 (1H, dd, J 11.0, 1.4 Hz), 5.83 (1H, d, J 8.5 Hz), 6.56 (1H, dd, J 17.3, 11.0 Hz), 6.95 (2H, d, J 8.8 Hz), 7.77 (2H, d, J 8.8 Hz), 7.88 (1H, bs); MS (NH$_3$DCI) m/z 498 (MH$^+$); (Found: C, 69.88; H, 7.67; N, 2.93. C$_{29}$H$_{39}$NO$_6$ requires C, 70.00; H, 7.90; N, 2.81)

EXAMPLE 32

Mutilin 14-[N-(4-nitrobenzoyl)carbamate]
Step 1. 4-Nitrobenzoylisocyanate
Silver cyanate (689 mg, 4.6 mmol) was suspended in dry dichloromethane (5 ml) under an atmosphere of argon. A solution of 4-nitrobenzoylchloride (682 mg, 4.0 mmol) in dichloromethane (5 ml) was added and the reaction treated as described in Example 31, Step 1. The solution was used immediately in the next reaction.
Step 2. (3R)-3-Deoxo-11-deoxy-3-methoxy-11-oxo-4-epi-mutilin 14-[N-(4-nitrobenzoyl)carbamate]
The solution from Step 1 was cooled to 0° C. and treated with (3R)-3-deoxo-11-deoxy-3-methoxy-11-oxo-4-epi-mutilin (335 mg, 1.0 mmol) and the reaction stirred for 1 hour. The title compound was isolated by the same procedure as described in Example 31. Step 2 (480 mg, 91%);

$v_{max}$ (CH$_2$Cl$_2$) 3406, 2959, 1780, 1733, 1698, 1607, and 1531 cm$^{-1}$; $^1$H NMR (CDCl$_3$) 0.90 (3H, d, J 6.8 Hz), 1.03 (3H, d, J 6.4 Hz), 1.08–1.59 (12H, m) including 1.20 (3H, s) and 1.31 (3H, s), 1.69 (1H, d, J 15.5 Hz), 1.75 (1H, d, J 11.6 Hz), 1.93–2.05 (2H, m), 2.15–2.25 (1H, m), 2.54 (1H, dd, J 15.2, 10.1 Hz), 2.89 (1H, q, J 6.4 Hz), 3.22 (3H, s), 3.41–3.50 (1H, m), 5.01 (1H, d, J 17.5 Hz), 5.28 (1H, d, J 10.7 Hz), 5.84 (1H, d, J 9.9 Hz), 6.64 (1H, dd, J 17.4, 10.7 Hz), 8.00 (2H, d, J 8.7 Hz), 8.22 (1H, bs), 8.35 (2H, d, J 8.9 Hz); MS (NH$_3$DCI) m/z 544 (MNH$_4^+$).

Step 3. Mutilin 14-[N-(4-nitrobenzoyl)carbamate]

The product of Step 2 (440 mg, 0.83 mmol) in dioxane (10 ml) was treated with a saturated solution of zinc chloride in conc. HCl (1 ml), as for Example 1 Step 2, to afford the title compound (282 mg, 66%); $v_{max}$(CH$_2$Cl$_2$) 3551, 3412, 2959, 1786, 1734, 1699, 1607, and 1531 cm$^{-1}$; $^1$H NMR (CDCl$_3$) 0.80 (3H, d, J 6.8 Hz), 0.88 (3H, d, J 7.0 Hz), 1.10–1.23 (4H, m), 1.41–1.82 (12H, m) including 1.50 (3H, s), 2.11 (1H, bs), 2.14–2.34 (3H, m), 3.37 (1H, dd, J 10.7, 6.6 Hz), 5.24 (1H, dd, J 17.3, 1.4 Hz), 5.36 (1H, dd, J 10.9, 1.3 Hz), 5.81 (1H, d, J 8.5 Hz), 6.49 (1H, dd, J 17.3, 11.0 Hz), 7.94 (2H, d, J 8.8 Hz), 8.04 (1H, bs), 8.33 (2H, d, J 8.8 Hz).

EXAMPLE 33

Mutilin 14-[N-(3-nitrobenzoyl)carbamate]

Step 1. 3-Nitrobenzoylisocyanate

Silver cyanate (689 mg, 4.6 mmol) was suspended in dry dichloroethane (5 ml) under an atmosphere of argon. A solution of 3-nitrobenzoylchloride (682 mg, 4.0 mmol) in dichloroethane (5 ml) was added and the reaction stirred at reflux for 4 hours before treating as described in Example 31, Step 1. The solution was used immediately in the next reaction. $v_{max}$ (CH$_2$Cl$_2$) 2247 cm$^{-1}$ Step 2. (3R)-3-Deoxo-11-deoxy-3-methoxy-11-oxo-4-epi-mutilin 14-[N-(3-nitrobenzoyl)carbamate]

The solution from Step 1 was cooled to 0° C. and treated with (3R)-3-deoxo-11-deoxy-3-methoxy-11-oxo-4-epi-mutilin (335 mg, 1.0 mmol) and the reaction stirred for 1 hour. The title compound was isolated by the same procedure as described in Example 31, Step 2 (523 mg, quant.); $v_{max}$ (CH$_2$Cl$_2$) 3406, 2930, 1781, 1720, 1698, 1618, and 1537 cm$^{-1}$; $^1$H NMR (CDCl$_3$) 0.91 (3H, d, J 6.8 Hz), 1.00 (3H, d, J 6.4 Hz), 1.08–1.60 (12H, m) including 1.20 (3H, s) and 1.30 (3H, s), 1.67–1.77 (2H, m), 2.00–2.05 (2H, m), 2.15–2.25 (1H, m), 2.55 (1H, dd, J 15.3, 10.1 Hz), 2.89 (1H, q, J 6.3 Hz), 3.22 (3H, s), 3.41–3.50 (1H, m), 5.01 (1H, d, J 17.5 Hz), 5.24 (1H, d, J 10.7 Hz), 5.86 (1H, d, J 10.0 Hz), 6.62 (1H, dd, J 17.4, 10.6 Hz), 7.73 (1H, t, J 8.0 Hz), 8.20 (1H, d, J 7.9 Hz), 8.23 (1H, s), 8.46 (1H, dd, J 7.8, 1.0 Hz), 8.67 (1H, m); MS (NH$_3$DCI) m/z 544 (MNH$_4^+$).

Step 3. Mutilin 14-[N-(3-nitrobenzoyl)carbamate]

The product of Step 2 (483 mg, 0.92 mmol) in dioxane (10 ml) was treated with a saturated solution of zinc chloride in conc. HCl (1 ml), as for Example 1 Step 2, to afford the title compound (280 mg, 66%); m.p. (CH$_2$Cl$_2$/hexane) 121° C.; $v_{max}$ (CH$_2$Cl$_2$) 3564, 3418, 2940, 1782, 1733, 1617, and 1537 cm$^{-1}$; $^1$H NMR (CDCl$_3$) 0.80 (3H, d, J 6.7 Hz), 0.88 (3H, d, J 6.9 Hz), 1.09–1.23 (4H, m), 1.40–1.81 (12H, m), 2.11 (1H, bs), 2.14–2.33 (3H, m), 3.36 (1H, dd, J 10.7, 6.7 Hz), 5.23 (1H, dd, J 17.4, 1.4 Hz), 5.31 (1H, dd, J 10.9, 1.2 Hz), 5.81 (1H, d, J 8.0 Hz), 6.49 (1H, dd, J 17.3, 11.0 Hz), 7.71 (1H, t, J 8.0 Hz), 8.17 (1H, dt, J 7.9, 1.3 Hz), 8.29 (1H, bs), 8.43 (1H, dt, J 8.0, 1.1 Hz), 8.64 (1H, t, J 1.9 Hz); MS (NH$_3$DCI) m/z 530 (MNH$_4^+$); (Found: C, 65.95; H, 7.23; N, 5.35. C$_{28}$H$_{36}$N$_2$O7 requires C, 65.61; H, 7.08; N, 5.46).

EXAMPLE 34

Mutilin 14-[N-(4-aminobenzoyl)carbamate]

Mutilin 14-[N-(4-nitrobenzoyl)carbamate] (79 mg, 0.15 mmol) was suspended in ethanol (10 ml). Addition of ethyl acetate (2 ml) brought about complete dissolution. Tin (II) chloride (146 mg, 0.75 mmol) was added and the reaction warmed to reflux whilst under an atmosphere of argon. After an hour the reaction was allowed to cool and poured into ethyl acetate/water before neutralising with sodium hydrogen carbonate. The organic phase was dried (MgSO$_4$) and purified by chromatography on silica gel eluting with 50% ethyl acetate in hexane. The title compound was isolated as a coloured foam (44 mg, 61%); $v_{max}$ (CH$_2$Cl$_2$) 3684, 3405, 2933, 1782, 1773, 1733, 1605, and 1473 cm$^{-1}$; $^1$H NMR (CDCl$_3$) 0.80 (3H, d, J 6.5 Hz), 0.88 (3H, d, J 7.0 Hz), 1.09–1.26 (4H, m), 1.40–1.81 (12H, m), 2.04–2.37 (4H, m), 3.36 (1H, dd, J 10.6, 6.6 Hz), 4.13 (2H, bs), 5.22 (1H, dd, J 17.4, 1.5 Hz), 5.36 (1H, dd, J 11.0, 1.3 Hz), 5.78 (1H, d, J 8.4 Hz), 6.56 (1H, dd, J 17.4, 11.0 Hz), 6.65 (2H, d, J 8.7 Hz), 7.64 (2H, d, J 8.7 Hz), 7.83 (1H, bs); MS (NH$_3$DCI) m/z 483 (MH$^+$).

EXAMPLE 35

Mutilin 14-[N-(3-aminobenzoyl)carbamate]

Mutilin 14-[N-(3-nitrobenzoyl)carbamate] (100 mg, 0.19 mmol) was suspended in ethanol (10 ml). Addition of ethyl acetate (2 ml) brought about complete dissolution. Tin (II) chloride (185 mg, 1.0 mmol) was added and the reaction treated as described in Example 34. The title compound was isolated as a coloured foam (55 mg, 60%); $v_{max}$ (CH$_2$Cl$_2$) 3395, 2932, 1778, 1733, 1716, 1624, and 1479 cm$^{-1}$; $^1$H NMR (CDCl$_3$) 0.80 (3H, d, J 6.6 Hz), 0.88 (3H, d, J 7.0 Hz), 1.10–1.82 (16H, m, including 1.19 (3H, s) and 1.51 (3H, s)), 2.09–2.37 (4H, m), 3.37 (1H, dd, J 10.8, 6.6 Hz), 3.86 (2H, bs), 5.23 (1H, dd, J 17.4, 1.5 Hz), 5.39 (1H, dd, J 11.0, 1.4 Hz), 5.82 (1H, d, J 8.5 Hz), 6.58 (1H, dd, J 17.3, 11.0 Hz), 6.86 (1H, dd, J 7.8, 2.4 Hz), 7.06 (1H, d, J 7.8 Hz), 7.13 (1H, t, J 2.0 Hz), 7.23 (1H, t, J 7.8 Hz), 7.88 (1H, bs); MS (ESI, –ve ion) m/z 481 (M–H$^-$).

EXAMPLE 36

Mutilin 14-[N-(2-hydroxybenzoyl)carbamate]

Step 1. 2-Acetoxybenzoylisocyanate

Silver cyanate (689 mg, 4.6 mmol) and O-acetylsalicoyl chloride (794 mg, 4.0 mmol) in dichloroethane (10 ml) were reacted in the manner described in Example 33, Step 1. The title compound was immediately used in the next reaction.

Step 2. (3R)-3-Deoxo-11-deoxy-3-methoxy-11-oxo-4-epi-mutilin 14-[N-(2-acetoxybenzoyl)carbamate]

The solution from Step 1 was cooled to 0° C. and treated with (3R)-3-deoxo-11-deoxy-3-methoxy-11-oxo-4-epi-mutilin (335 mg, 1.0 mmol) and the reaction stirred for 1 hour. The title compound (80% pure) was isolated by the same procedure as described in Example 31, Step 2 (385 mg, 70%); $v_{max}$ (CH$_2$Cl$_2$) 3411, 2981, 2931, 1778, 1732, 1698, 1606, and 1480 cm$^{-1}$; $^1$H NMR (CDCl$_3$) 0.89 (3H, d, J 6.8 Hz), 1.00 (3H, d, J 6.4 Hz), 1.08–1.60 (12H, m) including 1.20 (3H, s) and 1.26 (3H, s), 1.67–1.76 (2H, m), 1.95–2.05 (2H, m), 2.15–2.25 (1H, m), 2.38 (3H, s), 2.50 (1H, dd, J 15.3, 10.1 Hz), 2.88 (1H, q, J 6.3 Hz), 3.22 (3H, s), 3.42–3.48 (1H, m), 5.00 (1H, d, J 17.5 Hz), 5.30 (1H, d, J 10.7 Hz), 5.81 (1H, d, J 10.0 Hz), 6.72 (1H, dd, J 17.4, 10.6 Hz), 7.21–7.42 (2H, m), 7.68 (1H, dt, J 7.8, 1.4 Hz), 8.09 (1H, dd, J 7.9, 1.6 Hz), 8.36 (1H, bs), 8.46 (1H, dd, J 7.8, 1.0 Hz), 8.67 (1H, m); MS (EI) m/z 539 (MH$^+$); (NH$_3$DCI) m/z 540 (MH$^+$).

Step 3. Mutilin 14-[N-(3-hydroxybenzoyl)carbamate]

The product of Step 2 (385 mg, 0.50 mmol of 80% pure material) in dioxane (10 ml) was treated with a saturated solution of zinc chloride in conc. HCl (1 ml), as for Example 1 Step 2. The crude material was dissolved in ethanol (2 ml) and treated with 1.0M sodium hydroxide for 1 hour at room temperature. The solution was poured into ethyl acetate in hexane and water. The organic phase was washed with saturated sodium chloride and dried (MgSO$_4$). Purification was accomplished by chromatography on silica gel eluting with 10% acetone in toluene. The title compound was isolated as a white solid (115 mg, 47%); m.p. (CH$_2$Cl$_2$/hexane) 170° C.; $\nu_{max}$ (CH$_2$Cl$_2$) 3566, 3434, 2960, 1775, 1733, 1673, and 1493 cm$^{-1}$; $^1$H NMR (CDCl$_3$) 0.79 (3H, d, J 6.7 Hz), 0.89 (3H, d, J 6.9 Hz), 1.09–1.25 (4H, m), 1.37–1.81 (12H, m), 2.11–2.33 (4H, m), 3.37 (1H, dd, J 10.2, 6.6 Hz), 5.22 (1H, dd, J 17.4, 1.3 Hz), 5.35 (1H, dd, J 10.9, 1.1 Hz), 5.81 (1H, d, J 8.5 Hz), 6.52 (1H, dd, J 17.3, 11.0 Hz), 6.90 (1H, td, J 7.5, 0.8 Hz), 7.02 (1H, dd, J 8.3, 0.9 Hz), 7.18–7.28 (1H, m), 7.95 (1H, d, J 7.6 Hz), 8.45 (1H, bs), 11.31 (1H, bs); MS (ESI −ve ion) m/z 482 (M−H$^-$).

EXAMPLE 37

Mutilin 14-[N-(4-Acetoxybenzoyl)carbamate]

Step 1. 4-Acetoxybenzoylisocyanate

Silver cyanate (950 mg, 6.3 mmol) and 4-acetoxybenzoyl chloride (1.09 g, 5.5 mmol) in dichloroethane (10 ml) were reacted in the manner described in Example 34, Step 1. The title compound was immediately used in the next reaction; $\nu_{max}$ (CH$_2$Cl$_2$) 2240 cm$^{-1}$.

Step 2. (3R)-3-Deoxo-11-deoxy-3-methoxy-11-oxo-4-epi-mutilin 14-[N-(4-acetoxybenzoyl)carbamate]

The solution from Step 1 was cooled to 0° C. and treated with (3R)-3-deoxo-11-deoxy-3-methoxy-11-oxo-4-epi-mutilin (446 mg, 1.27 mmol) and the reaction stirred for 1 hour. The title compound was isolated by the same procedure as described in Example 31, Step 2 (620 mg, 91%); $\nu_{max}$ (CH$_2$Cl$_2$) 3420, 2930, 1777, 1762, 1731, 1714, 1698, 1604, and 1478 cm$^{-1}$; $^1$H NMR (CDCl$_3$) 0.89 (3H, d, J 6.8 Hz), 1.00 (3H, d, J 6.4 Hz), 1.07–1.56 (12H, m), 1.72 (1H, d, J 15.4 Hz), 1.74 (1H, d, J 11.2 Hz), 1.94–2.10 (2H, m), 2.15–2.48 (1H, m), 2.33 (3H, s), 2.53 (1H, dd, J 15.2, 10.0 Hz), 2.90 (1H, q, J 6.4 Hz), 3.22 (3H, s), 3.42–3.50 (1H, m), 5.02 (1H, d, J 17.5 Hz), 5.29 (1H, d, J 10.7 Hz), 5.85 (1H, d, J 9.9 Hz), 6.72 (1H, dd, J 17.5, 10.7 Hz), 7.24 (2H, d, J 8.7 Hz), 7.86 (2H, d, J 8.7 Hz), 8.02 (1H, bs).

Step 3. Mutilin 14-[N-(4-acetoxybenzoyl)carbamate]

The product of Step 2 (570 mg, 1.05 mmol) in dioxane (10 ml) was treated with a saturated solution of zinc chloride in conc. HCl (1 ml), as for Example 1 Step 2, to afford the title compound (56 mg, 11%); $\nu_{max}$ (CH$_2$Cl$_2$) 3563, 3419, 2960, 1778, 1761, 1733, 1718, 1604, and 1479 cm$^{-1}$; $^1$H NMR (CDCl$_3$) 0.40 (3H, d, J 6.6 Hz), 0.88 (3H, d, J 7.0 Hz), 1.10–1.28 (4H, m), 1.38–1.82 (13H, m), 2.12–2.37 (6H, m), 3.37 (1H, dd, J 10.8, 6.6 Hz), 5.24 (1H, dd, J 17.3, 1.4 Hz), 5.38 (1H, dd, J 11.1, 1.4 Hz), 5.83 (1H, d, J 8.7 Hz), 6.56 (1H, dd, J 17.4, 11.0 Hz), 7.22 (2H, d, J 8.7 Hz), 7.83 (2H, d, J 8.7 Hz), 8.22 (1H, bs); MS (FAB, NOBA/Na) m/z 548 (MNa$^+$).

EXAMPLE 38

Mutilin 14-[N-(4-hydroxybenzoyl)carbamate]

The title compound was isolated from the reaction described in Example 37, Step 3 (134 mg, 27%); $\nu_{max}$ (KBr disc) 1764, 1730, and 1690; $^1$H NMR (CDCl$_3$+CD$_3$OD) 0.76 (3H, d, J 6.4 Hz), 0.84 (3H, d, J 6.9 Hz), 1.05–1.21 (4H, m), 1.37–1.78 (11H, m), 2.00–2.34 (4H, m), 3.32 (1H, d, J 6.5 Hz), 5.19 (1H, dd, J 17.4, 1.4 Hz), 5.32 (1H, d, J 11.0 Hz), 5.77 (1H, d, J 8.7 Hz), 6.51 (1H, dd, J 17.4, 11.0 Hz), 6.82 (2H, d, J 8.7 Hz), 7.66 (2H, d, J 8.7 Hz); MS (FAB, NOBA/Na) m/z 506 (MH$^+$) m/z 548 (MNa$^+$).

EXAMPLE 39

Mutilin 14-[N-(3-methoxybenzoyl)carbamate]

Step 1. 3-Methoxybenzoylisocyanate

Silver cyanate (689 mg, 4.6 mmol) and 3-methoxybenzoylchloride (563 ul, 4.0 mmol) in dry dichloromethane (10 ml) were reacted according to the method described in Example 31, Step 1. The solution containing the title compound was immediately used in the next reaction.

Step 2. (3R)-3-Deoxo-11-deoxy-3-methoxy-11-oxo-4-epi-mutilin 14-[N-(3-methoxybenzoyl)carbamate]

The solution from Step 1 was cooled to 0° C. and treated with (3R)-3-deoxo-11-deoxy-3-methoxy-11-oxo-4-epi-mutilin (336 mg, 1.00 mmol) and the reaction stirred for 1 hour. The title compound was isolated by the same procedure as described in Example 31, Step 2 (430 mg, 84%); m.p. (CH$_2$Cl$_2$/hexane) 110–112° C.; $\nu_{max}$ (CH$_2$Cl$_2$) 3419, 2931, 1770, 1714, 1697, 1601, and 1585 cm$^{-1}$; $^1$H NMR (CDCl$_3$) 0.89 (3H, d, J 6.9 Hz), 1.00 (3H, d, J 6.4 Hz), 1.07–1.56 (12H, m) including 1.20 (3H, s) and 1.32 (3H, s), 1.72 (1H, d, J 15.4 Hz), 1.75 (1H, d, J 11.3 Hz), 1.94–2.06 (2H, m), 2.16–2.25 (1H, m), 2.53 (1H, dd, J 15.2, 10.1 Hz), 2.90 (1H, q, J 6.5 Hz), 3.23 (3H, s), 3.42–3.50 (1H, m), 3.86 (3H, s), 5.01 (1H, d, J 17.4 Hz), 5.30 (1H, d, J 10.8 Hz), 5.85 (1H, d, J 9.9 Hz), 6.73 (1H, dd, J 17.5, 10.7 Hz), 7.13 (1H, ddd, J 6.8, 2.6, 1.0 Hz), 7.31–7.43 (3H, m), 7.99 (1H, bs); MS (NH$_3$DCI) m/z 512 (MH$^+$); (Found: C, 70.38; H, 8.28; N, 2.91. C$_{30}$OH$_{41}$NO$_6$ requires C, 70.42; H, 8.08; N, 2.74)

Step 3. Mutilin 14-[N-(3-methoxybenzoyl)carbamate]

The product of Step 2 (440 mg, 0.85 mmol) in dioxane (5 ml) was treated with a saturated solution of zinc chloride in conc. HCl (1 ml), as for Example 1 Step 2, to afford the title compound (170 mg, 45%); m.p. (CH$_2$Cl$_2$/hexane) 117° C. (dec.); $\nu_{max}$ (CH$_2$Cl$_2$) 3556, 3423, 2961, 1779, 1733, and 1479 cm$^{-1}$; $^1$H NMR (CDCl$_3$) 0.80 (3H, d, J 6.6 Hz), 0.88 (3H, d, J 6.9 Hz), 1.10–1.81 (16H, m) including 1.23 (3H, s) and 1.52 (3H, s), 2.04–2.37 (4H, m), 3.36 (1H, dd, J 10.9, 6.5 Hz), 3.85 (3H, s), 5.23 (1H, dd, J 17.3, 1.5 Hz), 5.37 (1H, dd, J 10.9, 1.4 Hz), 5.83 (1H, d, J 8.5 Hz), 6.56 (1H, dd, J 17.3, 10.9 Hz), 7.11 (1H, ddd, J 8.0, 2.4, 1.3 Hz), 7.28–7.41 (3H, m), 7.98 (1H, bs); MS (NH$_3$DCI) m/z 498 (MH$^+$), m/z 515 (MNH$_4^+$).

EXAMPLE 40

Mutilin 14-[N-(2-methoxybenzoyl)carbamate]

Step 1. 2-Methoxybenzoylisocyanate

Silver cyanate (689 mg, 4.6 mmol) and 3-methoxybenzoylchloride (593 ul, 4.0 mmol) in dry dichloromethane (10 ml) were reacted according to the method described in Example 31, Step 1. The solution containing the title compound was immediately used in the next reaction: $\nu_{max}$ (CH$_2$Cl$_2$) 2250 cm$^{-1}$.

Step 2. (3R)-3-Deoxo-11-deoxy-3-methoxy-11-oxo-4-epi-mutilin 14-[N-(2-methoxybenzoyl)carbamate]

The solution from Step 1 was cooled to 0° C. and treated with (3R)-3-deoxo-11-deoxy-3-methoxy-11-oxo-4-epi-mutilin (336 mg, 1.00 mmol) and the reaction stirred for 1 hour. The title compound was isolated by the same procedure as described in Example 31, Step 2 (500 mg, 98%); $\nu_{max}$ (CH$_2$Cl$_2$) 3344, 2981, 2931, 1772, 1732, 1698, 1602, and 1509 cm$^{-1}$; $^1$H NMR (CDCl$_3$) 0.90 (3H, d, J 6.8 Hz), 1.01 (3H, d, J 6.4 Hz), 1.07–1.59 (12H, m) including 1.20 (3H, s) and 1.33 (3H, s), 1.75 (1H, d, J 11.2 Hz), 1.77 (1H, d, J 15.4 Hz), 1.95–2.04 (2H, m), 2.16–2.25 (1H, m), 2.50 (1H, dd, J 15.2, 10.1 Hz), 2.91 (1H, q, J 6.3 Hz), 3.23 (3H, s), 3.44–3.51 (1H, m), 4.04 (3H, s), 5.00 (1H, d, J 17.5 Hz), 5.30 (1H, d, J 10.7 Hz), 5.78 (1H, d, J 9.9 Hz), 6.82 (1H, dd, J 17.5, 10.7 Hz), 7.02 (1H, d, J 8.0 Hz), 7.10 (1H, td, J 7.5, 0.7 Hz), 7.54 (1H, td, J 7.8, 1.8 Hz), 8.24 (1H, dd, J 7.8, 1.8 Hz), 10.00 (1H, bs); MS (ESI, −ve ion) m/z 510 (M−H$^-$).

Step 3. Mutilin 14-[N-(2-methoxrbenzoyl)carbamate]

The product of Step 2 (430 mg, 0.83 mmol) in dioxane (5 ml) was treated with a saturated solution of zinc chloride in conc. HCl (1 ml), as for Example 1 Step 2, to afford the title compound (208 mg, 49%); m.p. ($CH_2Cl_2$/hexane) 142–145° C.; $v_{max}$ ($CH_2Cl_2$) 3626, 3563, 3346, 2953, 1773, 1733, 1701 and 1609 cm$^{-1}$; $^1$H NMR (CDCl$_3$) 0.81 (3H, d, J 6.6 Hz), 0.88 (3H, d, J 7.0 Hz), 1.15–1.81 (16H, m) including 1.22 (3H, s) and 1.52 (3H, s), 2.04–2.38 (4H, m), 3.36 (1H, dd, J 11.1, 6.5 Hz), 4.01 (3H, s), 5.23 (1H, dd, J 17.3, 1.5 Hz), 5.39 (1H, dd, J 10.9, 1.4 Hz), 5.78 (1H, d, J 8.5 Hz), 6.62 (1H, dd, J 17.4, 11.0 Hz), 7.11 (1H, t, J 7.6 Hz), 7.52 (1H, td, J 7.8, 1.8 Hz), 8.20 (1H, dd, J 7.8, 1.8 Hz), 9.89 (1H, bs); MS (ESI, +ve ion) m/z 520 (MNa$^+$).

EXAMPLE 41

Mutilin 14-[N-(phenylacetyl)carbamate]

Step 1. Phenylacetylisocyanate

Silver cyanate (689 mg, 4.6 mmol) and phenylacetylchloride (0.563 ml, 4.0 mmol) in dry dichloromethane (10 ml) were reacted according to the method described in Example 31, Step 1. The solution containing the title compound was immediately used in the next reaction.

Step 2. (3R)-3-Deoxo-11-deoxy-3-methoxy-11-oxo-4-epi-mutilin 14-[N-(phenylacetyl)carbamate]

The solution from Step 1 was cooled to 0° C. and treated with (3R)-3-deoxo-11-deoxy-3-methoxy-11-oxo-4-epi-mutilin (336 mg, 1.00 mmol) and the reaction stirred for 1 hour. The title compound was isolated by the same procedure as described in Example 31, Step 2 (500 mg, quant.); m.p. ($CH_2Cl_2$/hexane) 187–8° C.; $v_{max}$ ($CH_2Cl_2$) 3383, 2930, 1784, 1751, 1698, and 1479 cm$^{-1}$; $^1$H NMR (CDCl$_3$) 0.78 (3H, d, J 6.9 Hz), 1.00 (3H, d, J 6.4 Hz), 1.00–1.61 (13H, m), 1.72 (1H, d, J 11.3 Hz), 1.92–2.05 (2H, m), 2.14–2.23 (1H, m), 2.46 (1H, dd, J 15.3, 10.1 Hz), 2.88 (1H, q, J 6.5 Hz), 3.21 (3H, s), 3.38–3.48 (1H, m), 4.10 (2H, s), 5.03 (1H, d, J 17.4 Hz), 5.32 (1H, d, J 10.7 Hz), 5.72 (1H, d, J 9.9 Hz), 6.63 (1H, dd, J 17.5, 10.7 Hz), 7.24–7.38 (5H, m), 7.50 (1H, bs); MS (NH$_3$DCI) m/z 496 (MH$^+$), m/z 513 (MNH$_4^+$).

Step 3. Mutilin 14-[N-(phenylacetyl)carbamate]

The product of Step 2 (460 mg, 0.93 mmol) in dioxane (10 ml) was treated with a saturated solution of zinc chloride in conc. HCl (1 ml), as for Example 1 Step 2, to afford the title compound (202 mg, 45%); m.p. ($CH_2Cl_2$/hexane) 187° C.; $v_{max}$ ($CH_2Cl_2$) 3564, 3386, 2941, 1784, 1752, 1733, and 1477 cm$^{-1}$; $^1$H NMR (CDCl$_3$) 0.68 (3H, d, J 6.7 Hz), 0.89 (3H, d, J 7.0 Hz), 1.09–1.82 (15H, m) including 1.22 (3H, s) and 1.40 (3H, s), 2.00–2.38 (5H, m), 3.36 (1H, dd, J 10.4, 6.7 Hz), 4.02 and 4.12 (2H, ABq, J 15.7 Hz), 5.23 (1H, dd, J 17.5, 1.4 Hz), 5.38 (1H, dd, J 10.9, 1.3 Hz), 5.71 (1H, d, J 8.4 Hz), 6.57 (1H, dd, J 17.3, 11.1 Hz), 7.24–7.35 (5H, m), 7.51 (1H, bs); MS (NH$_3$DCI) m/z 482 (MH$^+$), m/z 499 (MNH$_4^+$).

EXAMPLE 42

Mutilin 14-[N-(4-carboxybenzoyl)carbamate]

Step 1. (3R)-3-Deoxo-11-deoxy-3-methoxy-11-oxo-4-epi-mutilin 14-[N-(4-formylbenzoyl)carbamate]

(3R)-3-deoxo-11-deoxy-3-methoxy-11-oxo-4-epi-mutilin (680 mg, 2.00 mmol) was combined with 4-formylbenzoyl chloride (1.68 g, 10.0 mmol), silver cyanate (1.50. g, 10.0 mmol) and tetrakis(triphenylphosphine) palladium (0) (25 mg) in dry dichloromethane (25 ml) and the reaction stirred at room temperature for 6 hours in subdued light and under an atmosphere of argon. The mixture was filtered through Kieselguhr and the filtrate washed with 1.0M hydrochloric acid followed by water and brine. After drying (MgSO$_4$) purification was accomplished by chromatography on silica gel, loading in dichloromethane and eluting with mixtures of ethyl acetate in hexane. The title compound was isolated as a crystalline solid (700 mg, 70%); $v_{max}$ ($CH_2Cl_2$) 3406, 2930, 1778, 1707, 1576, and 1480 cm$^{-1}$; $^1$H NMR (CDCl$_3$) 0.90 (3H, d, J 6.8 Hz), 1.00 (3H, d, J 6.4 Hz), 1.04–1.62 (12H, m), 1.73–1.77 (2H, m), 1.94–2.24 (2H, m), 2.15–2.25 (1H, m), 2.54 (1H, dd, J 15.2, 10.0 Hz), 2.88 (1H, q, J 6.3 Hz), 3.22 (3H, s), 3.41–3.48 (1H, m), 5.02 (1H, d, J 17.5 Hz), 5.28 (1H, d, J 10.7 Hz), 5.85 (1H, d, J 10.0 Hz), 6.67 (1H, dd, J 17.5, 10.0 Hz), 7.95–8.03 (5H, m), 8.13 (1H, bs), 10.11 (1H, s); MS (NH$_3$DCI) m/z 527 (MNH$_4^+$). (Found: C, 70.46; H, 8.03; N, 2.55. C$_{30}$H$_{39}$NO$_6$ requires C, 70.70: H, 7.71; N, 2.75).

Step 2. (3R)-3-Deoxo-11-deoxy-3-methoxy-11-oxo-4-epi-mutilin 14-[N-(4-carboxybenzoyl)carbamate]

(3R)-3-Deoxo-11-deoxy-3-methoxy-11-oxo-4-epi-mutilin 14-[N-(4-formylbenzoyl)carbamate] (200 mg, 0.4 mmol) was dissolved in acetone (5 ml) and treated with Jones' reagent (0.05 ml of 8M solution of [O], 0.4 mmol) and the reaction was stirred at room temperature for 5 minutes. More Jones' reagent (0.05 ml) was added and stirring continued at room temperature. The reaction mixture was treated with isopropanol (1 ml) and then partitioned between ethyl acetate and water. After washing the organic phase with water and brine it was dried (MgSO$_4$). Removal of solvent in vacuo gave the title compound as a foam (182 mg, 87%); $v_{max}$ ($CH_2Cl_2$) 3434, 3273, 2927, 17323, and 1699 cm$^{-1}$; $^1$H NMR (CDCl$_3$, CD$_3$OD)) 0.84 (3H, d, J 6.8 Hz), 0.93 (3H, d, J 6.3 Hz), 1.01–1.54 (13H, m), 1.62–1.69 (2H, m), 2.08–2.17 (2H, m), 2.44 (1H, dd, J 15.2, 10.0 Hz), 2.85 (1H, q, J 6.3 Hz), 3.16 (3H, s), 3.36–3.41 (1H, m), 4.94 (1H, d, J 17.4 Hz), 5.23 (1H, d, J 10.8 Hz), 5.78 (1H, d, J 9.8 Hz), 6.65 (1H, dd, J 17.5, 10.7 Hz), 7.84 (2H, d, J 8.5 Hz), 8.05 (2H, d, J 8.5 Hz); MS (NH$_3$DCI) m/z 543 (MNH$_4^+$).

Step 3. Mutilin 14-[N-(4-carboxybenzoyl)carbamate]

The product of Step 2 (600 mg, 1.14 mmol) in dioxane (15 ml) was treated with a saturated solution of zinc chloride in conc. HCl (3.5 ml), as for Example 1 Step 2, to afford the title compound (280 mg, 68%); $v_{max}$ (KBr disc) 1766, 1740, and 1709 cm$^{-1}$; $^1$H NMR (d$_6$-Acetone) 0.82 (3H, d, J 6.3 Hz), 0.96 (3H, d, J 7.0 Hz), 1.19–1.25 (4H, m), 1.39–1.84 (10H, m), 2.07–2.36 (5H, m), 3.36 (1H, bs, collapse to d in D$_2$O, J 6.0 Hz), 5.19 (1H, dd, J 11.2, 1.8 Hz), 5.27 (1H, dd, J 17.7, 1.6 Hz), 5.79 (1H, d, J 8.5 Hz), 6.45 (1H, dd, J 17.6, 11.2 Hz), 8.01 (1H, d, J 8.5 Hz), 8.14 (1H, d, J 8.1 Hz), 10.04 (1H, s, ex. in D$_2$O); MS (ESI, +ve ion) m/z 534 (MNa$^+$).

EXAMPLE 43

Mutilin 14-(N-phenoxycarbamate)

Step 1. (3R)-3-Deoxo-11-deoxy-3-methoxy-11-oxo-4-epi-mutilin 14-(N-phenoxycarbamate)

O-Phenylhydroxylamine hydrochloride (165 mg, 1.13 mmol) was reacted with (3R)3-deoxo-11-deoxy-3-methoxy-11-oxo-epi-mutilin 14-chloroformate (150 mg, 0.38 mmol) and diisopropylethylamine (0.33 ml, 1.9 mmol) in dichloromethane (3 ml), as for Example 12 Step 2, to afford the crude title compound (150 mg) which was used in the following step without purification; $v_{max}$ ($CH_2Cl_2$) 3368, 1753, 1698 cm$^{-1}$; $^1$H NMR inter alia(CDCl$_3$) 0.87 (3H, d, J 6.9 Hz), 0.98 (3H, d, J 6.4 Hz) 1.13 (3H, s), 1.20 (3H, s), 1.05–1.30 (4H, m), 1.52 (2H, m), 1.69 (1H, d, J 15.4 Hz), 1.71 (1H, d, J 11.2 Hz), 1.98 (2H, m), 2.18 (1H, m), 2.48 (1H, dd, J 15.3, 10.1 Hz), 2.88 (1H, q, J 6.4 Hz), 3.20 (3H, s), 3.44 (1H, m), 5.01 (1H, d, 17.5 Hz), 5.28 (1H, d, J 10.6 Hz), 5.76 (1H, d, J 10.0 Hz), 6.69 (1H, dd, J 17.4, 10.6 Hz), 7.08 (3H, m), 7.31 (2H, m), 7.63 (1H, s); MS(CI) m/z 487 (MNH$_4^+$).

Step 2. Mutilin 14-(N-phenoxycarbamate)

The product of Step 1 (112 mg) in dioxane (3 ml) was treated with a saturated solution of zinc chloride in conc. HCl (1 ml), as for Example 1 Step 2, to afford the title compound (11.5 mg); $v_{max}$ ($CH_2Cl_2$) 3562, 1735 cm$^{-1}$, $^1$H NMR (CDCl$_3$) 0.68 (3H,br), 0.86 (3H, d, J 6.9 Hz), 1.06–1.79 (9H, m), 1.16 (3H, s), 1.29 (3H, s), 2.05 (2H, m), 2.23 (3H, m), 3.33 (1H, m,), 5.21 (1H, dd, J 17.2, 1.3 Hz), 5.36 (1H, d, J 11.1 Hz), 5.75 (1H, d, J 8.3 Hz), 6.46 (1H, dd, J 17.3, 11.0 Hz), 6.91 (1H, d, J 7.9 Hz), 7.06 (1H, t, J 7.3 Hz), 7.28 (2H, m); MS(EI) m/z 456 (M$^+$) Found: 455.2677, $C_{27}H_{37}NO_5$ requires 455.2672.

EXAMPLE 44

Mutilin 14-[N-(4-trifluoromethylbenzoyl)carbamate]
Step 1. 4-Trifluoromethylbenzoylisocyanate Silver cyanate (690 mg, 4.6 mmol) and 4-trifluoromethylbenzoylchloride (0.6 ml, 4.0 mmol) in dry dichloromethane (5 ml) were reacted according to the method described in Example 31, Step 1. The solution containing the title compound was immediately used in the next reaction; $v_{max}$ (CH$_2$Cl$_2$) 2246 cm$^{-1}$.
Step 2. (3R)-3-Deoxo-11-deoxy-3-methoxy-11-oxo-4-epi-mutilin 14-[N-(4-trifluoromethylbenzoyl)carbamate]

The solution from step 1 was treated with (3R)-3-deoxo-11-deoxy-3-methoxy-11-oxo-4-epi-mutilin (335 mg, 1.00 mmol) and the reaction stirred for 1.5 hour. The title compound was isolated by the same procedure as described in Example 31, Step 2 (405 mg, 74%); $v_{max}$ (CH$_2$Cl$_2$) 3416, 1780, 1718, 1698 cm$^{-1}$; $^1$H NMR (CDCl$_3$) 0.85 (1H, m), 0.90 (3H, d, J 6.9 Hz), 1.01 (3H, d, J 6.4 Hz), 1.08–1.31 (3H, m), 1.21 (3H, s), 1.31 (3H, s), 1.52 (2H, m), 1.74 (2H, m), 2.03 (2H, m), 2.21 (1H, m), 2.54 (1H, dd, J 15.2, 10.1 Hz), 2.89 (1H, q, J 6.4 Hz), 3.23 (3H, s), 3.46 (1H, m), 5.02 (1H, d, J 17.4 Hz), 5.30 (1H, d, J 10.6 Hz), 5.85 (1H, d, J 10.0 Hz), 6.68 (1H, dd, J 17.4, 10.6 Hz), 7.77 (1H, d, J 8.3 Hz), 7.94 (1H, d, J 8.2 Hz), 8.02 (1H, s); MS (EI) m/z 549 (M$^+$) Found: 549.2703, $C_{30}H_{38}F_3NO_5$ requires 549.2702.
Step 3. Mutilin 14-[N-(4-trifluoromethylbenzoyl) carbamate]

The product of Step 2 (385 mg, 0.7 mmol) in dioxane (6 ml) was treated with a saturated solution of zinc chloride in conc. HCl (1 ml), as for Example 1 Step 2, to afford the title compound (148 mg, 40%); $v_{max}$ (CH$_2$Cl$_2$) 3421, 1781, 1734 cm$^{-1}$; $^1$H NMR (CDCl$_3$) 0.80 (3H, d, J 6.7 Hz), 0.89 (3H, d, J 7.0 Hz), 1.18 (1H, m) 1.20 (3H, s) 1.51 (3H, s), 1.41–1.82 (8H, m), 2.04–2.36 (5H, m), 3.37 (1H, dd, J 10.7, 6.6 Hz), 5.24 (1H, dd, J 17.4, 1.4 Hz), 5.37 (1H, dd, J 11.0, 1.3 Hz), 5.82 (1H, d, J 8.5 Hz), 6.53 (1H, dd, J 17.3, 11.0 Hz), 7.75 (2H, d, J 8.3 Hz), 7.90 (1H, d, J 8.2 Hz), 7.98 (1H, bs); MS (CI) m/z 553 (MNH$_4^+$).

EXAMPLE 45

Mutilin 14-[N-(3-trifluoromethylbenzoyl)carbamate]
Step 1. 3-Trifluoromethylbenzoylisocyanate Silver cyanate (690 mg, 4.6 mmol) and 3-trifluoromethylbenzoylchloride (0.6 ml, 3.98 mmol) in dry dichloromethane (5 ml) were reacted according to the method described in Example 31, Step 1. The solution containing the title compound was immediately used in the next reaction, $v_{max}$ (CH$_2$Cl$_2$) 2250 cm$^{-1}$.
Step 2. (3R)-3-Deoxo-11-deoxy-3-methoxy-11-oxo-4-epi-mutilin 14-[N-(3-trifluoromethylbenzoyl)carbamate]

The solution from step 1 was treated with (3R)-3-deoxo-11-deoxy-3-methoxy-11-oxo-4-epi-mutilin (335 mg, 1.0 mmol) and the reaction stirred for 1.5 hour. The title compound was isolated by the same procedure as described in Example 31, Step 2 (480 mg, 87%); $v_{max}$ (CH$_2$Cl$_2$) 3414, 1780, 1718, 1698 cm$^{-1}$; $^1$H NMR (CDCl$_3$) 0.90 (3H, d, J 6.8 Hz), 1.00 (3H, d, J 6.4 Hz), 1.05–1.43 (4H, m), 1.21 (3H, s), 1.30 (3H, s), 1.53 (2H, m), 1.71 (1H, d, J 15.3 Hz), 1.75 (1H, d, J 11.2 Hz), 2.00 (2H, m), 2.20 (1H, m), 2.55 (1H, dd, J 15.2, 10.1 Hz), 2.89 (1H, q, J 6.4 Hz), 3.22 (3H, s), 3.46 (1H, ddd, J 11.2, 5.3, 2.9 Hz), 5.02 (1H, d, J 17.5 Hz), 5.28 (1H, d, J 10.7 Hz), 5.86 (1H, d, J 10.0 Hz), 6.67 (1H, dd, J 17.5, 10.7 Hz), 7.65 (1H, t, J 7.8 Hz), 7.86 (1H, d, J 7.9 Hz), 8.01 (1H, d, J 7.9 Hz), 8.09 (2H, brs); MS (CI) m/z 567 (MNH$_4^+$) (Found: C, 65.50; H, 6.90; N, 2.71. $C_{30}H_{38}F_3NO_5$ requires C, 65.56; H, 6.97; N, 2.55).
Step 3. Mutilin 14-[N-(3-trifluoromethylbenzoyl) carbamate]

The product of Step 2 (350 mg, 0.64 mmol) in dioxane (5 ml) was treated with a saturated solution of zinc chloride in conc. HCl (1 ml), as for Example 1 Step 2, to afford the title compound (184 mg, 54%); $v_{max}$ (CH$_2$Cl$_2$) 3411, 1781, 1734 cm$^{-1}$; $^1$H NMR (CDCl$_3$) 0.80 (3H, d, J 6.7 Hz), 0.89 (3H, d, J 6.9 Hz), 1.15 (1H, m) 1.20 (3H, s) 1.51 (3H, s), 1.41–1.81 (8H, m), 2.11–2.35 (5H, m), 3.37 (1H, dd, J 10.9, 6.6 Hz), 5.23 (1H, dd, J 17.3, 1.4 Hz), 5.35 (1H, dd, J 11.0, 1.3 Hz), 5.82 (1H, d, J 8.5 Hz), 6.52 (1H, dd, J 17.3, 11.0 Hz), 7.63 (1H, t, J 7.8 Hz), 7.84 (1H, d, J 7.8 Hz), 7.98 (1H, d, J 7.8 Hz) 8.06 (1H, s), 8.12 (1H, s); MS (Electrospray) m/z 558 (MNa$^+$).

EXAMPLE 46

Mutilin 14-[N-(2-trifluoromethylbenzoyl)carbamate]
Step 1. 2-Trifluoromethylbenzoylisocyanate Silver cyanate (690 mg, 4.6 mmol) and 2-trifluoromethylbenzoylchloride (0.5 ml, 3.4 mmol) in dry dichloromethane (5 ml) were reacted according to the method described in Example 31, Step 1 for 3 hours. The solution containing the title compound was immediately used in the next reaction; $v_{max}$ (CH$_2$Cl$_2$) 2254 cm$^{-1}$
Step 2. (3R)-3-Deoxo-11-deoxy-3-methoxy-11-oxo-4-epi-mutilin 14-[N-(2-trifluoromethylbenzoyl)carbamate]

The solution from step 1 was treated with (3R)-3-deoxo-11-deoxy-3-methoxy-11-oxo-4-epi-mutilin (335 mg, 1.0 mmol) and the reaction stirred for 0.5 hour. The title compound was isolated by the same procedure as described in Example 31, Step 2 (231 mg, 42%); $v_{max}$ (CH$_2$Cl$_2$) 3384, 1782, 1760, 1698 cm$^{-1}$; $^1$H NMR (CDCl$_3$) 0.85 (3H, d, J 6.8 Hz), 0.95 (3H, d, J 6.4 Hz), 1.05–1.36 (4H, m), 1.19 (6H, s), 1.50 (2H, m), 1.62 (1H, d, J 15.4 Hz), 1.71 (1H, d, J 11.3 Hz), 1.98 (2H, m), 2.17 (1H, m), 2.48 (1H, dd, J 15.3, 10.1 Hz), 2.81 (1H, q, J 6.4 Hz), 3.21 (3H, s), 3.43 (1H, m), 4.98 (1H, d, J 17.5 Hz), 5.23 (1H, d, J 10.7 Hz), 5.72 (1H, d, J 10.0 Hz), 6.50 (1H, dd, J 17.4, 10.6 Hz), 7.50 (1H, m,), 7.64 (2H, m), 7.76 (2H, m); MS (CI) m/z 567 (MNH$_4^+$).
Step 3. Mutilin 14-[N-(2-trifluoromethylbenzoyl) carbamate]

The product of Step 2 (207 mg, 0.38 mmol) in dioxane (3 ml) was treated with a saturated solution of zinc chloride in conc. HCl (1 ml), as for Example 1 Step 2, to afford the title compound (149 mg, 74%); $v_{max}$ (CH$_2$Cl$_2$) 3390, 1784, 1763, 1734, 1705 cm$^{-1}$: $^1$H NMR (CDCl$_3$) 0.76 (3H, d, J 6.9 Hz), 0.83 (3H, d, J 7.0 Hz), 1.16 (1H, m) 1.18 (3H, s) 1.38 (3H, s), 1.36–1.49 (4H, m), 1.55–1.76 (4H, m), 2.04–2.28 (5H, m), 3.33 (1H, dd, J 10.6, 6.7 Hz), 5.19 (1H, dd, J 17.3, 1.3 Hz), 5.28 (1H, d, J 11.0 Hz), 5.67 (1H, d, J 8.4 Hz), 6.36 (1H, dd, J 17.2, 11.0 Hz), 7.44 (1H, m), 7.62 (2H, m), 7.72 (2H, m); MS (Cl) m/z 553 (MNH$_4^+$).

EXAMPLE 47

Mutilin 14-[N-iso-nicotinoylcarbamate]
Step 1. (3R)-3-Deoxo-11-deoxy-3-methoxy-11-oxo-4-epi-mutilin 14-[N-iso-nicotinoylcarbamate]

A mixture of silver cyanate (690 mg, 4.6 mmol), iso-nicotinoyl chloride hydrochloride (535 mg, 3.0 mmol), terrakis tipheylphosphine palladium (0) (18.5 mg, 0.016 mmol) and (3R)-3-deoxo-11-deoxy-3-methoxy-11-oxo-4-epi-mutilin (335 mg, 1.0 mmol) in dichloromethane (15 ml) was protected from light and stirred at room temperature under argon for 66 hour. Diisopropylethylamine (1 ml) was then added and the reaction mixture filtered through Kieselguhr. Concentration afforded a crude product which was purified by silica gel chromatography eluting with 50–75% ethyl acetate/hexane mixtures to give the title compound (212 mg, 44%); $v_{max}$ (CH$_2$Cl$_2$) 3406, 1781, 1721, 1698 cm$^{-1}$; $^1$H NMR (CDCl$_3$) 0.89 (3H, d, J 6.9 Hz), 1.01 (3H, d, J 6.4 Hz), 1.03–1.62 (6H, m), 1.21 (3H, s), 1.31 (3H, s), 1.70 (1H, d, J 15.5 Hz), 1.75 (1H, d, J 11.5 Hz), 2.00 (2H, m), 2.21 (1H, m), 2.54 (1H, dd, J 15.2, 10.1 Hz), 2.88 (1H, q, J 6.3 Hz), 3.22 (3H, s), 3.46 (1H, ddd, J 11.2, 8.3, 5.3 Hz), 5.02 (1H, d, J 17.5 Hz), 5.29 (1H, d, J 10.7 Hz), 5.85 (1H, d, J 10.0 Hz), 6.66 (1H, dd, J 17.5, 10.7 Hz), 7.64 (2H, dd, J 4.4, 1.6 Hz), 8.11 (1H, s), 8.84 (2H, dd, J 4.4, 1.5 Hz); MS (CI) m/z 483 (MNH$_4^+$).

Step 2. Mutilin 14-[N-iso-nicotinoylcarbamate]

The product of Step 1 (177 mg, 0.37 mmol) in dioxane (2 ml) was treated with a saturated solution of zinc chloride in conc. HCl (1 ml), as for Example 1 Step 2, to afford the title compound (29.6 mg, 17%); $v_{max}$(CH$_2$Cl$_2$) 3400, 1783, 1734 cm$^{-1}$; $^1$H NMR (CDCl$_3$) 0.79 (3H, d, J 6.8 Hz), 0.89 (3H, d, J 7.0 Hz), 1.16 (1H, m) 1.20 (3H, s) 1.50 (3H, s), 1.44–1.82 (8H, m), 2.11–2.35 (5H, m), 3.37 (1H, dd, J 10.7, 6.6 Hz), 5.23 (1H, dd, J 17.3, 1.4 Hz), 5.36 (1H, dd, J 10.9, 1.3 Hz), 5.82 (1H, d, J 8.5 Hz), 6.51 (1H, dd, J 17.3, 11.0 Hz), 7.62 (1H, dd, J 4.5, 1.5 Hz), 8.20 (1H, s), 8.79 (2H, dd, J 4.5, 1.7 Hz); MS (CI) m/z 469 (MH$^+$).

EXAMPLE 48

Mutilin 14-[N-nicotinoylcarbamate]

Step 1. (3R)-3-Deoxo-11-deoxy-3-methoxy-11-oxo-4-epi-mutilin 14-[N-nicotinoylcarbamate]

A mixture of silver cyanate (690 mg, 4.6 mmol), nicotinoyl chloride hydrochloride (712 mg, 4.0 mmol), terrakis tripheylphosphine palladium (0) (14 mg, 0.012 mmol), diisopropylethylamine (0.7 ml, 4.0 mmol) and (3R)-3-deoxo-11-deoxy-3-methoxy-11-oxo-4-epi-mutilin (335 mg, 1.0 mmol) in dichloromethane (14 ml) was protected from light and stirred at reflux under argon for 50 minutes. The reaction mixture was filtered through Kieselguhr and concentrated, to affored a crude product which was purified by silica gel chromatography to give the title compound (177 mg, 37%); $v_{max}$ (CH$_2$Cl$_2$) 3410, 1779, 1717, 1698 cm$^{-1}$; $^1$H NMR (CDCl$_3$) 0.90 (3H, d, J 6.8 Hz), 1.00 (3H, d, J 6.4 Hz), 1.08–1.56 (6H, m), 1.21 (3H, s), 1.30 (3H, s), 1.71 (1H, d, J 15.3 Hz), 1.75 (1H, d, J 11.2 Hz), 2.00 (2H, m), 2.21 (1H, m), 2.54 (1H, dd, J 15.3, 10.1 Hz), 2.89 (1H, q, J 6.4 Hz), 3.22 (3H, s), 3.46 (1H, ddd, J 11.2, 8.1, 5.4 Hz), 5.02 (1H, d, J 17.4 Hz), 5.28 (1H, d, J 10.7 Hz), 5.85 (1H, d, J 10.0 Hz), 6.67 (1H, dd, J 17.5, 10.7 Hz), 7.46 (1H, dd, J 7.6, 4.9 Hz), 8.16 (2H, m), 8.81 (1H, dd, J 4.9, 1.5 Hz) 9.02 (1H, d, J 2.3 Hz); MS (CI) m/z 483 (MNH$_4^+$).

Step 2. Mutilin 14-[N-nicotinoylcarbamate]

The product of Step 1 (153 mg, 0.32 mmol) in dioxane (2 ml) was treated with a saturated solution of zinc chloride in conc. HCl (1 ml), as for Example 1 Step 2, to afford the title compound (95 mg, 64%); $v_{max}$ (CH$_2$Cl$_2$) 3410, 1781, 1734 cm$^{-1}$; $^1$H NMR (CDCl$_3$) 0.81 (3H, d, J 6.7 Hz), 0.89 (3H, d, J 6.9 Hz), 1.18 (1H, m) 1.20 (3H, s) 1.50 (3H, s), 1.44–1.82 (5H, m), 2.11–2.35 (5H, m), 3.37 (1H, dd, J 10.6, 6.7 Hz), 5.23 (1H, d, J 17.4 Hz), 5.36 (1H, d, J 11.1 Hz), 5.82 (1H, d, J 8.4 Hz), 6.52 (1H, dd, J 17.3, 11.0 Hz), 7.44 (1H, dd, J 7.8, 4.9 Hz), 8.12 (2H, br), 8.80 (1H, d, J 3.4 Hz), 8.99 (1H, d, J 1.7 Hz); MS (EI) m/z 469 (MH$^+$), Found: 469.2704, C$_{27}$H$_{37}$N$_2$O$_5$ (MH$^+$) requires 469.2702.

EXAMPLE 49

Mutilin 14-[N-2-furoylcarbamate]

Step 1. (3R)-3-Deoxo-11-deoxy-3-methoxy-11-oxo-4-epi-mutilin 14-[N-2-furoylcarbamate]

A mixture of silver cyanate (690 mg, 4.6 mmol), 2-furoyl chloride (0.4 ml, 3.0 mmol), terrakis tripheylphosphine palladium (0) (17 mg, 0.015 mmol)and (3R)-3-deoxo-11-deoxy-3-methoxy-11-oxo-4-epi-mutilin (335 mg, 1.0 mmol) in 1,2-dichloroethane (10 ml) was protected from light and stirred at room temperature under argon for 41 hour. The reaction mixture was filtered through Kieselguhr and concentrated, to afforded a crude product, which was purified by silica gel chromatography to give the title compound (468 mg, 99%); $v_{max}$ (CH$_2$Cl$_2$) 3415, 1777, 1714, 1699 cm$^{-1}$; $^1$H NMR (CDCl$_3$) 0.89 (3H, d, J 6.9 Hz), 1.00 (3H, d, J 6.4 Hz), 1.07–1.42 (4H, m), 1.20 (3H, s), 1.33 (3H, s), 1.53 (2H, m), 1.71 (1H, d, J 15.3 Hz), 1.75 (1H, d, J 11.3 Hz), 2.02 (2H, m), 2.20 (1H, m), 2.53 (1H, dd, J 15.4, 10.1 Hz), 2.90 (1H, q, J 6.4 Hz), 3.23 (3H, s), 3.47 (1H, ddd, J 11.2, 8.3, 5.3 Hz), 5.01 (1H, d, J 17.4 Hz), 5.30 (1H, d, J 10.7 Hz), 5.84 (1H, d, J 9.9 Hz), 6.59 (1H, dd, J 3.5, 1.7 Hz), 6.73 (1H, dd, J 17.4, 10.6 Hz), 7.34 (1H, d, J 3.3 Hz), 7.54 (1H, s), 8.20 (1H, s); MS (CI) m/z 471 (M$^+$).

Step 2. Mutilin 14-[N-2-furoylcarbamate]

The product of Step 2 (200 mg, 0.42 mmol) in dioxane (2 ml) was treated with a saturated solution of zinc chloride in conc. HCl (1 ml), as for Example 1 Step 2, to afford the title compound (129 mg, 67%); $v_{max}$(CH$_2$Cl$_2$) 3412, 1777, 1733, 1716 cm$^{-1}$; $^1$H NMR (CDCl$_3$) 0.80 (3H, d, J 6.7 Hz), 0.89 (3H, d, J 7.0 Hz), 1.18 (1H, m) 1.19 (3H, s) 1.54 (3H, s), 1.37–1.82 (8H, m), 2.10–2.38 (5H, m), 3.37 (1H, dd, J 11.0, 6.6 Hz), 5.23 (1H, dd, J 17.3, 1.5 Hz), 5.38 (1H, dd, J 11.0, 1.5 Hz), 5.83 (1H, d, J 8.5 Hz), 6.56 (1H, dd, J 17.3, 11.0 Hz), 6.57 (1H, dd, J 3.5, 1.8 Hz), 7.32 (1H, d, J 3.3 Hz), 7.52 (1H, d, J 2.1 Hz), 8.15 (1H, s); MS (CI) m/z 475 (MNH$_4^+$).

EXAMPLE 50

Mutilin 14-[N-acetylcarbamate]

Step 1. Acetyl isocyanate

Silver cyanate (690 mg, 4.6 mmol) and acetyl chloride (0.28 ml, 3.94 mmol) in dry dichloromethane (5 ml) were reacted according to the method described in Example 31, Step 1 for 1.75 hours. The solution containing the title compound was immediately used in the next reaction; $v_{max}$ (CH$_2$Cl$_2$) 2257 cm$^{-1}$.

Step 2. (3R)-3-Deoxo-11-deoxy-3-methoxy-11-oxo-4-epi-mutilin 14-[N-acetylcarbamate]

The solution from step 1 was treated with (3R)-3-deoxo-11-deoxy-3-methoxy-11-oxo-4-epi-mutilin (335 mg, 1.0 mmol) and the reaction stirred for 10 minutes. The title compound was isolated by the same procedure as described in Example 31, Step 2 (420 mg, 100%); $v_{max}$ (CH$_2$Cl$_2$) 3388, 1753, 1713 cm$^{-1}$; $^1$H NMR (CDCl$_3$) 0.83 (3H, d, J 6.9 Hz), 1.00 (3H, d, J 6.4 Hz), 1.07–1.54 (6H, m), 1.21 (6H, s), 1.62 (1H, d, J 15.7 Hz), 1.73 (1H, d, J 11.3 Hz), 1.99 (2H, m), 2.20 (1H, m), 2.48 (3H, s), 2.49 (1H, dd, J 15.4, 10.0 Hz), 2.88 (1H, q, J 6.4 Hz), 3.22 (3H, s), 3.45 (1H, ddd, J 11.2, 8.1, 5.3 Hz), 5.03 (1H, d, J 17.5 Hz), 5.33 (1H, d, J 10.7 Hz), 5.72 (1H, d, J 10.0 Hz), 6.63 (1H, dd, J 17.5, 10.7 Hz), 7.45 (1H, s); MS (EI) m/z 419 (M$^+$), Found: 419.2674, C$_{24}$H$_{37}$NO$_5$ requires 419.2672.

Step 3. Mutilin 14-[N-acetylcarbamate]

The product of Step 2 (284 mg, 0.68 mmol) in dioxane (3 ml) was treated with a saturated solution of zinc chloride in conc. HCl (1 ml), as for Example 1 Step 2, to afford the title compound (190 mg, 69%); $v_{max}$(CH$_2$Cl$_2$) 3392, 1755, 1734, 1714 cm$^{-1}$; $^1$H NMR (CDCl$_3$) 0.74 (3H, d, J 6.7 Hz), 0.89 (3H, d, J 7.0 Hz), 1.16 (1H, m) 1.19 (3H, s) 1.43 (3H, s), 1.37–1.55 (5H, m), 1.59–1.85 (3H, m), 2.05–2.38 (5H, m), 2.42 (3H, s), 3.37 (1H, dd, J 10.6, 6.6 Hz), 5.23 (1H, dd, J 17.4, 1.3 Hz), 5.37 (1H, dd, J 11.0, 1.3 Hz), 5.72 (1H, d, J 8.4 Hz), 6.49 (1H, dd, J 17.4, 11.0 Hz), 7.51 (1H, s); MS (CI) m/z 423 (MNH$_4^+$).

EXAMPLE 51

Mutilin 14-[N-(4-chlorobenzenesulphonyl)]-carbamate (3R)-3-Deoxo-11-deoxy-3-methoxy-11-oxo-4-epi-mutilin 14-chloroformate (500 mg) in dry dichloromethane (7 ml) was treated with 4-chlorobenzenesulphonamide (265 mg), diisopropylethylamine (0.5 ml), and 4 dimethylaminopyridine (10 mg), and the solution was stirred for 30 minutes at room temperature. The solution was diluted with ethyl acetate (50 ml) and washed with dilute HCl (30 ml), water (30 ml), and saturated brine (30 ml). The solution was dried (sodium sulphate) and the solvent was removed by evaporation under reduced pressure to yield a white foam (780 mg).

The foam was dissolved in 1,4-dioxane (8 ml) and treated with a saturated solution of zinc chloride in conc. HCl (2.5 ml). The solution was stirred for 2.5 hours at room temperature, and was then diluted with ethyl acetate (50 ml) and washed three times with water. The solution was dried (sodium sulphate) and the solvent was removed by evaporation under reduced pressure to yield a pink foam. Crystallisation from dichloromethane-hexane gave the title compound as colourless crystals (555 mg), m.p. 216–218° C.; $\lambda_{max}$ (EtOH) 230 nm ($\epsilon$ 12,100);$\nu_{max}$ (CHCl$_3$) 3380, 1735, and 1210 cm$^{-1}$; $\delta_H$ (CDCl$_3$) 7.94 (2H, d, J 5 Hz), 7.52 (2H, d, J 5 Hz), 6.27 (1H, dd, J 17.4 and 11 Hz), 5.61 (1H, d, J 8.4 Hz), 5.24 (1H, dd, J 11 and 1.2 Hz), 5.10 (1H, dd, J 17.4 and 1.2 Hz), 3.30 (1H, dd, J 10.1 and 6.7), 2.20 (3H, m), 1.95 (2H, m), 1.8–1.0 (overlapping multiplets), 1.34 (3H, s), 1.09 (3H, s), 0.83 (3H, d, J 7 Hz), and 0.52 (3H, d, J 6.8 Hz); MS (CI) m/z 555 (M.NH$_4^+$).

EXAMPLE 52

Mutilin 14-[N-(4-fluorobenzenesulphonyl)]-carbamate

Step 1. (3R)-3-Deoxo-11-deoxy-3-methoxy-11-oxo-4-epi-mutilin 14-[N-(4-fluorobenzenesulphonyl)]-carbamate (3R)-3-Deoxo-11-deoxy-3-methoxy-11-oxo-4-epi-mutilin 14-chloroformate (200 mg) in dry dichloromethane (3 ml) was treated with 4-fluorobenzenesulphonamide (180 mg), diisopropylethylamine (0.2 ml), and 4-dimethylaminopyridine (2 mg), and the solution was stirred for 30 minutes at room temperature. The solution was diluted with ethyl acetate (50 ml) and washed with dilute HCl (20 ml), water (20 ml), and saturated brine (20 ml). The solution was dried (sodium sulphate) and the solvent was removed by evaporation under reduced pressure to yield a colourless gum. Chromatography on silica gel using ethyl acetate-hexane gave the title compound as a colourless gum (240 mg); $\nu_{max}$ (CHCl$_3$) 3379, 1737, 1697, and 1594 cm$^{-1}$; MS (EI) m/z 535 (M$^+$) (Found: M$^+$, 535.2408. C$_{28}$H$_{38}$NO$_6$FS requires M, 535.2404).

Step 2. Mutilin 14-[N-(4-fluorobenzenesulphonyl)]-carbamate (3R)-3-Deoxo-11-deoxy-3-methoxy-11-oxo-4-epi-mutilin 14-[N-(4-fluoro-benzenesulphonyl)]-carbamate (200 mg) in 1,4-dioxane (4 ml) was treated with a saturated solution of zinc chloride in conc. HCl (1.5 ml) and the solution was kept at room temperature for 1.5 hours. The solution was diluted with ethyl acetate (50 ml) and was washed three times with water (20 ml portions). The solution was dried (sodium sulphate) and the solvent was removed by evaporation under reduced pressure to give a colourless gum. Chromatography on silica gel using ethyl acetate-hexane gave the title compound as colourless crystals (140 mg). Recrystallisation from dichloromethane-hexane gave colourless needles, m.p. 228–229° C.; $\lambda_{max}$ (EtOH) 217 nm ($\epsilon$ 11,660); $\delta_H$ (CDCl$_3$) 8.01 (2H, dd, J 9 and 5 Hz), 7.20 (2H, t, J 9 Hz), 6.27 (1H, dd, J 17.5 and 11 Hz), 5.58 (1H, d, J 8.3 Hz), 5.20 (1H, dd, J 11 and 1.2 Hz), 5.06 (1H, dd, J 17.5 and 1.2 Hz), 3.20 (1H, d, J 6.2 Hz), 2.22 (2H, m), 1.97 (2H, m), 1,8–1.0 (overlapping multiplets), 1.35 (3H, s), 1.09 (3H, s), 0.85 (3H, d, J 7 Hz), 0.51 (3H, d, J 6.7 Hz); MS (CI) m/z 539 (M.NH$_4^+$).

EXAMPLE 53

Mutilin 14-[N-(4-n-propylbenzenesulphonyl)]-carbamate

Step 1. (3R)-3-Deoxo-11-deoxy-3-methoxy-11-oxo-4-epi-mutilin 14-[N-(4-n-propylbenzenesulphonyl)]-carbamate Using the process described in Example 52, Step 1, (3R)-3-deoxo-11-deoxy-3-methoxy-11-oxo-4-epi-mutilin 14-chloroformate (200 mg) and 4-n-propylbenzenesulphonamide (150 mg) were converted into the title compound, which was obtained as a colourless gum (220 mg); MS (CI) m/z 577 (M.NH$_4^+$).

Step 2. Mutilin 14-[N-(4-n-propylbenzenesulphonyl)]-carbamate

Using the process described in Example 52, Step 2, (3R)-3-deoxo-11-deoxy-3-methoxy-11-oxo-4-epi-mutilin 14-[N-(4-n-propylbenzenesulphonyl)]-carbamate (190 mg) was converted into the title compound, which was obtained as a colourless gum (150 mg); $\nu_{max}$ (CHCl$_3$) 3565, 3384, 1735, 1598, and 1421 cm$^{-1}$; $\delta_H$ (CDCl$_3$) 7.85 (2H, d, J 8.5 Hz), 7.32 (2H, d, J 8.5 Hz), 6.28 (1H, dd, J 17.3 and 11 Hz), 5.61 (1H, d, J 8.3 Hz), 5.23 (1H, dd, J 11 and 1.3 Hz), 5.08 (1H, dd, J 17 and 1.3 Hz), 3.29 (1H, dd, J 10.2 and 6.6 Hz), 2,67 (2H, t, J 7.3 Hz), 2.20 (2H, m), 1.95 (2H, m), 1.8–0.8 (overlapping multiplets), 0.49 (3H, d, J 6.7 Hz); MS (CI) m/z 563 (M.NH$_4^+$).

EXAMPLE 54

Mutilin 14-[N-(4-hydroxybenzenesulphonyl)]-carbamate (3R)-3-Deoxo-11-deoxy-3-methoxy-11-oxo-4-epi-mutilin 14-chloroformate (300 mg) in dry dichloromethane (5 ml) was treated with 4-hydroxybenzenesulphonamide (170 mg), diisopropylethylamine (0.35 ml), and 4-dimethylaminopyridine (8 mg), and the solution was stirred for 30 minutes at room temperature. The solution was diluted with ethyl acetate (50 ml) and washed with dilute HCl (20 ml), water (20 ml), and saturated brine (20 ml). The solution was dried (sodium sulphate) and the solvent was removed by evaporation under reduced pressure to yield a colourless gum. Chromatography on silica gel using ethyl acetate-hexane gave the product as a white foam (410 mg).

The above product was dissolved in 1,4-dioxane (8 ml) and the solution was treated with a saturated solution of zinc chloride in conc. HCl (3 ml); the solution was kept at room temperature for 3.5 hours. The solution was diluted with ethyl acetate (50 ml) and was washed three times with water (20 ml portions). The solution was dried (sodium sulphate) and the solvent was removed by evaporation under reduced pressure to five a pale yellow gum. Chromatography on silica gel using ethyl acetate-hexane gave the product as a white foam (180 mg). The NMR spectrum of this product showed that it contained two different mutilin moieties, and suggested that it had been derived by simultaneous reaction of 4-epi-mutilin chlomformate molecules with both the hydroxyl and the sulphonamido groups of 4-hydroxybenzenesulphonamide:

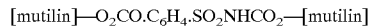

[mutilin]—O$_2$CO.C$_6$H$_4$.SO$_2$NHCO$_2$—[mutilin]

The above product was dissolved in methanol (8 ml) and the solution was treated with 1M NaOH (1 ml) and kept at room temperature for 6 hours. The solution was diluted with ethyl acetate (50 ml) and was washed with dilute HCl (20 ml) and saturated brine (20 ml). The solution was dried (sodium sulphate) and the solvent was removed by evaporation under reduced pressure to give a yellow gum. Chromatography on silica gel using ethyl acetate-hexane gave the title compound as a white solid (107 mg); $\lambda_{max}$ (EtOH) 239 nm (ε 12,340); $v_{max}$(CHCl$_3$) 3690, 3583, 3382, 1734, 1602, 1418, and 1157 cm$^{-1}$; $\delta_H$ (CDCl$_3$-d$_4$-MeOH) 7.77 (2H, d, J 7 Hz), 6.84 (2H, d, J 7 Hz), 6.28 (1H, dd, J 17.3 and 11 Hz), 5.56 (1H, d, J 8.3 Hz), 5.21 (1H, d, J 11 Hz), 5.07 (1H, d, J 17.3 Hz), 3.26 (1H, d, J 6.4 Hz), 2.5–1.0 (overlapping multiplets), 0.82 (3H, d, J 7 Hz), 0.51 (3H, d, J 6.5 Hz); MS (CI) m/z 537 (M.NH$_4^+$), 519. (M$^+$).

EXAMPLE 55

Mutilin 14-[N-(3,4-dimethoxybenzoyl)carbamate]
Step 1. 3,4-Dimethoxybenzoylisocyanate Silver cyanate (690 mg, 4.6 mmol) and 3,4-dimethoxybenzoylchloride (800 mg, 4.0 mmol) in dry dichloromethane (5 ml) were reacted according to the method described in Example 31, Step 1. The solution containing the title compound was immediately used in the next reaction; $v_{max}$ (CH$_2$Cl$_2$) 2238 cm$^{-1}$.
Step 2. (3R)-3-Deoxo-11-deoxy-3-methoxy-11-oxo-4-epi-mutilin 14-[N-(3,4-dimethoxybenzoyl)carbamate]

The solution from step 1 was treated with (3R)-3-deoxo-11-deoxy-3-methoxy-11-oxo-4-epi-mutilin (335 mg, 1.0 mmol) and the reaction stirred for 40 minutes. The title compound was isolated by the same procedure as described in Example 31, Step 2 (392 mg, 72%); $v_{max}$(CH)Cl$_2$) 3430, 1774, 1698 cm$^{-1}$; $^1$H NMR (CDCl$_3$) 0.91 (3H, d, J 6.8 Hz), 1.00 (3H, d, J 6.4 Hz), 1.05–1.57 (6H, m), 1.21 (3H, s), 1.34 (3H, s), 1.73 (1H, d, J 15.3 Hz), 1.75 (1H, d, J 10.5 Hz), 2.02 (2H, m), 2.20 (1H, m), 2.54 (1H, dd, J 15.2, 10.1 Hz), 2.91 (1H, q, J 6.2 Hz), 3.23 (3H, s), 3.47 (1H, m), 3.95 (6H, s), 5.02 (1H, d, J 17.5 Hz), 5.30 (1H, d, J 10.7 Hz), 5.85 (1H, d, J 9.9 Hz), 6.79 (1H, dd, J 17.5, 10.7 Hz), 6.90 (1H, d, J 8.4 Hz), 7.34 (1H, dd, J 8.4, 2.0 Hz), 7.46 (1H, d, J 2.0 Hz), 7.94 (1H, s); MS (CI) m/z 542 (MH$^+$).
Step 3. Mutilin 14-[N-(3,4-dimethoxybenzoyl)carbamate]

The product of Step 2 (275 mg, 0.51 mmol) in dioxane (2 ml) was treated with a saturated solution of zinc chloride in conc. HCl (1 ml), as for Example 1 Step 2, to afford the title compound (75 mg, 28%); $v_{max}$ (KBr disc) 3305, 1768, 1730, 1687 cm$^{-1}$; $^1$H NMR (CDCl$_3$) 0.82 (3H, d, J 6.6 Hz), 0.89 (3H, d, J 6.9 Hz), 1.20 (1H, m), 1.23 (3H, s), 1.54 (3H, s), 1.44–1.82 (8H, m), 2.12–2.38 (5H, m), 3.38 (1H, dd, J 10.7, 6.6 Hz), 3.94 (6H, s), 5.24 (1H, dd, J 17.4, 1.4 Hz), 5.38 (1H, dd, J 10.9, 1.4 Hz), 5.84 (1H, d, J 8.5 Hz), 6.58 (1H, dd, J 17.3, 11.0 Hz), 6.88 (1H, d, J 8.4 Hz), 7.30 (1H, dd, J 8.4, 2.0 Hz), 7.43 (1H, d, J 2.1 Hz), 7.86 (1H, s); MS (EI) m/z 527 (M$^+$), Found: 527.2884, C$_{30}$H$_{41}$NO$_7$ requires 527.2883.

EXAMPLE 56

Mutilin 14-[N-(3,4-methylenedioxybenzoyl)carbamate]
Step 1. 3,4-Methylenedioxybenzoylisocyanate Silver cyanate (690 mg, 4.6 mmol) and piperonyloyl chloride (738 mg, 4.0 mmol) in dry dichloromethane (5 ml) were reacted according to the method described in Example 31, Step 1. The solution containing the title compound was immediately used in the next reaction: $v_{max}$ (CH$_2$Cl$_2$) 2238 cm$^{-1}$.
Step 2. (3R)-3-Deoxo-11-deoxy-3-methoxy-11-oxo-4-epi-mutilin 14-[N-(3,4-methylenedioxybenzoyl)carbamate]

The solution from step 1 was treated with (3R)-3-deoxo-11-deoxy-3-methoxy-11-oxo-4-epi-mutilin (335 mg, 1.0 mmol) and the reaction stirred for 40 minutes. The title compound was isolated by the same procedure as described in Example 31, Step 2 (283 mg, 54%); $v_{max}$ (CH$_2$Cl$_2$) 3428, 1775, 1698 cm$^{-1}$; $^1$H NMR (CDCl$_3$) 0.90 (3H, d, J 6.9 Hz), 1.00 (3H, d, J 6.4 Hz), 1.07–1.56 (6H, m), 1.20 (3H, s), 1.31 (3H, s), 1.71 (1H, d, J 15.3 Hz), 1.75 (1H, d, J 11.2 Hz), 1.99 (2H, m), 2.20 (1H, m), 2.52 (1H, dd, J 15.2, 10.1 Hz), 2.90 (1H, q, J 6.5 Hz), 3.23 (3H, s), 3.46 (1H, ddd, J 11.2, 8.2, 5.3 Hz), 5.01 (1H, d, J 17.4 Hz), 5.29 (1H, d, J 10.7 Hz), 5.84 (1H, d, J 10.0 Hz), 6.07 (2H, s), 6.72 (1H, dd, J 17.5, 10.7 Hz), 6.87 (1H, d, J 8.0 Hz), 7.32 (1H, d, J 1.5 Hz), 7.36 (1H, dd, J 7.9, 1.8 Hz), 7.89 (1H, s); MS (CI) m/z 543 (MNH$_4^+$), 526 (MH$^+$).
Step 3. Mutilin 14-[N-(3,4-methylenedioxybenzoyl)carbamate]

The product of Step 2 (237 mg, 0.45 mmol) in dioxane (2 ml) was treated with a saturated solution of zinc chloride in conc. HCl (1 ml), as for Example 1 Step 2, to afford the title compound (151 mg, 65%); $v_{max}$(CH$_2$Cl$_2$) 3432, 1777, 1733, 1712 cm$^{-1}$; $^1$H NMR (CDCl$_3$) 0.80 (3H, d, J 6.6 Hz), 0.89 (3H, d, J 7.0 Hz), 1.18 (1H, m), 1.19 (3H, s), 1.38–1.83 (8H, m), 1.51 (3H, s), 2.09–2.37 (5H, m), 3.37 (1H, dd, J 10.9, 6.6 Hz), 5.23 (1H, dd, J 17.4, 1.5 Hz), 5.38 (1H, dd, J 11.0, 1.5 Hz), 5.82 (1H, d, J 8.5 Hz), 6.06 (2H, s), 6.56 (1H, dd, J 17.4, 11.0 Hz), 6.85 (1H, d, J 8.0 Hz), 7.29 (1H, d, J 1.6 Hz), 7.32 (1H, dd, J 8.1, 1.8 Hz), 7.81 (1H, s); MS (EI) m/z 511 (M$^+$), Found: 511.2566, C$_{29}$H$_{37}$NO$_7$ requires 511.2570.

EXAMPLE 57

Mutilin 14-(N-p-methoxysulphonylcarbamate)
Step 1. Mutilin 11-dichloroacetate

Mutilin (1.0 g, 3.12 mmol) was disolved in dry THF (10 ml) under argon and treated with pyridine (0.33 ml, 4.06 mmol), dichloroacetic anhydride (820 mg, 3.42 mmol) in THF (2 ml), and N,N-4-dimethylaminopyridine (5 mg). After 24 hours the reaction was diluted with ethyl acetate, washed with 1M hydrochloric acid, saturated sodium hydrozen carbonate and saturated sodium chloride solutions. The solution was dried over magnesium sulphate and concentrated to afford the crude product (1.5 g). Purification by silica gel chromatography (15–25% ethyl acetate/hexane) afforded the title compound (925 mg, 69%); $v_{max}$ (CH$_2$Cl$_2$) 3635, 1756, 1735 cm$^{-1}$; $^1$H NMR (CDCl$_3$) 0.86 (3H, d, J 7.1 Hz), 0.97 (3H, d, J 7.0 Hz), 1.06 (3H, s), 1.15 (1H, m), 1.32–1.50 (4H, m), 1.39 (3H, s), 1.63–2.02 (5H, m), 2.10 (1H, s), 2.22 (2H, m), 2.37 (1H, quintet, J 7.0 Hz), 4.31 (1H, t, J 6.4 Hz), 4.91 (1H, d, J 6.9 Hz), 5.32 (1H, dd, J 11.2, 0.7 Hz), 5.48 (1H, dd, J 17.7, 0.8 Hz), 6.00 (1H, s), 6.12 (1H, dd, J 18.0, 11.2 Hz); MS (CI) m/z 448/450/452 (MNH$_4^+$).
Step 2. Mutilin 14-chloroformate-11-dichloroacetate The product of Step 1 (882 mg, 2.04 mmol) was disolved in dry THF (15 ml) under argon, cooled in an ice-bath, and treated with trichloromethyl chloroformate (0.25 ml, 2.07 mmol) and pyridine (0.21 ml, 2.6 mmol). The resultant heterogeneous mixture was rapidly stirred for 1 hour, diluted with ethyl acetate and washed with saturated sodium chloride solution. The solution was dried over magnesium sulphate and concentrated to afford the title compound which was used without purification (982 mg, 97%); $v_{max}$ (CH$_2$Cl$_2$) 1760, 1737 cm$^{-1}$; $^1$H NMR (CDCl$_3$) 0.83 (3H, d, J 7.1 Hz), 0.88 (3H, d, J 7.1 Hz), 1.13 (3H, s), 1.16 (1H, m), 1.37–1.54 (3H, m), 1.48 (3H, s), 1.61–1.92 (4H, m), 2.13–2.37 (4H, m), 2.46 (1H, quintet. J 7.0 Hz), 4.93 (1H, t, J 6.8 Hz), 5.31 (1H, d, J 17.2 Hz), 5.37 (1H, d, J 10.7 Hz), 5.61 (1H, d, J 8.4 Hz), 5.99 (1H, s), 6.25 (1H, dd, J 17.5, 11.2 Hz); MS (EI) m/z 498–492 (M$^+$).
Step 3. Mutilin 11-dichloroacetate-14-(N-p-methoxysulphonylcarbamate)

The product of Step 2 (250 mg, 0.51 mmol) was disolved in dichloromethane (5 ml) under argon and treated with p-methoxysulphonamide (187 mg, 1.0 mmol) in DMF (0.5 ml), N,N-diisopropylethylamine (0.2 ml, 1.15 mmol) and N,N-4-dimethylaminopyridine (5 mg). After stirring at room temperature for 3 hours the solution was diluted with dichloromethane and washed with 1M hydrochloric acid. The solution was dried over magnesium sulphate and concentrated to afford the crude product (746 mg). Purification by silica gel chromatography (50% ethyl acetate/hexane)

afforded the title compound (294 mg, 90%); $\nu_{max}$ (CH$_2$Cl$_2$) 3368, 1736 cm$^{-1}$; $^1$H NMR (CDCl$_3$) 0.53 (3H, d, J 6.7 Hz), 0.83 (3H, d, J 7.0 Hz), 0.99 (3H, s), 1.06–1.89 (8H, m), 1.35 (3H, s), 1.94–2.29 (4H, m), 2.45 (1H, m), 3.88 (3H, s), 4.86 (1H, d, J 6.8 Hz), 5.09 (1H, d, J 17.6 Hz), 5.19 (1H, d, J 11.2 Hz), 5.52 (1H, d, J 8.0 Hz), 5.96 (1H, s), 6.16 (1H, dd, J 17.6, 11.2 Hz), 6.99 (2H, d, J 8.9 Hz), 7.94 (2H, d, J 8.9 Hz); MS (CI) m/z 665/663/661(MNH$_4^+$).

Step 4. Mutilin 14-(N-p-methoxysulphonylcarbamate)

The product of Step 3 (262 mg, 0.41 mmol) was disolved in THF (3 ml) and methanol (1 ml) and treated with 1M sodium hydroxide (1 ml, 1.0 mmol). After 1 hour the solution was diluted with ethyl acetate and washed with 1M hydrochloric acid and water. The solution was dried over magnesium sulphate and concentrated to afford the crude product (260 mg). Purification by silica gel chromatography (50% ethyl acetate/hexane) afforded the title compound (206 mg, 95%); $\nu_{max}$ (CH$_2$Cl$_2$) 3367, 1736 cm$^{-1}$; $^1$H NMR (CDCl$_3$) 0.53 (3H, d, J 6.7 Hz), 0.83 (3H, d, J 7.0 Hz), 1.08 (1H, m), 1.10 (3H, s), 1.25–1.75 (8H, m), 1.35 (3H, s), 1.97 (2H, m), 2.20 (3H, m), 3.29 (1H, dd, J 10.2,6.6 Hz), 3.88 (3H, s), 5.09 (1H, dd, J 17.4, 1.3 Hz), 5.24 (1H, d, J 11.0, 1.2 Hz), 5.61 (1H, d, J 8.4 Hz), 6.28 (1H, dd, J 17.4, 11.0 Hz), 6.98 (2H, d, J 9.0 Hz), 7.43 (1H, s), 7.93 (2H, d, J 9.0 Hz); MS (CI) m/z 551(MNH$_4^+$); (Found: C, 63.13; H, 7.54; N, 2.61. C$_{28}$H$_{39}$NO$_7$S requires C, 63.02; H, 7.37; N, 2.62).

EXAMPLE 58

Mutilin 14-[N-(4-hydroxybenzoyl)carbamate]

Step 1. 11-O-Dichloroacetylmutilin

Mutilin (4.0 g, 12.5 mmol) was dissolved in dry tetrahydrofuran (20 ml) and treated with pyridine (1.31 ml, 16.2 mmol), dichloroacetic anhydride (3.29 g, 13.7 mmol), and N,N-dimethylaminopyridine (20 mg). The reaction was stirred under argon for 2 h at room temperature. Reaction mixture partitioned between ethyl acetate and water. The organic phase was washed with 1.0M HCl, water and saturated sodium chloride solution before drying (MgSO$_4$). Purification was accomplished by chromatography on silica gel. The product was isolated as a crystalline solid (3.57 g, 66%); $\nu_{max}$ (CH$_2$Cl$_2$) 3635, 2936, 1756, 1735 and 1463; $^1$H NMR (CDCl$_3$) 0.86 (3H, d, J 7.1 Hz), 0.97 (3H, d, J 7.0 Hz), 1.06 (3H, s), 1.15 (1H, m) 1.39 (3H, s), 1.32–1.50 (4H, m), 1.63–2.02 (5H, m), 2.10(1H, s), 2.22 (2H, m), 2.37 (1H, quint., J 6.5 Hz), 4.31 (1H, t, J 6.4 Hz), 4.91 (1H, d, J 6.9 Hz), 5.32 (1H, dd, J 11.2, 0.7 Hz), 5.48 (1H, dd, J 17.7, 0.7 Hz), 6.00 (1H, s), 6.12 (1H, dd, J 18.0, 11.2 Hz); MS (NH3DCI) m/z 448,450,452 (MNH$_4^+$).

Step 2. 11-O-Dichloroacetylmutilin-14-[N-(4-acetoxybenzoyl)carbamate]

A solution of 4-acetoxybenzoylisocyanate (6 mmol) in dichloroethane (20 ml) (prepared as described in Example 33, Step 1) was treated with 11-O-dichloroacetylmutilin (650 mg, 1.5 mmol) and the title compound isolated as described in Example 31, Step 2 (716 mg, 72%); $\nu_{max}$ (CH$_2$Cl$_2$) 3420, 2943, 1779, 1734, 1604 and 1479; $^1$H NMR (CDCl$_3$) 0.80 (3H, d, J 6.5 Hz), 0.87 (3H, d, J 7.0 Hz), 1.11–1.23 (4H, m), 1.38–1.93 (11H, m), 2.14–2.32 (5H, m), 2.56–2.52 (1H, m), 4.96 (1H, d, J 6.7 Hz), 5.33 (1H, d, J 17.6 Hz), 5.36 (1H, dd, J 11.1 Hz), 5.75 (1H, d, J 8.1 Hz), 5.99 (1H, s), 6.44 (1H, dd, J 17.3, 11.3 Hz), 7.22 (2H, d, J 8.7 Hz), ), 7.84 (2H, d, J 8.7 Hz), 7.89 (1H, bs); MS (ESI, +ve ion) m/z 653 (NNH$_4^+$); (Found: C, 60.34; H, 6.42; N, 2.13. C$_{32}$H$_{39}$Cl$_2$NO$_8$ requires C, 60.38; H, 6.18; N, 2.20)

Step 3. Mutilin 14-[N-(4-hydroxybenzoyl)carbamate]

11-O-Dichloroacetylmutilin-14-[N-(4-acetoxybenzoyl) carbamate] (671 mg, 1.05 mmol) was dissolved in tetrahydrofuran (5 ml) and methanol (1.0 ml) before treating with 1.0M sodium hydroxide (3.2 ml, 3.2 mmol). The reaction was stirred at room temperature for 1 h. The reaction was partitioned between ethyl acetate and 1.0M HCl and the organic phase washed with water, sodium hydrogen carbonate solution, and finally brine. After drying (MgSO$_4$) the crude product was purified by chromatography on silica gel, loading and eluting with 50% ethyl acetate in hexane followed by ethyl acetate. The title compound was isolated as a solid (409 mg, 80%).

EXAMPLE 59

Mutilin 14-[N-(4-hydroxymethylbenzoyl)]-carbamate

Step 1. (3R)-3-Deoxo-11-deoxy-3-methoxy-11-oxo-4-epi-mutilin 14-[N-(4-hydroxymethylbenzoyl)carbamate]

(3R)-3-Deoxo-11-deoxy-3-methoxy-11-oxo-4-epi-mutilin 14-[N-(4-formylbenzoyl)carbamate] (250 mg, 0.49 mmol) (prepared as described in Example 42, Step 1) was dissolved in dry tetrahydrofuran (2.5 ml) and treated with diisobutyl aluminium hydride (0.54 ml of 1.0M solution in toluene, 0,8 mmol). After stirring at room temperature for 15 minutes the reaction was partitioned between ethyl acetate and water. After washing the organic phase with water, saturated sodium hydroren carbonate solution and brine the solution was dried (MgSO$_4$). Purifcation was accomplished by chromatography on silica gel elutina with mixtures of ethyl acetate in hexane. The title compound was isolated as a foam (184 mg, 73%); $\nu_{max}$ (CH$_2$Cl$_2$) 3605, 3426, 2930, 1776, 1731, 1698, 1613, and 1479 cm$^{-1}$; $^1$H NMR (CDCl$_3$) 1.00 (3H, d, J 6.4 Hz), 1.31 (3H, d, J 6.8 Hz), 1.07–1.60 (12H, m), 1.69–1.73 (2H, m), 1.91–2.04 (2H, m), 2.15–2.24 (1H, m), 2.53 (1H, dd, J 15.2, 10.1 Hz), 2.90 (1H, q, J 6.3 Hz), 3.22 (3H, s), 3.42–3.50 (1H, m), 4,79 and 4.81 (2H, s+s), 5.00 (1H, d, J 17.4 Hz), 5.30 (1H, d, J 10.7 Hz), 5.85 (1H, d, J 9.9 Hz), 6.72 (1H, dd, J 17.4, 10.7 Hz), 7.49 (2H, d, J 8.2 Hz), 7.82 (1H, d, J 8.3 Hz), 8.00 (1H, bs); MS (NH$_3$DCI) m/z 512 (MH$^+$), m/z 529 (MNH$_4^+$)

Step 2. Mutilin 14-[N-(4-hydroxymethylbenzoyl) carbamate]

The product of Step 1 (164 mg, 0.32 mmol) in dioxane (2.0 ml) was treated with a saturated solution of zinc chloride in conc. HCl (0.5 ml), as for Example 1 Step 2, to afford the title compound (52 mg, 33%); $\nu_{max}$ (CH$_2$Cl$_2$) 3604, 3431, 1778, 1733, 1714, and 1613 cm$^{-1}$; $^1$H NMR (CDCl$_3$) 0.81 (3H, d, J 6.6 Hz), 0.88 (3H, d, J 7.0 Hz), 1.19–1.81 (16H, m), 1.86 (1H, bs), 2.10–2.37 (4H, m), 3.37 (1H, dd, J 10.5, 6.5 Hz), 4.79 (2H, bs), 5.23 (1H, dd, J 17.4, 1.4 Hz), 5.38 (1H, dd, J 11.0, 1.4 Hz), 5.83 (1H, d, J 8.5 Hz), 6.55 (1H, dd, J 17.3, 11.0 Hz), 7.50 (1H, d, J 8.2 Hz), 7.80 (1H, d, J 8.3 Hz), 7.96 (1H, bs); MS (NH$_3$DCI) m/z 498 (MH$^+$), m/z 515 (MNH$_4^+$).

EXAMPLE 60

Mutilin 14-[N-(4-methanesulfonamidobenzoyl)]-carbamate

Step 1. (3R)-3-Deoxo-11-deoxy-3-methoxy-11-oxo-4-epi-mutilin 14-[N-(4-aminobenzoyl)carbamate]

(3R)-3-Deoxo-11-deoxy-3-methoxy-11-oxo-4-epi-mutilin 14-[N-(4-nitrobenzoyl)carbamate] (460 mg, 0.87 mmol) was converted to the title compound by the method described in Example 34 (268 mg, 64%); $\nu_{max}$ (CH$_2$Cl$_2$) 3405, 2930, 1771, 1698, 1623, and 1477 cm$^{-1}$; $^1$H NMR (CDCl$_3$) 0.89 (3H, d, J 6.9 Hz), 1.00 (3H, d, J 6.4 Hz), 1.07–1.61 (12H, m), 1.69–1.76 (2H, m), 1.94–2.04 (2H, m), 2.15–2.24 (1H, m), 2.52 (1H, dd, J 15.2, 10.1 Hz), 2.91 (1H, q, J 6.4 Hz), 3.22 (3H, s), 3.42–3.50 (1H, m), 4.15 (2H, bs), 5.00 (1H, d, J 17.5 Hz), 5.29 (1H, d, J 10.7 Hz), 5.83 (1H, d, J 9.9 Hz), 6.64–6.80 (3H, m), 7.66 (2H, d, J 8.6 Hz), 7.86 (1H, bs); MS (NH$_3$DCI) m/z 497 (MH$^+$).

Step 2. (3R)-3-Deoxo-11-deoxy-3-methoxy-11-oxo-4-epi-mutilin 14-[N-(4-methanesulfonamidobenzoyl)carbamate]

(3R)-3-Deoxo-11-deoxy-3-methoxy-11-oxo-4-epi-mutilin 14-[N-(4-aminobenzoyl)carbamate] (248 mg, 0.50 mmol) was dissolved in dry dichloromethane (5 ml) whilst under argon at room temperature. The reaction was treated with pyridine (0.132 ml, 1.65 mmol) and methanesulfonyl chloride (0.126 ml, 1.65 mmol) which were added in three separate portions over a period of 3 h. The reaction was diluted with dichloromethane and washed with saturated sodium hydrogen carbonate, 1.0M HCl, water, and saturated sodium chloride solution before drying ($MgSO_4$). The crude material was triturated with hexane to give the title compound as a solid (236 mg, 82%); $v_{max}$ (KBr disc) 1762, 1695, 1603 $cm^{-1}$; $^1$H NMR ($d_6$-acetone) 0.94 (3H, d, J 6.9 Hz), 1.01 (3H, d, J 6.4 Hz), 1.0–1.97 (12H, m), 2.04–2.10 (m, obscured by solvent), 2.53 (1H, dd, J 15.6, 10.5 Hz), 2.80–3.00 (m, obscured by solvent), 3.11 (3H, s), 3.21 (3H, s), 3.46–3.52 (1H, m), 4.99 (1H, d, J 17.5 Hz), 5.30 (1H, d, J 10.7 Hz), 5.80 (1H, d, J 9.9 Hz), 6.82 (1H, dd, J 17.5, 10.7 Hz), 7.43 (2H, d, J 8.8 Hz), 7.94 (2H, d, J 8.7 Hz), 9.11 (1H, bs), 9.91 (1H, s).

Step 3: Mutilin 14-[N-(4-methanesulfonamidobenzoyl)]-carbamate (3R)-3-Deoxo-11-deoxy-3-methoxy-11-oxo-4-epi-mutilin 14-[N-(4-methanesulfonamidobenzoyl)carbamate] (208 mg, 0.36 mmol) was dissolved in dioxan (2.0 ml) and treated with a saturated solution of zinc chloride in conc. HCl (0.5 ml), as for Example 1 Step 2, to afford the title compound (72 mg, 36%); $v_{max}$ (KBr disc) 1733 and 1608 $cm^{-1}$; $^1$H NMR ($d_6$-acetone) 0.67 (3H, d, J 6.3 Hz), 0.82 (3H, d, J 7.1 Hz), 0.91–1.71 (15H, m), 1.96–2.05(1H, m), 2.19 (1H, quint., J 6.8 Hz), 2.26 (1H, bs), 2.96 (3H, s), 3.30 (1H, d, J 7.3 Hz, ex. in $D_2O$), 3.50 (1H, m, collapse to d in $D_2O$, J 5.9 Hz), 5.05 (1H, dd, J 11.0, 1.7 Hz), 5.11 (1H, dd, J 17.7, 1.7 Hz), 5.64 (1H, d, J 8.3 Hz), 6.32 (1H, dd, J 17.7, 11.1 Hz), 7.26 (1H, d, J 8.8 Hz), 7.80 (1H, d, J 8.7 Hz), 9.72 (1H, bs, ex in $D_2O$); MS ($NH_3DCI$) m/z 561 ($MH^+$), m/z 578 ($MNH_4^+$).

EXAMPLE 61

Mutilin 14-[N-(4-Aminosulphonylphenyl)]-carbamate

Step 1. (3R)-3-Deoxo-11-deoxy-3-methoxy-11-oxo-4-epi-mutilin 14-[N-(4-aminosulphonylphenyl)]-carbamate (3R)-3-Deoxo-11-deoxy-3-methoxy-11-oxo-4-epi-mutilin (336 mrg, 1 mmol) in dry $CH_2Cl_2$ (7.5 ml) was treated with 4-chlorosulphonylphenyl isocyanate (283 mg, 1.3 mmol) and N,N-di-iso-propylethylamine (1 drop) and the solution was kept at room temperature, with exclusion of moisture, for 2 days, and then in a refrigerator for 70 h. The solvent was then removed using a rotary eveporator and replaced by tetrahydrofuran (7.5 ml). 0.880 S.G. Aqueous ammonia (0.5 ml) was then added and the mixture was stirred for 1.5 h. The solution was diluted with ethyl acetate (50 ml) and was washed with brine. The aqueous layer was re-extracted with ethyl acetate (50 ml) and the combined ethyl acetate solutions were washed with 1M HCl (5 ml)/brine (15 ml). The solution was dried ($MgSO_4$) and the solvent was removed by evaporation under reduced pressure to yield a colourless foam. The foam was chromatographed on silica gel, using 4:6, followed by 1:1, followed by 7:3 ethyl acetate-hexane, to give (3R)-3-deoxo-11-deoxy-3-methoxy-11-oxo-4-epi-mutilin 14-[N-(4-aminosulphonylphenyl)]-carbamate as a colourless solid foam (460 mg, 86%); $v_{max}$ ($CH_2Cl_2$) 3420, 3335, 2980, 2930, 1731, 1698, 1592, 1218, and 1163 $cm^{-1}$; $^1$H NMR ($CDCl_3$) 0.87 (3H, d, J 6.9 Hz), 1.00 (3H, d, J 6.37 Hz), 1.01–1.8 (ca 14 H, m), 1.9–21. (2H, m), 2.1–2.3 (1H, m), 2.50 (1H, dd, J 10.0, 15.2 Hz), 2.94 (1Hq, J 6.4 Hz), 3.23 (3H, s), 3.4–3.6 (1H, m), 4.84 (2H, s), 5.03 (1H, d, J 17.5 Hz), 5.34 (1H, d, J 10.7 Hz), 5.81 (1H, d, J 9.8 Hz), 6.70 (1H, dd, J 10.6, 17.5 Hz), 6.88 (1H, s), 7.59 (2H, d, J 8.7 Hz), 7.88 (2H, d, J 8.8 Hz); MS (CI) m/z 550 ($MNH_4$)$^+$.

Step 2. Mutilin 14-[N-(4-Aminosulphonylphenyl)]-carbarmate (3R)-3-deoxo-11-deoxy-3-methoxy-11-oxo-4-epi-mutilin [N-(4-aminosulphonyl-phenyl)]-carbamate (410 mg, 0.77 mmol) in dioxane (7.5 ml) was treated with a saturated solution of zinc chloride in conc. HCl (1 ml) and the solution was stirred at room temperature for 5 hours. As the reaction had not proceded to completion more of a saturated solution of zinc chloride in conc. HCl (2 ml) was added and stirring was continued for 2 h. The mixture was diluted with ethyl acetate (50 ml) and the solution was washed with saturated NaCl solution (20 ml) and saturated $NaHCO_3$ solution (20 ml). The solution was dried ($MgSO_4$) and the solvent was removed by evaporation under reduced pressure to yield a colourless solid. The solid was chromatographed on silica gel, loading in $CH_2Cl_2$/toluene containing a trace of ethyl acetate and using 1:1 ethyl acetate-hexane, followed by ethyl acetate-toluene mixtures; 3:7; followed by 6:4; followed by 1:1; to give mutilin [N-(4-aminosulphonylphenyl)]-carbamate as a colourless solid (281 mg, 70%); $v_{max}$ (KBr) 1725, 1595, 1530, 1337, 1317, 1228 and 1160 $cm^{-1}$; $^1$H NMR [$(CD_3)_2SO$] 0.90 (3H, d, J 6.8 Hz), 1.00 (3H, d, J 6.3 Hz), 1.0–1.8 (14 H, m, including singlets at 1.08 and 1.43), 2.04–2.27 (4H, m), 2.42 (1h, br s), 3.45 (1H, br t, J ca. 5.8 Hz: d, J 5.5 Hz after $D_2O$ exch.), 4.52 (1H, d, J 6.1 Hz, exch $D_2O$), 5.05–5.15 (2H, m), 5.38 (1H, br d, J 7.8 Hz), 6.27 (1H, dd, J 11.1, 17.7 Hz), 7.21 (2H, s, exch $D_2O$), 7.59 (2H, d, J 8.8 Hz), 7.71 (2H, d, J 8.8 Hz), 9.82 (1H, s); MS(CI) m/z 536 ($M+NH_4^+$).

EXAMPLE 62

Mutilin 14-{N-[4-([2R]-2,3-dihydroxypropyloxy)-benzoyl]}-carbamate

Step 1. (3R)-3-Deoxo-11-deoxy-3-methoxy-11-oxo-4-epi-mutilin 14-[N-(4-hydroxybenzoyl)]-carbamate (3R)-3-Deoxo-11-deoxy-3-methoxy-11-oxo-4-epi-mutilin 14-[N-4-acetoxybenzoyl)]-carbamate (Example 37, Step 2) (809 mg, 1.5 mmol) in 1,4-dioxan (10 ml) was treated with aqueous 1M NaOH (4.5 ml) and the mixture was stirred for 2.5 h. Ethyl acetate (100 ml) and aqueous 1M HCl (10 ml), followed by water (50 ml) were added. After separation of the layers the aqueous layer was washed with ethyl acetate. The combined ethyl acetate layers were dried ($MgSO_4$) and evaporated. The residue was chromatographed on silica gel, loading with $CH_2Cl_2$, and eluting with ethyl acetate/hexane mixtures: 1:1, foowed by 6:4, followed by 7:3, followed by 8:2, to eive the title compound (677 mg, 90%) as a colourless solid; $v_{max}$ ($CH_2Cl_2$) 3565, 3417, 2930, 1774, 1729, 1698, 1608, 1478, 1187, and 1167 $cm^{-1}$; $^1$H NMR ($CDCl_3$) 0.90 (3H, d, J 6.8 Hz), 1.00 (3H, d, J 6.3 Hz), 1.0–1.8 (14 H, m, including s at 1.20 and s at 1.31), 1.99 (2H, m), 2.21 (1H, dt, J 10.0, 2.7 Hz), 2.52 (1h, dd, J 10.1, 15.2 Hz), 2.91 (1H, q, J 6.4 Hz), 3.23 (3H, s), 3.46 (1H, m), 5.01 (1H, d, J 17.5 Hz), 5.28 (1H, d, J 10.8 Hz), 5.84 (1H, d, J 9.9 Hz), 6.71 (1H, dd, J 10.7, 17.5 Hz), 6.94 (2H, d, J 8.7 Hz), 7.75 (2H, d, J 8.7 Hz), 7.96 (1H, s); MS(CI) m/z 498 ($MH^+$), 515 ($MNH_4^+$).

Step 2. (3R)-3-Deoxo-11-deoxy-3-methoxy-11-oxo-4-epi-mutilin 14-{N-[4-([2R]-2,3-dihydroxypropyloxy)-benzoyl]}carbamate (3R)-3-Deoxo-11-deoxy-3-methoxy-11-oxo-4-epi-mutilin 14-[N-(4-hydroxybenzoyl)]-carbamate (497 mg, 1 mmol) in tert-butanol (5 ml) under an atmosphere of argon was warmed to effect dissolution, and then treated with sodium hydride (40 mg of a 60% dispersion in oil, 1 mmol). When effervescence had ceased (ca. 30 min) (R)-(+)- glycidol (0.06 ml, 74 mg, 1 mmol) in dichloromethane (2.5 ml) was added, followed by titanium(IV) isopropoxide (0.36 ml, 341 mg, 1.2 mmol). The mixture was strirred under an argon atmosphere for 18 h , and then heated under reflux (oil bath 50°) for 6.5 h. Ethyl acetate (50 ml)/1M HCl (25 ml) were added the layers separated. The aqueous layers was re-extracted with ethyl acetate and combined ethyl acetate layers were washed with brine and dried ($MgSO_4$). After removal of solvent the crude product was chromatographed on silica gel, loading in $CH_2Cl_2$, and eluting with ethylacetate/hexane mixtures: 1:1, follwed by 6:4, followed by 7:3, followed by 8:4. Fractions containing the product were combined and evaporated to give the title compound as a solid foam (297 mg, 52%); $v_{max}$ ($CH_2Cl_2$) 3585, 2931, 1774, 1729, 1698, 1605, 1478, and 1171 $cm^{-1}$; $^1$H NHMR ($CDCl_3$) 0.90 (3H, d, J 6.8 Hz), 1.00 (3H,d, J 6.3 Hz), 1.0–1.6 (12H, m, including s at 1.20 and s at 1.30) 1.70 (1H, d, J 9.9 Hz), 1.70 (1H, d, J 5.7 Hz), 1.9–2.3 (4H, m; 1H exch. $D_2O$), 2.53 (1H, dd, J 10.1, 15.2 Hz), 2.60 (1H, br s, exch. $D_2O$), 2.90 (1H, q, J 6.4 Hz), 3.22 (3H, s), 3.41–3.50 (1H, m), 3,7–4.0 (2H, m, signal sharpens on $D_2O$ exch.), 4.07–4.16 (3H, m), 5.01 (1H, d, J 17.4 Hz), 5.29 (1H, d, J 17.4 Hz), 5.29 (1H, d, J 10.8 Hz), 5.84 (1H, d J 9.9 Hz), 6.71 (1H, dd, J 10.6, 17.4 Hz), 6.97 (2H, d, J 8.8 Hz), 7.79 (2H, d, J 8.8 Hz), 8.00 (1H, s); MS (Electrospray) m/z 572 ($MH^+$), 1143 $(2M+H)^+$.

Step 3. Mutilin 14-{N-[4-([2R]-2,3-dihydroxypropyloxy]-benzoyl]}-carbamate

The product of Step 2 (256 mg, 0.45 mmol) in dioxane (3 ml) was treated with a saturated solution of zinc chloride in conc. HCl (1.0 ml), as for Example 1 Step 2, to afford the title compound (105 mg, 42%); $v_{max}$ (KBr) 1761, 1732, 1605, 1497, 1255, 1204, and 1174 $cm^{-1}$; $^1$H NMR ($CDCl_3$+$CD_3OH$) 0.77 (3H, d, J 6.4 Hz) 0.85 (3H, d, J 6.9 Hz), 1.0–2.4 (19 H, m, including s at 1.15 and s at 1.48), 3.33 (1h, d, J 6.5 Hz), 3.60–3.83 92h, m), 3.9–4.2 (3H, m), 5.19 (1H, dd, J 1.4, 17.4 Hz), 5.33 (1H, dd, J 1.3, 11.0 Hz), 5.78 (1H, d, J 8.3 Hz), 6.51 (1h, dd, J 11.0, 17.3 Hz), 6.92 (2H, d, J 8.8 Hz), 7.74 (2H, d, J 8.8 Hz); MS (Electrospray) m/z 558 ($MH^+$), 1115 $(2M+H)^+$.

EXAMPLE 63

Mutilin 14-(N-Chloroacetyl)-carbamate

Step 1. (3R)-3-Deoxo-11-deoxy-3-methoxy-11-oxo-4-epi-mutilin 14-(N-chloracetyl)-carbamate (3R)-3-Deoxo-11-deoxy-3-methoxy-11-oxo-4-epi-mutilin (335 mg, 1.0 mmol) and silver cyanate (225 mg, 1.5 mmol) in dichloromethane (5 ml) under an argon atmosphere in a flask wrapped in aluminium foil was treated with chloroacetyl chloride (0.12 ml, 169 mg, 1.5 mmol), and the mixture was stirred for 1 h. The mixture was filtered through kieselguhr and evaporated. Toluene was then added and removed. The residue was chromatographed on silica gel, loading in dichloromethane and eluting with ethyl acetate/hexane mixtures: 2:8, followed by 3:7 to give the title compound (456 mg, quant.); $v_{max}$ ($CH_2Cl_2$) 3381, 2981, 1787, 1754, 1728, 1698, 1489, 1459, and 1198 $cm^{-1}$; $^1$H NMR ($CDCl_3$) 0.83 (3H, d, J 6.8 Hz), 1.00 (3H, d, J 6.4 Hz), 1.01–1.40 (10H, m, including s at 1.20 and s at 1.23), 1.40–1.56 (2H, m), 1.62 (1H, d, J 15.3 Hz), 1.73 (1H, d, J 11.3 Hz), 1.8–2.1 (2H, m), 2.20 (1H, dt, J 2.8, 12.7 Hz), 2.51 (1H, dd, J 10.1, 15.3 Hz), 2.86 (1H, q, J 6.3 Hz), 3.22 (3H, s), 3.35–3.50 (1H, m), 4.51 (2H, s), 5.03 (1H, d, J 17.5 Hz), 5.32 (1H, d, J 10.7 Hz), 5.75 (1H, d, J 10.0 Hz) 6.60 (1H, dd, J 10.7, 17.5 Hz), 7.88 (1H, s, exch $D_2O$); MS(CI) m/z 471 ($MNH_4^+$).

Step 2. Mutilin 14-(N-Chloroacetyl)-carbamate

The product of Step 2 (400 mg, 0.88 mmol) in dioxane (4.5 ml) was treated with a saturated solution of zinc chloride in conc. HCl (1.5 ml), as for Example 1 Step 2, to afford the title compound (185 mg, 52%); $v_{max}$ ($CH_2Cl_2$) 3564, 3388, 2960, 2895, 1783, 1755, 1732, 1605, and 1478 $cm^{-1}$; $^1$H NMR ($CDCl_3$) 0.74 (3H, d, J 6.8 Hz), 0.89 (3H, d, J 7.1 Hz), 1.0–1.3 (4H, m, including s at 1.19), 1.3–1.9 (12H, m, including s at 1.44), 2.0–2.4 (4H, m), 3.37 (1 H, dd, J 6.6, 10.7 Hz; d, J 6.5 Hz after $D_2O$ exch.), 4.47 (2H, s), 5.23 (1H, dd, J 1.4, 17.4 Hz), 5.38 (1H, dd, J 1.3, 10.9 Hz), 5.72 (1H, d, J 8.5 Hz), 6.47 (1H, dd, J 11.0, 17.4 Hz), 7.81 (1H, exch $D_2O$); MS(CI) m/z 457 ($MNH_4^+$).

EXAMPLE 64

19,20-Dihydromutilin 14-[N-(4-hydroxybenzoyl)]-carbamate

Mutilin 14-[N-(4-hydroxybenzoyl)]-carbamate (130 mg) in ethyl acetate (10 ml) containing 10% Pd-C catalyst (44 mg) and the mixture was hydrogenated at atmospheric pressure for 30 min. The mixture was filtered through kieselguhr and the ethyl acetate was removed. chloroform/methanol was then added and removed and the chloroform was added and removed to leave the title compound (131 mg) as a solid foam. $v_{max}$ (KBr) 1781, 1725, 1697, 1609, 1459, 1299, and 1201 $cm^{-1}$; $^1$H NMR ($CDCl_3$+$CD_3OD$+$D_2O$) 0.7–1.27 (15H, m), 1.27–1.90 (10 H, m, including s at 1.46), 1.9–2.5 (5H, m), 3.39 (1h, d, J 5.4 Hz), 5.65 (1H, d, J 7.9 Hz), 6.84 (2H, d, J 8.7 Hz), 7.69 2H, d, J 8.7 Hz); MS(CI) m/z 486 ($MH^+$) 503 ($MNH_4^+$); MS(Electrospray) 503 ($MNH_4^+$) 544 ($MNH_4^+$+MeCN).

EXAMPLE 65

Mutilin 14-[N-(3-Amino-1,2,4-triazolylthioacetyl)]-carbamate

Mutilin 14-(N-Chloroacetyl)-carbamate (1100 mg, 0.23 mmol) in N,N-dimethylformamide (2.5 ml) was treated with 3-amino-5-mercapto-1,2,4-triazole (29 mg, 0.25 mmol), followed by N,N-diisopropylethylamine (0.043 ml, 32 mg, 0.25 mmol). The mixture was stirred for 4.5 h and then ethyl acetate (25 ml) and water (15 ml) were added and the mixture was separated. The aqueous phase was re-extracted with ethyl acetate, and combined ethyl acetate layers were washed with brine, dried ($MgSO_4$) and evaporated. the residual oil was taken up in dichloromethane and loaded onto a silica gel column. Elution with ethyl acetate/hexane (1:1), followed by ethyl acetate, followed by ethyl acetate/ethanol gave the title compound, contaminated by a little DMF. The material was taken up in ethyl acetate and washed with water, followed by brine, dried ($MgSO_4$) and evaporated. Triturarion of the residue with diethyl ether gave the title compound (102 mg, 85%); $^1$H NMR ($CDCl_3$+$CD_3OD$+$D_2O$) inter alia 0.63 (3H, d, J 6.4 Hz), 0.81 (3H, d, J 6.9 Hz), 0.9–1.8 (14H, m, including s at 1.04 and s at 1.32), 1.9–2.3 (5H, m). 3.65 and 3.72 (2H, ABq, J 15.2 Hz), 5.08 (1H, dd, J 1.4, 17.3 Hz), 5.22 (1H,dd, J 1.3, 11.1 Hz), 5.55 (1H, d, J 8.4 Hz), 6.35 (1H, dd, J 11.0, 17.4 Hz); MS(CI) 520 ($MH^+$).

EXAMPLE 66

Mutilin 14-[N-(2-N,N-Diethylaminoethylthio-acetyl)]-carbamate

Mutilin 14-(N-Chloroacetyl)-carbamate (100 mg, 0.23 mmol) in tetrahydrofuran (2 ml) was treated with N,N-diethylaminoethane thiol hydrochloride (39 mg, 0.23 mmol) followed by 1M aqueous NaOH (0.5 ml). After stirring for 4.5 h ethyl acetate (25 ml) and water (20 ml) were added and the layers were separated. The aqueous layer was re-extracted with ethyl acetate and the combined extracts were washed ($MgSO_4$) and evaporated. the residue was chromatographed on silica gel, eluting with $CH_2Cl_2$/MeOH/

0.880 NH$_4$OH mixtures: 95:4.5:0.5, followed by 90:9:1 to give the title compound (20 mg); $^1$H NMR (CDCl$_3$+ CD$_3$OD+D$_2$O) 0.73 (3H, d, J 6.4 Hz), 0.85 (3H, d, J 6.9 Hz), 1.00 (6H, t, J 7.1 Hz), 1.1–1.25 (4H, s superimposed on m), 1.25–1.9 (11H, m, including s at 1.42), 2.0–2.4 (6H, m), 2.53 (4H, q, J 7.1 Hz), 2.65 (4H, br. s), 3.33 (1H, d, J 6.3 Hz), 5.19 (1H, d, J 17.2 Hz), 5.33 (1H, d J 11.0 Hz), 5.70 (1H, d, J 8.3 Hz), 6.46 (1H, dd, J 11.0, 17.4 Hz).

EXAMPLE 67

Mutilin 14-[N-(4-nitrobenzenesulphonyl)]-carbamate

Step 1. (3R)-3-Deoxo-11-deoxy-3-methoxy-11-oxo-4-epi-mutilin 14-[N-(4-nitrobenzenesulphonyl)]-carbamate (3R)-3-Deoxo-11-deoxy-3-methoxy-11-oxo-4-epi-mutilin 14-chloroformate (500 mg) in dry dichloromethane (10 ml) was treated with 4-nitrobenzenesulphonamide (508 mg), diisopropylethylamine (0.5 ml), and 4-dimethylaminopyridine (5 mg), and the solution was stirred for 2 hours at room temperature. The solution was diluted with ethyl acetate (100 ml) and washed with dilute HCl (100 ml), water (100 ml), and saturated brine (100 ml). The solution was dried (sodium sulphate) and the solvent was removed by evaporation under reduced pressure to yield the crude product as a colourless gum.

Step 2. Mutilin 14-[N-(4-nitrobenzenesulphonyl)]-carbamate

The crude (3R)-3-Deoxo-11-deoxy-3-methoxy-11-oxo-4-epi-mutilin 14-[N-(4-nitrobenzenesulphonyl)]-carbamate from Step 1. was dissolved in 1,4-dioxane (12 ml) and treated with a saturated solution of zinc chloride in conc. HCl (4 ml). The solution was kept at room temperature for 4 hours, diluted with ethyl acetate (150 ml) and washed three times with water (100 ml portions). The solution was dried (sodium sulphate) and the solvent was removed by evaporation under reduced pressure to give a colourless gum. Chromatoaraphy on silica gel using ethyl acetate-hexane gave the title compound as a white solid (272 mg); $\nu_{max}$ (CH$_2$Cl$_2$) 3624, 3353, 1736, and 1608 cm$^{-1}$; $\delta_H$ (CDCl$_3$) 8.32 (2H, d, J 8.5 Hz), 8.18 (2H, d, J 8.5 Hz), 6.27 (1H, dd, J 17.5 and 11 Hz), 5.60 (1H, d, J 8.3 Hz), 5.22 (1H, d, J 11 Hz), 5.09 (1H, d, J 17.5 Hz), 3.30 (1H, dd, J 6.5 and 10 Hz), 2.22 (2H, m), 2.00 (2H, m), 1.8–1.0 (overlapping multiplets), 1.35 (3H, s), 1.09 (3H, s), 0.85 (3H, d, J 6.9 Hz), 0.51 (3H, d, J 6.7 Hz); MS (CI) m/z 566 (M.NH$_4^+$).

EXAMPLE 68

Mutilin 14-[N-(4-cyanobenzenesulphonyl)]-carbamate

Step 1. (3R)-3-Deoxo-11-deoxy-3-methoxy-11-oxo-4-epi-mutilin 14-[N-(4-cyanobenzenesulphonyl)]-carbamate (3R)-3-Deoxo-11-deoxy-3-methoxy-11-oxo-4-epi-mutilin 14-chloroformate (400 mg) in dry dichloromethane (20 ml) was treated with 4-cyanobenzenesulphonamide (273 mg), diisopropylethylamine (0.4 ml), and 4-dimethylaminopyridine (4 mg), and the solution was stirred for 16 hours at room temperature. The solution was diluted with ethyl acetate (100 ml) and washed with dilute HCl (100 ml), water (100 ml), and saturated brine (100 ml). The solution was dried (sodium sulphate) and the solvent was removed by evaporation under reduced pressure to yield the crude product as a colourless gum.

Step 2. Mutilin 14-[N-(4-cyanobenzenesuiphonyl)]-carbamate

The crude (3R)-3-Deoxo-11-deoxy-3-methoxy-11-oxo-4-epi-mutilin 14-[N-(4-cyanobenzenesulphonyl)]-carbamate from Step 1. was dissolved in 1,4-dioxane (12 ml) and treated with a saturated solution of zinc chloride in conc. HCl (4 ml). The solution was kept at room temperature for 4 hours, diluted with ethyl acetate (150 ml) and washed three times with water (100 ml portions). The solution was dried (sodium sulphate) and the solvent was removed by evaporation under reduced pressure to give a colourless gum. Chromatography on silica gel using ethyl acetate-hexane gave the title compound as a white foam (185 mg); $\nu_{max}$ (CH$_2$Cl$_2$) 3627, 3348, and 1735 cm$^{-1}$; $\delta_H$ (CDCl$_3$) 8.12 (2H, d, J 8.5 Hz), 7.82 (2H, d, J 8.5 Hz), 6.27 (1H, dd, J 17.5 and 11 Hz), 5.60 (1H, d, J 8.4 Hz), 5.21 (1H, d, J 10.5 Hz), 5.10 (1H, d, J 17.5 Hz), 3.30 (1H, dd, J 6.5 and 10 Hz), 2.21 (2H, m), 2.00 (2H, m), 1,8–1.0 (overlapping multiplets), 1.33 (3H, s), 1.10 (3H, s), 0.86 (3H, d, J 6.9 Hz), 0.51 (3H, d, J 6.9 Hz); MS (CI) m/z 546 (M.NH$_4^+$).

EXAMPLE 69

Mutilin 14-[N-(4-aminobenzenesulphonyl)]-carbamate

Mutilin 14-[N-(4-nitrobenzenesulphonyl)]-carbamate (265 mg) was dissolved in ethanol (30 ml) and ethyl acetate (5 ml) and heated to gentle reflux with tin(II) chloride (458 mg) for 5 hours under an atmosphere of argon. After cooling, the solvent was evaporated and the residue was chromatographed over silica gel, eluting with ethyl acetate-hexane mixtures. The title compound was obtained as a white solid (80 mg); $\nu_{max}$ (CH$_2$Cl$_2$) 3407, 1735, 1624 and 1596 cm$^{-1}$; $\delta_H$ (d$_6$-DMSO) 11.23 (1H, s, exchanges with D$_2$O), 7.44 (2H, d, J 8.8 Hz), 6.90 (1H, s, exchanges with D$_2$O), 6.59 (2H, d, J 8.8 Hz), 6.10 (1H, s. exchanges with D$_2$O), 6.10 (1H, dd, J 17.7 and 11.2 Hz), 5.32 (1H, d, J 7.6 Hz), 4.87 (1H, dd, J 11.2 and 1.4 Hz), 4.78 (1H, dd, J 17.8 and 1.4 Hz), 4.51 (1H, d, J 6.0 Hz, exchanges with D$_2$O), 3.30 (1H, d), 2.3–1.0 (overlapping multiplets), 1.30 (3H, s),0.98 (3H, s), 0.78 (3H, d, J 6.9 Hz), 0.48 (3H, d, J 6.3 Hz); MS (CI) m/z 536 (M.NH$_4^+$).

EXAMPLE 70

Mutilin 14-[N-(6-Ethoxybenzothiazolyl-2-sulphonyl)]-carbamate

Step 1. 11-O-Dichloroacetyl-Mutilin 14-[N-(6-Ethoxybenzotriazolyl-2-sulphonyl)]-carbamate A solution of mutilin 14-chloroformate-11-dichloroacetate (246 mg, 0.5 mmol) in dichloromethane (1 ml) was added to an ice-cooled solution of 6-ethoxybenzothiazole-2-sulphonamide (130 mg, 0.5 mmol) and N,N-di-isopropylethylamine (0.092 ml, 1.05 eq) in dichloromethane (2 ml)-DMF (0.5 ml). The cooling bath was removed and the solution stirred at room temperature for 3 days. The solution was diluted with ethyl acetate and washed with dil. HCl, with water and with brine. Drying (MgSO$_4$) and evaporation gave a foam (ca 350 mg) which was chromatographed on silica gel, using 5% methanol-chloroform to give the product as a white solid (142 mg); $\nu_{max}$ (CHCl$_3$) 3500, 3368, 1734, 1740 (shoulder), 1601 cm$^{-1}$.

Step 2. Mutilin 14-[N-(6-Ethoxybenzothiazolyl-2-sulphonyl)]-carbamate

The product of Step 1 (130 mg, 0.18 mmol) was dissolved in methanol (2 ml) and 1N NaOH (0.18 ml) was added. After stirring for 1 hr a further portion of 1N NaOH (0.18 ml) was added. After a total of 3 hr the mixture was acidified by adding 2N HCl (0.2 ml) and extracted with ethyl acetate. The extract was washed with brine, dried (MgSO$_4$) and evaporated to give a gum (140 mg). Chromatography on silica gel, using 10% methanol-chloroform gave the title compound as a white solid (96 mg, 87%); $\nu_{max}$ (CHCl$_3$) 3370, 1737, 1602 cm$^{-1}$; $^1$H NMR (CDCl$_3$) 0.59 (3H, d, J 6.7), 0.82 (3H, d, J 6.9), 0.94 (3H, s), 0.9–1.1 (ca 12H, m), 1.25–1.7 (ca 15H, m) 1.8–2.25 (ca 4H, m), 3.24 (1H, dd, J 9, 7 collapse to d, J 6 with $D_2O$), 4.13 (2H, q, J 7), 5.00 (1H, d, 17), 5.11 (1H, d, J 11), 5.62 (1H, d, J 8), 6.2 (1H, br, collapse to dd, J 17,11 with $D_2O$), 7.2 1H, dd J 2.2, 9), 7.35 (1H, d, J 2.3), 8.0 (1H, d, J 9); MS ($NH_3DCI$) m/z 605 ($MH^+$), 622 ($MNH_4^+$)

EXAMPLE 71

Mutilin 14-[N-(2,4-Dimethylthiazolyl-5-sulphonyl)]-carbamate

Step 1. 11-O-Dichloroacetyl-Mutilin-14-[N-(2,4-Dimethlithiazolyl-5-sulphonyl)]-carbamate A solution of mutilin 14-chloroformate-11-dichloroacetate (493 mg, 1 mmol) in dichloromethane (4 ml) was added to an ice-cooled solution of 2,4-dimethylthiazole-5-sulphonamide (192 mg, 1 mmol) and N,N-di-isopropylethylamine (0.175 ml, 1 mmol) in dichloromethane (5 ml)-DMF (0.5 ml). The cooling bath was removed and the solution stirred at room temperature overnight, refluxed for 5 hr and left again at room temperature overnight. Examination by tlc showed that reaction was almost complete. Evaporation of solvent followed by chromatography on silica gel, using 2% methanol-chloroform gave an impure product which was further chromatographed using 1:1 ethyl acetate-hexane. The product was obtained as a white solid (188 mg); $v_{max}$ ($CHCl_3$) 3378, 1735 $cm^{-1}$; $^1H$ NMR ($CDCl_3$) inter alia 2.70 (3H, s), 4.89 (1H, d, J 7), 5.17 (1H, d, J 17), 5.24 (1H, d, J 11), 5.58 (1H, d, J 8), 5.98 (1H, s), 6.21(1H, dd J 17, 11), 7.5–7.8 (1H, br); MS ($NH_3DCI$) m/z 649/651 ($MH^+$).

Step 2. Mutilin 14-[N-(2,4-Dimethylthiazolyl-5-sulphonyl)]-carbamnate

The product of Step 1 (175 mg, 0.27 mmol) was dissolved in methanol (5 ml)-tetahydrofuran (2 ml) and 1N NaOH (0.50 ml; 1.85 eq) was added. After 3 hr at room temperature the mixture was acidified by adding 2N HCl (0.25 ml) and extracted with ethyl acetate (50 ml). The extract was washed with water and with brine, dried ($MgSO_4$) and evaporated to give a gum (140 mg). Chromatography on silica gel, using 1:1 ethyl acetate-hexane gave the title compound as a white foam (85 mg); $v_{max}$ ($CHCl_3$) 3694, 3562, 1736 $cm^{-1}$; $^1H$ NMR ($CDCl_3$) 0.61 (3H, d, J 6.8), 0.86 (3H, d, J 7), 1.1–1.8 (ca 15H, m), 2.0–2.25 (ca 5H, m), 2.64 (3H, s), 2.70 (3H, s), 3.32 (1H, d, J 6.5), 5.14 (1H, dd, J 17, 1.3), 5.30 (1H, dd, J 10, 1.3), 5.66 (1H, d, J 8), 6.32 (1H, dd, J 17,11), 7.71(1H, br, exch $D_2O$); MS (EI) m/z 538 ($M^+$). Found: 538.2171, $C_{26}H_{38}N2O_6S_2$ requires 538.2172.

EXAMPLE 72

Mutilin 14-[N-(Thiophene-2-sulphonyl)]-carbamate

Step 1. 11-O-Dichloroacetyl-Mutilin 14-[N-(Thiophene-2-sulphonyl)]-carbamate

A solution of mutilin 14-chloroformate-11-dichloroacetate (370 mg, 0.75 mmol) in dichloromethane (1 ml) was added to an ice-cooled solution of thipohene-2-sulphonamide (122 mg, 0.75 mmol), N,N-di-isopropylethylamine (0.13 ml) and 4-dimethylaminopyridine (2 mg) in dichloromethane (3 ml)-DMF (0.4 ml). The cooling bath was removed and the solution stirred at room temperature overnight. The solution was diluted with ethyl actetate and washed with dil. HCl and with brine. The solution was dried ($MgSO_4$) and evaporated to give a gum which was chromatographed on silica gel, using 5% acetone-toluene to give the product as a white foam (280 mg); $v_{max}$ ($CHCl_3$) 3381, 1736 $cm^{-1}$; $^1H$ NMR ($CDCl_3$) inter alia 4.88 (1H, d, J 6.9), 5.15 (1H, d, J 17), 5.24 (1H, d, J 11), 5.58 (1H, d, J 8), 5.97 (1H, s), 6.21 (1H, dd, J 17, 11), 7.12 (1H, dd, J 5, 3.8), 7.70 (1H, dd, J 5, 1.4), 7.85 (1H, dd, J 3.8, 1.4); MS ($NH_3DCI$) m/z 637/639 ($MNH_4^+$).

Step 2. Mutilin 14-[N-(Thiophene-2-sulphonyl)]-carbamate

The product from Step 1 (248 mg, 0.4 mmol) was dissolved in methanol (4 ml) and 1N NaOH (0.8 ml, 2 eq) was added. After 4 hr the mixture was acidified by adding 2N HCl and extracted with ethyl acetate. The extract was washed with brine, dried ($MgSO_4$) and evaporated to give a gum which was purified by chromatography on silica giel, using 1:1 ethyl acetate-hexane. The title compound was obtained as a white solid (155 mg); $v_{max}$ ($CHCl_3$) 3380, 1736 $cm^{-1}$; $^1H$ NMR ($CDCl_3$) 0.57 (3H, d, J 6.8), 0.85 (3H, d, J 7), 1.11 (3H, s), 1.38 (3H, s), 1.2–1.75 (ca 11H, m), 1.92–2.05 (2H, m), 2.22 (2H, q, J 8), 3.31 (1H, dd, J 10, 6.8), 5.12 (1H, dd J 17, 1.4), 5.28 (1H, dd, J 11, 1.4), 5.67 (1H, d, J 8.,4), 7.11 (1H, dd, J 5, 4), 7.69 (1H, dd J 5 1.2), 7.84 (1H, dd, J 4, 1.2), 7.5 (1H, br); MS ($NH_3DCI$) m/z 527 ($MNH_4^+$).

EXAMPLE 73

Mutilin 14-[N-(5-Acetamido-1,3,4-thiadiazolyl-2-sulphonyl)]-carbamate

Step 1. 11-O-Dichloroacetyl-Mutilin 14-[N-(5-Acetamido-1,3,4-thiadiazolyl-2-sulphonyl)carbamate]

A solution of mutilin 14-chloroformate-11-dichloroacetate (246 mg, 0.5 mmol) in DMF (1 ml) was added to a solution of 5-acetamido-1,3,4-thiadiazole-2-sulphonamide (111 m, 0.5 mmol), N,N-di-isopropylethylamine (0.09 ml, 1.05 eq) and 4-dimethylaminopyridine (cat.) in DMF (1 ml). The solution was stirred at room temperature overnight, diluted with ethyl actetate and washed with dil. HCl and with brine. The solution was dried ($MgSO_4$) and evaporated to give a gum which was chromatographed on silica gel, using 10% methanol-chloroform to give the product as a white solid (97 mg).

Step 2. Mutilin 14-[N-(5-Acetamido-1,3,4-thiadiazolyi-2-sulphonyly]-carbamate

The product of Step 1 (95 mg) was dissolved in THF (0.5 ml) and methanol (1.5 ml). 1N NaOH (0.28 ml, 2 eq) was added and the solution left at room tempeature for ca 24 hr during which time a further portion of 1N NaOH (0.14 ml) was added. The solution was acidified with 2N HCl and extracted with ethyl acetate. The extract was washed with brine, dried ($MgSO_4$) and evaporated to give a gum which was purified by chromatography on silica gel, using 10% methanol-chloroform and rechromatographed using using ethyl acetate. The title compound was obtained as a white solid (19 mg, 24%); $^1H$ NMR ($d_6$-acetone-$D_2O$) inter alia 2.36 (3H, s), 3.54 (1H, d J 6), 5.0–5.1 (ca 2H, m), 5.58 (1H, d J 8), 6.18 (1H, dd, J 17, 11); MS (Electrospray) m/z 569 ($MH^+$).

EXAMPLE 74

Mutilin 14-[N-(3-amino-4-methoxybenzoyl)]-carbamate

Step 1. 4-Methoxy-3-nitrobenzoylisocyanate

Silver cyanate (967 mg, 6.5 mmol) was suspended in dry dichloromethane (6 ml) under an atmosphere of argon. A solution of 4-methoxy-3-nitrobenzoyl chloride (1.29 g, 6.0 mmol) in dichloromethane (4 ml) was added and the heterogeneous mixture stirred at reflux under subdued light. After 40 minutes the reaction was allowed to cool and filtered through Kieselguhr. The solution was used immediately in the next reaction. $v_{max}$ ($CH_2C_2$) 2337 $cm^{-1}$.

Step 2. (3R)-3-Deoxo-11-deoxy-3-methoxy-11-oxo-4-epi-mutilin 14-[N-(4-methoxy-3-nitrobenzoyl)]-carbamate The solution from step 1 was cooled to 0° C. and treated with (3R)-3-deoxo-11-deoxy-3-methoxy-11-oxo-4-epi-mutilin (500 mg, 1.5 mmol) and the reaction stirred for 1 hour. The mixture was diluted with dichloromethane and washed with 1.0M hydrochloric acid followed by water and saturated sodium chloride solution. After drying (MgSO$_4$) the crude material was purified by chromatography on silica gel eluting with 40% ethyl acetate in hexane to yield the tide compound (770 mg, 92%). m.p. 178–180° C.; $v_{max}$ (CH$_2$Cl$_2$) 3300, 2980, 1777, 1697, 1619 and 1476 cm$^{-1}$; $^1$H NMR (CDCl$_3$) 0.90 (3H, d, J 6.8 Hz), 0.99 (3H, d, J 6.4 Hz), 1.07–1.58 (12H, m) including 1.21 (3H, s) and 1.31 (3H, s), 1.68–1.76 (2H, m), 1.94–2.04 (2H, m), 2.20 (1H, m), 2.54 (1H, dd, J 15.3, 10.0 Hz), 2.90 (1H, q, J 6.2 Hz), 3.24 (3H, s), 3.48 (1H, m), 4.05 (3H, s), 5.01 (1H, d, J 17.4 Hz), 5.26 (1H, d, J 10.7 Hz), 5.86 (1H, d, J 9.9 Hz), 6.67 (1H, dd, J 17.4, 10.7 Hz), 7.20 (1H, d, J 8.9 Hz), 8.09 (1H, s), 8.12 (1H, dd, J 8.9, 2.4 Hz); 8.33 (1H, d, J 2.4 Hz); MS (Electrospray) m/z 574 (MNH$_4^+$); (Found: C, 64.33; H, 7.48; N, 4.68. C$_{30}$H$_{40}$N$_2$O$_8$ requires C, 64.73; H. 7.24; N. 5.03).

Step 3. (3R)-3-Deoxo-11-deoxy-3-methoxy-11-oxo-4-epi-mutilin 14-[N-(3-amino-4-methoxybenzoyl)]-carbamate (3R)-3-Deoxo-11-deoxy-3-methoxy-11-oxo-4-epi-mutilin 14-[N-(4-methoxy-3-nicrobenzoyl)carbamate] (720 mg, 1.29 mmol) was suspended in ethanol (30 ml). Addition of ethyl acetate (6 ml) brought about complete dissolution. Tin (II) chloride (1.26 g, 6.65 mmol) was added and the reaction warmed to reflux whilst under an atmosphere of argon. After 3 hours the reaction was allowed to cool and poured into ethyl acetate and water before neutralising with sodium hydrogen carbonate. The organic phase was dried (MgSO$_4$) and purified by chromatography on silica gel eluting with 40% ethyl acetate in hexane. The title compound was isolated as a colourless foam (297 mg, 44%); $v_{max}$ (CH$_2$Cl$_2$) 3393, 2981, 1773, 1698, 1605 and 1474 cm$^{-1}$; $^1$H NMR (CDCl$_3$) 0.90 (3H, d, J 6.6 Hz), 0.99 (3H, d, J 6.4 Hz), 1.05–1.55 (12H, m) including 1.21 (3H, s) and 1.34 (3H, s), 1.70–1.79 (2H, m), 1.94–2.08 (2H, m), 2.21 (1H, m), 2.53 (1H, dd, J 15.3, 10.0 Hz), 2.92 (1H, q, J 6.1 Hz), 3.26 (3H, s), 3.48 (1H, m), 3.93 (3H, s), 3.99 (2H, bs), 5.03 (1H, d, J 17.5 Hz), 5.30 (1H, d, J 10.8 Hz), 5.84 (1H, d, J 9.9 Hz), 6.73 (1H, dd, J 17.5, 10.8 Hz), 6.82 (1H, d, J 8.6 Hz), 7.18 (1H, dd, J 8.6, 2.3 Hz), 7.23 (1H, d, J 2.3 Hz), 7.90 (1H, s); MS (Electrospray) m/z 527 (MH$^+$).

Step 4. Mutilin-14-[N-(3-amino-4-methoxybenzoyl)]-carbamate

The product of Step 3 (100 mg, 0.19 mmol) in dioxane (1 ml) was created with a saturated solution of zinc chloride in conc. HCl (1 ml) and the reaction stirred at room for 30 minutes. The solution was poured into ethyl acetate and saturated sodium hydrogen carbonate solution. The aqueous phase was re-extracted with ethyl acetate and the combined orcanic phases were washed with saturated sodium chloride solution. The organic phase was dried (MgSO$_4$) and purified by chromatography on silica gel eluring with 70% ethyl acetate in hexane. The title compound was isolated as a colourless foam (53 mg, 54%); $v_{max}$ (CH$_2$Cl$_2$) 3393, 2939, 1774, 1733, 1615 and 1476 cm$^{-1}$; $^1$H NMR (CDCl$_3$) 0.80 (3H, d, J 6.6 Hz), 0.88 (3H, d, J 7.0 Hz), 1.12–1.80 (16H, m) including 1.19 (3H,s) and 1.51 (3H, s), 2.08–2.40 (4H, m), 3.37 (1H, dd, J 11.0, 6.6 Hz), 3.91 (3H, s), 3.93 (2H, bs), 5.22 (1H, dd, J 17.4, 1.4 Hz), 5.39 (1H, dd, J 10.9, 1.4 Hz), 5.81 (1H, d, J 8.5 Hz), 6.59 (1H, dd, J 17.4, 10.9 Hz), 6.89 (1H, d, J 8.4 Hz), 7.11–7.20 (2H, m), 7.80 (1H, bs); MS (Electrospray) m/z 513 (MH$^+$).

EXAMPLE 75

Mutilin 14-[N-(3-methanesulphonamido-4-methoxybenzoyl)]-carbamate

Step 1. (3R)-3-Deoxo-11-deoxy-3-methoxy-11-oxo-4-epi-mutilin 14-[N-(3-methanesulphonamido4-methoxybenzoyl)]-carbamate (3R)-3-Deoxo-11-deoxy-3-methoxy-11-oxo-4-epi-mutilin 14-[N-(3-amino4-methoxybenzoyl)carbamate] (158 mg, 0.30 mmol) was dissolved in dichloromethane (5 ml) and treated with pyridine (81 ul, 1.05 mmol) followed by methanesulphonyl chloride (81 ul, 1.05 mmol). After stirring for 3 hours, the reaction mixture was diluted with dichloromethane and washed successively with 0.5M hydrochloric acid, saturated aqueous sodium hydrogem carbonate, water and brine. The organic phase was dried over magnesium sulphate and concentrated in vacuo. The residue was purified by chromatography eluting with 70% ethyl acetate in hexane to yield a colourless foam (159 mg, 88%); $v_{max}$ (CH$_2$Cl$_2$) 3338, 2981, 1775, 1697, 1607 and 1476 cm$^{-1}$; $^1$H NMR (CDCl$_3$) 0.90 (3H, d, J 6.8 Hz), 1.02 (3H, d, J 6.4 Hz), 1.05–1.59 (12H, m) including 1.20 (3H, s) and 1.31 (3H, s), 1.70–1.78 (2H, m), 1.96–2.07 (2H, m), 2.22 (1H, m), 2.55 (1H, dd, J 15.2, 10.1 Hz), 2.91 (1H, q, J 6.4 Hz), 3.02 (3H, s), 3.23 (3H, s), 3.48 (1H, m), 3.99 (3H, s), 5.01 (1H, d, J 17.5 Hz), 5.30 (1H, d, J 10.8 Hz), 5.83 (1H, d, J 9.9 Hz), 6.72 (1H, dd, J 17.5, 10.8 Hz), 6.86 (1H, bs), 7.02 (1H, d, J 8.6 Hz), 7.72 (1H, dd, J 8.6, 2.2 Hz), 7.93 (1H, d, J 2.2 Hz), 7.99 (1H, s).

Step 2. Mutilin-14-[N-(3-methanesulphonamido-4-methoxybenzoyl)]-carbamate

The product of Step 1 (128 mg, 0.21 mmol) in dioxane (1 ml) was treated with a saturated solution of zinc chloride in conc. HCl (1 ml) and the reaction stirred at room for 30 minutes. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel elutint with 70% ethyl acetate in hexane. The title compound was isolated as a colourless foam (46 mg, 37%); $v_{max}$ (CH$_2$Cl$_2$) 3340, 2941, 1776, 1733, 1607 and 1477 cm$^{-1}$; $^1$H NMR (CDCl$_3$) 0.81 (3H, d, J 6.6 Hz), 0.89 (3H, d, J 6.9 Hz), 1.10–1.82 (16H, m) including 1.21 (3H, s) and 1.52 (3H, s), 2.10–2.38 (4H, m), 2.99 (3H, s), 3.38 (1H, dd, J 10.8, 6.5 Hz), 3.96 (3H, s), 5.22 (1H, dd, J 17.4, 1.4 Hz), 5.38 (1H, dd, J 11.1, 1.4 Hz), 5.82 (1H, d, J 8.4 Hz), 6.54 (1H, dd, J 17.4, 11.1 Hz), 6.84 (1H, bs), 6.99 (1H, d, J 8.6 Hz), 7.70 (1H, dd, J 8.6, 2.3 Hz), 7.88 (1H, d, J 2.3 Hz), 7.95 (1H, bs).

EXAMPLE 76

Mutilin 14-[N-(isoxaxol-5-oyl)]-carbamate

Step 1. (3R)-3-Deoxo-11-deoxy-3-methoxy-11-oxo-4-epi-mutilin 14-[N-(isoxazol-5-oyl)]-carbamate (3R)-3-Deoxo-11-deoxy-3-methoxy-11-oxo-4-epi-mutilin (633 mg, 1.89 mmol) was combined with isoxazole-5-carbonyl chloride (1.0 g, 7.60 mmol), silver cyanate (1.22 g, 8.14 mmol) and tetrakis(triphenylphosphine) palladium (0) (32 mg) in dry dichloromethane (15 ml) and the reaction stirred at room temperature for 30 minutes in subdued light and under an atmosphere of argon. The mixture was filtered through Kieselguhr and the filtrate washed with saturated aqueous sodium hydrogen carbonate (×2) and brine. After drying (MgSO$_4$) purification was accomplished by chromatography on silica gel eluting with 30% ethyl acetate in hexane. The title compound was isolated as a colourless foam (850 mg, 95%); $v_{max}$ (CH$_2$Cl$_2$) 3393, 2929, 1783, 1726, 1597 and 1496 cm$^{-1}$; $^1$H NMR (CDCl$_3$) 0.88 (3H, d, J 6.8 Hz), 1.01 (3H, d, J 6.4 Hz), 1.08–1.59 (12H, m) including 1.20 (3H, s) and 1.31 (3H, s), 1.69–1.77 (2H, m), 1.93–2.07 (2H, m), 2.21 (1H, m), 2.56 (1H, dd, J 15.3, 10.1 Hz), 2.89 (1H, q, J 6.3 Hz), 3.22 (3H, s), 3.48 (1H, m), 5.02 (1H, d, J 17.5 Hz), 5.31 (1H, d, J 10.7 Hz), 5.86 (1H, d, J 10.0 Hz), 6.68 (1H, dd, J 17.5, 10.7 Hz), 7.03 (1H, d, J 1.8 Hz), 8.39 (1H, bs), 8.43 (1H, d, J 1.8 Hz); MS(CI) m/z 490 (MNH$_4^+$).

Step 2. Mutilin-14-[N-(isoxazol-5-oyl)]-carbamate

The product of Step 1 (810 mg, 1.71 mmol) in dioxane (6 ml) was treated with a saturated solution of zinc chloride in conc. HCl (3 ml) and the reaction stirred at room for 30 minutes. The solution was poured into ethyl acetate and saturated sodium hydrogen carbonate solution. The aqueous phase was re-extracted with ethyl acetate and the combined organic phases were washed with saturated sodium chloride solution. The organic phase was dried ($MgSO_4$) and purified by chromatography on silica gel eluting with 50% ethyl acetate in hexane to yield the title compound (540 mg, 69%); $v_{max}$ ($CH_2Cl_2$) 3395, 2959, 1785, 1731 and 1496 cm$^{-1}$; $^1$H NMR ($CDCl_3$) 0.79 (3H, d, J 6.8 Hz), 0.90 (3H, d, J 7.0 Hz), 1.10–1.83 (16H, m) including 1.20 (3H, s) and 1.50 (3H, s), 2.10–2.37 (4H, m), 3.38 (1H, dd, J 10.8, 6.6 Hz), 5.23 (1H, dd, J 17.3, 1.4 Hz), 5.40 (1H, dd, J 10.9, 1.4 Hz), 5.85 (1H, d, J 8.5 Hz), 6.53 (1H, dd, J 17.3, 10.9 Hz), 7.10 (1H, d, J 1.9 Hz), 8.36 (1H, bs), 8.41 (1H, d, J 1.9 Hz); MS(CI) m/z 476 ($MNH_4^+$).

EXAMPLE 77

Mutilin 14-[N-(methoxyacetyl)]-carbamate
Step 1. (3R)-3-Deoxo-11-deoxy-3-methoxy-11-oxo-4-epi-mutilin 14-[N-(methoxyacetyl)]-carbamate
(3R)-3-deoxo-11-deoxy-3-methoxy-11-oxo-4-epi-mutilin (500 mg, 1.50 mmol) was combined with methoxyacetyl chloride (547 ul, 6.0 mmol) and silver cyanate (965 mg, 6.40 mmol) in dry dichloromethane (15 ml) and the reaction stirred at room temperature for 10 minutes in subdued light and under an atrnosphere of argon. The mixture was filtered through Kieselguhr and the filtrate washed with saturated aqueous sodium hydrogen carbonate (×2) and brine. After drying ($MgSO_4$) purification was accomplished by chromatography on silica gel eluting with 30% ethyl acetate in hexane. The title compound was isolated as a colourless foam (630 mg, 94%); $v_{max}$ ($CH_2Cl_2$) 3388, 2932, 1786, 1722 and 1488 cm$^{-1}$; $^1$H NMR ($CDCl_3$) 0.85 (3H, d, J 6.9 Hz), 1.00 (3H, d, J 6.4 Hz), 1.08–1.58 (12H, m) including 1.19 (3H, s) and 1.28 (3H, s), 1.64–1.77 (2H, m), 1.94–2.06 (2H, m), 2.21 (1H, m), 2.51 (1H, dd, J 15.3, 10.1 Hz), 2.88 (1H, q, J 6.4 Hz), 3.21 (3H, s), 3.42 (1H, m), 3.49 (3H, s), 4.08 (2H, s), 5.01 (1H, d, J 17.6 Hz), 5.30 (1H, d, J 10.7 Hz), 5.77 (1H, d, J 10.0 Hz), 6.69 (1H, dd, J 17.6, 10.7 Hz), 8.26 (1H, bs).
Step 2. Mutilin-14-[N-(methoxyacetyl)]-carbamate
The product of Step 1 (600 mg, 1.34 mmol) in dioxane (6 ml) was treated with a saturated solution of zinc chloride in conc. HCl (3 ml) and the reaction stirred at room for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried ($MgSO_4$) and purified by chromatography on silica gel eluting with 40% ethyl acetate in hexane to yield the title compound as a colourless foam (210 mg, 36%); $v_{max}$ ($CH_2Cl_2$) 3388, 2941, 1787, 1726 and 1488 cm$^{-1}$; $^1$H NMR ($CDCl_3$) 0.74 (3H, d, J 6.7 Hz), 0.90 (3H, d, J 7.0 Hz), 1.10–1.85 (16H, m) including 1.17 (3H, s) and 1.48 (3H, s), 2.04–2.37 (4H, m), 3.35 (1H, dd, J 10.9, 6.6 Hz), 3.45 (3H, s), 4.06 (2H, s), 5.22 (1H, dd, J 17.4, 1.5 Hz), 5.38 (1H, dd, J 11.0, 1.5 Hz), 5.75 (1H, d, J 8.5 Hz), 6.52 (1H, dd, J 17.4, 11.0 Hz), 8.20 (1H, bs); MS(CI) m/z 453 ($MNH_4^+$).

EXAMPLE 78

Mutilin 14-[N-(6-methoxynicotinoyl)]-carbamate
Step 1. (3R)-3-Deoxo-11-deoxy-3-methoxy-11-oxo-4-epi-mutilin 14-[N-(6-methoxynicotinoyl)carbamate]
(3R)-3-deoxo-11-deoxy-3-methoxy-11-oxo-4-epi-mutilin (500 mg, 1.50 mmol) was combined with 6-methoxynicotinoyl chloride (430 mg, 2.5 mmol) and silver cyanate (400 mg, 2.67 mmol) in dry dichloromethane (20 ml) and the reaction stirred at room temperature for 4.5 hours in subdued light and under an atmosphere of argon. The mixture was filtered through Kieseiguhr and the filtrate washed with saturated aqueous sodium hydrogen carbonate (×2) and brine. After drying ($MgSO_4$) purification was accomplished by chromatography on silica gel eluting with 30% ethyl acetate in hexane. The title compound was isolated as a colourless foam (750 mg, 98%); $v_{max}$ ($CH_2Cl_2$) 3423, 2930, 1776, 1729, 1603 and 1477 cm$^{-1}$; $^1$H NMR ($CDCl_3$) 0.91 (3H, d, J 6.8 Hz), 1.01 (3H, d, J 6.4 Hz), 1.10–1.59 (12H, m) including 1.27 (3H, s) and 1.36 (3H, s), 1.68–1.78 (2H, m), 1.96–2.04 (2H, m), 2.21 (1H, m), 2.52 (1H, dd, J 15.3, 10.1 Hz), 2.91 (1H, q, J 6.4 Hz), 3.23 (3H, s), 3.49 (1H, m), 4.02 (3H, s), 5.03 (1H, d, J 17.4 Hz), 5.30 (1H, d, J 10.8 Hz), 5.84 (1H, d, J 10.0 Hz), 6.69 (1H, dd, J 17.4, 10.8 Hz), 6.83 (1H, d, J 8.8 Hz), 7.91 (1H, bs), 8.05 (1H, dd, J 8.8, 2.6 Hz), 8.63 (1H, d, J 2.6 Hz); MS(CI) ml-513 (MH$^+$).
Step 2. Mutilin-14-[N-(6-methoxynicotinoyl)]-carbamate
The product of Step 1 (720 mg, 1.41 mmol) in dioxane (5 ml) was treated with a saturated solution of zinc chloride in conc. HCl (3 ml) and the reaction stirred at room for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried ($MgSO_4$) and purified by chromatography on silica gel eluting with 50% ethyl acetate in hexane to yield the title compound as a colourless foam (600 mg, 85%); $v_{max}$ ($CH_2Cl_2$) 3423, 2949, 1777, 1733, 1603 and 1475 cm$^{-1}$; $^1$H NMR ($CDCl_3$) 0.82 (3H, d, J 6.7 Hz), 0.89 (3H, d, J 7.0 Hz), 1.10–1.82 (16H, m) including 1.20 (3H, s) and 1.49 (3H, s), 2.06–2.37 (4H, m), 3.36 (1H, dd, J 10.9, 6.5 Hz), 3.99 (3H, s), 5.24 (1H, dd, J 17.4, 1.4 Hz), 5.39 (1H, dd, J 11.0, 1.4 Hz), 5.82 (1H, d, J 8.5 Hz), 6.54 (1H, dd, J 17.4, 11.0 Hz), 6.81 (1H, d, J 8.8 Hz), 7.92 (1H, bs), 8.01 (1H, dd, J 8.8, 2.5 Hz), 8.62 (1H, d, J 2.5 Hz); MS(CI) m/z 499 (MH$^+$).

EXAMPLE 79

Mutilin 14-[N-(pyrazin-2-oyl)]-carbamate
Step 1. (3R)-3-Deoxo-11-deoxy-3-methoxy-11-oxo-4-epi-mutilin 14-[N-(pyrazin-2-oyl)carbamate]
(3R)-3-deoxo-1-deoxy-3-methoxy-11-oxo-4-epi-mutilin (500 mg, 1.50 mmol) was combined with pyrazin-2-oyl chloride (1.14 g, 8.0 mmol) and silver cyanate (1.20 g, 8.0 mmol) in dry dichloromethane (15 ml) and the reaction stirred at room temperature for 10 minutes in subdued light and under an atmosphere of argon. The mixture was filtered through Kieselguhr and the filtrate washed with saturated aqueous sodium hydrogen carbonate (×2) and brine. After drying ($MgSO_4$) purification was accomplished by chromatography on silica gel eluting with 40% ethyl acetate in hexane. The title compound was isolated as a colourless foam (498 mg, 69%); $v_{max}$ ($CH_2Cl_2$) 3364, 2931, 1781, 1720, 1697 and 1490 cm$^{-1}$; $^1$H NMR ($CDCl_3$) 0.90 (3H, d, J 6.8 Hz), 1.01 (3H, d, J 6.4 Hz), 1.09–1.61 (12H, m) including 1.20 (3H, s) and 1.38 (3H, s), 1.69–1.79 (2H, m), 1.94–2.06 (2H, m), 2.21 (1H, m), 2.56 (1H, dd, J 15.3, 10.1 Hz), 2.92 (1H, q, J 6.4 Hz), 3.24 (3H, s), 3.50 (1H, m), 5.03 (1H, d, J 17.4 Hz), 5.32 (1H, d, J 10.7 Hz), 5.89 (1H, d, J 9.9 Hz), 6.75 (1H, dd, J 17.4, 10.7 Hz), 8.62 (1H, d, J 2.5 Hz), 8.88 (1H, d, J 2.5 Hz), 9.51 (1H, d, J 1.5 Hz), 9.76 (1H, bs).
Step 2. Mutilin-14-[N-(pyrazin-2-oyl)]-carbamate
The product of Step 1 (450 mg, 0.93 mmol) in dioxane (2 ml) was treated with a saturated solution of zinc chloride in conc. HCl (2 ml) and the reaction stirred at room for 1 hour. The solution was poured into ethyl acetate and saturated sodium hydrogen carbonate solution. The aqueous phase was re-extracted with ethyl acetate and the combined orzanic phases were washed with saturated sodium chloride solution. The organic phase was dried (MgSO$_4$) and purified by chromatography on silica gel eluting with 50% ethyl acetate in hexane to yield the title compound as a colourless foam (420 mg, 96%); $v_{max}$ (CH$_2$Cl$_2$) 3364, 2939, 1782, 1734 and 1491 cm$^{-1}$; $^1$H NMR (CDCl$_3$) 0.79 (3H, d, J 6.7 Hz), 0.91 (3H, d, J 7.0 Hz), 1.10–1.85 (16H, m) including 1.20 (3H, s) and 1.58 (3H, s), 2.10–2.43 (4H, m), 3.39 (1H, dd, J 10.9, 6.6 Hz), 5.24 (1H, dd, J 17.4, 1.5 Hz), 5.40 (1H, dd, J 10.9, 1.4 Hz), 5.85 (1H, d, J 8.5 Hz), 6.59 (1H, dd, J 17.4, 10.9 Hz), 8.60 (1H, d, J 2.3 Hz), 8.84 (1H, d, J 2.5 Hz), 9.45 (1H, d, J 2.3 Hz), 9.72 (1H, bs); MS(CI) m/z 487 (MNH$_4^+$).

EXAMPLE 80

Mutilin 14-(N-thiophen-2-oyl)-carbamate

Step 1. (3R)-3-Deoxo-11-deoxy-3-methoxy-11-oxo-4-epi-mutilin 14-(N-thiophen-2-oyl)-carbamate A suspension of silver cyanate in dichloromethane (10 ml) was treated with 2-thiophene carbonyl chloride and the mixture heated under reflux for 45 mins. IR analysis showed no starting material. The reaction mixture was cooled and filtered through Kieselguhr affording a pale yellow solution. (3R)-3-Deoxo-11-deoxy-3-methoxy-11-oxo-4-epi-mutilin (0.5 g) was added to the solution. After 20 mins. the solution was washed with dilute hydrochloric acid, saturated sodium chloride and then dried over anhydrous magnesium sulphate. Removal of solvent in vacuo afforded the product as a white solid which was purified by silica gel chromatography eluting with dichloromethane then 1% and 2% acetone/dichloromethane to give the title compound as a white solid (0.686 g, 94%); $v_{max}$ (CH$_2$CH$_2$) 3422, 1773, 1726(w), 1698, 1521 and 1481 cm$^{-1}$; $^1$H NMR (CDCl$_3$) 0.89 (3H, d, J 6.8 Hz), 1.01 (3H, d, J 6.4 Hz), 1.07–1.78 (8H, m), 1.20 (3H, s), 1.34 (3H, s), 1.99 (2H, m), 2.21 (1H,m), 2.55 (1H, dd, J 10.1,15.3 Hz), 2.90 (1H, q, J 6.4 Hz), 3.22 (3H, s), 3.46 (1H, m), 5.01 (1H, d, J 17.5), 5.28 (1H, d, J 10.7 Hz), 5.86 (1H, d, J 10.0 Hz), 6.70 (1H, d, J 10.7,17.5 Hz), 7.13 (1H, m), 7.66 (2H, m) and 8.03 (1H, s); MS (NH$_3$DCI) m/z 488 (MH$^+$) and 505 (MNH$_4^+$).

Step 2. Mutilin 14-(N-thiophen-2-oyl)-carbamate

The product from Step 1 (0.45 g) in dioxan (1.5 ml) was treated with Lukas reagent (sat. ZnCl$_2$/conc. HCl; 1.5 ml), at room temperature. The reaction mixture darkened and became warm. After 5 min. t.l.c. analysis showed no staring material. The reaction mixture was diluted with ethyl acetate and the solution washed with water. The organic phase was extracted with ethyl acetate and the combined organic extracts washed with saturated sodium hydrogen carbonate, saturated sodium chloride, dried and concentrated to an orange gum. Silica gel chromatography eluting with ethyl acetate/hexane gave the product as a white solid, (0.173 g, 40%); $v_{max}$ (CH$_2$Cl$_2$) 3564, 3424, 1775, 1733, 1705, 1521 and 1482 cm$^{-1}$; $^1$H NMR (CDCl$_3$) 0.80 (3H, d, J 6.7 Hz), 0.89 (3H, d, 7.0 Hz), 1.14 (1H, m), 1.19 (3H, s), 1.37–1.82 (9H, m), 1.54 (3H, s), 2.12–2.37 (4H, m), 3.37 (1H, dd, J 6.6,10.6 Hz), 5.23 (1h, dd, J 1.5,17.4 Hz), 5.36 (1H, dd, J 1.5,11.1 Hz), 5.83 (1H, d, J 8.5 Hz), 6.54 (1H, J, 11.0,17.4 Hz), 7.12 (1H, m), 7.63 (2H, m) and 7.95 (1H, s); MS (NH$_3$ DCI) m/z 474 (MH$^+$) and 491 (MNH$_4^+$).

EXAMPLE 81

Mutilin 14-[(S)-Tetrahydrofuran-2-oyl]-carbamate

Step 1. (3R)-3-Deoxo-11-deoxy-3-methoxy-11-oxo-4-epi-mutilin 14-[(S)-tetrahydrofuran-2-oyl]-carbamate (S)-(−)-Tetrahydrofuroic acid (0.464 g) in dichloromethane (3 ml) at room temperature was treated with oxalyl chloride (0.635 ml) and one drop of DMF for 1 h. IR analysis showed complete conversion to the acid chloride. The solvent and excess oxalyl chloride were removed in vacuo and the residue redissolved in dry dichloromethane. The acid chloride was reacted with silver cyanate (0.645 g) and (3R)-3-deoxo-11-deoxy-3-methoxy-11-oxo-4-epi-mutilin (0.322 g) as previously described in Example 80, Step 1. Following purification by silica gel chromatography the product was isolated as a colourless foam, (0.43 g, 91%); $v_{max}$ (CH$_2$Cl$_2$) 3381, 1783, 1744, 1717 and 1698 cm$^{-1}$; $^1$H NMR (CDCl$_3$) 0.83 (3H, d, J 6.9 Hz), 0.99 (3H, d, J 6.4 Hz), 1.06–1.75 (9H, m), 1.19 (3H, s), 1.29 (3H, s), 1.87–2.38 (7H, m), 2.50 (1H, dd, J 10.1,15.3 Hz), 2.88 (1H, q, J 6.4 Hz), 3.22 (3H, s), 3.46 (1H, m), 3.96 (2H, m), 4.43 (1H, dd, J 5.7,8.4 Hz), 5.00 (1H, d, J 17.4 Hz), 5.29 (1H, d, J 10.7 Hz), 6.71 (1H, dd, J 10.7,17.5 Hz) and 8.59 (1H, s); MS (NH$_4$ DCI) m/z 494 (MNH$_4^+$).

Step 2. Mutilin 14-[(S)-tetrahydrofuran-2-oyl]-carbamate

The product from Step 1, (0.388 g) in dioxan (1 ml) was treated with Lukas reagent as described in Example 80, Step 2. After purification by silica gel chromatography the product was isolated as a colourless foam, (0.242 g, 64%); $v_{max}$ (CH$_2$)Cl$_2$) 3562, 3381, 1784, 1733 and 1480 cm$^{-1}$; $^1$H NMR (CDCl$_3$) 0.75 (3H, d, J 6.7 Hz), 0.89 (3H, d, J 7. lHz), 1.15 (1H, m), 1.18 (3H, s), 1.42–2.35 (19H, m), 1.50 (3H, s), 3.36 (1H, dd, J 6.7,10.9 Hz), 3.94 (2H, m), 4.40 (1H, dd, J 5.8,8.4 Hz), 5.22 (1H, dd, J 1.5,17.4 Hz), 5.37 (1H, dd, J 1.5,10.9 Hz), 5.77 (1H, d, J 8.5 Hz), 6.54 (1H, dd, J 11.0,17.4 Hz) and 8.51 (1H, s); MS (NH$_4$ DCI) m/z 479 (MNH$_4^+$).

EXAMPLE 82

Mutilin 14-[(R)-Tetrahydrofuran-2-oyl]carbamate

Step 1. (3R)-3-Deoxo-11-deoxy-3-methoxy-11-oxo-4-epi-mutilin 14-[(R)-tetrahydrofuran-2-oylcarbamate]

(R)-(+)-Tetrahydrofuroic acid (0.464 g) and (3R)-3-deoxo-11-deoxy-3-methoxy-11-oxo-4-epi-mutilin (0.322 g) were converted into the title compound as described in Example 80, Step 1. Following purification by silica gel chromatography the title compound was obtained as a colourless foam (0.432 g, 91%), $v_{max}$ (CH$_2$Cl$_2$) 3383, 1782, 1718, 1698 and 1474 cm$^{-1}$; $^1$H NMR (CDCl$_3$) 0.86 (3H, d, J 6.9 Hz), 1.00 (3H, d, J 6.4 Hz), 1.06–1.75 (9H, m), 1.17 (3H, s), 1.28 (3H, s), 1.87–2.38 (7H, m), 2.50 (1H, dd, J 10.1,15.3 Hz), 2.88 (1H, q, J 6.4 Hz), 3.22 (3H, s), 3.46 (1H, m), 3.884.06 (2H, m), 4.43 (1H, dd, J 5.7,8.4 Hz), 5.00 (1H, d, J 17.4 Hz), 5.29 (1H, d, J 10.7 Hz), 6.71 (1H, dd, J 10.7,17.5 Hz) and 8.59 (1H, s); MS (NH$_3$ DCI) m/z 494 (MNH$_4^+$).

Step 2. Mutilin 14-[(R)-tetrahydrofuran-2-oyl]-carbamate

The product from Step 1 (0.38 g) in dioxan (1 ml) was treated with Lukas reagent as described in Example 80, Step 2. After purification by silica gel chromatography the product was isolated as a colourless foam (0.195 g, 53%); $v_{max}$ (CH$_2$Cl$_2$) 3560, 3382, 1783, 1733 and 1480 cm$^{-1}$; $^1$H NMR (CDCl$_3$) 0.76 (3H, d, J 6.7 Hz), 0.88 (3H, d, J 7.1 Hz), 1.15 (1H, m), 1.18 (3H, s), 1.42–2.35 (19H, m), 1.48 (3H, s), 3.36 (1H, dd, J 6.7,10.9 Hz), 3.86–4.05 (2H, m), 4.40 (1H, dd, J 5.8,8.4 Hz), 5.22 (1H, dd, J 1.5,17.4 Hz), 5.37 (1H, dd, J 1.5,10.9 Hz), 5.77 (1H, d, J 8.5 Hz), 6.54 (1H, dd, J 11.0,17.4 Hz) and 8.51 (1H, s); MS (NH$_4$ DCI) m/z 479 (MNH$_4^+$).

EXAMPLE 83

Mutilin 14-[N-(2,4-Difluorobenzoyl)]-carbamate

Step 1. (3R)-3-Deoxo-11-deoxy-3-methoxy-11-oxo-4-epi-mutilin 14-[N-(2,4-difluorobenzoyl)]-carbamate (3R)-3-Deoxo-11-deoxy-3-methoxy-11-oxo-4-epi-mutilin (200 mg), 2,4-difluoro-benzoyl chloride (212 mg), and silver cyanate (180 mg) in dichloromethane (5 ml) were stirred at room temperature for 2 hours. The mixture was diluted with ethyl acetate (100 ml) and filtered. The filtrate was washed with water (2×30 ml) and saturated sodium bicarbonate solution (30 ml), the solution was dried (sodium sulphate), and the solvent was evaporated under reduced pressure to give the title compound as a coloirless gum (400 mg); $^1$H NMR (CDCl$_3$) inter alia 3.23 (3H, s), 3.46 (1H, m), 5.00 (1H, d, J 17.5 Hz), 5.30 (1H, d, J 10.5 Hz), 5.81 (1H, d, J 10 Hz), 6.72 (1H, dd, J 17.5, 10.5 Hz), 6.90 (1H, m), 7.03 (1H, m), 8.10 (1H, m), 8.40 (1H, d, J 13 Hz).

Step 2. Mutilin 14-[N-(2,4-Dinluorobenzoyl)]-carbamate (3R)-3-Deoxo-11-deoxy-3-methoxy-11-oxo-4-epi-mutilin 14-[N-(2,4-difluoro-benzoyl)]-carbamate from Step 1 (400 mg) in 1,4-dioxane (5 ml) was treated with a saturated solution of zinc chloride in conc. HCl (2 ml) and the solution was kept at room temperature for 3 hours. The solution was diluted with ethyl acetate (50 ml) and washed with water (2×30 ml) and saturated sodium bicarbonate solution (30 ml). The solution was dried (sodium sulphate) and the solvent was evaporated under reduced pressure to give a pale yellow gum. The gum was chromato-graphed on silica gel using gradient elution from 1:4 to 2:3 ethyl acetate/hexane, to give the title compound as a white foam. Crystallisation from dichloromethane/hexane gave colourless crystals (250 mg), m.p. 178–180° C.; $^1$H NMR (CDCl$_3$) inter alia 3.37 (1H, dd, J 11, 6.6 Hz), 5.23 (1H, dd, J 17.3, 1.4 Hz), 5.38 (1H, dd, J 11, 1.4 Hz), 5.80 (1H, d, J 8.5 Hz), 6.55 (1H, dd, J 17.3, 11 Hz), 6.91 (1H, m), 7.03 (1H, m), 8.10 (1H, m), 8.30 (1H, d, J 13 Hz).

EXAMPLE 84

Mutilin 14-[N-(3,4-Difluorobenzoyl)]-carbamate

Using the methods described in Example 83, (3R)-3-deoxo-11-deoxy-3-methoxy-11-oxo-4-epi-mutilin (250 mg) and 3,4-difluorobenzoyl chloride (210 mg) were converted into (3R)-3-deoxo-11-deoxy-3-methoxy-11-oxo-4-epi-mutilin 14-[N-(3,4-difluorobenzoyl)]-carbamate [MS(EI) m/z 517 (M$^+$)], and hence into the title compound, which was obtained as colourless crystals (120 mg), m.p. 144–146° C. (dichloromethane/hexane); $^1$H NMR (CDCl$_3$) inter alia 3.37 (1H, dd, J 10.7, 6.6 Hz), 5.23 (1H, dd, J 17.3, 1.4 Hz), 5.32 (1H, dd, J 11, 1.3 Hz), 5.82 (1H, d, J 8.5 Hz), 6.50 (1H, dd, J 17.3, 11 Hz), 7.30 (1H, m), 7.60 (1H, m), 7.70 (1H, m), 8.13 (1H, s).

EXAMPLE 85

Mutilin 14-[N-(1-tert-butyloxycarbonyl-azetidin-3-oyl)]-carbamate

Step 1. 1-tert-Butyloxycarbonyl-azetidine-3-carboxylic acid

3-Azetidine carboxylic acid (250 mg) in water (2 ml) was treated with a solution of di-tert-butyl dicarbonate (650 mg) in 1,4-dioxane (3 ml) and the mixture was stirred at room temperature for 17 hours. The mixture was acidified by adding a few drops of 1M HCl, was diluted with water (10 ml), and extracted with ethyl acetate (2×20 ml). The organic extract was washed with water (2×10 ml). The solution was dried (sodium sulphate) and the solvent was evaporated under reduced pressure to give a colourless gum. Crystallisation from diethyl ether/pentane gave the title compound as colourless crystals (470 mg), m.p. 102.5–104° C.; $^1$H NMR (CDCl$_3$) 1.44 (9H, s), 3.38 (1H, quin, J 7.4 Hz), 4.13 (4H, d, J 7.4 Hz).

Step 2. Mutilin 11-trifluoroacetate

Mutilin (960 mg) in dry tetrahydrofuran (12 ml) was treated with pyridine (0.3 ml) and the solution was cooled to 0° C. Trifluoroacetic anhydride (0.48 ml) was added dropwise over 3 minutes to the stirred solution. The solution was kept at 0° C. for 2 hours, and was then diluted with ethyl acetate (100 ml) and washed with water (2×30 ml), sodium bicarbonate solution (30 ml), and saturated sodium chloride solution (30 ml). The solution was dried (sodium sulphate) and the solvent was evaporated under reduced pressure to give a colourless gum. The gum was chromatographed on silca gel using 1:9 to 1:4 ethyl acetate/hexane to give the title compound as colourless crystals (570 mg). Recrystallisation from dichloromethane/hexane gave colourless rods, m.p. 170–171° C.; $v_{max}$ (CHCl$_3$) 3636, 1777, and 1736 cm$^{-1}$; MS(EI) m/z 416 (M$^+$).

Step 3. Mutilin 14-[N-(1-tert-butyloxycarbonyl-azetidin-3-oyl)]-carbamate 11-trifluoroacetate 1-terr-Butyloxycarbonyl-azetidine-3-carboxylic acid (345 mg) in dry dichloromethane (10 ml) was treated with oxalyl chloride (254 mg; 0.175 ml) and N,N-dimethylformamide (1 drop). The solution was stirred for 1.5 hours, and then the solvent was removed by evaporation under reduced pressure. The residue was dissolved in toluene (10 ml), and the toluene was evaporation under reduced pressure to give 1-terr-butyloxycarbonyl-azetidine-3-carbonyl chloride as a colourless oil.

The oil was dissolved in dichloromethane (6 ml) and the solution was treated with silver cyanate (525 mg). The mixture was stirred for 10 minutes, and then mutilin 11-trifluoroacetate (535 mg) in dichloromethane (9 ml) was added. The mixture was stirred for 20 hours. Ethyl acetate (50 ml) was added and the mixture was filtered. The filtrate was washed with saturated sodium bicarbonate solution (20 ml) and saturated sodium chloride solution (20 ml). The solution was dried (sodium sulphate) and the solvent was removed under reduced pressure to yield a colourless gum. The gum was chromatographed on silica gel using 1:4 to 1:2 ethyl acetate/hexane to give the title compound as a colourless gum (485 mg); $^1$H NMR (CDCl$_3$) inier alia 1.43 (9H, s), 3.93 (1H, quin, J 7.2 Hz), 4.98 (1H, d, J 6.9 Hz), 4.14 (4H, m), 5.23 (1H, d, J 17.5 Hz), 5.29 (1H, d, J 11.2 Hz), 5.58 (1H, d, J 8 Hz), 6.31 (1H, dd, J 17.5, 11.2 Hz), 7.57 (1H, s).

Step 4. Mutilin 14-[N-(1-tert-butyloxycarbonyl-azetidin-3-oyl)]-carbamate

Mutilin 14-[N-(1-terr-butyloxycarbonyl-azetidin-3-oyl)]-carbamate 11-trifluoroacetate (450 mg) was dissolved in tetrahydrofuran (10 ml)/water (2 ml) and the solution was treated with 0.5M sodium hydroxide (1.5 ml). The mixture was stirred for 4.5 hours, and was then diluted with ethyl acetate (50 ml) and washed with water (2×30 ml). The solution was dried (sodium sulphate) and the solvent was removed by evaporation under reduced pressure to give the title compound as a white foam (380 mg); $v_{max}$ (CHCl$_3$) 3551, 3396, and 1706 cm$^{-1}$; $^1$H NMR (CDCl$_3$) inter alia 1.43 (9H, s), 3.35 (1H, m), 3.94 (1H, quin, J 7.5 Hz), 4.10 (4H, m), 5.22 (1H, d, J 17.3 Hz), 5.35 (1H, d, J 11 Hz), 5.65 (1H, d, J 8.4 Hz), 6.42 (1H, dd, J 17.3, 11 Hz), 7.26 (1H,s).

EXAMPLE 86

Mutilin 14-(N-azetidin-3-oyl)-carbamate

Mutilin 14-[N-(1-tert-butyloxycarbonyl-azetidin-3-oyl)]-carbamate (350 mg) in dichloromethane (8 ml) was treated with trifluoroacetic acid (0.5 ml) and the solution was kept at room temperature for 5 hours. The solvent was removed under reduced pressure and the residue was dissolved in ethyl acetate (20 ml). The solution was extracted with dilute HCl (10 ml), and the extract was washed with ethyl acetate (10 ml). The aqueous solution was basified (pH 10) using potassium carbonate, and was then extracted with ethyl acetate (3×10 ml). The organic extract was washed with saturated sodium chloride and dried (sodium sulphate). The solvent was removed under reduced pressure to give a white waxy solid (125 mg). The solid was chromatographed on silca gel using 1:9:90 ammonia solution (35%)/methanol/dichloromethane to give the title compound as a white foam (100 mg); $^1$H NMR (1:9 CD$_3$OD:CDCl$_3$) inter alia 3.33 (1H, d, J 6.3 Hz), 4.01 (4H, m), 5.20 (1H, d, J 17.4 Hz), 5.32 (1H, d, J 11.2 Hz), 5.64 (1H, d, J 8.3 Hz), 6.41 (1H, dd, J 17.4, 11.2 Hz); MS(ES) m/z 447 (MH$^+$).

EXAMPLE 87

Mutilin 14-[N-(1-ethyl-piperidin-4-oyl)]-carbamate

Step 1. Ethyl 1-ethyl-isonipecotate

Ethyl isonipecotate (6.28 g) in ethanol (35 ml) was treated with ethyl iodide (6.86 g) and powdered potassium carbonate (10 g). The mixture was stirred and heated under reflux for 20 hours. The mixture was cooled to room temperature and the solid was removed by filtration and was washed with ethanol (2×10 ml). The ethanol was removed from the filtrate by evaporation under reduced pressure, and the resulting residue was partitioned between chloroform (100 ml) and water (50 ml). The organic layer was separated, washed with saturated sodium chloride solution, and dried (sodium sulphate). The solvent was removed by evaporation under reduced pressure to give the title compound as a yellow oil (6.62 g); MS(EI) m/z 185 (M$^+$).

Step 2. 1-Ethyl-isonipecotic acid hydrochloride Ethyl 1-ethyl-isonipecotate (5.5 g) was dissolved in water (22 ml)/c.HCl (39 ml) and the solution was heated under reflux for 4 hours. The solvent was removed by evaporation under reduced pressure. The residue was dissolved in water (30 ml), and the water was removed by evaporation under reduced pressure. The residue was triturated with toluene (50 ml), and the toluene was removed by evaporation under reduced pressure to give a solid which was dried in vacua for 18 hours. The title compound was thus obtained as a white powder (5.4 g); MS(EI) m/z 157 (M$^+$).

Step 3. (3R)-3-Deoxo-11-deoxy-3-methoxy-11-oxo-4-epi-mutilin 14-[N-(1-ethyl-piperidin-4-oyl)]-carbamate 1-Ethyl-isonipecotic acid hydrochloride (0.95 g) was suspended in thionyl chloride (8 ml) and the mixture was stirred and heated under reflux for 3 hours to give a clear yellow solution. The thionyl chloride was removed by evaporation under reduced pressure and the resulting residue was suspended in toluene (5 ml) and the toluene was removed by evaporation under reduced pressure to give 1-ethyl-isonipecotoyl chloride hydrochloride as a white solid. The acid chloride was suspended in dry dichloromethane (20 ml) and silver cyanate (1.5 g) was added. The mixture was stirred and heated under reflux for 1 hour. The mixture was cooled to room temperature and (3R)-3-deoxo-11-deoxy-3-methoxy-11-oxo-4-epi-mutilin (1 g) and triethylamine (0.5 g) were added. The mixture was stirred at room temperature for 16 hours. The mixture was diluted with ethyl acetate (50 ml) and the solid was removed by filtration. The filtrate was washed with saturated sodium bicarbonate and saturated sodium chloride. The solution was dried (sodium sulphate), and the solvent was removed by evaporation under reduced pressure to give a yellow gum. The gum was chromatographed on silica gel using 1:3 ethyl acetate/chloroform and 1:9:90 ammonia solution (35%)/methanol/dichloromethane to give the title compound as a colourless gum (134 mg); $^1$H NMR (CDCl$_3$) inter alia 2.88 (2H, q, J 6.5 Hz), 3.08 (3H, m), 3.22 (3H, s), 3.42 (1H, m), 5.04 (1H, d, J 17.5 Hz), 5.33 (1H, d, J 10.7 Hz), 5.74 (1H, d, J 9.9 Hz), 6.63 (1H, dd, J 17.5, 10.7 Hz), 7.47 (1H, s).

Step 4. Mutilin 14-[N-(1-ethyl-piperidin-4-oyl)]-carbamate (3R)-3-Deoxo-11-deoxy-3-methoxy-11-oxo-4-epi-mutilin 14-[N-(1-ethyl-piperidin-4-oyl)]-carbamate (110 mg) in 1,4-dioxane (0.7 ml) was treated with c.HCl (0.7 ml) and the solution was kept at room temperature for 2.5 hours. The solution was diluted with water (10 ml) and washed with dichloromethane (10 ml). The aqueous phase was basified by careful addition of solid potassium carbonate and the resulting mixture (pH 10) was extracted with chloroform (3×10 ml). The organic extract was dried (sodium sulphate) and the solvent was removed by evaporation under reduced pressure to give the title compound as a white solid (80 mg); $^1$H NMR (CDCl$_3$) inter alia 1.12 (3H, t, J 7.1 Hz), 2.48 (2H, q, J 7.1 Hz), 2.97 (3H, m), 3.37 (1H, dd, J 10.3, 6.6 Hz), 5.24 (1H, d, J 17.5 Hz), 5.37 (1H, d, J 11 Hz), 5.70 (1H, d, J 8.4 Hz), 6.50 (1H, dd, J 17.5, 11 Hz), 7.35 (1H, s); MS(EI) m/z 502 (M$^+$).

EXAMPLE 88

Mutilin 14-{N-[1-(1-methyl-ethyl)-piperidin-4-oyl]}-carbamate

Step 1. Ethyl 1-(1-methyl-ethyl)-isonipecotate

Using the process described in Example 87, Step 1, ethyl isonipecotate (6.28 g) and 2-iodo-propane (7.48 g) were converted into the title compound, which was obtained as a pale yellow oil (7.17 g); MS(EI) m/z 199 (M$^+$).

Step 2. 1-(1-Methyl-ethyl)-isonipecotic acid hydrochloride

Using the process described in Example 87, Step 2, ethyl 1-(1-methyl-ethyl)-isonipecorate (6 g) was converted into the title compound, which was obtained as a white powder (6.1 g); MS(EI) m/z 171 (M$^+$).

Step 3. (3R)-3-Deoxo-11-deoxy-3-methoxy 11-oxo-4-epi-mutilin 14-{N-[1-(1-methyl-ethyl)-piperidin-4-oyl]}-carbamate Using the process described in Example 87, Step 3, 1-(1-methyl-ethyl)-isonipecotic acid hydrochloride (0.96 g) and (3R)-3-deoxo-11-deoxy-3-methoxy-11-oxo-4-epi-mutilin (1 g) were converted into the title compound, which was obtained as a pale yellow gum (195 mg); MS(EI) m/z 530 (M$^+$).

Step 4. Mutilin 14-{N-[1-(1-methyl-ethyl)-piperidin-4-oyl]}-carbamate

Using the process described in Example 87, Step 4, (3R)-3-deoxo-11-deoxy-3-methoxy-11-oxo-4-epi-mutilin 14-{N-[1-(1-methyl-ethyl)-piperidin-4-oyl]}-carbamate (170 mg) was converted into the title compound, which was obtained as a white solid (110 mg); $^1$H NMR (CDCl$_3$) inter alia 1.01 (6H, d, J 6.5 Hz), 2.74 (1H, m), 2.92 (3H, m), 3.37 (1H, dd, J 10.5, 6.6 Hz), 5.23 (1H, d, J 17.4 Hz), 5.36 (1H, d, J 11 Hz), 5.71 (1H, d, J 8.4 Hz), 6.50 (1H, dd, J 17.4, 11 Hz), 7.32 (1H, s); MS(EI) m/z 516 (M$^+$).

EXAMPLE 89

Mutilin 14-{N-[1-(2-methoxy-ethyl)-piperidin-4-oyl]}-carbamate

Step 1. Ethyl 1-(2-methoxy-ethyl)-isonipecotate

Using the process described in Example 87, Step 1, ethyl isonipecotate (6.28 g) and 2-bromoethyl methyl ether (6.12 g) were converted into the title compound, which was obtained as a light yellow oil (8.47 g); MS(EI) m/z 216 (MH$^+$); Found: 216.1601, C$_{11}$H$_{22}$NO$_3$ requires 216.1599.

Step 2. 1-(2-Methoxy-ethyl)-isonipecotic acid hydrochloride

Using the process described in Example 87, Step 2, ethyl 1-(2-methoxy-ethyl)-isonipecotate (7.3 g) was converted into the title compound, which was obtained as a yellow gum (7.1 g); MS(EI) m/z 187 (M$^+$).

Step 3. (3R)-3-Deoxo-11-deoxy-3-methoxy-11-oxo-4-epi-mutilin 14-{N-[1-(2-methoxy-ethyl)-piperidin-4-oyl]}-carbamate Using the process described in Example 87, Step 3, 1-(2-methoxy-ethyl)-isonipecotic acid hydrochloride (0.98 g) and (3R)-3-deoxo-11-deoxy-3-methoxy-11-oxo-4-epi-mutilin (1 g) were converted into the title compound, which was obtained as a pale yellow solid (80 mg); MS(EI) m/z 546 (M$^+$).

Step 4. Mutilin 14-{N-[1-(2-methoxy-ethyl)-piperidin-4-oyl]}-carbamate

Using the process described in Example 87, Step 4, (3R)-3-deoxo-11-deoxy-3-methoxy-11-oxo-4-epi-mutilin 14-{N-[1-(2-methoxy-ethyl)-piperidin-4-oyl]}-carbamate (65 mg) was converted into the title compound, which was obtained as a white solid (50 mg); $^1$H NMR (CDCl$_3$) inter alia 2.58 (2H, t, 5.7 Hz), 3.00 (3H, m), 3.36 (4H, s overlapping m), 3.51 (2H, t, J 5.7 Hz), 5.24 (1H, d, J 17.3 Hz), 5.37 (1H, d, J 11 Hz), 5.70 (1H, d, J 8.4 Hz), 6.50 (1H, dd, J 17.3, 11 Hz), 7.31 (1H, s); MS(EI) m/z 532 (M$^+$); Found: 532.3523, C$_{30}$H$_{48}$N$_2$O$_6$ requires 532.3512.

EXAMPLE 90

Mutilin 14-[N-(1-propyl-piperidin-4-oyl)]-carbamate
Step 1. Ethyl 1-propyl-isonipecotate Using the process described in Example 87, Step 1, ethyl isonipecotate (4.2 g) and propyl iodide (5 g) were converted into the title compound, which was obtained as a light yellow oil (4.39 g); MS(EI) m/z 199 (M$^+$).
Step 2. 1-propyl-isonipecotic acid hydrochloride Using the process described in Example 87, Step 2, ethyl 1-propyl-isonipecotate (4.3 g) was converted into the title compound, which was obtained as an off-white solid (4.4 g); MS(EI) m/z 171 (M$^+$).
Step 3. (3R)-3-Deoxo-11-deoxy-3-methoxy-11-oxo-4-epi-mutilin 14-[N-(1-propyl-piperidin-4-oyl)]-carbamate Using the process described in Example 87, Step 3, 1-propyl-isonipecotic acid hydrochloride (0.5 g) and (3R)-3-deoxo-11-deoxy-3-methoxy-11-oxo-4-epi-mutilin (0.5 g) were converted into the title compound, which was obtained as a colourless gum (65 mg); MS(EI) m/z 530 (M$^+$).
Step 4. Mutilin 14-[N-(1-propyl-piperidin-4-oyl)]-carbamate Using the process described in Example 87, Step 4, (3R)-3-deoxo-11-deoxy-3-methoxy-11-oxo-4-epi-mutilin 14-[N-(1-propyl-piperidin-4-oyl)]-carbamate (50 mg) was converted into the title compound, which was obtained as a white solid (37 mg); $^1$H NMR (CDCl$_3$) inter alia 3.00 (3H, m), 3.36 (1H, dd, J 10. 6.6 Hz), 5.24 (1H, d, J 17.3 Hz), 5.36 (1H, d, J 11 Hz), 5.70 (1H, d, J 8.6 Hz), 6.48 (1H, dd, J 17.3, 11 Hz), 7.34 (1H, s); MS(EI) m/z 516 (M$^+$).

EXAMPLE 91

Mutilin 14-[N-(quinuclidin-4-oyl)]-carbamate
Step 1. (3R)-3-Deoxo-11-deoxy-3-methoxy-11-oxo-4-epi-mutilin 14-[N-(quinuclidin-4-oyl)]-carbamate Using the process described in Example 87, Step 3, quinuclidine 4-carboxylic acid hydrochloride (*Helverica Chimica Acta*, 1974, 57, 2332) (230 mg) and (3R)-3-deoxo-1-deoxy-3-methoxy-11-oxo-4-epi-mutilin (330 mg) were converted into the title compound, which was obtained as a white foam (160 mg); $^1$H NMR (CDCl$_3$) inter alia 1.90 (6H, dd, J 8, 7.4 Hz), 3.10 (6H, dd, J 8, 7.4 Hz)), 3.21 (3H, s), 5.00 (1H, d, J 17.5 Hz), 5.27 (1H, d, J 10.7 Hz), 5.77 (1H, d, J 10 Hz), 6.68 (1H, dd, J 17.5, 10.7 Hz), 7.85 (1H, broad s); MS(ES) m/z 515 (MH$^+$).
Step 2. Mutilin 14-[N-(quinuclidin-4-oyl)]-carbamate Using the process described in Example 87, Step 4, (3R)-3-deoxo-11-deoxy-3-methoxy-11-oxo-4-epi-mutilin 14-[N-(quinuclidin-4-oyl)]-carbamate (140 mg) was converted into the title compound, which was obtained as a white solid (86 mg); $^1$H NMR (CDCl$_3$) inter alia 0.73 (3H, d, J 6.7 Hz), 0.87 (3H, d, J 7 Hz), 1.17 (3H, s), 1.49 (3H, s), 1.68 (6H, dd, J 8, 7.3 z), 2.93 (6H, dd, J 8, 7.3 Hz), 3.34 (1H, dd, J 10, 6.6 Hz), 5.22 (1H, d, J 17.3 Hz), 5.36 (1H, d, J 11 Hz), 5.76 (1H, d, J 8.5 Hz), 6.54 (1H, dd, J 17.3, 11 Hz); MS(ES) m/z 501 (MH$^+$).

EXAMPLE 92

Mutilin 14-[N-(quinuclidin-4-oyl)]-carbamate Hydrochloride

Mutilin 14-[N-(quinuclidin-4-oyl)]-carbamate (71 mg) was dissolved in ethyl acetate (5 ml)/1,4-dioxane (2 ml) and 4M HCl in dioxane (0.2 ml) was added. The solution was concentrated to ca. 1 ml by evaporation of solvent under reduced pressure, and toluene (5 ml) was added to give a white precipitate. The precipitate was collected by filtration, washed with toluene (2 ml), and dried in vacuo to give the title compound as a white solid (79 mg); $^1$H NMR (D$_2$O) inter alia 0.69 (3H, d, J 6 Hz), 0.92 (3H, d, J 6.8 Hz), 1.15 (3H, s), 1.39 (3H, s), 2.16 (6H, dd, J 8.2, 7.5 Hz), 3.42 (6H, dd, J 8.2, 7.5 Hz), 3.58 (1H, d, J 6 Hz), 5.20 (1H, d, J 17.5 Hz), 5.28 (1H, d, J 11.1 Hz), 5.68 (1H, d, J 8.1 Hz), 6.36 (1H, dd, J 17.5, 11.1 Hz).

EXAMPLE 93

Mutilin 14-{N-(1-azabicyclo[2.2.1]heptan-4-oyl)}-carbamate
Step 1. (3R)-3-Deoxo-11-deoxy-3-methoxy-11-oxo-4-epi-mutilin 14-{N-(1-azabicycio[2.2.1]heptan-4-oyl)}-carbamate Using the process described in Example 87, Step 3, 1-azabicyclo[2.2.1]heptane 4-carboxylic acid hydrochloride (*Chemical Abstracrs*, 1989, 110, 95016) (700 mg) and (3R)-3-deoxo-11-deoxy-3-methoxy-11-oxo-4-epi-mutilin (1 g) were converted into the title compound, which was obtained as a white solid (330 mg); $^1$H NMR (CDCl$_3$) inter alia 2.05 (4H, m), 2.72 (4H, m), 3.08 (2H, m), 3.22 (3H, s), 3.44 (1H, m), 5.02 (1H, d, J 17.5 Hz), 5.30 (1H, d, J 11.6 Hz), 5.80 (1H, d, J 9.9 Hz), 6.69 (1H, dd, J 17.5, 11.6 Hz), 7.48 (1H, s); MS(ES) m/z 501 (MH$^+$).
Step 2. Mutilin 14-{N-(1-azabicyclo[2.2.1]heptan-4-oyl)}-carbamate Using the process described in Example 87, Step 4, (3R)-3-deoxo-11-deoxy-3-methoxy-11-oxo-epi-mutilin 14-{N-(1-azabicyclo[2.2.1]heptan 4oyl)}-carbamate (300 mg) was converted into the title compound, which was obtained as a white solid (250 mg); $^1$H NMR (CDCl$_3$) inter alia 2.28 (4H, m), 3.06 (2H, m), 3.37 (1H, broad s), 5.24 (1H, dd, J 17,3, 1.4 Hz), 5.38 (1H, dd, J 11, 1.4 Hz), 5.78 (1H, d, J 8.5 Hz), 6.64 (1H, dd, J 17.3, 11 Hz), 7.38 (1H, s); MS(EI) m/z 486 (M$^+$); Found: 486.3085, C$_{28}$H$_{42}$N$_2$O$_5$ requires 486.3094.

EXAMPLE 94

Mutilin 14-[N-(N,N-dimethylcarbamoyl)]-carbamate
Step 1. (3R)-3-Deoxo-11-deoxy-3-methoxy-11-oxo-4-epi-mutilin 14-[N-(N,N-dimethylcarbamoyl)]-carbamate (3R)-3-Deoxo-11-deoxy-3-methoxy-11-oxo-4-epi-mutilin (270 mg, 0.80 mmol) was combined with dimethylcarbamoyl chloride (0.088 ml, 0.96 mmol) and silver cyanate (197 mg, 1.31 mmol) in dry dichloromethane (15 ml) and the reaction stirred at room temperature for 3 days in subdued light and under an atmosphere of argon. The mixture was filtered through Kieselguhr and the filtrate washed with saturated aqueous sodium hydrogen carbonate (×2) and brine. After drying (MgSO$_4$) purification was accomplished by chromatography on silica gel eluting with 40% ethyl acetate in hexane. The title compound was isolated as a colourless foam (135 mg, 38%); $\nu_{max}$ (CH$_2$Cl$_2$) 3052, 2981, 1771, 1695, 1490 and 1459 cm$^{-1}$; MS(CI) m/z 449 (MH$^+$), 466 (MNH$_4^+$).
Step 2. Mutilin-14-[N-(N,N-dimethylcarbamoyl)]-carbamate The product of Step 1 (110 mg, 0.25 mmol) in dioxane (2 ml) was treated with a saturated solution of zinc chloride in conc. HCl (1 ml) and the reaction stirred at room temperature for 30 minutes. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 70% ethyl acetate in hexane to yield the title compound (90 mg, 83%); v$_{max}$ (CH$_2$Cl$_2$) 3402, 2935, 1774, 1735, 1686 and 1489 cm$^{-1}$; $^1$H NMR (CDCl$_3$) 0.78 (3H, d, J 6.6 Hz), 0.89 (3H, d, J 7.0 Hz), 1.10–1.83 (16H, m) including 1.19 (3H, s) and 1.43 (3H, s), 2.06–2.37 (4H, m), 2.99 (6H, s), 3.37 (1H, dd, J 10.8, 6.7 Hz), 5.20 (1H, dd, J 17.3, 1.5 Hz), 5.36 (1H, dd, J 11.1, 1.5 Hz), 5.71 (1H, d, J 8.4 Hz), 6.53 (1H, dd, J 17.3, 11.1 Hz), 6.54 (1H, bs), MS(CI) m/z 435 (MH$^+$).

EXAMPLE 95

Mutilin 14-[N-(1-methyl (6H)-6-oxopyridine-3-carbonyl)]-carbamate

Step 1. (3R)-3-Deoxo-11-deoxy-3-methoxy-11-oxo-4-epi-mutilin 14-[N-(1-methyl (6H)-6-oxopyridine-3-carbonyl)]-carbamate (3R)-3-Deoxo-11-deoxy-3-methoxy-11-oxo-4-epi-mutilin (500 mg, 1.50 mmol) was combined with 1-methyl (6H)-6oxopyridine-3-carbonyl chloride (600 mg, 3.50 mmol) and silver cyanate (539 mg, 3.59 mmol) in dry dichloromethane (30 ml) and the reaction stirred at room temperature for 20 hours in subdued light and under an atmosphere of argon. The mixture was filtered through Kieselguhr and the filtrate washed with saturated aqueous sodium hydrogen carbonate (×2) and brine. After drying (MgSO$_4$) purification was accomplished by chromatography on silica gel eluting with 80% ethyl acetate in hexane. The title compound was isolated as a colourless foam (559 mg, 73%); v$_{max}$ (CH$_2$Cl$_2$) 3382, 2959, 1779, 1735, 1704 and 1473 cm$^{-1}$; MS(CI) m/z 513 (MH$^+$), 530 (MNH$_4^+$).

Step 2. Mutilin-14-[N-(1-methyl (6H)-6-oxopyridine-3-carbonyl)]-carbamate

The product of Step 1 (550 mg, 1.07 mmol) in dioxane (5 ml) was treated with a saturated solution of zinc chloride in conc. HCl (5 ml) and the reaction stirred at room temperature for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with ethyl acetate to yield the title compound (360 mg, 67%); v$_{max}$ (CH$_2$Cl$_2$) 3427, 2935, 1778, 1734, 1662 and 1479 cm$^{-1}$; $^1$H NMR (CDCl$_3$) 0.78 (3H, d, J 6.6 Hz), 0.87 (3H, d, J 7.0 Hz), 1.08–1.83 (16H, m) including 1.18 (3H, s) and 1.48 (3H, s), 2.08–2.34 (4H, m), 3.36 (1H, dd, J 10.8, 6.6 Hz), 3.59 (3H, s), 5.22 (1H, dd, J 17.3, 1.5 Hz), 5.38 (1H, dd, J 11.1, 1.5 Hz), 5.79 (1H, d, J 8.5 Hz), 6.52 (1H, dd, J 17.3, 11.1 Hz), 6.54 (1H, d, J 9.5 Hz), 7.62 (1H, dd, J 9.5, 2.6 Hz), 7.87 (1H, bs), 8.16 (1H, d, J 2.6 Hz); MS (EI) m/z 498 (M$^+$). Found: 498.2741, C$_{28}$H$_{38}$N$_2$O$_6$ requires 498.2730.

EXAMPLE 96

Mutilin 14-[N-(6-chloronicotinoyl)]-carbamate

Step 1. (3R)-3-Deoxo-11-deoxy-3-methoxy-11-oxo-4-epi-mutilin 14-[N-(6-chloronicotinoyl)]-carbamate (3R)-3-Deoxo-11-deoxy-3-methoxy-11-oxo-4-epi-mutilin (250 mg, 0.75 mmol) was combined with 6-chloronicotinoyl chloride (1.21 g. 7.0 mmol) and silver cyanate (1.0 g, 6.67 mmol) in dry dichloromethane (15 ml) and the reaction stirred at room temperature for 10 minutes in subdued light and under an atmosphere of argon. The mixture was filtered through Kieselguhr and the filtrate washed with saturated aqueous sodium hydrogen carbonate (×2) and brine. After drying (MgSO$_4$) purification was accomplished by chromatography on silica gel eluting with 20% ethyl acetate in hexane. The title compound was isolated as a colourless foam (311 mg, 80%); v$_{max}$ (CH$_2$Cl$_2$) 3413, 2930, 1780, 1719, 1697 and 1488 cm$^{-1}$; MS(CI) m/z 517 (MH$^+$), 534 (MNH$_4^+$).

Step 2. Mutilin-14-[N-(6-chloronicotinoyl)]-carbamate

The product of Step 1 (300 mg, 0.58 mmol) in dioxane (2 ml) was treated with a saturated solution of zinc chloride in conc. HCl (2 ml) and the reaction stirred at room temperature for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 50% ethyl acetate in hexane to yield the title compound (85 mg, 29%); v$_{max}$ (CH$_2$Cl$_2$) 3413, 2939, 1782, 1735, 1697, 1586 and 1489cm$^{-1}$; $^1$H NMR (CDCl$_3$) 0.78 (3H, d, J 6.6 Hz), 0.89 (3H, d, J 7.0 Hz), 1.07–1.82 (16H, m) including 1.18 (3H, s) and 1.50 (3H, s), 2.08–2.33 (4H, m), 3.36 (1H, dd, J 10.7, 6.6 Hz), 5.21 (1H, dd, J 17.3, 1.5 Hz), 5.33 (1H, dd, J 11.1, 1.5 Hz), 5.79 (1H, d, J 8.5 Hz), 6.49 (1H, dd, J 17.3, 11.1 Hz), 7.45 (1H, d, J 8.3 Hz), 8.07 (1H, dd, J 8.3, 2.3 Hz), 8.08 (1H, bs), 8.74 (1H, d, J 2.3 Hz); 6 Hz); MS (EI) m/z 512 (M$^+$). Found: 512.2882, C$_{29}$H$_{40}$N$_2$O$_6$ requires 512.2886.

EXAMPLE 97

Mutilin 14-[N-(2-methoxyisonicotinoyl)]-carbamate

Step 1. (3R)-3-Deoxo-11-deoxy-3-methoxy-11-oxo-4-epi-mutilin 14-[N-(2-methoxyisonicotinoyl)]-carbamate (3R)-3-Deoxo-11-deoxy-3-methoxy-11-oxo-4-epi-mutilin (500 mg, 1.50 mmol) was combined with 2-methoxyisonicorinoyl chloride (600 mg, 3.2 mmol) and silver cyanate (500 mg, 3.30 mmol) in dry dichloromethane (20 ml) and the reaction stirred at room temperature for 3 hours in subdued light and under an atmosphere of argon. The mixture was filtered through Kieselguhr and the filtrate washed with saturated aqueous sodium hydrogen carbonate (×2) and brine. After drying (MgSO$_4$) purification was accomplished by chromatography on silica gel eluting with 30% ethyl acetate in hexane. The title compound was isolated as a colourless foam (598 mg, 78%); v$_{max}$ (CH$_2$Cl$_2$) 3410, 2931, 1781, 1720, 1698, 1559 and 1473 cm$^{-1}$; MS(CI) m/z 517 (MH$^+$), 534 (MNH$_4^+$).

Step 2. Mutilin-14-[N-(2-methoxyisonicotinoyl)]-carbamate

The product of Step 1 (560 mg, 1.09 mmol) in dioxane (4 ml) was treated with a saturated solution of zinc chloride in conc. HCl (4 ml) and the reaction stieed at room temperature for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 50% ethyl acetate in hexane to yield the title compound (374 mg, 69%); v$_{max}$ (CH$_2$Cl$_2$) 3412, 2946, 1782, 1735, 1610, 1559 and 1474 cm$^{-1}$; $^1$H NMR (CDCl$_3$) 0.78 (3H, d, J 6.6 Hz), 0.89 (3H, d, J 7.0 Hz), 1.08–1.84 (16H, m) including 1.20 (3H, s) and 1.49 (3H, s), 2.10–2.37 (4H, m), 3.38 (1H, dd, J 10.6, 6.7 Hz), 3.99 (3H, s), 5.24 (1H, dd, J 17.3, 1.5 Hz), 5.39 (1H, dd, J 11.1, 1.5 Hz), 5.72 (1H, d, J 8.5 Hz), 6.53 (1H, dd, J 17.3, 11.1 Hz), 7.05 (1H, d, J 1.1 Hz), 7.18 (1H, dd, J 5.2, 1.1 Hz), 7.92 (1H, bs), 8.31 (1H, d, J 5.2 Hz); MS (EI) m/z 498 (M$^+$). Found: 498.2726, C$_{28}$H$_{29}$N$_2$O$_6$ requires 498.2730.

EXAMPLE 98

Mutilin 14-[N-(morpholine-4-ylcarbonyl)]-carbamate

Step 1. (3R)-3-Deoxo-11-deoxy-3-methoxy-11-oxo-4-epi-mutilin 14-[N-(morpholine-4-ylcarbonyl)]-carbamate (3R)-3-Deoxo-11-deoxy-3-methoxy-11-oxo-4-epi-mutilin (1.0 g, 3.0 mmol) was combined with 4-morpholine carbonyl chloride (1.40 ml, 12.0 mmol) and silver cyanate (2.0 g, 13.3 mmol) in dry dichloromethane (45 ml) and the reaction stirred at room temperature for 17 days in subdued light and under an atmosphere of argon. The mixture was filtered through Kieselguhr and the filtrate washed with saturated aqueous sodium hydrogen carbonate (×2) and brine. After drying (MgSO$_4$) purification was accomplished by chromatography on silica gel eluting with 50% ethyl acetate in hexane. The title compound was isolated as a colourless foam (990 mg, 67%); $v_{max}$(CH$_2$Cl$_2$) 3394, 2985, 1771, 1736, 1695 and 1421 cm$^{-1}$; MS(CI) m/z 491 (MH$^+$).

Step 2. Mutilin-14-[N-(morpholine-4-ylcarbonyl)]-carbamate

The product of Step 1 (500 mg, 1.02 mmol) in dioxane (5 ml) was treated with a saturated solution of zinc chloride in conc. HCl (5 ml) and the reaction stirred at room temperature for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 70% ethyl acetate in hexane to yield the title compound (180 mg, 37%); $v_{max}$(CH$_2$Cl$_2$) 3391, 2928, 1773, 1735, 1684, 1488 and 1458 cm$^{-1}$; $^1$H NMR (CDCl$_3$) 0.78 (3H, d, J 6.6 Hz), 0.85 (3H, d, J 7.0 Hz), 1.06–1.82 (16H, m) including 1.18 (3H, s) and 1.42 (3H, s), 2.04–2.38 (4H, m), 3.33 (1H, dd, J 10.4, 6.6 Hz), 3.45 (4H, m), 3.70 (4H, m), 5.20 (1H, dd, J 17.3, 1.5 Hz), 5.32 (1H, dd, J 11.1, 1.5 Hz), 5.69 (1H, d, J 8.4 Hz), 6.51 (1H, dd, J 17.3, 11.1 Hz), 6.68 (1H, bs); MS (CI) m/z 477 (MH$^+$).

EXAMPLE 99

Mutilin 14-[N-(thiomorpholine-4-ylcarbonyl)]-carbamate

Step 1. (3R)-3-Deoxo-11-deoxy-3-methoxy-11-oxo-4-epi-mutilin 14-[N-(thiomorpholine-4-ylcarbon yl)]-carbamate A solution of (3R)-3-deoxo-11-deoxy-3-methoxy-11-oxo-4-epi-mutilin (250 mg, 0.75 mmol) in diethyl ether (5 ml) was added to a solution of N-(chlorocarbonyl)-isocyanate (0.060 ml, 0.75 mmol) in diethyl ether (5 ml) under an atmosphere of argon at −50° C. The temperature was raised to 0° C. over 1.5 hours and then a solution of thiomorpholine (0.075 ml, 0.75 mmol) and triethylamine (0.079 ml, 0.75 mmol) in diethyl ether (5 ml) was added dropwise. The reaction mixture was stirred for 2 hours at room temperature and then partitioned between 0.5M hydrochloric acid and ethyl acetate. The organic layer was washed with brine. After drying (MgSO$_4$) purification was accomplished by chromatography on silica gel eluting with 30% ethyl acetate in hexane. The title compound was isolated as a colourless foam (144 mg, 38%); $v_{max}$(CH$_2$Cl$_2$) 3393, 2928, 1771, 1739, 1682 and 1458 cm$^{-1}$; MS(Electrospray) m/z 505 [M−H]$^-$.

Step 2. Mutilin-14-[N-(thiomorpholine-4-ylcarbonyl)]-carbamate

The product of Step 1 (170 mg, 0.34 mmol) in dioxane (1.5 ml) was treated with a saturated solution of zinc chloride in conc. HCl (1.5 ml) and the reaction stirred at room temperature for 1 hour. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 50% ethyl acetate in hexane to yield the title compound (115 mg, 69%); $v_{max}$(CH$_2$Cl$_2$) 3393, 2930, 1772, 1736, 1682, 1458 and 1426 cm$^{-1}$; $^1$H NMR (CDCl$_3$) 0.75 (3H, d, J 6.6 Hz), 0.89 (3H, d, J 7.0 Hz), 1.09–1.83 (16H, m) including 1.18 (3H, s) and 1.45 (3H, s), 2.04–2.35 (4H, m), 2.69 (4H, m), 3.34 (1H, dd, J 10.6, 6.6 Hz), 3.73 (4H, m), 5.20 (1H, dd, J 17.3, 1.5 Hz), 5.33 (1H, dd, J 11.1, 1.5 Hz), 5.69 (1H, d, J 8.7 Hz), 6.50 (1H, dd, J 17.3, 11.1 Hz), 6.65 (1H, bs); MS (CI) m/z 493 (MH$^+$).

EXAMPLE 100

Mutilin 14-[N-(thiomorpholine-4-ylcarbonyl-1,1-dioxide)]-carbamate

Step 1. (3R)-3-Deoxo-11-deoxy-3-methoxy-11-oxo-4-epi-mutilin 14-[N-(thiomorpholine-4-ylcarbonyl-1,1-dioxide)]-carbarnate A solution of (3R)-3-deoxo-11-deoxy-3-methoxy-11-oxo-4-epi-mutilin 14-[N-(thiomorpholine-4-ylcarbonyl)] carbamate (120 mg, 0.24 mmol) in methanol (2 ml) was cooled to 0° C. and treated with a solution of oxone (442 mg, 0.72 mmol) in water (2 ml). The reaction mixture was stirred for 1 hour at room temperature and then partitioned between water and dichloromethane. The organic layer was washed with water and brine. After drying (MgSO$_4$) purification was accomplished by chromatography on silica gel eluting with 50% ethyl acetate in hexane. The title compound was isolated as a colourless foam (73 mg, 57%); $v_{max}$(CH$_2$Cl$_2$) 3387, 2931, 1775, 1742, 1694 and 1461 cm$^{-1}$; MS(CI) ml: 539 (MH$^+$).

Step 2. Mutilin-14-[N-(thiomorpholine-4-ylcarbonyl-1,1-dioxide)]-carbamate

The product of Step 1 (220 mg, 0.40 mmol) in dioxane (2 ml) was treated with a saturated solution of zinc chloride in conc. HCl (2 ml) and the reaction stirred at room temperature for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 80% ethyl acetate in hexane to yield the title compound (120 mg, 57%); $v_{max}$(CH$_2$Cl$_2$) 3388, 2938, 1776, 1736, 1692, 1465 and 1426 cm$^{-1}$; $^1$H NMR (CDCl$_3$) 0.72 (3H, d, J 6.6 Hz), 0.90 (3H, d, J 7.0 Hz), 1.09–1.83 (16H, m) including 1.18 (3H, s) and 1.42 (3H, s), 2.07–2.34 (4H, m), 3.18 (4H, m), 3.37 (1H, dd, J 10.6, 6.5 Hz), 3.92 (4H, m), 5.22 (1H, dd, J 17.3, 1.5 Hz), 5.33 (1H, dd, J 11.1, 1.5 Hz), 5.67 (1H, d, J 8.4 Hz), 6.46 (1H, dd, J 17.3, 11.1 Hz), 6.80 (1H, bs); MS (CI) m/z 542 (MNH$_4^+$).

EXAMPLE 101

Mutilin 14-[N-(1-methylpiperazin-4-ylcarbonyl)]-carbamate

Step 1. (3R)-3-Deoxo-11-deoxy-3-methoxy-11-oxo-4-epi-mutilin 14-[N-(1-methylpiperazin-4-ylcarbonyl)]-carbamate A solution of (3R)-3-deoxo-11-deoxy-3-methoxy-11-oxo-4-epi-mutilin (500 mg, 1.5 mmol) in diethyl ether (10 ml) was added to a solution of N-(chlorocarbonyl)-isocyanate (0.12 ml, 1.5 mmol) in diethyl ether (10 ml) under an atmosphere of argon at −50° C. The temperature was raised to 0° C. over 1.5 hours and then a solution of 1-methylpiperazine (0.16 ml, 1.5 mmol) and triethylamine (0.16 ml, 1.5 mmol) in diethyl ether (10 ml) was added dropwise. The reaction mixture was stirred for 2 hours at room temperature and then partitioned between 0.5M hydrochloric acid and ethyl acetate. The organic layer was washed with brine. After drying (MgSO$_4$) purification was accomplished by chromatography on silica gel eluting with 20% methanol in ethyl acetate. The title compound was isolated as a colourless foam (170 mg, 23%); $v_{max}$(CH$_2$Cl$_2$) 3394, 2942, 1769, 1740, 1684 and 1458 cm$^{-1}$; MS(CI) m/z 504 (MH$^+$).

Step 2. Mutilin-14-[N-(1-methyvpiperazin-4-ylcarbonyl)]-carbamate

The product of Step 1 (165 mg, 0.32 mmol) in dioxane (2 ml) was treated with a saturated solution of zinc chloride in conc. HCl (2 ml) and the reaction stirred at room temperature for 3 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 30% methanol in ethyl acetate to yield the title compound (81 mg, 52%); $v_{max}$ (CH$_2$Cl$_2$) 3392, 2941, 1771, 1736, 1683, 1488 and 1458 cm$^{-1}$; $^1$H NMR (CDCl$_3$) 0.75 (3H, d, J 6.6 Hz), 0.86 (3H, d, J 7.0 Hz), 1.00–1.80 (16H, m) including 1.12 (3H, s) and 1.38 (3H, s), 2.02–2.25 (4H, m), 2.30 (3H, s), 2.41 (4H, m), 3.35 (1H, m), 3.45 (4H, m), 5.20 (1H, dd, J 17.3, 1.5 Hz), 5.35 (1H, dd, J 11.1, 1.5 Hz), 5.70 (1H, d, J 8.4 Hz), 6.50 (1H, dd, J 17.3, 11.1 Hz), 6.60 (1H, bs); MS (CI) m/z 490 (MH$^+$).

EXAMPLE 102

Mutilin 14-[N-(4-{4-(2-morpholinoethyloxy)}-benzoyl)]-carbamate

Step 1. (3R)-3-Deoxo-11-deoxy-3-methoxy-11-oxo-4-epi-mutilin 14-[N-(4-acetoxybenzoyl)]-carbamate (3R)-3-Deoxo-11-deoxy-3-methoxy-11-oxo-4-epi-mutilin (1.0 mg, 3.0 mmol) was combined with 4-acetoxybenzoyl chloride (2.3 g, 11.0 mmol) and silver cyanate (1.7 g, 11.3 mmol) in dry dichloromethane (30 ml) and the reaction stirred at room temperature for 3 hours in subdued light and under an atmosphere of argon. The mixture was filtered through Kieselguhr and the filtrate washed with saturated aqueous sodium hydrogen carbonate (×2) and brine. After drying (MgSO$_4$) purification was accomplished by chromatography on silica gel eluting with 40% ethyl acetate in hexane. The title compound was isolated as a colourless foam (1.5 g, 93%); $^1$H NMR (CDCl$_3$) 0.90 (3H, d, J 6.6 Hz), 1.02 (3H, d, J 7.0 Hz), 1.10–1.77 (12H, m) including 1.22 (3H, s) and 1.30 (3H, s), 1.69–1.76 (2H, m), 1.95–2.05 (2H, m), 2.22 (1H, m), 2.32 (3H, s), 2.53 (1H, dd, J 15.3, 10.1 Hz), 2.90 (1H, q, J 6.5 Hz), 3.20 (3H, s), 3.47 (1H, m), 5.02 (1H, d, J 17.5 Hz), 5.30 (1H, d, J 10.7 Hz), 5.87 (1H, d, J 10.0 Hz), 6.72 (1H, dd, J 17.5, 10.7 Hz), 7.20 (2H, d, J 8.7 Hz), 7.88 (2H,d, J 8.7 Hz), 7.95 (1H, bs).

Step 2. (3R)-3-Deoxo-11-deoxy-3-methoxy-11-oxo-4-epi-mutilin 14-[N-(4-hydroxybenzoyl)]-carbamate The product of Step 1 (1.50 g, 2.78 mmol) in dioxane (20 ml) was treated with 1M aqueous sodium hydroxide solution (9 ml). The reaction mixture was stirred at room temperature for 30 minutes under an atmosphere of argon. The mixture was diluted with ethyl acetate and dilute aqueous hydrochloric acid, the layers separated, and the organic phase washed with brine. After drying (MgSO$_4$) purification was accomplished by chromatography on silica gel eluting with 50% ethyl acetate in hexane. The title compound was isolated as a colourless foam (1.30 g, 94%); $^1$H NMR (CDCl$_3$) 0.89 (3H, d, J 6.6 Hz), 1.00 (3H, d, J 7.0 Hz), 1.09–1.70 (12H, m) including 1.20 (3H, s) and 1.30 (3H, s), 1.70–1.79 (2H, m), 1.97–2.03 (2H, m), 2.20 (1H, m), 2.53 (1H, dd, J 15.3, 10.1 Hz), 2.92 (1H, q, J 6.5 Hz), 3.23 (3H, s), 3.49 (1H, m), 5.01 (1H, d, J 17.5 Hz), 5.29 (1H, d, J 10.7 Hz), 5.85 (1H, d, J 10.0 Hz), 6.12 (1H,exch), 6.70 (1H, dd, J 17.5, 10.7 Hz), 6.94 (1H, d, J 8.7 Hz), 7.74 (2H,d, J 8.7 Hz), 7.94 (1H, bs).

Step 3. (3R)-3-Deoxo-11-deoxy-3-methoxy-11-oxo-4-epi-mutilin 14-[N-(4-{4-(2-morpholinoethyloxy)}benzoyl)]-carbamate The product of Step 2 (700 mg, 1.41 mmol) in acetone (14 ml) was treated with potassium carbonate (389 mg, 2.82 mmol) and 4-(2-chloroethyl)morpholine hydrochloride (262 mg, 1.41 mmol). The reaction mixture was heated to reflux for 16 hours under an atmosphere of argon. The mixture was diluted with ethyl acetate and water and the layers separated. After drying (MgSO$_4$) purification was accomplished by chromatography on silica gel eluting with 5% ethanol in ethyl acetate. The title compound was isolated as a colourless foam (275 mg, 32%); $v_{max}$ (CH$_2$Cl$_2$) 3421, 2932, 1774, 1726, 1698, 1605 and 1474 cm$^{-1}$; MS(Electrospray) m/z 611 (MH$^+$).

Step 4. Mutilin-14-[N-(4-{4-(2-morpholinoethyloxy)}benzoyl)]-carbamate

The product of Step 3 (265 mg, 0.43 mmol) in dioxane (2 ml) was treated with a saturated solution of zinc chloride in conc. HCl (2 ml) and the reaction stirred at room temperature for 1 hour. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 70% ethyl acetate in hexane to yield the title compound (160 mg, 62%); $v_{max}$ (CH$_2$Cl$_2$) 3418, 2939, 1775, 1732, 1605 and 1476 cm$^{-1}$; $^1$H NMR (CDCl$_3$) 0.79 (3H, d, J 6.6 Hz), 0.86 (3H, d, J 7.0 Hz), 1.10–1.82 (16H, m) including 1.15 (3H, s) and 1.49 (3H, s), 2.08–2.39 (4H, m), 2.54 (4H, m), 2.80 (2H, t, J 5.7 Hz), 3.36 (1H, dd, J 10.8, 6.5 Hz), 3.72 (4H, m), 4.13 (2H, t, J 5.7 Hz), 5.21 (1H, dd, J 17.3, 1.5 Hz), 5.37 (1H, dd, J 11.1, 1.5 Hz), 5.82 (1H, d, J 8.4 Hz), 6.55 (1H, dd, J 17.3, 11.1 Hz), 6.92 (2H, d, J 8.9 Hz), 7.78 (2H, d, J 8.9 Hz), 7.83 (1H, bs); MS(CI) m/z 597 (MH$^+$).

EXAMPLE 103

Mutilin 14-[N-(3-(2-dimethylaminoethoxy)-benzoyl)]-carbamate

Step 1. (3R)-3-Deoxo-11-deoxy-3-methoxy-11-oxo-4-epi-mutilin 14-[N-(3-acetoxybenzoyl)]-carbamate (3R)-3-Deoxo-1-deoxy-3-methoxy-11-oxo-4-epi-mutilin (1.0 mg, 3.0 mmol) was combined with 3-acetoxybenzoyl chloride (1.8 g, 8.4 mmol) and silver cyanate (1.31 g, 8.7 mmol) in dry dichloromethane (30 ml) and the reaction stirred at room temperature for 2 hours in subdued light and under an atmosphere of argon. The mixture was filtered through Kieselguhr and the filtrate washed with saturated aqueous sodium hydrogen carbonate (×2) and brine. After drying (MgSO$_4$) purification was accomplished by chromatography on silica gel eluting with 5% ethyl acetate in dichloromethane to yield the title compound (960 mg, 59%); $v_{max}$ (CH$_2$Cl$_2$) 3414, 2929, 1775, 1715, 1698 and 1475 cm$^{-1}$; MS (EI) m/z 539 (M$^+$). Found: 539.2883, C$_{31}$H$_{41}$NO$_7$ requires 539.2883.

Step 2. (3R)-3-Deoxo-11-deoxy-3-methoxy-11-oxo-4-epi-mutilin 14-[N-(3-hydroxybenzoyl)]-carbamate The product of Step 1 (940 mg, 1.74 mmol) in dioxane (14 ml) was treated with 1M aqueous sodium hydroxide solution (5.6 ml). The reaction mixture was stirred at room temperature for 30 minutes under an atmosphere of argon. The mixture was diluted with ethyl acetate and dilute aqueous hydrochloric acid, the layers separated, and the organic phase washed with brine. After drying (MgSO$_4$) purification was accomplished by chromatography on silica gel eluting with 40% ethyl acetate in hexane to yield the title compound (629 mg, 73%); $v_{max}$ (CH$_2$Cl$_2$) 3575, 3414, 2929, 1776, 1713, 1697 and 1479 cm$^{-1}$; MS (CI) m/z 498 (MH$^+$), 515 (MNH$_4^+$).

Step 3. (3R)-3-Deoxo-11-deoxy-3-methoxy-11-oxo-4-epi-mutilin 14-[N-(3-(2-dimethylaminoethoxy)benzoyl)]-carbamate The product of Step 2 (590 mg, 1.19 mmol) in acetone (10 ml) was treated with potassium carbonate (328 mg, 2.38 mmol) and 2-dimethylaminoethyl chloride hydrochloride (171 mg, 1.19 mmol). The reaction mixture was heated to reflux for 16 hours under an atmosphere of argon. The mixture was diluted with ethyl acetate and water and the layers separated. After drying (MgSO$_4$) purification was accomplished by chromatography on silica gel eluting with 10% ethanol in ethyl acetate to yield the title compound (138 mg, 20%); $v_{max}$ (CH$_2$Cl$_2$) 3419, 2943, 1776, 1713, 1698, 1583 and 1477 cm$^{-1}$; MS (EI) m/z 568 (M$^+$). Found: 568.3516, C$_{33}$H$_{48}$N$_2$O$_6$ requires 568.3512.

Step 4. Mutilin-14-[N-(3-(2-dimethylaminoethoxy)benzoyl)]-carbamate

The product of Step 3 (120 mg, 0.21 mmol) in dioxane (2 ml) was treated with a saturated solution of zinc chloride in conc. HCl (1 ml) and the reaction stirred at room temperature for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 3% (9:1 methanol:ammonia (35%)) in dichloromethane to yield the title compound (69 mg, 59%); $v_{max}$ (CH$_2$Cl$_2$) 3412, 2961, 1778, 1732, 1706 and 1479 cm$^{-1}$; $^1$H NMR (CDCl$_3$) 0.80 (3H, d, J 6.6 Hz), 0.89 (3H, d, J 7.0 Hz), 1.15–1.83 (16H, m) including 1.19 (3H, s) and 1.52 (3H, s), 2.03–2.28 (4H, m), 2.34 (6H, s), 2.74 (2H, t, J 5.6 Hz), 3.39 (1H, m), 4.10 (2H, t, J 5.6 Hz), 5.22 (1H, dd, J 17.3, 1.5 Hz), 5.39 (1H, dd, J 11.1, 1.5 Hz), 5.83 (1H, d, J 8.4 Hz), 6.56 (1H, dd, J 17.3, 11.1 Hz), 7.12 (1H, m), 7.28–7.40 (3H, m), 7.92 (1H, bs); MS (EI) m/z 554 (M$^+$). Found: 554.3368, C$_{32}$H$_{48}$N$_2$O$_6$ requires 554.3356.

EXAMPLE 104

Mutilin 14-[N-(4-(3-dimethylaminopropyl)-benzoyl)]-carbamate

Step 1. (3R)-3-Deoxo-11-deoxy-3-methoxy-11-oxo-4-epi-mutilin 14-[N-(4-(3-dimethylaminopropyl)benzoyl)]-carbamate (3R)-3-Deoxo-11-deoxy-3-methoxy-11-oxo-4-epi-mutilin 14-[N-(4-hydroxy-benzoyl)]-carbamate (370 mg, 0.74 mmol) in acetone (10 ml) was treated with potassium carbonate (207 mg, 1.50 mmol) and 3-dimethylaminopropyl chloride hydrochloride (118 mg, 0.75 mmol). The reaction mixture was heated to reflux for 16 hours under an atmosphere of argon. The mixture was diluted with ethyl acetate and water, and the layers separated. After drying (MgSO$_4$) purification was accomplished by chromatography on silica gel eluting with 5% (9:1 methanol:ammonia (35%)) in dichloromethane to yield the title compound (170 mg, 39%); $v_{max}$ (CH$_2$Cl$_2$) 3425, 2943, 1774, 1697, 1605 and 1468 cm$^{-1}$; MS (EI) m/z 582 (M$^+$). Found: 582.3675, C$_{34}$H$_{50}$N$_2$O$_6$ requires 582.3669.

Step 2. Mutilin-14-[N-(4-(3-dimethylaminopropyl)benzoyl)]-carbamate

The product of Step 1 (152 mg, 0.26 mmol) in dioxane (1 ml) was treated with a saturated solution of zinc chloride in conc. HCl (1 ml) and the reaction stirred at room temperature for 1.5 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 5% (9:1 methanol:ammonia (35%)) in dichloromethane to yield the title compound (80 mg, 54%); $v_{max}$ (CH$_2$Cl$_2$) 3418, 2956, 1775, 1732, 1605 and 1477 cm$^{-1}$; $^1$H NMR (CDCl$_3$) 0.78 (3H, d, J 6.6 Hz), 0.87 (3H, d, J 7.0 Hz), 1.05–1.85 (16H, m) including 1.18 (3H, s) and 1.50 (3H, s), 1.95–2.30 (6H, m), 2.34 (6H, s), 2.55 (2H, t, J 7.1 Hz), 3.42 (1H, m), 4.08 (2H, t, J 6.3 Hz), 5.21 (1H, dd, J 17.3, 1.5 Hz), 5.37 (1H, dd, J 11.1, 1.5 Hz), 5.82 (1H, d, J 8.4 Hz), 6.56 (1H, dd, J 17.3, 11.1 Hz), 6.93 (2H, d, J 8.8 Hz), 7.74 (2H, d, J 8.8 Hz), 7.85 (1H, bs); MS (EI) m/z 568 (M$^+$). Found: 568.3499, C$_{33}$H$_{48}$N$_2$O$_6$ requires 568.3512.

EXAMPLE 105

Mutilin 14-[N-(4-[2-pyrrolidin-1-yl-ethoxy])-benzoyl)]-carbamate

Step 1. (3R)-3-Deoxo-11-deoxy-3-methoxy-11-oxo-4-epi-mutilin 14-[N-(4-[2-pyrrolidin-1-yl-ethoxy]benzoyl)]-carbamate (3R)-3-Deoxo-11-deoxy-3-methoxy-11-oxo-4-epi-mutilin 14-[N-(4-hydroxy-benzoyl)]-carbamate (600 mg, 1.21 mmol) in acetone (10 ml) was treated with potassium carbonate (333 mg, 2.41 mmol) and 1-(2-chloroethyl) pyrrolidine hydrochloride (205 mg, 1.21 mmol). The reaction mixture was heated to reflux for 16 hours under an atmosphere of argon. The mixture was diluted with ethyl acetate and water and the layers separated. After drying (MgSO$_4$) purification was accomplished by chromatography on silica gel eluting with 3% (9:1 methanol:ammonia (35%)) in dichloromethane to yield the title compound (302 mg, 42%); $v_{max}$ (CH$_2$Cl$_2$) 3053, 2985, 1774, 1697, 1605 and 1421 cm$^{-1}$; MS (CI) m/z 595 (MH$^+$).

Step 2. Mutilin-14-[N-(4-[2-pyrrolidin-1-yl-ethoxy]benzoyl)]-carbamate

The product of Step 1 (280 mg, 0.47 mmol) in dioxane (2 ml) was treated with a saturated solution of zinc chloride in conc. HCl (2 ml) and the reaction stirred at room temperature for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 4% (9:1 methanol:ammonia (35%)) in dichloromethane to yield the title compound (52 mg, 19%); $v_{max}$ (CH$_2$Cl$_2$) 3427, 1775, 1732, 1711, 1606 and 1478 cm$^{-1}$; $^1$H NMR (CDCl$_3$) 0.79 (3H, d, J 6.6 Hz), 0.89 (3H, d, J 7.0 Hz), 1.10–1.85 (20H, m) including 1.18 (3H, s) and 1.52 (3H, s), 2.09–2.40 (4H, m), 2.62 (4H, m), 2.92 (2H, t, J 5.8 Hz), 3.46 (1H, m), 4.12 (2H, t, J 5.8 Hz), 5.22 (1H, dd, J 17.3, 1.5 Hz), 5.38 (1H, dd, J 11.1, 1.5 Hz), 5.82 (1H, d, J 8.4 Hz), 6.58 (1H, dd, J 17.3, 11.1 Hz), 6.97 (2H, d, J 8.8 Hz), 7.75 (2H, d, J 8.8 Hz), 7.80 (1H, bs); MS (CI) m/z 581 (MH$^+$).

EXAMPLE 106

Mutilin 14-[N-(4-[3-(4-methylpiperazin-1-yl)-propyloxy]-benzoyl)]-carbamate

Step 1. (3R)-3-Deoxo-11-deoxy-3-methoxy-11-oxo-4-epi-mutilin 14-[N-(4-[3-(4-methylpiperazin-1-yl)-propyloxy]benzoyl)]-carbamate (3R)-3-Deoxo-11-deoxy-3-methoxy-11-oxo-4-epi-mutilin 14-[N-(4-hydroxybenzoyl)]-carbamate (600 mg, 1.21 mmol) in acetone (10 ml) was treated with potassium carbonate (480 mg, 3.47 mmol) and 1-(3-chloropropyl)-4-methylpiperazine dihydrochloride (302 mg, 1.21 mmol). The reaction mixture was heated to reflux for 16 hours under an atmosphere of argon. The mixture was diluted with ethyl acetate and water and the layers separated. After drying (MgSO$_4$) purification was accomplished by chromatography on silica gel eluting with 5% (9:1 methanol:ammonia (35%)) in dichloromethane to yield the title compound (230 mg, 30%); $v_{max}$ (CH$_2$Cl$_2$) 3420, 2941, 1774, 1697, 1605 and 1467 cm$^{-1}$; MS (EI) m/z 637 (M$^+$). Found: 637.4085, C$_{37}$H$_{55}$N$_3$O$_6$ requires 637.4091.

Step 2. Mutilin-14-[N-(4-[3-(4-methylpiperazin-1-yl)-propyloxy)benzoyl)]-carbamate The product of Step 1 (200 mg, 0.31 mmol) in dioxane (2 ml) was treated with a saturated solution of zinc chloride in conc. HCl (2 ml) and the reaction stirred at room temperature for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried ($MgSO_4$) and purified by chromatography on silica gel eluting with 5% (9:1 methanol:ammonia (35%)) in dichloromethane to yield the title compound (80 mg, 41%); $v_{max}$ (KBr) 3427, 2924, 1753, 1727, 1689, 1605 and 1465 $cm^{-1}$; $^1H$ NMR ($CDCl_3$) 0.80 (3H, d, J 6.6 Hz), 0.87 (3H, d, J 7.0 Hz), 1.14–2.52 (35H, m) including 1.18 (3H, s), 1.52 (3H, s) and 2.29 (3H, s), 3.36 (1H, m), 4.08 (2H, t, J 6.3 Hz), 5.21 (1H, dd, J 17.3, 1.5 Hz), 5.38 (1H, dd, J 11.1, 1.5 Hz), 5.82 (1H, d, J 8.4 Hz), 6.57 (1H, dd, J 17.3, 11.1 Hz), 6.94 (2H, d, J 8.8 Hz), 7.73 (2H, d, J 8.8 Hz), 7.81 (1H, bs); MS (EI) m/z 623 ($M^+$). Found: 623.3921, $C_{36}H_{53}N_3O_6$ requires 623.3921.

EXAMPLE 107

Mutilin 14-[N-(3-fluoro-4-hydroxybenzoyl)]-carbamate

Step 1. (3R)-3-Deoxo-11-deoxy-3-methoxy-11-oxo-4-epi-mutilin 14-[N-(4-acetoxy-3-fluorobenzoyl)]-carbamate (3R)-3-Deoxo-11-deoxy-3-methoxy-11-oxo-4-epi-mutilin (1.0 mg, 3.0 mmol) was combined with 4-acetoxy-3-fluorobenzoyl chloride (1.7 g, 7.5 mmol) and silver cyanate (1.20 g, 8.0 mmol) in dry dichloromethane (30 ml) and the reaction stirred at room temperature for 2 hours in subdued light and under an atmosphere of argon. The mixture was filtered through Kieselguhr and the filtrate washed with saturated aqueous sodium hydrogen carbonate (×2) and brine. After drying ($MgSO_4$) purification was accomplished by chromatography on silica gel eluting with 5% ethyl acetate in dichloromethane to yield the title compound (1.61 g, 96%); $v_{max}$ ($CH_2Cl_2$) 3413, 2930, 1777, 1716, 1697 and 1479 $cm^{-1}$; MS (CI) m/z 575 ($MNH_4^+$).

Step 2. (3R)-3-Deoxo-11-deoxy-3-methoxy-11-oxo-4-epi-mutilin 14-[N-(3-fluoro-4-hydroxybenzoyl)]-carbamate The product of Step 1 (1.59 g, 2.85 mmol) in dioxane (20 ml) was treated with 1M aqueous sodium hydroxide solution (9 ml). The reaction mixture was stirred at room temperature for 30 minutes under an atmosphere of argon. The mixture was diluted with ethyl acetate and dilute aqueous hydrochloric acid, the layers separated, and the organic phase washed with brine. After drying ($MgSO_4$) purification was accomplished by chromatography on silica gel eluting with 40% ethyl acetate in hexane to yield the title compound (1.42 g, 96%); $v_{max}$ ($CH_2Cl_2$) 3547, 3417, 2930, 1776, 1713, 1697, 1618 and 1479 $cm^{-1}$; MS (Electrospray) m/z 514 [M-H]$^-$.

Step 3. Mutilin-14-[N-(3-nluoro-4-hydroxybenzoyl)]-carbamate

The product of Step 2 (200 mg, 0.39 mmol) in dioxane (1 ml) was treated with a saturated solution of zinc chloride in conc. HCl (2 ml) and the reaction stirred at room temperature for 1.5 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried ($MgSO_4$) and purified by chromatography on silica gel eluting with 60% ethyl acetate in hexane to yield the title compound (110 mg, 56%); $v_{max}$ (KBr) 3307, 2931, 1731, 1690, 1618, 1504 and 1457 $cm^{-1}$; $^1H$ NMR ($CDCl_3$ + $d_6DMSO$) 0.72 (3H, d, J 6.6 Hz), 0.83 (3H, d, J 7.0 Hz), 1.05–1.76 (16H, m) including 1.10 (3H, s) and 1.42 (3H, s), 1.85–2.34 (5H, m), 3.39 (1H, dd, J 10.1, 6.6 Hz), 5.13 (1H, dd, J 17.3, 1.5 Hz), 5.26 (1H, dd, J 11.1, 1.5 Hz), 5.72 (1H, d, J 8.4 Hz), 6.50 (1H, dd, J 17.3, 11.1 Hz), 6.92 (1H, m), 7.45 (1H, m), 7.58 (1H,m), 8.99 (1H, bs); MS (CI) m/z 519 ($MNH_4^+$).

EXAMPLE 108

Mutilin 14-[N-(4-[2-dimethylaminoethoxy]-3-fluorobenzoyl)]-carbamate

Step 1. (3R)-3-Deoxo-11-deoxy-3-methoxy-11-oxo-4-epi-mutilin 14-[N-(4-[2-dimethylaminoethoxy]-3-fluorobenzoyl)]-carbamate (3R)-3-Deoxo-11-deoxy-3-methoxy-11-oxo-4-epi-mutilin 14-[N-(3-fluoro-4-hydroxybenzoyl)]-carbamate (613 mg, 1.19 mmol) in acetone (10 ml) was treated with potassium carbonate (328 mg, 2.38 mmol) and 2-dimethylaminoethyl chloride hydrochloride (171 mg, 1.19 mmol). The reaction mixture was heated to reflux for 16 hours under an atmosphere of argon. The mixture was diluted with ethyl acetate and water and the layers separated. After drying ($MgSO_4$) purification was accomplished by chromatography on silica gel eluting with 2% (9:1 methanol:ammonia (35%)) in dichloromethane to yield the title compound (360 mg, 52%); $v_{max}$ ($CH_2Cl_2$) 3419, 2943, 1776, 1697, 1615 and 1497 $cm^{-1}$; MS (CI) m/z 587 ($MH^+$).

Step 2. Mutilin-14-[N-(4-[dimethylaminoethoxy]-3-fluorobenzoyl)]-carbamate

The product of Step 1 (350 mg, 0.59 mmol) in dioxane (2 ml) was treated with a saturated solution of zinc chloride in conc. HCl (2 ml) and the reaction stirred at room temperature for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried ($MgSO_4$) and purified by chromatography on silica gel eluting with 5% (9:1 methanol:ammonia (35%)) in dichloromethane to yield the title compound (203 mg, 60%); $v_{max}$ ($CH_2Cl_2$) 3414, 2944, 1777, 1732, 1713, 1615 and 1479 $cm^{-1}$; $^1H$ NMR ($CDCl_3$) 0.80 (3H, d, J 6.6 Hz), 0.89 (3H, d, J 7.0 Hz), 1.16–1.83 (16H, m) including 1.18 (3H, s) and 1.49 (3H, s), 2.10–2.29 (4H, m), 2.33 (6H, s), 2.79 (2H, t, J 5.7 Hz), 3.36 (1H, m), 4.17 (2H, t, J 5.7 Hz), 5.21 (1H, dd, J 17.3, 1.5 Hz), 5.38 (1H, dd, J 11.1, 1.5 Hz), 5.82 (1H, d, J 8.4 Hz), 6.54 (1H, dd, J 17.3, 11.1 Hz), 7.01 (1H, m), 7.52–7.60 (2H, m), 7.82 (1H, bs); MS (CI) m/z 573 ($MH^+$).

EXAMPLE 109

Mutilin 14-[N-(4-[2-dimethylaminoethoxy]-3-methoxybenzoyl)]-carbamate

Step 1. (3R)-3-Deoxo-11-deoxy-3-methoxy-11-oxo-4-epi-mutilin 14-[N-(4-acetoxy-3-methoxybenzoyl)]-carbamate (3R)-3-Deoxo-11-deoxy-3-methoxy-11-oxo-4-epi-mutilin (1.0 mg, 3.0 mmol) was combined with 4-acetoxy-3-methoxybenzoyl chloride (820 mg, 4.75 mmol) and silver cyanate (715 mg, 4.77 mmol) in dry dichloromethane (30 ml) and the reaction stirred at room temperature for 2 hours in subdued light and under an atmosphere of argon. The mixture was filtered through Kieselguhr and the filtrate washed with saturated aqueous sodium hydrogen carbonate (×2) and brine. After drying ($MgSO_4$) purification was accomplished by chromatography on silica gel eluting with 50% ethyl acetate in dichloromethane to yield the title compound (1.37 g, 80%); $v_{max}$ ($CH_2Cl_2$) 3417, 2931, 1775, 1713, 1698, 1604 and 1479 $cm^{-1}$; MS (EI) m/z 569 ($M^+$). Found: 569.2991, $C_{32}H_{43}NO_8$ requires 569.2989.

Step 2. (3R)-3-Deoxo-11-deoxy-3-methoxy-11-oxo-4-epi-mutilin 14-[N-(4-hydroxy-3-methoxybenzoyl)]-carbamate The product of Step 1 (1.30 mg, 2.28 mmol) in dioxane (20 ml) was treated with 1M aqueous sodium hydroxide solution (7.3 ml). The reaction mixture was stirred at room temperature for 2 hours under an atmosphere of argon. The mixture was diluted with ethyl acetate and dilute aqueous hydrochloric acid, the layers separated, and the organic phase washed with brine. After drying (MgSO$_4$) purification was accomplished by chromatography on silica gel eluring with 20% ethyl acetate in dichloromethane to yield the title compound (1.08 g, 90%); $v_{max}$ (CH$_2$Cl$_2$) 3519, 3424, 2930, 1773, 1697 and 1479 cm$^{-1}$; MS (EI) m/z 527 (M$^+$). Found: 527.2889, C$_{30}$H$_{41}$NO$_7$ requires 527.2883.

Step 3. (3R)-3-Deoxo-11-deoxy-3-methoxy-11-oxo-4-epi-mutilin 14-[N-4-[2-dimethylaminoethoxy]-3-methoxybenzoyl)]-carbamate The product of Step 2 (1.04 g, 1.97 mmol) in acetone (20 ml) was treated with potassium carbonate (545 mg, 3.95 mmol) and 2-dimethylaminoethyl chloride hydrochloride (284 mg, 1.97 mmol). The reaction mixture was heated to reflux for 16 hours under an atmosphere of argon. The mixture was diluted with ethyl acetate and water and the layers separated. After drying (MgSO$_4$) purification was accomplished by chromatography on silica gel eluting with 4% (9:1 methanol:ammonia (35%)) in dichloromethane to yield the title compound (185 mg, 16%); $v_{max}$ (CH$_2$Cl$_2$) 3421, 2941, 1773, 1697, 1599 and 1477 cm$^{-1}$; MS (CI) m/z 599 (MH$^+$).

Step 4. Mutilin-14-[N-4-[2-dimethylaminoethoxy]-3-methoxybenzoyl)]-carbamate

The product of Step 3 (160 mg, 0.27 mmol) in dioxane (1.5 ml) was treated with a saturated solution of zinc chloride in conc. HCl (1.5 ml) and the reaction stirred at room temperature for 2 hours. The solution was poured into ethyl acetate and saturated sodium hydrogen carbonate solution. The aqueous phase was re-extracted with ethyl acetate and the combined organic phases were washed with saturated sodium chloride solution. The organic phase was dried (MgSO$_4$) and purified by chromatography on silica gel eluting with 4% (9:1 methanol:ammonia (35%)) in dichloromethane to yield the title compound (65 mg, 41%); $v_{max}$ (CH$_2$Cl$_2$) 3418, 2962, 1776, 1732, 1600 and 1478 cm$^{-1}$; $^1$H NMR (CDCl$_3$) 0.80 (3H, d, J 6.6 Hz), 0.89 (3H, d, J 7.0 Hz), 1.12–1.90 (16H, m) including 1.19 (3H, s) and 1.52 (3H, s), 2.05–2.30 (4H, n), 2.35 (6H, s), 2.80 (2H, t, J 6.0 Hz), 3.39 (1H, m), 3.90 (3H, s), 4.12 (2H, t, J 6.0 Hz), 5.23 (1H, dd, J 17.3, 1.5 Hz), 5.39 (1H, dd, J 11.1, 1.5 Hz), 5.85 (1H, d, 18.4 Hz), 6.58 (1H, dd, J 17.3, 11.1 Hz), 6.90 (1H, m), 7.29–7.42 (2H, m), 7.85 (1H, bs); MS (EI) m/z 584 (M$^+$). Found: 584.3474, C$_{33}$H$_{48}$N$_2$O$_7$ requires 584.3474.

EXAMPLE 110

Mutilin 14-{N-[(3S,4R)-1-azabicyclo[2.2.1]hept-3-ylcarbonyl]}-carbamate

Step 1. (3R)-3-Deoxo-11-deoxy-3-methoxy-11-oxo-4-epi-mutilin 14-{N-[(3S,4R)-1-azabicyclo(2.2.1]hept-3-ylcarbonyl]}-carbamate (3R)-3-Deoxo-11-deoxy-3-methoxy-11-oxo-4-epi-mutilin (490 mg, 1.46 mmol) was combined with (3S,4R)-1-azabicyclo[2.2.1]hept-3-ylcarbonyl chloride (280 mg, 1.46 mmol) and silver cyanate (550 mg, 3.67 mmol) in dry dichloromethane (20 ml). Triethylamine (0.20 ml, 1.46 mmol) was added and the reaction stirred at room temperature for 16 hours in subdued light and under an atmosphere of argon. The mixture was filtered through Kieselguhr and the filtrate washed with saturated aqueous sodium hydrogen carbonate (×2) and brine. After drying (MgSO$_4$) purification was accomplished by chromatography on silica gel eluting with 4% (9:1 methanol:ammonia (35%)) in dichloromethane to yield the title compound (276 mg, 38%); $v_{max}$ (CH$_2$Cl$_2$) 3383, 2981, 1780, 1749, 1698, 1460 and 1374 cm$^{-1}$; MS (EI) m/z 500 (M$^+$). Found: 500.3248, C$_{29}$H$_{44}$N$_2$O$_5$ requires 500.3250.

Step 2. Mutilin-14 {N-[(3S,4R)-1-azabicycio[2.2.1]hept-3-ylcarbonyl]}-carbamate

The product of Step 1 (260 mg, 0.52 mmol) in dioxane (3 ml) was treated with conc. HCl (3 ml) and the reaction stirred at room for 30 minutes. The solution was diluted with water and washed with dichloromethane (×2). The aqueous phase was basified with saturated aqueous sodium hydrogen carbonate and the product extracted into dichloromethane. The organic phase was dried (MgSO$_4$) and concentrated to yield the title compound (187 mg, 74%); $v_{max}$ (CH$_2$Cl$_2$) 3386, 2962, 1782, 1735, 1699 and 1467 cm$^{-1}$; $^1$H NMR (d$_6$-DMSO) 0.63 (3H, d, J 6.6 Hz), 0.81 (3H, d, J 7.0 Hz), 1.05–3.12 (29H, m) including 1.09 (3H, s) and 1.42 (3H, s), 4.52 (1H, d, J 6.0 Hz, exch), 5.03–5.12 (2H, m), 5.51 (1H, d, J 7.8 Hz), 6.21 (1H, dd, J 17.7, 11.1 Hz), 10 40 (1H, bs); MS(CI) m/z 487 (MH$^+$).

EXAMPLE 111

Mutilin 14-(piperidin-4-oyl)-carbamate

Step 1. Mutilin 11-dichloroacetyl-14-(1-tert-butoxycarbonylpiperidin-4-oyl)-carbamate 1-tert-Butoxycarbonylpiperidine-4-carboxylic acid [J. Med. Chem., (1996), 39(10), 1943–5] (229 mg) was converted to the acid chloride with oxalyl chloride (152 mg, 0.105 ml) and 1 drop of DMF in dichloromethane. Silver cyanate (300 mg) was added to the reaction mixture and the mixture refluxed for 1 hr. After cooling mutilin 11-dichloroacetate (216 mg) and tetrakis(triphenyl-phosphine)-palladium(0) (5 mg) was added and the reaction mixture stirred at room temperature for 16 h. The mixture was filtered through celite and the solvent removed from the filtrate in vacuo. Following purification by silica gel chromatography the title compound was obtained as a colourless foam, (154 mg, 45%); $v_{max}$ (CH$_2$Cl$_2$) 3382, 1786, 1754, 1736, 1686 and 1473 cm$^{-1}$; MS(CI) m/z 702 (M+NH$_4$)$^+$.

Step 2. Mutilin 14-(1-tert-butoxycarbonylpiperidin-4-oyl)-carbamate

Mutilin 11-dichloroacetate-14-(1-tert-butoxycarbonylpiperidin-4-oyl)-carbamate (150 mg) in tetrahydrofuran (1 ml) was treated with 1M aqueous sodium hydroxide (1.5 ml) and vieorously stirred at room temperature for 1.5 hr. The reaction mixture was diluted with ethyl acetate and washed with 5% citric acid, brine, dried over anhydrous magnesium sulfate and concentrated. After purification by silica gel chromatography, the title compound was obtained as a colourless solid, (47 mg, 37%); $v_{max}$ (CH$_2$Cl$_2$) 3385, 1784, 1735, 1699 and 1686 cm$^{-1}$; MS(CI) m/z 575 (M+H)$^+$.

Step 3. Mutilin 14-(piperidin-4-oyl)-carbamate

Mutilin 14-(1-terr-butoxycarbonylpiperidin-4-oyl)-carbamate (45 mg) in dichloromethane at room temperature was treated with trifluoroacetic acid (90 mg, 0.06 ml) and the solution left 16 h. The solution was concentrated and dried in vacuo to a colouriess solid, (36 mg, 97%); Crystallization from acetone/hexane afforded the title compound as colourless prisms, m.p. 190–195° C.; $v_{max}$ (CH$_2$Cl$_2$) 3382, 1780, 1735, 1704 and 1677 cm$^{-1}$; $^1$H NMR (CDCl$_3$) inter alia 0.73 (3H, d, J 6.6 Hz), 0.90 (3H, d, J 6.8 Hz), 1.19 (3H, s), 1.43 (3H, s), 2.87 (2H, t, J 11.6 Hz), 3.32 (3H, m), 5.23 (1H, d, J 18.6 Hz), 5.35 (1H, d, J 11.1 Hz), 5.69 (1H, d, J 8.4 Hz), 6.48 (1H, dd, J 11.1, 18.6 Hz) and 7.90 (1H, vbr s); MS(CI) m/z 475 (M+H)$^+$.

EXAMPLE 112

Mutilin 14-(2,3-dihydroimidazol[2,1-b]thiazol-6-oyl)-carbamate

Step 1. 2,3-Dihydroimidazol[1,2-b]thiazole-6-carboxylic acid

Ethyl 2,3-dihydroimidazol[1,2-b]thiazole-6-carboxylate, (Patent, WO 94/10178, 11th May 1994) (760 mg) in ethanol (5 ml) was hydrolysed with aqueous sodium hydroxide at 60° C. for 3 hr. The solvent was removed in vacuo and the residue re-dissolved in water and acidified to pH 3 with 5M hydrochloric acid. No precipitate was formed. The aqueous solution was freeze-dried and the solid residue extracted with hot ethanol. After filtration and removal of solvent the title compound was obtained as a pale yellow amorphous solid, (621 mg, quant.); $^1$HNMR (CDCl$_3$) 3.93 (2H, t, J 7.0 Hz), 4.25 (2H, t, J 7.6 Hz) and 7.93 (1H, s).

Step 2. (3R)-3-Deoxo-11-deoxy-3-methoxy-11-oxo-4-epi-mutilin 14-(2,3-dihydroimidazol[2,1-b]thiazol-6-oyl)-carbamate A suspension of 2,3-dihydroimidazol[1,2-b]thiazole-6-carboxylic acid (316 mg) in dry dichloromethane (3 ml) was treated with oxalyl chloride (381 mg, 0.26 ml) for 3 hr. The slurry that was formed was concentrated in vacua to remove excess oxalyl chloride and the solid residue re-suspended in dry dichloromethane. The reaction mixture was cooled in an ice bath and triethylamine (202 mg, 0.28 ml) was slowly added. The pale yellow solution/solid was warmed to room temperature and silver cyanate (600 mg) was added. The mixture was stirred at room temperature 16 h. and (3R)-3-deoxo-11-deoxy-3-methoxy-11-oxo-4-epi-mutilin (334 mg) added. The reaction mixture was stirred for 2 h. The mixture was filtered through celite. The filtrate was then washed with water, saturated aqueous sodium hydrogen carbonate dried over anhydrous magnesium sulfate and concentrated. Purification by silica gel chromatography eluting with 80% and then 90% ethyl acetate/hexane afforded the title compound as a colourless foam, (113 mg, 21%); $v_{max}$ (CH$_2$Cl$_2$) 3374, 1769, 1728, 1698, 1543, 1945 and 1468 cm$^{-1}$; MS(CI) m/z 530 (M+H)$^+$.

Step 3. Mutilin 14-(2,3-dihydroimidazol [2,1-b]thiazol-6-oyl)-carbamate (3R)-3-Deoxo-11-deoxy-3-methoxy-11-oxo-4-epi-mutilin 14-(2,3-dihydroimidazol[2,1-b]thiazol-6-oyl)-carbamate (214 mg) in dioxan (1 ml) was treated at room temperature with Lukas reacent (1 ml). The reaction was exothermic and darkened. After 1 h, t.l.c. analysis showed complete conversion to the product. The reaction mixture was diluted with ethyl acetate and neutralized with saturated aqueous sodium hydrogen carbonate. The aqueous phase was extracted with ethyl acetate and the combined organic phases washed with brine, dried over anhydrous magnesium sulfate and concentrated to a colourless solid. Trituration with dichloromethane and filtering gave the title compound as a white amorphous solid, (97 mg, 47%); $v_{max}$ (KBr) 1762, 1732, 1637, 1543, 1509 and 1464 cm$^{-1}$; $^1$HNMR (CDCl$_3$) inter alia 0.63 (3H, d, J 6.0 Hz), 0.81 (3H, d, J 6.7 Hz), 1.05 (3H, s), 1.39 (3H, s), 3.41 (1H, d, J 5.5 Hz), 3.90 (2H, t, J 7.0 Hz) 4.24 (2H, t, J 7.0 Hz), 5.09 (2H, m), 5.53 (7.8 Hz), 6.20 (1H, dd, J 11.2, 17.6 Hz), 7.98 (1H, s) and 9.66 (1H, s exchangeable with D$_2$O); MS(ES) m/z 516 (M+H)$^+$.

EXAMPLE 113

Mutilin 14-(2,3-dihydroimidazol[2,1-b]thiazol-5-oyl)-carbamate

Step 1. 2,3-Dihydroimidazol[1,2-b]thiazole-5-carboxylic acid

Ethyl 2,3-dihydroimidazol[1,2-b]thiazole-5-carboxylate (formed as a side-product in the preparation of the thiazol-6-carboxylate, Example 112) (3.84 g) was hydrolysed to the acid with aqueous sodium hydroxide (50 ml) as described in Example 112, Step 1. After acidification a white precipitate was formed. This was filtered off, washed with water and dried overnight in vacua. The title compound was obtained as a white solid, (2.86 g, 93%); $^1$HNMR (d6-DMSO) 3.96 (2H, t, J 7.3 Hz), 4.37 (2H, t, J 7.3 Hz), 7.51 (1H, s) and 12.89 (1H vbr s).

Step 2. (3R)-3-Deoxo-11-deoxy-3-methoxy-11-oxo-4-epi-mutilin 14-(2,3-dihydroimidazol[2,1-b]thiazol-5-oyl)-carbamate 2,3-dihydroimidazol[1,2-b]thiazole-5-carboxylic acid (316 mg) was converted to the acid chloride and coupled to (3R)-3-deoxo-11-deoxy-3-methoxy-11-oxo4-epi-mutilin on the same scale, and using the same procedure described in Example 112, Step 2. Purification by silica gel chromatography using 50% and then 60% ethyl acetate/hexane afforded the title compound as a colourless solid, (353, 67%); $v_{max}$ (CH$_2$Cl$_2$) 3419, 1769, 1723, 1697, 1520 and 1484 cm$^{-1}$; MS(EI) m/z 529 (M$^+$).

Step 3. Mutilin 14-(2,3-dihydroimidazol[2,1-b]thiazoi-5-oyl)-carbamate (3R)-3-Deoxo-11-deoxy-3-methoxy-11-oxo-4-epi-mutilin 14-(2,3-dihydroimidazol[2,1-b]thiazol-5-oyl)-carbamate (324 mg) in dioxan (2 ml) was treated with concentrated hydrochloric acid (1 ml) at room temperature for 2 days. The reaction mixture was worked up as described in Example 113, Step 3. The resultant colourless foam crystallized on addition of dichloromethane. The title compound was obtained as a colourless crystalline solid, (206 mg, 65%); $v_{max}$ (KBr) 1735, 1712, 1527 and 1433 cm$^{-1}$; $^1$HNMR (d$_6$-DMSO) inter alia 0.67 (3H, d, J 5.9 Hz), 0.83 (3H, d, J 6.8 Hz), 1.08 (3H, s) 1.45 (3H, s), 3.45 (1H, t, J 5.5 Hz), 3.95 (2H, d, J 7.8 Hz), 4.54 (1H, d, J 6.0 Hz), 5.09 (2H, m), 5.60 (1H, d, J 7.9 Hz), 7.87 (1H, s) and 10.5 (1H, s); MS(CI) m/z 515 (M$^+$); Found: 515.2458, C$_{27}$H$_{37}$N$_3$O$_5$S requires 515.2452.

EXAMPLE 114

Mutilin 14-(1-Methylpiperidin-4-oyl)-carbamate

Step 1. (3R)-3-Deoxo-11-deoxy-3-methoxy-11-oxo-4-epi-mutilin 14-(1-methylpiperidin-4-oyl)-carbamate 1-Methylpiperidin-4-carboxylic acid (500 mg) was converted to the corresponding acid chloride with thionyl chloride [J. Med. Chem., (1990), 33(6), 1599]. A suspension of the acid chloride in dry dichloromethane (5 ml) was treated with silver cyanate (1.04 g) and the reaction mixture refluxed for 1 h. After cooling, (3R)-3-deoxo-11-deoxy-3-methoxy-11-oxo-4-epi-mutilin (334 mg) was added followed by triethylamine (281 mg, 0.39 ml) after 10 m. The reaction mixture was filtered through celite, and the filtrate washed with saturated aqueous sodium hydrogen carbonate. Following purification by silica gel chromatography, the title compound was obtained as a colourless foam, (426 mg, 85%); $v_{max}$ (CH$_2$Cl$_2$) 3381, 1781, 1749, 1698 and 1474 cm$^{-1}$; MS(EI) m/z 502 (M$^+$); Found: 502.3411, C$_{29}$H$_{46}$N$_2$O$_5$ requires 502.3407.

Step 2. Mutilin 14-(1-methylpiperidin-4-oyl)-carbamate (3R)-3-Deoxo-11-deoxy-3-methoxy-11-oxo-4-epi-mutilin 14-(1-methylpiperidin-4-oyl)-carbamate (1.08 g) in dioxan (8 ml), was treated wih concentrated hydrochloric acid (4 ml) at room temperature for 5 h. T.l.c. analysis showed complete conversion to the product. The solvents were removed in vacuo and the residual material dissolved in water. The solution was extracted with dichloromethane. The aqueous solution was basified with saturated aqueous sodium hydrogen carbonate to pH 8 and extracted with dichloromethane (three times). The combined organic phases were subsequently washed with brine, dried over anhydrous magnesium sulfate and concentrated to give a colourless foam. Trituration with hexane afforded the title compound as a colourless amporphous solid, (574 mg, 55%); $v_{max}$ (CH$_2$Cl$_2$) 3385, 1782, 1736, 1704 and 1474 cm$^{-1}$; $^1$HNMR (CDCl$_3$) inter alia 0.73 (3H, d, J 6.7 Hz), 0.89 (3H, d, J 7.0 Hz), 1.18 (3H, s), 1.42 (3H, s), 2.28 (3H, s), 3.36 (1H, dd, J 6.7, 10.2 Hz), 5.22 (1H, d, J 17.5 Hz), 5.36 (1H, d, J 1.0 Hz), 5.70 (1H, d, J 8.4 Hz), 6.49 (1H, dd, J 11.0, 17.3 Hz) and 7.43 (1H, s);MS(EI) m/z 488 (M$^+$), Found: 488.3225, C$_{28}$H$_{44}$N$_2$O$_5$ requires 488.3250.

EXAMPLE 115

Mutilin 14-(1-Methylpiperidin-4-oyl)-carbamate Hydrochloride salt

Mutilin 14-(1-methylpiperidin-4-oyl)-carbamate (350 mg) in ethyl acetate (5 ml) at room temperature was treated with a solution of 4M hydrogen chloride in dioxan in a dropwise fashion until no more precipitate was formed. The white solid was removed by filtration, washed with ethyl acetate and dried in vacuo. The title compound was obtained as an amporphous white solid, (300 mgs, 80%); $^1$HNMR (D$_2$O) inter alia 0.69 (3H, d, J 5.8 Hz), 0.92 (3H, d, J 6.8 Hz), 1.14 (3H, s), 1.38 (3H, s), 2.89 (3H, s), 3.05 (2H, t, J 12.7 Hz), 5.19 (1H, d, J 17.5 Hz), 5.26 (1H, d, J 11.1 Hz), 5.61 (1H, d, J 8.1 Hz) and 6.35 (1H, d, J 11.1,17.5 Hz).

EXAMPLE 116

Mutilin 14-(2-Chloropropionyl)-carbamate

Step 1. (3R)-3-Deoxo-11-deoxy-3-methoxy-11-oxo-4-epi-mutilin 14-(2Chloropropionyl)-carbamate 3-Chloropropionyl chloride (889 mg, 0.67 ml), silver cyanate (2.05 g) and (3R)-3-deoxo-11-deoxy-3-methoxy-11-oxo-4-epi-mutilin (668 mg), in dichloromethane (10 ml) were allowed to react at room temperature for 3 days. The mixture was filtered through celite, washed with saturated aqueous sodium hydrogen carbonate, dried over anhydrous magnesium sulfate and concentrated, to give a gum. Purification by silica gel chromatography afforded the title compound as a crisp white foam, (909 mg, 97%); $v_{max}$ (CH$_2$Cl$_2$) 3382, 1785, 1752, 1711, 1699 and 1473 cm$^{-1}$; MS(CI) m/z 485 (M+NH$_4$)$^+$.

Step 2. Mutilin 14-(2-Chloropropionyl)-carbamate (3R)-3-Deoxo-11-deoxy-3-methoxy-11-oxo-4-epi-mutilin 14-(2-chloro-propionyl)-carbamate (300 mg) in dioxan (2 ml), cooled to 0–5° C. was treated with Lukas reagent (2 ml) and allowed to warmi to room temperature. After 2 h, the reaction mixture was diluted with dichloromethane and washed with water, saturated aqueous sodium hydrogen carbonate, brine and then dried over anhydrous magnesium sulfate. After purification by silica gel chromatography, the title compound was obtained as a colourless foam, (223 mg, 77%); $v_{max}$ (CH$_2$Cl$_2$) 3624, 3564, 3384, 1786, 1754, 1734, 1710 and 1473 cm$^{-1}$; $^1$HNMR (CDCl$_3$) inter alia 0.74 (3H, d, J 6.8 Hz), 0.89 (3H, d, J 7.0 Hz), 1.19 (3H, s), 1.42 (3H, s), 3.29 (2H, t, J 7.0 Hz), 3.37 (1H, dd, J 6.7, 10.7 Hz), 3.80 (3H, t, J 7.0 Hz), 5.24 (1H, d, J 17.4 Hz), 5.34 (1H, d, J 11.0 Hz), 5.70 (1H, d, J 8.5 Hz), 6.48 (1H, dd, J 11.0, 17.4 Hz) and 7.50 (1H, s); MS(ES) m/z 452 (M−H)$^-$.

EXAMPLE 117

Mutilin 14-(2-diethylaminopropionyl)-carbamate

Step 1. (3R)-3-Deoxo-11-deoxy-3-methoxy-11-oxo-4-epi-mutilin 14-(2-Diethylaminopropionyl)-carbamate (3R)-3-Deoxo-11-deoxy-3-methoxy-11-oxo-4-epi-mutilin 14-(2-chloro-propionyl)-carbamate (200 mg) in ethyl acetate (2 ml) at room temperature was treated with diethylamine (312 mg, 0.44 ml). After 2 h, no remaining starting material by t.l.c. analysis. The solution was washed with saturated aqueous sodium hydrogen carbonate, water (two times), brine and then dried over anhydrous magnesium sulfate. The solution was concentrated to give the title compound as a colourless foam, (197 mg, 92%); $v_{max}$ (CH$_2$Cl$_2$) 1770, 1697, 1520 and 1458 cm$^{-1}$; MS(EI) m/z 504 (M$^+$), Found: 504.3548, C$_{29}$H$_{48}$N$_2$O$_5$ requires 504.3563.

Step 2. Mutilin 14-(2-diethylaminopropionyl)-carbamate (3R)-3-Deoxo-11-deoxy-3-methoxy-11-oxo-4-epi-mutilin 14-(2-diethylamiino-propionyl)-carbamate, (320 mg) was converted to the title compound as described in Example 116, Step 2. The product was obtained as a colourless foam, (153 mg, 49%); $v_{max}$ (CH$_2$Cl$_2$) 1772, 1735, 1703 and 1520 cm$^{-1}$; $^1$HNMR (CDCl$_3$) inter alia 0.76 (3H, d, J 6.6 Hz), 0.87 (3H, d, J 7.0 Hz), 1.08 (6H, t, J 7.2 Hz), 1.17 (3H, s), 1.43 (3H, s), 3.34 (1H, dd, J 6.5, 11.2 Hz), 5.21 (1H, d, J 17.4 Hz), 5.37 (1H, d, J 11.0 Hz), 5.71 (1H, d, J 8.5 Hz) and 6.59 (1H, dd, J 11.0, 17.4 Hz); MS(EI) m/z 490 (M$^+$), Found: 490.3414, C$_{28}$H$_{46}$N$_2$O$_5$ requires 490.3407.

EXAMPLE 118

Mutilin 14-(Acryloyl)-carbamate

Step 1. Mutilin 14-(acryoyl)-carbamate

Mutilin 14-(2-chloropropionyl)-carbamate (150 mg) in dichloromethane (1 ml) at room temperature was treated with triethylamine (67 mg, 0.092 ml). After 2 h., t.l.c. analysis showed no starting material, The solution was purified by silica gel chromatography to give the title compound as a colourless foam, (135 mg, 98%); $v_{max}$ (CH$_2$Cl$_2$) 3625, 3563, 3389, 1779, 1735, 1697, 1625 and 1485 cm$^{-1}$; $^1$HNMR (CDCl$_3$) inter alia 0.75 (3H, d, J 6.8 Hz), 0.89 (3H, d, J 7.0 Hz), 1.12 (3H, s), 1.45 (3H, s), 3.37 (1H, dd, J 6.6, 10.7 Hz), 5.23 (1H, d, J 17.3 Hz), 5.37 (1H, d, J 11.1 Hz), 5.72 (1H, d, J 8.5 Hz), 5.89 (1H, d, J 10.4 Hz), 6.50 (2H, dd, J 10.4, 17.4 Hz), 7.06 (1H, dd, J 11.1, 17.3 Hz) and 7.60 (1H, s); MS(CI) m/z 435 (M+NH$_4$)$^+$.

EXAMPLE 119

Mutilin 14-(1-Benzylpiperidin-4-oyl)-carbamate

Step 1. 1-Benzylpiperidine-4-carboxylic acid

Ethyl 1-benzylpiperidine-4-carboxylate (13.73 g) in methanol (10 ml) was treated with 40% aqueous sodium hydroxide (8.3 ml) at room temperature 16 h. The solvent was removed in vacuo and the residue re-dissolved in water (100 ml), acidified with dilute hydrochloric acid to pH 4 and concentrated. The residue was extracted with hot ethanol (200 ml), filtered and concentrated again. Addition of dichloromethane resulted in crystallization giving the title compound as a colourless crystaline solid, (3.24 g, 27%). Removal of solvent from the filtrate and trituration with ether gave a second batch as an amorphous white solid, (9.24 g, 73%); $v_{max}$ (CH$_2$Cl$_2$) 2496 (vbr), 1720 and 1604 (br) cm$^{-1}$.

Step 2. (3R)-3-Deoxo-11-deoxy-3-methoxy-11-oxo-4-epi-mutilin 14-(1-Benzylpiperidin-4-oyl)-carbamate 1-Benzylpiperidine-4carboxylic acid (500 mg) in dichloromethane (5 ml) was converted to the acid chloride with oxalyl chloride (319 mg, 0.22 ml) and 1 drop of DMF over 1 h. To this homogeneous solution was added silver cyanate (684 mg) and the reaction mixture refluxed for 1 h. The mixture was cooled to room temperature and (3R)-3-deoxo-11-deoxy-3-methoxy-11-oxo-4-epi-mutilin (334 mg) added. After 5 m. triethylamine (0.32 ml) was added dropwise. After 2 h. the reaction mixture was filtered through celite, washed with water, saturated aqueous sodium hydrogen carbonate, brine and dried over anhydrous magnesium sulfate. Removal of solvent in vacuo, and purification of the residue by silica gel chromatography, afforded the title compound as a colourless foam, (355 mg, 61%); $v_{max}$ (CH$_2$Cl$_2$) 3384, 1782, 1784, 1699 and 1478 cm$^{-1}$; MS(ES) m/z 579 (M+H)$^+$.

Step 3. Mutilin 14-(1-Benzylpiperidin-4-oyl)-carbamate (3R)-3-Deoxo-11-deoxy-3-methoxy-11-oxo-4-epi-mutilin 14-(1-benzylpiperidin-4-oyl)-carbamate (304 mg) in dioxan (0.5 ml) was treated with concentrated hydrochloric acid (0.5 ml) until t.l.c. analysis showed no starting material. The solvents were removed under vacuum and the residue partitioned between saturated aqueous sodium hydrogen carbonate and dichloromethane. The organic phase was dried over anhydrous magnesium sulfate and the solvent removed in vacuo. The crude product was purified by silica gel chromatography to give the title compound as a foam, (172 mg, 58%); $v_{max}$ (CH$_2$Cl$_2$) 3622, 3562, 3383, 1782, 1735, 1703 and 1477 cm$^{-1}$; $^1$HNMR (CDCl$_3$) inter alia 0.72 (3H, d, J 6.6 Hz), 0.88 (3H, d, J 7.0 Hz), 1.18 (3H, s), 1.42 (3H, s), 3.36 (1H, dd, J 6.6,10.5 Hz), 3.51 (2H, s), 5.21 (1H, d, J 17.3 Hz), 5.35 (1H, d, J 10.9 Hz), 5.69 (1H, d, J 8.4 Hz), 6.48 (1H, d, J 10.9,17.3 Hz) and 7.30 (4H, m); MS(CI) m/z 564 (M$^+$), Found: 564.3538, C$_{34}$H$_{48}$N$_2$O$_5$ requires 564.3564.

EXAMPLE 120

Mutilin 14-[1-(4-Methoxybenzyl)piperidin-4-oyl]-carbamate

Step 1. Ethyl 1-(4-methoxybenzyl)piperidine-4-carboxylate

Ethyl isonipecotate (5 g, 4.9 ml) and 4-methoxybenzyl chloride (5 g, 4.44 ml) in DMF (40 ml) with potassium carbonate (8.8 g) was heated to 70° C. for 2 h, then room temperature for 2 days, and again at 70° C. for 2 h. The reaction mixture was partitioned between ethyl acetate/water. The organic layer was washed with water (2×), brine, dried over anhydrous magnesium sulfate and concentrated. The title compound was obtained as a yellow oil, (8.05 g, quant.); $v_{max}$ (CH$_2$Cl$_2$) 1725, 1611, 1585, 1511 and 1466 cm$^{-1}$; MS(EI) m/z 277 (M$^+$), Found: 277.1682, C$_{16}$H$_{23}$NO$_3$ requires 277.1678.

Step 2. 1-(4-methoxybenzyl)piperidine-4-carboxylic acid

Ethyl 1-(4-methoxybenzyl)piperidine-4-carboxylate, (8.05 g) was hydrolysed to the corresponding acid with sodium hydroxide as described in Example 119, Step 1. Following isolation of the crude product, the foam was tnturated with ether overnight to give the title compound as a white, crystalline solid, (6.23 g, 86%); $v_{max}$ (KBr) 1731, 1613, 1516 and1457 cm$^{-1}$; MS(EI) m/z 249 (M$^+$), Found 249.1368, C$_{14}$H$_{19}$NO$_3$ requires 249.1365.

Step 3. (3R)-3-Deoxo-11-deoxy-3-methoxy-11-oxo-4-epi-mutilin 14-[1-(4-methoxybenzyl)piperidin-4-oyl]-carbamate 1-(4-Methoxybenzyl)piperidine-4-carboxylic acid (747 mg) was converted to the acid chloride with oxalyl chloride (0.27 ml) in dichloromethane (10 ml) and then reacted with silver cyanate (600 mg) and coupled to (3R)-3-deoxo 11-deoxy-3-methoxy-11-oxo-4-epi-mutilin (500 mg) in the presence of triethylamine (0.42 ml) as described in example 119, Step 2. After purification the title compound was obtained as a colourless foam, (515 mg, 56%); $v_{max}$ (CH$_2$Cl$_2$) 3383, 1782, 1749, 1699, 1611, 1511 and 1468 cm$^{-1}$; MS(EI) m/z 608 (M$^+$), Found: 608.3813, C$_{36}$H$_{52}$N$_2$O$_6$ requires 608.3825.

Step 4. Mutilin 14-[1-(4-Methoxybenzyl)piperidin-4-oyl]-carbamate (3R)-3-Deoxo-11-deoxy-3-methoxy-11-oxo-4-epi-mutilin 14-[1-(4-methoxybenzyl)piperidin-4-oyl]-carbamate (485 mg) in dioxan (2 ml) was converted to the title compound as described in Example 119, Step 3. After purification the product was obtained as a colourless foam, (433 mg, 92%); $v_{max}$ (CH$_2$Cl$_2$) 3624, 3565, 3385, 1783, 1734, 1705, 1611, 1511 and 1468 cm$^{-1}$; $^1$HNMR (CDCl$_3$) inter alia 0.73 (3H, d, J 6.7 Hz), 0.89 (3H, d, J 6.9 Hz), 1.18 (3H, s), 1.43 (3H, s), 2.61 (2H, s), 3.81 (3H, s), 5.22 (1H, d, J 19.4 Hz), 5.36 (1H, d, J 1.1 Hz), 5.70 (1H, d, J 8.0 Hz), 6.49 (1H, dd, J 11.1, 19.4 Hz), 6.85 (2H, d, J 8.6 Hz), 7.22 (2H, d, J 8.6 Hz) and 7.32 (1H, s); MS(EI) m/z 594 (M$^+$), Found: 594.3657, C$_{35}$H$_{50}$N$_2$O$_6$ requires 594.3669.

EXAMPLE 121

Mutilin 14-[1-(4-Methoxybenzyl)piperidin-4-oyl]-carbamate Hydrochloride salt

Mutilin 14-[1-(4-methoxybenzyl)piperidin-4-oyl]-carbamate (100 mg) in ethyl acetate (1 ml) was treated with 4M hydrogen chloride in dioxan, dropwise until no further precipitation was observed. The white solid was filtered off, washed with ethyl acetate and dried under vacuum. The title compound was obtained as an amorphous white solid, (70 mg, 66%); $^1$HNMR (d$_6$-DMSO) inter alia 0.63 (3H, d, J 6.2 Hz), 0.83 (3H, d, J 6.7 Hz), 1.08 (3H, s), 1.40 (3H, s), 3.79 (3H, s), 4.20 (2H, br s), 4.56 (1H, d, J 5.9 Hz), 5.06 (1H, d, J 11.0 Hz), 5.10 (1H, d, J 17.6 Hz), 5.50 (1H, d, J 7.8 Hz), 6.22 (1H, dd, J 11.0, 17.6 Hz), 7.01 (2H, d, J 8.5 Hz), 7.50 (2H, d, J 8.5 Hz), 10.30 (1H, br s) and 10.51 (1H, s).

EXAMPLE 122

Mutilin 14-[1-(4-Fluorobenzyl)piperidin-4-oyl]-carbamate

Step 1. Ethyl 1-(4-Fluorobenzyl)piperidine-4-carboxylate

Ethyl isonipecotate (5 g, 4.9 ml) was alkylated with 4-fluorobenzyl bromide, (6.02 g, 3.97 ml) in DMF (40 ml) in the presence of potassium carbonate (8.8 g) as described in Example 120, Step 1. The title compound was obtained as a yellow oil, (7.52 g, 89%); $v_{max}$ (CH$_2$Cl$_2$) 1725, 1603, 1508 and 1449 cm$^{-1}$; MS(EI) m/z 265 (M$^+$), Found: 265.1478, C$_{15}$H$_{20}$FNO$_2$ requires 265.1478.

Step 2. 1-(4-Fluorobenzyl)piperidine-4-carboxylic acid

Ethyl 1-(4-fluorobenzyl)piperidine-4-carboxylate (7.52 g) was hydrolysed with 40% sodium hydroxide (4.3 ml) as described in Example 120, Step 2. After work-up the title compound was obtained as a colourless solid, (4.26 g, 63%); $v_{max}$ (KBr) 1722, 1605, 1511 and 1447 cm$^{-1}$; MS(EI) m/z 237 (M$^+$), Found: 237.1160, C$_{13}$H$_{16}$FNO$_2$ requires 237.1165.

Step 3. (3R)-3-Deoxo-11-deoxy-3-methoxy-11-oxo-4-epi-mutilin 14-[1-(4-Fluorobenzyl)piperidin-4-oyl]-carbamate 1-(4-Fluorobenzyl)piperidine-4-carboxylic acid (711 mg) was converted to the acid chloride with oxalyl chloride (0.27 ml), treated with silver cyanate (600 mg) and coupled to (3R)-3-deoxo-11-deoxy-3-methoxy-11-oxo-4-epi-mutilin (500 mg) in the presence of triethylamine (0.42 ml) as described in Example 120, Step 3. Following purification the title compound was isolated as a colourless foam, (539 mg, 60%); $v_{max}$ (CH$_2$Cl$_2$) 3678, 3381, 1781, 1748, 1699, 1603, 1508 and 1478 cm$^{-1}$; MS(ES) m/z 597 (MH)$^+$.

Step 4. Mutilin 14-[1-(4-Fluorobenzyl)piperidin-4-oyl]-carbamate (3R)-3-Deoxo-11-deoxy-3-methoxy-11-oxo-4-epi-mutilin 14-[1-(4-fluoro-benzyl)piperidin-4-oyl]-carbamate (510 mg) was converted to the title compound as described in Example 120, Step 4. After purification the product was obtained as a colourless foam, (346 mg, 70%); $v_{max}$ (CH$_2$Cl$_2$) 3563, 3386, 1783, 1735, 1705, 1604, 1508 and 1478 cm$^{-1}$; $^1$HNMR (CDCl$_3$) inter alia 0.72 (3H, d, J 6.6 Hz), 0.89 (3H, d, J 8.0 Hz), 1.19 (3H, s), 1.43 (3H, s), 3.37 (1H, dd, J 6.6, 10.2 Hz), 3.45 (2H, s), 5.22 (1H, d, J 17.5 Hz), 5.36 (1H, d, J 9.9 Hz), 5.70 (1H, d, J 8.4 Hz), 6.49 (1 H, dd, J 9.9, 17.5 Hz), 7.00 (2H, m), 7.26 (2H, m) and 7.35 (1H, s); MS(EI) m/z 582 (M$^+$), Found: 582.3472, C$_{35}$H$_{47}$FN$_2$O$_5$ requires 582.3469.

EXAMPLE 123

Mutilin 14-[1-(pyridin-2-ylmethyl)piperidin-4-oyl]-carbamate

Step 1. Ethyl 1-(pyridin-2-ylmethyl)piperidine-4-carboxylate

Ethyl isonipecotate (4.79 g, 4.7 ml) was alkylated with 2-chloromethylpyridine hydrochloride (5 g) and potassium carbonate (12.62 g) in DMF (40 ml) as described in Example 120, Step 1. The title compound was obtained as a yellow oil, (6.09 g, 81%); $v_{max}$ (CH$_2$Cl$_2$) 1724, 1590, 1570, 1476, 1449 and 1433 cm$^{-1}$; MS(ES) m/z 249 (MH)$^+$.

Step 2. 1-(pyridin-2-ylmethyl)piperidine-4-carboxylic acid

Ethyl 1-(pyridin-2-ylmethyl)piperidine-4-carboxylate (6.08 g) was hydrolysed with 40% sodium hydroxide (3.7 ml) in methanol (50 ml) as dscribed in Example 120, Step 2. After isolation the title compound was obtained as a pale green foam, (5.0 g, 93%). A portion of the material was shown to crystallize from dichloromethane to give a colourless crystalline solid; $v_{max}$ (KBr) 1685 (br), 1601 and 1463 cm$^{-1}$; MS(ES) m/z 221 (MH)$^+$.

Step 3. (3R)-3-Deoxo-11-deoxy-3-methoxy-11-oxo-4-epi-mutilin 14-[1-(pyridin-2-ylmethyl)piperidin-4-oyl]-carbamate 1-(Pyridin-2-ylmethyl)piperidine-4-carboxylic acid (440 mg) was coverted to the acid chloride with oxalyl chloride (267 mg, 0.18 ml) and treated with silver cyanate (450 mg) and then coupled to (3R)-3-deoxo-11-deoxy-3-methoxy-11-oxo-4-epi-mutilin (334 mg) in the presence of triethylamine (0.28 ml), as described in Example 120, Step 3. After purification the title compound was isolated as a pale yellow foam, (267 mg, 46%); $v_{max}$ (CH$_2$Cl$_2$) 3382, 1782, 1749, 1699, 1590 and 1475 cm$^{-1}$; MS(EI) m/z 580 (MH)$^+$, Found: 580.3741, C$_{34}$H$_{50}$N$_3$O$_5$ requires 580.3750.

Step 4. Mutilin 14-[1-(pyridin-2-ylmethyl)piperidin-4-oyl]-carbamate (3R)-3-Deoxo-11-deoxy-3-methoxy-11-oxo-4-epi-mutilin 14-[1-(pyridin-2-ylmethyl)piperidin-4-oyl]-carbamate (248 mg) was converted with concentrated hydrochloric acid as described in Example 120, Step 4. After work-up, the crude product was re-dissolved in dilute hydrochloric acid washed with dichloromethane, basified with saturated aqueous sodium hydrogen carbonate and re-extracted. After drying and removal of solvent the title compound was obtained as a pale yellow solid, (135 mg, 56%); $v_{max}$ (CH$_2$Cl$_2$) 3676, 3622, 3564, 3384, 1782, 1735, 1703, 1590 and 1475 cm$^{-1}$; $^1$HNMR (CDCl$_3$) inter alia 0.73 (3H, d, J 6.6 Hz), 0.89 (3H, d, J 6.9 Hz), 1.18 (3H, s), 1.42 (3H, s), 3.36 (1H, dd, J 6.6, 10.5 Hz), 3.67 (3H, s), 5.22 (1H, d, J 17.3 Hz), 5.36 (1H, d, J 11.1 Hz), 5.70 (1H, d, J 8.4 Hz), 6.49 (1H, dd, J 11.1, 17.3 Hz), 7.17 (1H, m), 7.45 (2H, m), 7.66 (1H, m) and 8.55 (1H, d, J 4.0 Hz); MS (ES) m/z 565 (M$^+$); Found 565.3527, C$_{33}$H$_{47}$N$_3$O$_5$ requires 565.3516.

EXAMPLE 124

Mutilin 14-{1-[(2-methylthiazol-4-yl)methyl]-piperidin-4-oyl}-carbamate

Step 1. Ethyl 1-[(2-methylthiazol-4-yl)methyl]piperidine-4-carboxylate

Ethyl isonipecotate (3.14 g, 3.08 ml) was alkylated with 4-chloromethyl-2-methylthiazole hydrochloride (3.68 g) in DMF (40 ml) with potassium carbonate (8.28 g) as peviously described in Example 120, Step 1. After purification by silica gel chromatography the title compound was isolated as a yellow oil, (3.26 g, 61%); $v_{max}$ (CH$_2$Cl$_2$) 1724 cm$^{-1}$; MS(EI) m/z 269 (MH)$^+$, Found: 269.1318, C$_{13}$H$_{21}$N$_2$O$_2$S requires 269.1324.

Step 2. 1-[(2-methylthiazol-4-yl)methyl]piperidine-4-carboxylic acid

Ethyl 1-[(2-methylthiazol-4-yl)methyl]piperidine-4-carboxylate (3.06 g) was hydrolysed to the acid with 40% sodium hydroxide (1.73 ml) as described in Example 120, Step 2. After purification the title compound was isolated as a colourless solid, (3.08 g, 99%); $v_{max}$ (KBr) 1719, 1665, 1591 and 1392 cm$^{-1}$; MS(EI) m/z 240 (M$^+$), Found: 240.0934, C$_{11}$H$_{16}$N$_2$O$_2$S requires 240.0932.

Step 3. (3R)-3-Deoxo-11-deoxy-3-methoxy-11-oxo-4-epi-mutilin 14-{1-[(2-methylthiazol-4-yl)methyl]piperidin-4-oyl}-carbamate 1-[(2-Methylthiazol-4-yl)methyl]piperidine-4-carboxylic acid (720 mg) was converted to the acid chloride with oxalyl chloride (0.27 ml), treated with silver cyanate (600 mg) and coupled to (3R)-3-deoxo-11-deoxy-3-methoxy-11-oxo-4-epi-mutilin (500 mg) in the presence of trsethylamine (0.42 ml), as previously outlined in Example 120, Step 3. Following purification the title compound was obtained as a pale yellow foam, (405 mg, 45%); $v_{max}$ (CH$_2$Cl$_2$) 3382, 1781, 1784, 1698 and 1478 cm$^{-1}$; MS (EI) m/z 599 (M$^+$); Found 599.3406, C$_{33}$H$_{49}$N$_3$O$_5$S requires 599.3392.

Step 4. Mutilin 14-{1-[(2-methylthiazol-4-yl)methyl]piperidin-4-oyl}-carbamate (3R)-3-Deoxo-11-deoxy-3-methoxy-11-oxo-4-epi-mutilin 14-{1-[(2-methylthiazol-4-yl)methyl]piperidin-4-oyl}-carbamate (391 mg) was converted to the title compound as described in Example 121, Step 4. The product was obtained as a white solid, (241 mg, 63%); $v_{max}$ (CH$_2$Cl$_2$) 3677, 3384, 1783, 1735, 1705 and 1477 cm$^{-1}$; $^1$H NMR (CDCl$_3$) inter alia 0.73 (3H, d, J 6.6 Hz), 0.89 (3H, d, J 6.9 Hz), 1.18 (3H, s), 1.42 (3H, s), 2.71 (3H, s), 2.99 (2H, d, J 10.3 Hz), 3.36 (1H, dd, J 6.6, 10.5 Hz), 3.63 (2H, s), 5.24 (1H, d, J 17.0 Hz), 5.36 (1H, d, J 11.1 Hz), 5.72 (1H, d, J 8.4 Hz), 6.48 (1H, dd, J 11.1, 17.0 Hz), 6.95 (1H, s) and 7.38 (1H, s).

EXAMPLE 125

Mutilin 14-(N-3-pyridylacetyl)-carbamate

Step 1. (3R)-3-Deoxo-11-deoxy-3-methoxy-11-oxo-4-epi-mutilin 14-(N-3-pyridylacetyl)-carbamate 3-Pyridylacetic acid (520 mg, 3 mmol) in dichloromethane (5 ml) was treated with oxalyl chloride (0.45 ml, 5.2 mmol) and one drop of DMF at room temperature for 2 h. The solvent and excess oxalyl chloride were removed in vacuo. The residue was dissolved in toluene and the solvent again removed in vacuo.

The crude acid chloride in dry dichloromethane (10 ml) was treated with silver cyanate (900 mg, 6 mmol) and (3R)-3-deoxo-11-deoxy-3-methoxy-11-oxo-4-epi-mutilin (335 mg, 1 mmol). After stirring at room temperature for 18 h the title compound was isolated by the procedure described in Example 31, Step 2, (360 mg, 72%); $v_{max}$ (CH$_2$Cl$_2$) 3380, 1752 and 1699 cm$^{-1}$; $^1$H NMR (CDCl$_3$) 0.80 (3H, d, J 6.9 Hz), 1.01 (3H, d, J 6.4 Hz), 1.08–1.37 (3H, m), 1.19 (3H, s), 1.21 (3H, s), 1.56 (4H, m), 1.73 (1H, d, J 11.3 Hz), 1.99 (2H, m), 2.20 (1H, m), 2.49 (1H, dd, J 15.2, 10.1 Hz), 2.88 (1H, q, J 6.3 Hz), 3.21 (3H, s), 3.44 (1H, m), 4.18 (2H, m), 5.04 (1H, d, J 17.5 Hz), 5.34 (1H, d, J 10.8 Hz), 5.74 (1H, d, J 9.9 Hz), 6.62 (1H, dd, J 17.5, 10.6 Hz), 7.28 (2H, m), 7.65 (1H, dt, J 7.8, 1.9 Hz) 7.72 (1H, s), 8.54 (1H, s); MS (NH$_3$ DCI) m/z 497 (MH$^+$), Found: 496.2948, C$_{29}$H$_{40}$N$_2$O$_5$ requires 496.2937.

Step 2. Mutilin 14-(N-3-pyridylacetyl)-carbamate

The product from step 1, (310 mg) in dioxan (2 ml) was treated with a saturated solution of zinc chloride in conc. HCl (2 ml), as for Example 1 Step 2, to afford the title compound, (173 mg, 58%); $v_{max}$ (CH$_2$Cl$_2$) 3383, 1754, 1734, 1716 cm$^{-1}$; $^1$H NMR (CDCl$_3$) 0.70 (3H, d, J 6.7 Hz), 0.91 (3H, d, J 7.0 Hz), 1.17 (1H, m), 1.19 (3H, s), 1.40 (3H, s), 1.36–1.82 (8H, m), 2.05–2.36 (5H, m), 3.37 (1H, dd, J 10.1, 6.7 Hz), 4.14 (2H, AB quartet, J 16.3 Hz), 5.24 (1H, dd, J 17.4, 1.4 Hz), 5.39 (1H, dd, J 11.1, 1.3 Hz), 5.71 (1H, d, 18.4 Hz), 6.49 (1H, dd, J 17.4, 11.0 Hz), 7.26 (1H, m), 7.56 (1H, s), 7.63 (1H, d, J 7.8 Hz), 8.52 (2H, m); MS (NH$_4$ DCI) m/z 483 (MH$^+$), Found: 483.2856, C$_{28}$H$_{38}$N$_2$O$_5$ requires 483.2859.

EXAMPLE 126

Mutilin 14-(N-2-pyridylmethyl)-carbamate

Step 1. (3R)-3-Deoxo-11-deoxy-3-methoxy-11-oxo-4-epi-mutilin 14-(N-2-pyridylmethyl)-carbamate 2-Aminomethylpyridine (0.31 ml, 3 mmol) was reacted with (3R)-3-deoxo-11-deoxy-3-methoxy-11-oxo-4-epimutilin-14-chloroformate (400 mg, 1 mmol) in dichloromethane (10 ml), as for Example 12 Step 2, to afford the title compound (463 mg, 98%); $v_{max}$ ($CH_2Cl_2$) 3446, 1709 cm$^{-1}$; $^1$H NMR (CDCl$_3$) 0.85 (3H, d, J 6.9 Hz), 0.98 (3H, d, J 6.5 Hz), 1.05–1.61 (6H, m), 1.19 (3H, s), 1.22 (3H, s), (1H, d, J 15.3 Hz), 1.71 (1H, d, J 11.2 Hz), 1.99 (2H, m), 2.19 (1H, m), 2.43 (1H, dd, J 15.1, 10.1 Hz), 2.94 (1H, q, 36.4 Hz), 3.22 (3H, s), 3.46 (1H, ddd, J 11.3, 8.2, 5.3 Hz), 4.52 (2H, t, J 5.3 Hz), 5.00 (1H, d, J 17.5 Hz), 5.29 (1H, d, J 10.7 Hz), 5.68 (2H, m), 6.77 (1H, dd, J 17.5, 10.6 Hz), 7.20 (1H, dd, J 7.5, 5.3 Hz), 7.29 (1H, m) 7.67 (1H, s), 8.55 (1H, d, 34.5 Hz); MS (EI) m/z 468 (M$^+$), (NH, DCI) m/z 469 (MH$^+$), Found: 468.2991, $C_{28}H_{40}N_2O_4$ requires 468.2988.

Step 2. Mutilin 14-(N-2-pyridylmethyl)-carbamate

The product from step 1, (398 mg) in dioxan (2 ml) was treated with a saturated solution of zinc chloride in conc. HCl (2 ml), as for Example 1 Step 2, to afford the title compound, (184 mg, 48%); $v_{max}$ ($CH_2Cl_2$) 3445, 1732, 1713 cm$^{-1}$; $^1$H NMR (CDCl$_3$) 0.75 (3H, d, J 6.0 Hz), 0.86 (3H, d, J 7.0 Hz), 1.1 (1H, m), 1.17 (3H, s), 1.42 (3H, s), 1.43 (4H, m), 1.71 (4H, m), 2.04 (2H, m), 2.21 (2H, m), 2.37 (1H, quintet, J 6.8 Hz), 3.35 (1H, dd, J 10.8, 6.7 Hz), 4.48 (2H, m), 5.20 (1H, dd, 17.4, 1.5 Hz), 5.34 (1H, d, J 11.1 Hz), 5.68 (2H, includes 1H d, J 8.4 Hz), 6.59 (1H, dd, J 17.4, 11.0 Hz), 7.20 (2H, m), 7.62 (1H, td, J 7.6, 1.7 Hz), 8.53 (1H, d, J 4.3 Hz); MS (EI) m/z 455 (MH$^+$), (NH$_3$ DCI) m/z 455 (MH$^+$), Found: 454.2833, $C_{27}H_{38}N_2O_4$ requires 454.2832.

EXAMPLE 127

(E)-Mutilin 14-[N-3-(1-methyl-1,2,3-triazol-4-yl) acryloyl]-carbamate

Step 1: Methyl-(E)-3-(1-methyl-1,2,3-triazol-4-yl)acrylate

1-Methyl-1,2,3-triazol-4-carboxald-hyde (1 g, 9 mmol) was added to a solution of methoxycarbonylmethylene triphenylphosphorane (4.5 g, 13.5 mmol) in dichloromethane (50 ml) and stirred at room temperture for 3.5 hours. The solvent was removed and the residue purified by silica gel chromatography to afford the title compound, (3.2 g).

Step 2: (E)-3-(1-Methyl-1,2,3-triazol-4-yl)acrylic acid

10% Sodium hydroxide solution (3 ml) was added to a solution of the product from step 1 (3.2 g). The mixture was stirred at room temperature for 15 hours, further 10% sodium hydroxide solution (2 ml) added and then heated to reflux for 3 hours. On cooling the reaction mixture was partitioned between ethyl acetate and water. The organics were re-extracted with saturated sodium hydrogen carbonate solution and the combined aqueous extracts acidified to pH 1 with conc. hydrochloric acid. After extraction into ethyl acetate and dying over magnesium sulphate the solvent was removed to afford the title compound, (748 mg); $^1$H NMR (d$^6$-DMSO) 4.07 (3H, s), 6.53 (1H, d, J 16.0 Hz), 7.53 (1H, d, J 16.0 Hz), 8.44 (1H, s), 12.48 (1H, br).

Step 3: (E)-(3R)-3-Deoxo-11-deoxy-3-methoxy-11-oxo-4-epi-mutilin 14-[N-3-(1-methyl-1,2,3-triazol-4-yl)acryloyl]-carbamate (E)-3-(1-Methyl-1,2,3-triazo-4-yl)acrylic acid (306 mg, 2 mmol) in dichloromethane (10 ml) was treated with oxalyl chloride (0.35 ml, 4 mmol) and one drop of DMF at room temperature for 2 h. The solvent and excess oxalyl chloride were removed in vacua. The residue was dissolved in toluene and the solvent again removed in vacuo.

The crude acid chloride was disolved in dry dichloromethane (10 ml) and treated with silver cyanate (450 mg, 3 mmol) and (3R)-3-deoxo-11-deoxy-3-methoxy-11-oxo-4-epi-mutilin (335 mg, 1 mmol). After stirring at room temperature for 1.5 h the title compound was isolated by the procedure described in Example 31, Step 2, (310 mg, 60%); $v_{max}$ ($CH_2Cl_2$) 3388, 1775, 1748 and 1691 cm$^{-1}$; $^1$H NMR (CDCl$_3$) 0.86 (3H, d, J 6.8 Hz), 1.00 (3H, d, J 6.4 Hz), 1.07–1.55 (6H, m), 1.21 (3H, s), 1.24 (3H, s), 1.67 (1H, d, J 15.5 Hz), 1.73 (1H, d, J 11.5 Hz), 2.02 (2H, m), 2.20 (1H, m), 2.50 (1H, dd, J 15.3, 10.1 Hz), 2.89 (1H, q, J 6.3 Hz), 3.23 (3H, s), 3.46 (1H, m), 4.15 (3H, s), 5.03 (1H, d, J 17.5 Hz), 5.34 (1H, d, J 10.7 Hz), 5.76 (1H, d, 19.9 Hz), 6.69 (1H, dd, J 17.5, 10.7 Hz), 7.62 (1H, s), 7.65 (1H, d, J 15.5 Hz) 7.76 (1H, s), 7.84 (1H, d, J 15.7 Hz); MS (NH$_3$ DCI) m/z 513 (MH$^+$).

Step 4: (E)-Mutilin 14-[N-3-(1-methyl-1,2,3-triazol-4-yl) acryloyl]-carbamate.

The product from step 3, (272 mg) in dioxan (2 ml) was treated with a saturated solution of zinc chloride in conc. HCl (1 ml), as for Example 1 Step 2, to afford the title compound, (173 mg, 65%); $v_{max}$($CH_2Cl_2$) 3390, 1777, 1735 cm$^{-1}$; $^1$H NMR (CDCl$_3$) 0.76 (3H, d, J 6.6 Hz), 0.89 (3H, d, J 7.0 Hz), 1.18 (3H, s), 1.19 (1H, m), 1.45 (3H, s), 1.46 (3H, m), 1.57–1.81 (2H, m), 1.62 (3H, s), 2.05–2.36 (5H, m), 3.37 (1H, dd, J 10.7, 6.6 Hz), 4.14 (3H, s), 5.24 (1H, dd, J 17.4, 1.3 Hz), 5.40 (1H, dd, J 11.1, 1.3 Hz), 5.75 (1H d, J 8.4 Hz), 6.53 (1H, dd J 17.3, 11.0 Hz), 7.54 (1H, s), 7.60 (1H, d, J 15.7 Hz), 7.74 (1H, s), 7.81 (1H, d, J 15.7 Hz); MS (EI) m/z 498 (M$^+$), (NH$_3$ DCI) m/z 516 (MH$_4$$^+$), 499 (MH$^+$), Found: 498.2844. $C_{27}H_{38}N_4O_5$ requires 498.2842.

EXAMPLE 128

Mutilin 14-N-{[2-(N,N-Diethylamino)-ethylthio]-acetyl}-carbamate Hydrochloride

Mutilin 14-N-{[2-(N,N-diethylamino)ethylthio] acetyl}carbamate (110 mg, 0.2 mmol) in methanol (4 ml) was treated with chlorotrimethylsilane (0.1 ml) and the mixture was left to stand for 10 min. The solvents were removed. Chloroform was added and removed (×2). The residue was triturated under diethyl ether, and the resultant solid was isolated by filtration and then dried over $P_2O_5$ in vacua to give the title compound (70 mg, 59%), $v_{max}$ (KBr) 2926, 2674, 1770, 1728, 1512, 1506, 1453, and 1215 cm$^{-1}$; $^1$H NMR [(CD$_3$)$_2$SO] 0.65 (3H, d, J 6.3 Hz), 0.82 (3H, d, J 6.7 Hz), 1.08 (4H, s at 1.07 superposed on m), 1.15–1.80 (ca. 16H, m including t, J 7.2 Hz at 1.20 and s at 1.40), 2.0–2.3 (ca. 3H, m), 2.41 (1H, br s), 2.95–3.00 (2H, m), 3.05–3.18 (4H, m), 3.18–3.30 (2H, m), 3.46 (1H, br t; d, J 5.4 after D$_2$O exch.), 3.52 (2H, s), 4.57 (1H, d, J 6.0 Hz, exch D$_2$O), 5.04–5.15 (2H, m), 5.49 (1H, d, J 8.0 Hz), 6.21 (1H, dd, J 10.4, 17.7 Hz), 9.98 (1H, br s, exch D$_2$O), and 10.64 (1H, s, exch D$_2$O).

EXAMPLE 129

Mutilin 14-N-(Formyloxy-acetyl)-carbamate

Mutilin 14-N-(chloroacetyl)carbamate (110 mg, 0.25 mmol) and potassium iodide (332 mg) in N,N-dimethylforrnamide (4 ml) was stirred for 10 minutes and then treated with sodium formate (68 mg), followed by more N,N-dimethylformamide (1 ml). The mixture was stirred for four days and then ethyl acetate and water were added, and the aqueous layer was re-extracted with ethyl acetate. The combined extracts were washed with brine, dried (MgSO$_4$) and evaporated. The residue was chromatographed on silica gel eluting with ethyl acetate hexane mixtures to give, after evaporation of requisite fractions, the title compound (120 mg, quantitative), $v_{max}$ ($CH_2Cl_2$) 3564, 3381, 2944, 1791 (w), 1755 (sh), 1739, 1724, 1472, 1393, 1214, 1160, 1116, 1016, 978, and 936 cm$^{-1}$; $^1$H NMR (CDCl$_3$) inter alia 0.74 (3H, d, J 6.9 Hz), 0.90 (3H, d, J 7.0 Hz), 1.20 (s), 1.42 (s), 3.37 (1H, dd, J 6.6, 10.6 Hz), 5.12 and 5.21 (2H, ABq J 17.2 Hz), 5.24 (1H, dd, J 1.4, 17.5 Hz), 5.38 (1H, dd, J 1.3, 11.1 Hz), 5.69 (1H, d J 8.5 Hz), 6.45 (1H, dd, J 11.1, 17.4 Hz), 7.67 (1H, br s), 8.06 (1H, s); MS(CI) m/z 467 (MNH$_4$$^+$).

EXAMPLE 130

Mutilin 14-N-(Hydroxyacetyl)-carbamate

Mutilin 14-N-(formyloxyacetyl)carbamate (140 mg, 0.31 mmol) in methanol (5 ml) was stirred for 78 h and the methanol was then removed. Chromatography of the residue on silica gel, eluting with ethyl acetate/hexane mixtures gave the title compound as a solid (58 mg, 44%), $v_{max}$ (CH$_2$Cl$_2$) 3564, 3386, 2932, 1786(w), 1756, 1735, 1712, 1472, and 1209 cm$^{-1}$; $^1$H NMR (CDCl$_3$) inter alia 0.73 (3H, d, J 6.8 Hz), 0.89 (3H, d, J 7.1 Hz), 1.19 (s), 1.42 (s), 2.99 (1H, t, J 4.9 Hz), 3.37 (1H, dd, J 6.6, 10.6 Hz), 4.4–4.6 (2H, m), 5.22 (1H, dd, J 1.4, 17.5 Hz), 5.37 (1H, dd, J 1.3, 11.1 Hz), 5.71 (1H, d, J 8.5 Hz), 6.45 (1H, dd, J 11.0, 17.4 Hz), 7.81 (1H, br s); MS(ES+) m/z 534(M−H+TFA)$^+$; MS(ES−) m/z 420 (M−H)$^-$.

EXAMPLE 131

Mutilin 14-N-(Iodoacetyl)-carbamate

Mutilin 14-N-(chloroacetyl)carbamate (400 mg, 0.91 mmol) in acetone (50 ml) was treated with potassium iodide (1.2 g, 7.2 mmol), and the mixture was stirred at room temperature for 5 days. Water and ethyl acetates were added and the layers were separated. The ethyl acetate layer was washed with brine, dried (MgSO$_4$) and evaporated. The crude product was chromatographed on silica gel, eluting with ethyl acetate/hexane mixtures to give the title compound (475 mg, 86%), $^1$H NMR (CDCl$_3$) 0.77 (3H, d, J 6.7 Hz), 0.90 (3H, d, J 7.0 Hz), 1.0–1.3 (4H, m, including s at 1.20), 1.3–1.9 (12H, m, including s at 1.42), 2.0–2.4 (4H, m), 3.37 (1H, dd, J 6.6, 10.5 Hz), 4.18 and 4.32 (2H, ABq J 9.6 Hz), 5.24 (1H, dd, J 1.4, 17.4 Hz), 5.39 (1H, dd, J 1.3, 10.9 Hz), 5.74 (1H, d, J 8.5 Hz), 6.48 (1H, dd, J 11.0, 17.4 Hz), 7.47 (1H, s).

EXAMPLE 132

Mutilin 14-N-(Azidoacetyl)-carbamate

Mutilin 14-N-(iodoacetyl)carbamate (133 mg, 0.25 mmol) and sodium azide (16 mg, 0.25 mmol) were stirred together in N,N-dimethyl-formamide for 24 h. Ethyl acetate and water were added and the layers separated. The aqueous layer was re-extracted with ethyl acetate and combined ethyl acetate layers were washed with brine, dried (MgSO$_4$) and evaporated. Chromatography on silica gel, eluting with ethyl acetate 1 hexane 6:4, and evaporation of requisite fractions, gave the title compound (101 mg, 90%), $v_{max}$ (CH$_2$Cl$_2$) 3381, 2931, 2111, 1789(w), 1755, 1724, 1470, and 1206 cm$^{-1}$; $^1$H NMR (CDCl$_3$) 0.73 (3H, d, J 6.7 Hz), 0.89 (3H, d, J 7.0 Hz), 1.0–1.3 (4H, m, including s at 1.19), 1.3–1.9 (12H, m, including s at 1.43), 2.0–2.4 (4H, m), 3.36 (1H, dd, J 6.6, 10.6 Hz), 4.31 and 4.40 (2H, ABq J 18.3 Hz), 5.23 (1H, dd, J 1.4, 17.4 Hz), 5.37 (1H, dd, J 1.3, 11.1 Hz), 5.69 (1H, d, J 8.5 Hz), 6.45 (1H, dd, J 11.0, 17.4 Hz), 7.72 (1H, s); MS(ES−) m/z 445 (M−H$^-$).

EXAMPLE 133

Mutilin 14-N-[2-(3-Hydroxypyrid-2-ylthio)-acetyl]-carbamate

Mutilin 14-N-(chloroacetyl)carbamate (110 mg, 0.25 mmol) in N,N-dimethyl-formamide (4 ml) was treated with potassium iodide (166 mg, 1 mmol). After 10 min 3-hydroxy-2-mercaptopyridine (35 mg, 0.275 mmol) and potassium carbonate (35 mg, 0.25 mmol) and N,N-dimethylformamide (1 ml) were added. The mixture was stirred for 24 h and then added to ethyl acetate 1 water. After separation the aqueous layer was re-extracted with ethyl acetate. The combined ethyl acetate layers were dried (MgSO$_4$) and evaporated. The residue was chromatographed on silica gel, eluting with ethyl acetate/hexane mixtures to yield the title compound (110 mg, 83%); $v_{max}$ (KBr) 2956, 1782, 1725, 1711, 1523, 1491, 1449, and 1299 cm$^{-1}$; $^1$H NMR [(CD$_3$)$_2$SO] 0.66 (3H, d, J 6.1 Hz), 0.82 (3H, d, J 6.7 Hz), 0.9–1.8 (ca 15 H, m, including s at 1.14 and s at 1.39), 2.0–2.3 (4H, m), 2.41 (1H, br s), 3.44 (1H, br t, d, J 5.4 Hz after D$_2$O exch), 4.04 (2H, s), 4.53 (1, d J 6.0 Hz, exch D$_2$O) 5.04–5.15 (2H,m), 5.50 (1H, d, J 7.9 Hz), 6.22 (1H, dd, J 11.1, 17.7 Hz), 6.94–7.06 (2H, m), 7.83 (1H, dd J 1.4 and 4.6 Hz), 10.43 (1H, br s, exch. D$_2$O), 10.65 (1H, s, exch. D$_2$O); MS(CI) m/z 531 (M+H)$^+$.

EXAMPLE 134

Mutilin 14-N-[2-(4-Methylpyrimidin-2-ylthio)-acetyl]-carbamate

Using a simliar procedure to that described in Example 133, 2-mercapto4-methylpyrimidine (42 mg, 0.26 mmol) was converted over 3 days into the title compound (95 mg, 71%), $v_{max}$ (CH$_2$Cl$_2$) 3377, 3179, 2961, 1782(w), 1734, 1576, 1545, 1332, 1217, 1116, and 1016 cm$^{-1}$; $^1$H NMR (CDCl$_3$) inter alia 0.61 (3H, d, J 6.5 Hz), 0.87 (3H, d, J 7.0 Hz), 1.19 (s, 1.43 (s), 2.51 (3H, s), 3.34 (1H, dd, J 6.6, 11.1 Hz), 3.84 and 3.92 (2H, ABq J 15.1 Hz), 5.22 (1H, dd, J 1.4, 17.3 Hz), 5.37 (1H, dd, J 1.4, 10.9 Hz), 5.71 (1H, d, J 8.5 Hz), 6.54 (1H, dd, J 11.0, 17.4 Hz), 6.96 (1H, d J 5.1 Hz), 8.41 (1H, d J 5.2 Hz), 9.57 (1H, br s); MS(EI) m/z 589 (M$^+$); Found: 529.2607, C$_{28}$H$_{39}$N$_3$O$_5$S requires 529.2610.

EXAMPLE 135

Mutilin 14-N-[2-(1-Oxopyrid-2-ylthio)-acetyl]-carbamate

Using a simliar procedure to that described in Example 133, 2-mercaptopyridine-1-oxide (32 mg, 0.25 mmol) was converted in 3 days into the title compound (87 mg, 65%), $v_{max}$ (CH$_2$Cl$_2$) 3386, 2962, 2932, 1783, 1734, 1484, 1204, 1116, and 1016 cm$^{-1}$; $^1$H NMR (CDCl$_3$) inter alia 0.72 (3H, d, J 6.7 Hz), 0.89 (3H, d, J 7.0 Hz), 1.18 (s), 1.42 (s), 3.36 (1H, dd, J 6.6, 10.5 Hz), 4.06 (2H, s), 5.24 (1H, dd, J 1.3, 17.4 Hz), 5.41 (1H, dd, J 1.3, 11.0 Hz), 5.73 (1H, d, J 8.4 Hz), 6.50 (1H, dd, J 11.0, 17.4 Hz), 7.3 (1H, dt J 1.7, 6.5 Hz), 7.27 (1H, dt, J ca. 1.2, 8 Hz) 7.51 (1H, dd J 1.7, 8.2 Hz), 8.27 (1H, dd, J 0.9, 6.4), 8.36 (1H, br s); MS(CI) m/z 531 (MH)$^+$.

EXAMPLE 136

Mutilin 14-N-(Ethylthio-acetyl)-carbamate

Using a simliar procedure to that described in Example 133, the chloroacetyl compound (280 mg, 0.64 mmol) and sodium ethane thiolate (79 mg), with no potassium carbonate, was converted in 26 hours into the title compound (194 mg, 65%), $v_{max}$ (CH$_2$Cl$_2$) 3386, 2962, 2932, 1782, 1756 (sh),1734, 1716 (sh), 1484, 1204, 1116, and 1016 cm$^{-1}$; $^1$H NMR (CDCl$_3$) inter alia 0.76 (3H, d, J 6.7 Hz), 0.89 (3H, d, J 7.1 Hz), 1.18 (s), 1.26 (t, J 7.4 Hz), 1.44 (s), 2.56 (2H, q, J 7.4 Hz), 3.36 (1H, dd, J 6.6, 11.7 Hz), 3.51 and 3.60 (2H, ABq, J 15.2 Hz), 5.22 (1H, dd, J 1.5, 17.4 Hz), 5.38 (1H, dd, J 1.4, 10.9 Hz), 5.73 (1H, d, J 8.5 Hz), 6.51 (1H, dd, J 11.0, 17.3 Hz), 7.95 (1H, br s); MS(CI) m/z 483 (MNH$_4$)$^+$.

EXAMPLE 137

Mutilin 14-N-(Ethylsulfinyl-acetyl)-carbamate

Mutilin 14-N-(ethylthio-acetyl)carbamate (74 mg, 0.16 mmol) in dichloromethane (4 ml) was cooled in an ice-bath and treated with m-chloroperbenzoic acid (55% pure, 50 mg, 0.16 mmol) and the mixture was stirred for 2 h. The mixture was diluted with dichloromethane and washed with aqueous NaHCO$_3$, dried (MgSO$_4$) and evaporated. The residue was chromatographed on silica gel, eluting with ethyl acetate/hexane mixtures to give the title compound as a mixture of diasteroisomeric sulphoxides (57 mg, 73%), $v_{max}$ (CH$_2$Cl$_2$) 3380, 2940, 2932, 1781, 1735, 1518, 1470, 1211, 1116, 1014, and 910 cm$^{-1}$; MS(ES−) m/z 480 (M−H)$^-$.

EXAMPLE 138

Mutilin 14-N-(Ethylsulfonyl-acetyl)-carbamate

The Mutilin 14-N-(ethylthio-acetyl)carbamate (74 mg, 0.16 mmol) in dichloromethane (4 ml) was cooled in an ice-bath and treated with m-chloroperbenzoic acid (55% pure, 100 mg, 0.32 mmol) and the mixture was stirred for 2 h. The mixture was diluted with dichloromethane and washed with dilute aqueous NaHCO$_3$ dried (MgSO$_4$) and evaporated. The residue was chromatographed on silica gel, eluting with ethyl acetate/hexane mixtures to give the title compound (36 mg, 45%), $v_{max}$ (CH$_2$Cl$_2$) 3373, 2944, 1787, 1757, 1733, 1706, 1469, 1324, 1208, 1153, 1116, 1016, 939, and 910 cm$^{-1}$; $^1$H NMR (CDCl$_3$) inter alia 0.75 (3H, d, J 6.8 Hz), 0.89 (3H, d, J 7.0 Hz), 1.18 (s), 3.25 (2H, q, J 7.5 Hz), 3.37 (1H, dd, J 6.7, 9.8 Hz), 4.50 (2H, br ABq), 5.24 (1H, dd, J 1.3, 17.3 Hz), 5.37 (1H, dd, J 1.3, 10.9 Hz), 5.71 (1H, d, J 8.4 Hz), 6.47 (1H, dd, J 11.1, 17.4 Hz), 8.19 (1H, br s); MS(ES−) m/z 496 (M−H)$^-$.

EXAMPLE 139

Mutilin 14-N-[tert-Butyloxycarbonylmethylthio-acetyl]-carbamate

Mutilin 14-N-(chloroacetyl)carbamate (55 mg, 0.125 mmol) in N,N-dimethyl-formamide (2 ml) was treated with potassium iodide (84 mg, 0.5 mmol) and potassium carbonate (18 mg, 0.125 mmol). tert-Butyl 2-mercaptoacetate (18.5 mg, 0.125 mmol) in N,N-dimethyl-formamide (0.5 ml) was then added. The mixture was shaken for 17 h and then treated with ethyl acetate (5 ml)/water (7.5 ml). After separation the ethyl acetate layer was washed with 1M NaOH and dried (MgSO$_4$) and evaporated. The residue was chromatographed on silica gel, eluting with ethyl acetate/hexane mixtures to yield the title compound (44 mg, 63%), $^1$H NMR (CDCl$_3$) inter alia 0.76 (3H, d, J 6.7 Hz), 0.88 (3H, d, J 7.0 Hz), 1.18 (s), 1.44 (s), 1.47 (s), 3.26 (2H, s), 3.36 (1H, dd, J 6.6, 10.8 Hz), 3.64 (2H br s), 5.22 (1H, dd, J 1.4, 17.3 Hz), 5.37 (1H, dd, J 1.3, 11.0 Hz), 5.71 (1H, d, J 8.4 Hz), 6.51 (1H, dd, J 11.0, 17.3 Hz), 8.35 (1H, br s).

EXAMPLE 140

Mutilin 14-N-[2-(Ethyloxycarbonyl)ethylthio-acetyl]-carbamate

Using the process described in Example 139 mutilin 14-N-(chloroacetyl)carbamate (55 mg, 0.125 mmol) and ethyl 3-mercaptopropionate (16.8 mg, 0.125 mmol) were converted into the title compound (51 mg, 75%), $^1$H NMR (CDCl$_3$) inter alia 0.75 (3H, d, J 6.7 Hz), 0.88 (3H, d, J 7.0 Hz), 1.19 (s), 1.26 (t, J 7.2 Hz), 1.44 (s), 2.62 (2H, t, J 6.8 Hz), 2.84 (2H, t, J 6.7 Hz), 3.36 (1H, dd, J 6.6, 10.6 Hz), 3.56 and 3.64 (2H, ABq, J 15.0 Hz), 5.22 (1H, dd, J 1.4, 17.3 Hz), 5.37 (1H, dd, J 1.3, 11.0 Hz), 5.71 (1H, d, J 8.4 Hz), 6.48 (1H, dd, J 11.0, 17.3 Hz), 7.90 (1H, br s).

EXAMPLE 141

Mutilin 14-N-[(5-Methyl-1,3,4-thiadiazol-2-ylthio)-acetyl]-carbamate

Using the process described in Example 139 mutilin 14-N-(chloroacetyl)-carbamate (55 mg, 0.125 mmol) and 2-mercapto-5-methyl-1,3,4-thiadiazole (16.5 mg, 0.125 mmol) were converted into the title compound (38 mg, 56%), $^1$H NMR (CDCl$_3$) inter alia 0.65 (3H, d, J 6.7 Hz), 0.88 (3H, d, J 7.0 Hz), 1.18 (s), 1.42 (s), 2.74 (s, 3H), 3.35 (1H, dd, J 6.6, 10.9 Hz), 4.14 and 4.33 (2H, ABq, J 15.5 Hz), 5.22 (1H, dd, J 1.4, 17.3 Hz), 5.38 (1H, dd, J 1.4, 11.0 Hz), 5.70 (1H, d, J 8.4 Hz), 6.53 (1H, dd, J 11.0, 17.3 Hz), 9.05 (1H, br s).

EXAMPLE 142

Mutilin 14-N-[(1-Methyltetrazol-5-ylthio)-acetyl]-carbamate

Using the process described in Example 139 mutilin 14-N-(chloroacetyl)-carbamate (55 mg, 0.125 mmol) and 5-mercapto-1-methyl-tetrazole (14.5 mg, 0.125 mmol) were converted into the title compound (28 mg, 43%), $^1$H NMR (CDCl$_3$) inter alia 0.71 (3H, d, J 6.7 Hz), 0.89 (3H, d, J 6.9 Hz), 1.19(s), 1.41 (s), 3.36 (1H, dd, J 6.6, 10.7 Hz), 3.98 (3H, s), 4.46 and 4.54 (2H, ABq, J 16.8 Hz), 5.24 (1H, dd, J 1.4, 17.4 Hz), 5.39 (1H, dd,. 1.3, 11.1 Hz), 5.71 (1H, d, J 8.4 Hz), 6.49 (1H, dd, J 11.0, 17.3 Hz), 8.44 (1H, br s).

EXAMPLE 143

Mutilin 14-N-[(1-Phenyl-tetrazol-5-ylthio)-acetyl]-carbamate

Using the process described in Example 139 mutilin 14-N-(chloroacetyl)-carbamate (55 mg, 0.125 mmol) and 5-mercapto-1-phenyl-tetrazole (22.3 mg, 0.125 mmol) were converted into the title compound, (60 mg, 82%), $^1$H NMR (CDCl$_3$) inter alia 0.72 (3H, d, J 6.7 Hz), 0.89 (3H, d, J 7.0 Hz), 1.20 (s), 1.44 (s), 3.37 (1H, dd, J 6.6. 10.8 Hz), 4.50 and 4.60 (2H, ABq, J 16.6 Hz), 5.24 (1H, dd, J 1.4, 17.4 Hz), 5.38 (1H, dd, J 1.3, 11.0 Hz), 5.73 (1H, d, J 8.7 Hz), 6.50 (1H, dd, J 11.0, 17.4 Hz), 7.58 (5H, s), 8.39 (1H, br s).

EXAMPLE 144

Mutilin 14-N-[(1,3,4-Thiadiazol-2-ylthio)-acetyl]-carbamate

Using the process described in Example 139 mutilin 14-N-(chloroacetyl)-carbamate (55 mg, 0.125 mmol) and 2-mercapto-1,3,4-thiadiazole (14.9 mg, 0.125 mmol) were converted into the title compound (37 mg, 60%), $^1$H NMR (CDCl$_3$) inter alia 0.67 (3H, d, J 6.7 Hz), 0.88 (3H, d, J 6.9 Hz), 1.19 (s), 1.42 (s), 3.36 (1H, dd, J 6.5, 10.9 Hz), 4.29 and 4.47 (2H, ABq, J 15.8 Hz), 5.24 (1H, d, J 17.3 Hz), 5.38 (1H, d, J 12.0 Hz), 5.70 (1H, d, J 8.4 Hz), 6.51 (1H, dd, J 11.0, 17.4 Hz), 8.77 (1H, br s), 9.13 (1H, s).

EXAMPLE 145

Mutilin 14-N-[(5-Aminocarbonyl-1,3,4-thiadiazol-2-ylthio)-acetyl]-carbamate

Using the process described in Example 139 mutilin 14-N-(chloroacetyl)-carbamate (55 mg, 0.125 mmol) and 2-mercapto-1,3,4-thiadiazole-5-carbamate (16.1 mg, 0.125 mmol) were converned into the title compound (21 mg, 29%), $^1$H NMR (CDCl$_3$) inter alia 0.67 (3H, d, J 6.7 Hz), 0.88 (3H, d, J 7.0 Hz), 1.19 (s), 1.42 (s), 3.36 (1H, dd, J 6.5, 10.8 Hz), 4.29 and 4.47 (2H, ABq, J 15.8 Hz), 5.24 (1H, d, J 17.5 Hz), 5.39 (1H, d, J 10.9 Hz), 5.71 (1H, d, J 8.4 Hz), 5.86 (1H, s), 6.51 (1H, dd, J 11.0, 17.3 Hz), 7.10 (1H, s), 8.48 (1H, br s).

EXAMPLE 146

Mutilin 14-N-[(5-Aminocarbonyl-1,3,4-oxadiazol-2-ylthio)-acetyl]-carbamate

Using the process described in Example 139 mutilin 14-N-(chloroacetyl)-carbamate (55 mg, 0.125 mmoi) and 2-mercapto-1,3,4-oxadiazole-5-carbamate (20.1 mg, 0.125 mmol) were converted into the title compound (8 mg, 11%), $^1$H NMR (CDCl$_3$) inter alia 0.73 (3H, d, J 6.8 Hz), 0.90 (3H, d, J 6.8 Hz), 1.19 (s), 1.43 (s),3.37 (1H, dd), 4.54 and 4.61 (2H, ABq, J 17.0 Hz), 5.25 (1H, dd, J 1.3, 17.4 Hz), 5.39 (1H, dd, J 1.2, 11.0 Hz), 5.72 (1H, d, J 8.4 Hz), 6.01 (1H, br s), 6.48 (1H, dd, J 11.1, 17.4 Hz), 7.01 (1H, br s), 8.21 (1H, br s).

EXAMPLE 147

Mutilin 14-N-[1-(2-Dimethylaminoethyl)-tetrazol-5-ylthio]-acetyl}-carbamate

Mutilin 14-N-(iodoacetyl)carbamate (133 mg, 0.25 mmol) in N,N-dimethylformamide (2 ml) was treated with potassium carbonate (35 mg, 0.25 mmol) and 1-(2-dimethylaminoethyl)-5-mercaptotetrazole (43 mg, 0.25 mmol). The mixture was shaken for 17 h and then treated with ethyl acetate (5 ml)/water (5 ml). After separation the aqueous layer was re-extracted with ethyl acetate (5 ml). The combined ethyl acetate layers were washed with brine, and dried (MgSO$_4$) and evaporated. The residue was chromatographed on silica gel, eluting with ethyl acetate/hexane mixtures to yield the title compound (96 mg, 66%), $v_{max}$ (CH$_2$Cl$_2$)3384, 2948, 1782, 1733, 1468, 1390, 1215, 112, 1116, 1016, and 938 cm$^{-1}$; $^1$H NMR (CDCl$_3$) inter alia 0.68 (3H, d, J 6.7 Hz), 0.87 (3H, d, J 7.0 Hz), 1.17 (s), 1.42 (s), 2.23 (s), 2.73 (2H, t, J 6.2 Hz), 3.34 (1H, dd, J 6.5, 10.5 Hz), 4.33 (4H, t J 6.1 Hz), 5.21 (1H, dd, J 1.3, 17.3 Hz), 5.37 (1H, dd, J 1.3, 11.0 Hz), 5.69 (1H, d, J 8.4 Hz), 6.49 (1H, dd, J 11.0, 17.4 Hz), 8.68 (1H, br s); MS(EI) m/z 576 (M$^+$); Found: 576.3072, C$_{28}$H$_{44}$N$_6$O$_5$S req. 576.3094.

EXAMPLE 148

Mutilin 14-N-[(1,2,3-Triazol-5-ylthio)-acetyl]-carbamate

Using the process described in Example 147 mutilin 14-N-(iodoacetyl)-carbamate (133 mg, 0.25 mmol) and the sodium salt of 5-mercapto-1,2,3-triazole (31 mg, 0.25 mmol), in the absence of potassium carbonate, were converted into the title compound (75 mg, 55%), $v_{max}$ (CH$_2$Cl$_2$) 3408, 3220, 2930, 1781, 1733, 1471, 1410, 1387, 1209, 1116, and 1016 cm$^{-1}$; $^1$H NMR (CDCl$_3$) interalia 0.70 (3H, d, J 6.7 Hz), 0.87 (3H, d, J 7.0 Hz), 1.17 (s), 1.42 (s), 3.35 (1H, br s), 3.93 (2H, s), 5.21 (1H, dd, J 1.3, 17.4 Hz), 5.35 (1H, dd, J 1.2. 11.1 Hz), 5.69 (1H, d, J 8.4 Hz), 6.49 (1H, dd, J 11.0, 17.4 Hz), 7.67 (1H, s), 8.65 (1H, br s); MS(CI) m/z 522 (MNH$_4$)$^+$.

EXAMPLE 149

Mutilin 14-N-{[1-(Methoxycarbonylmethyl)-tetrazol-5-ylthio]-acetyl}-carbamate

Using the process described in Example 147 mutilin 14-N-(iodoacetyl)-carbamate (133 mg, 0.25 mmol) and methyl 5-(mercapto-tetrazol-1-yl)-acetate (44 mg, 0.25 mmol) were converted into the title compound (77 mg, 53%), $v_{max}$ (CH$_2$Cl$_2$) 3380, 2958, 1783, 1759, 1733, 1459, 1217, 1183, 1116, 1016, and 939 cm$^{-1}$; $^1$H NMR (CDCl$_3$) inter alia 0.69 (3H, d, J 6.8 Hz), 0.87 (3H, d, J 7.0 Hz), 1.17 (s), 1.41 (s), 3.35 (1H, dd, J 6.5, 10.7 Hz), 4.46 and 4.56 (2H, ABq J 16.9 Hz), 5.13 (2H, s), 5.22 (1H, dd, J 1.3, 17.3 Hz), 5.37 (1H, dd, J 1.3, 11.1 Hz), 5.69 (1H, d, J 8.4 Hz), 6.47 (1H, dd, J 11.0, 17.4 Hz), 8.26 (1H, br s); MS(CI) m/z 595 (MNH$_4$)$^+$.

EXAMPLE 150

Mutilin 14-N-{[3-(Methoxycarbonyl)-pyrid-2-ylthio]-acetyl}-carbamate

Using the process described in Example 147 mutilin 14-N-(iodoacetyl)-carbamate (133 mg, 0.25 mmol) and methyl methyl 2-mercapto-pyridine-3-carboxylate (42 mg, 0.25 mmol) were converted into the title compound (48 mg, 33%), $v_{max}$ (CH$_2$Cl$_2$) 3380, 2956, 1781, 1720, 1401, 1214, 1139, 1116, 1071, and 1016 cm$^{-1}$; $^1$H NMR (CDCl$_3$) inmer alia 0.55 (3H, d, J 6.6 Hz), 0.84 (3H, d, J 7.0 Hz), 1.14 (s), 1.36 (s), 3.31 (1H, dd, J 6.6, 11.0 Hz), 3.91 (2H, s), 3.94 (3H, s), 5.19 (1H, dd, J 1.4, 17.3 Hz), 5.35 (1H, dd, J 1.4, 10.9 Hz), 5.65 (1H, d, J 8.5 Hz), 6.47 (1H, dd, J 11.0, 17.4 Hz), 7.20 (1H, dd J 5.0, 7.8 Hz), 8.30 (1H, dd J 1.8, 7.8 Hz), 8.55 (1H, dd, J 1.7, 4.8 Hz), 9.45 (1H, br s); MS(CI) m/z 573 (MH)$^+$.

EXAMPLE 151

Mutilin 14-N-[(2-Furylmethylthio)-acetyl]-carbamate

Using the process described in Example 147 mutilin 14-N-(iodoacetyl)-carbamate (133 mg, 0.25 mmol) and (2-furyl)-methyl mercaptan (29 mg, 0.25 mmol) were converted into the title compound (43 mg, 53%), $v_{max}$ (CH$_2$Cl$_2$) 3382, 2930, 1783, 1734, 1483, 1206, 1152, 1116, 1014, and 938 cm$^{-1}$; $^1$H NMR (CDCl$_3$) inter alia 0.73 (3H, d, J 6.6 Hz), 0.87 (3H, d, J 7.0 Hz), 1.18 (s), 1.42 (s), 3.35 (1H, dd, J 6.7, 10.7 Hz), 3.48 and 3.56 (2H, ABq J 15.7 Hz), 3.76 (2H, s), 5.21 (1H, dd, J 1.4, 17.3 Hz), 5.36 (1H, dd, J 1.3, 11.1 Hz), 5.70 (1H, d, J 8.4 Hz), 6.21 (1H, d, J 3.4 Hz), 6.28 (1H, J d 1.9, 5.01 Hz), 6.48 (1H, dd, J 11.0, 17.4 Hz), 7.34 (1H, dd J 0.8, 1.9 Hz), 7.80 (1H, br s): MS(CI) m/z 535 (MNH$_4$)$^+$.

EXAMPLE 152

Mutilin 14-N-[(2,3-Dihydroxypropylthio)-acetyl]-carbamate

Using the process described in Example 147 mutilin 14-N-(iodoacetyl)-carbamate (133 mg, 0.25 mmol) and 3-mercapto-1,2-propane-diol (0.021 ml, 27 mg, 0.25 mmol) were converted into the title compound (37 mg, 28%); $v_{max}$ (CH$_2$Cl$_2$) 3380, 2929, 1782, 1733, 1471, 1409, 1206, 1115, and 1016 cm$^{-1}$; $^1$H NMR (CDCl$_3$) inter alia 0.74 (3H, d, J 6.5 Hz), 0.87 (3H, d, J 7.0 Hz), 1.17 (s), 1.42 (s), 2.56–2.81 (2H,m), 3.12 (1H, s, exch. D$_2$O), 3.35 (1H, dd, J 6.6, 10.5 Hz; d, J 6.4 after D$_2$O exch.), 3.50–3.58 (1H, m), 3.96–4.11 (2H, m), 4.13–4.21 (1H, m), 5.21 (1H, dd, J 1.3, 17.4 Hz), 5.36 (1H, d, J 11.1 Hz), 5.69 (1H, d, J 8.4 Hz), 6.47 (1H, dd, J 11.0, 17.4 Hz), 7.99 (1H, br s); MS(ES+) m/z 529 (MNH$_4$)$^+$.

EXAMPLE 153

Mutilin 14-N-[(Pyrid-2-ylthio)-acetyl]-carbamate

Using the process described in Example 147 mutilin 14-N-(iodoacetyl)-carbamate (133 mg, 0.25 mmol) and 2-mercapto-pyridine (28 mg, 0.25 mmol) were converted into the title compound (107 mg, 83%), $v_{max}$ (CH$_2$Cl$_2$) 3557, 3379, 3151, 2932, 1779, 1733, 1584, 1527, 1456, 1417, 1220, 1152, 1116, 1034, and 1016 cm$^{-1}$; $^1$H NMR (CDCl$_3$) inter alia 0.56 (3H, d, J 6.4 Hz), 0.84 (3H, d, J 7.0 Hz), 1.14 (s), 1.38 (s), 3.32 (1H, d, J 6.5, Hz), 3.70 and 3.84 (2H, ABq, J 14.5 Hz), 5.19 (1H, dd, J 1.5, 17.4 Hz), 5.35 (1H, dd, J 1.5, 10.9 Hz), 5.65 (1H, d, J 8.6 Hz), 6.57 (1H, dd, J 10.9, 17.3 Hz), 7.06–7.16 (1H, m), 7.24–7.30 (2H, m), 7.55 (1H, m), 8.42–8.45 (1H, m), 10.71 (1H, br s); MS(EI) m/z 514 (M$^+$); Found: 514.2485, C$_{28}$H$_{38}$N$_2$O$_5$S requires 514.2501.

EXAMPLE 154

Mutilin 14-N-[(Cyanothio)-acetyl]-carbamate

Using the process described in Example 147 mutilin 14-N-(iodoacetyl)-carbamate (133 mg, 0.25 mmol) and ammonium thiocyanate (19 mg, 0.25 mmol), in the absence of potassium carbonate, were converted into the title compound (105 mg, 90%), $v_{max}$ ($CH_2Cl_2$) 3376, 2931, 1752, 1735, 1721, 1472, 1216, 1188, 1116, 1016, and 939 cm$^{-1}$; $^1$H NMR (CDCl$_3$) inter alia 0.72 (3H, d, J 6.9 Hz), 0.88 (3H, d, J 7.0 Hz), 1.18 (s), 1.41 (s), 3.36 (1H, dd, J 6.6, 10.4 Hz), 4.37 (2H, s), 5.23 (1H, dd, J 1.3, 17.3 Hz), 5.38 (1H, dd, J 1.2, 10.9 Hz), 5.68 (1H, d, J 8.5 Hz), 6.41 (1H, dd, J 11.0, 17.4 Hz), 7.94 (1H, br s); MS(ES-) m/z 461 (M-H)$^-$.

EXAMPLE 155

Mutilin 14-N-[N-Acetylglycyl]carbamate

Mutilin 14-N-(azidoacetyl)carbamate (113 mg, 0.25 mmol) in dry tetrahydrofuran (1 ml) under argon was treated with tri-n-butylphosphine (0.045 ml, 55 mg, 0.275 mmol) and the mixture was stirred under argon for 1 h. The solution was then cooled to –50° C. and acetyl chloride (0.024 ml, 21 mg, 0.275 mmol) was added. The mixture was stirred for 45 min and then saturated aqueous NaHCO$_3$ (0.5 ml) was added and the mixture was allowed to warm to room temperature. Ethyl acetate and brine were added. the layers were separated and the ethyl acetate layer was dried (MgSO$_4$)and evaporated. The residue was chromatographed on silica gel, eluting with ethyl acetate hexane mixtures to give the title compound (20 mg, 17%), $v_{max}$ (CH$_2$Cl$_2$) 3427, 3385, 2961, 2935, 1783, 1756, 1732, 1674, 1509, and 1474 cm$^{-1}$; $^1$H NMR (CDCl$_3$) inter alia 0.71 (3H, d, J 6.8 Hz), 0.87 (3H, d, J 7.0 Hz), 1.17 (s), 1.41 (s), 2.04 (s), 2.54 (1H, br d J 6.0 Hz\), 4.38 and 4.47 (2H, dABq, J 4.9 and 19 Hz), 5.21 (1H, dd, J 1.1, 17.3 Hz), 5.36 (1H, dd, J 1.1, 10.9 Hz), 5.68 (1H, d, J 8.4 Hz), 6.26 (1H, br t. J ca. 4.6 Hz), 6.46 (1H, dd, J 11.1, 17.4 Hz), 8.06 (1H, br s); (MS) (ES-) 461 (M–H)$^-$.

EXAMPLE 156

Mutilin 14-N-(N,N-Diethylglycyl)carbamate

Mutilin 14-N-(iodoacetyl)carbamate (133 mg, 0.25 mmol) in diethylether (1.5 ml) was treated with diethylamine (0.03 ml). After 2 h and 6 h further aliquots of diethylamine (0.03 ml) were added and stirring was continued for a further 17 h. Ethyl acetate/water were added followed by 1M NaOH (2 ml). The aqueous layer was re-extracted with ethyl acetate, and combined ethyl acetate layers were dried (MgSO$_4$). and evaporated. Chromatography on silica gel, luuing with ethyl acetate 1 hexane 6:4, and evaporation of requisite fractions gave the title compound (103 mg, 83%), MS(CI) m/z 477 (MH)$^+$.

EXAMPLE 157

Mutilin 14-{N-[(1-Methyl-1,2,3-triazol-4-yl) carbonyl]-carbamate}

Step 1. (3R)-3-Deoxo-11-deoxy-3-methoxy-11-oxo-4-epi-mutilin 14-{N-[(1-methyl-1,2,3-triazol-4-yl) carbonylcarbamate]

1-Methyl-1,2,3-tniazole-4-carboxylic acid (2.00 g) in dichloromethane (50 ml) at room temperature was treated with oxalyl chloride (2.40 g) and two drops of DMF for 3 h. IR analysis showed complete conversion to the acid chloride. The solvent and excess oxalyl chloride were removed in vacuo and the residue was re-evaporated from toluene to yield the acid chloride as a white solid.

The acid chloride (0.436 g), silver cyanate (0.450 g) and (3R)-3-deoxo-11-deoxy-3-methoxy-11-oxo-4-epi-mutilin (0.334 g) were then suspended in dry dichloromethane (5 ml) and stirred at room temperature for 4 h. The resulting suspension was filtered throuzh Celite. washing well with dichloromethane. The organic solution was washed with water, saturated sodium chloride solution and dried (MgSO$_4$). After filtration, the solvent was evaporated to yield the crude product. Purification by silica gel chromatography, eluting with ethyl acetate-hexane mixtures, proylded the pure product as a colourless foam, (0.486 g); $^1$H NMR (CDCl$_3$) 0.90 (3H, d, J 6.9 Hz), 1.00 (3H, d, J 6.4 Hz), 1.05–1.80 (m), 1.21 (3H, s), 1.30 (3H, s), 1.90–2.10 (2H, m), 2.14–2.28 (1H, m) 2.52 (1H, dd, J 10.1,15.3 Hz), 2.90 (1H, q, J 6.4 Hz), 3.24 (3H, s), 3.40–3.55 (1H, m), 4.20 (3H, s), 5.00 (1H, d), J 17.5 Hz), 5.30 (1H, d, J 10.8 Hz), 5.83 (1H, d, J 9.9 Hz), 6.78 (1H, dd, J 10.7,17.5 Hz), 8.20 (1H, s) and 9.10 (1H, s).

Step 2. Mutilin 14-{N-[(1-Methyl-1,2,3-triazol-4-yl) carbonyl]carbamate}

The product from step 1, (0.450 g) in 1,4-dioxan (4 ml) was stirred at room temperature for 8 h with Lukas reagent (1.25 ml). The solution was then diluted with ethyl acetate and neutralized with saturated sodium hydrogen carbonate solution. The organic solution was washed with saturated sodium chloride solution, dried (MgSO$_4$) and evaporated to yield the crude product. After purification by silica gel chromatography, the title compound was isolated as a white solid, (0.405 g); $^1$H NMR (CDCl$_3$) 0.79 (3H, d, J 6.5 Hz), 0.89 (3H, d, J 7.0 Hz), 1.20 (3H, s), 1.40–1.90 (m), 1.52 (3H, s), 2.08–2.45 (5H, m), 3.39 (1H, dd, J 6.6,11.0 Hz), 4.19 (3H, 3), 5.22 (1H, dd, J 1.5,17.4 Hz), 5.39 (1H, dd, J 1.4,10.9 Hz), 5.83 (1H, d, J 8.4 Hz), 6.59 (1H, dd, J 10.95,17.3 Hz) 8.19 (1H, s) and 9.03 (1H, s); MS (NH$_4$ DCI) m/z 490 (MNH$_4^+$), 473 (MH$^+$).

EXAMPLE 158

Mutilin 14-{N-[(1,2,3-thiadiazol-4-yl)-carbonyl] carbamate}

Step 1. (3R)-3-Deoxo-11-deoxy-3-methoxy-11-oxo-4-epi-mutilin 14-{N-[(1,2,3-thiadiazol-4-yl)-carbonyl]carbamate}

1,2,3-Thiadiazole-4-carboxylic acid was converted to the acid chloride and reacted with (3R)-3-deoxo-11-deoxy-3-methoxy-11-oxo-4-epi-mutilin (0.334 g) as described for Example 157. Following purification by silica gel chromatography the title compound was obtained as a colourless foam (0.490 g); $^1$H NMR (CDCl$_3$) 0.90 (3H, d, J 6.9 Hz), 1.00 (3H, d, J 6.4 Hz), 1.05–1.68 (m), 1.21 (3H, s), 1.30 (3H, s), 1.7–1.82 (2H, m), 1.92–2.10 (2H, m), 2.14–2.28 (1H, m) 2.58 (1H, dd, J 10.1,15.3 Hz), 2.90 (1H, q, J 6.3 Hz), 3.25 (3H, s), 3.40–3.55 (1H, m), 5.02 (1H, d, J 17.5 Hz), 5.32 (1H, d, J 10.0 Hz), 5.89 (1H, d, J 9.9 Hz), 6.77 (1H, dd, J10.6,17.5 Hz), 9.42 (1H, s) and 9.43 (1H, s).

Step 2. Mutilin 14-(N-[(1,2,3-thiadiazol-4-yl)carbonyl] carbamate}

The product from step 1, (0.460 g) in 1,4-dioxan (4 ml) was stirred at room temperature for 7 h with Lukas reagent (1.25 ml). The solution was then diluted with ethyl acetate and neutralized with saturated sodium hydrogen carbonate solution. The organic solution was washed with saturated sodium chloride solution. dried (MgSO$_4$) and evaporated to yield the crude product. After purification by silica gel chromatography, the title compound was isolated as a white solid, (0.359 g); $^1$H NMR (CDCl$_3$) 0.81 (3H, d, J 6.7 Hz), 0.90 (3H, d, J 7.0 Hz), 1.20 (3H, s), 1.38–1.88 (m), 1.55 (3H, s), 2.10–2.45 (5H, m), 3.39 (1H, dd, J 6.6,10.9 Hz), 5.22 (1H, dd, J 1.5,17.2 Hz), 5.40 (1H, dd, J 1.4,11.1 Hz), 5.89 (1H, d, J 8.5 Hz), 6.59 (1H, dd, J 11.05,17.4 Hz) and 9.40 (2H, s): MS (NH$_4$ DCI) m/z 493 (MNH$_4^+$).

EXAMPLE 159

Mutilin 14-{N-[(1-ethyl-5-methylpyrazol-3-yl)-carbonyl]carbamate}

Step 1. (3R)-3-Deoxo-11-deoxy-3-methoxy-11-oxo-4-epi-mutilin 14-{N-[(1-ethyl-5-methylpyrazol-3-yl)carbonyl] carbamate}

1-Ethyl-5-methylpyrazole-3-carboxylic acid was converted to the acid chloride and reacted with (3R)-3-deoxo-11-deoxy-3-methoxy-11-oxo-4-epi-mutilin (0.334 g) as described for Example 157. Following purification by silica gel chromatography the title compound was obtained as a colourless foam (0.140 g); $^1$H NMR (CDCl$_3$) 0.90 (3H, d, J 6.9 Hz), 1.00 (3H, d, J 6.4 Hz), 1.05–1.64 (m), 1.20 (3H, s), 1.37 (3H, s), 1.42 (3H, t, J 7.3 Hz), 1.71(1H, d, 35.5 Hz), 1.79 (1H, s), 1.95–2.10 (2H, m), 2.12–2.29 (1H, m), 2.31 (3H, s), 2.52 (1H, dd, J 10.1,15.3 Hz), 2.92 (1H, q, J 6.3 Hz), 3.22 (3H, s), 3.40–3.55 (1H, m), 4.12 (2H, q, J 7.25 Hz), 5.02 (1H, d, J 17.5 Hz), 5.28 (1H, d, J 10.7 Hz), 5.83 (1H, d, J 9.9 Hz), 6.63 (1H, s), 6.78 (1H, dd, J 10.7,17.5 Hz), and 8.88 (1H, s).

Step 2. Mutilin 14-{N-[(1-ethyl-5-methylpyrazol-3-yl) carbonyl]carbamate}

The product from step 1, (0.130 g) in 1,4-dioxan (3.5 ml) was stirred at room temperature for 5 h with Lukas reagent (1.0 ml). The solution was then diluted with ethyl acetate and neutralized with saturated sodium hydrogen carbonate solution. The organic solution was washed with saturated sodium chloride solution, dried (MgSO$_4$) and evaporated to yield the crude product. After purification by silica gel chromatography, the title compound was isolated as a white solid, (0.133 g); $^1$H NMR (CDCl$_3$) 0.80 (3H, d, J 6.5 Hz), 0.90 (3H, d, J 7.0 Hz), 1.19 (3H, s), 1.35–1.88 (m), 1.46 (3H, t, J 7.22 Hz), 1.55 (3H, s), 2.30 (3H, s), 2.05–2.45 (5H, m), 3.38 (1H, dd, J 6.5,10.9 Hz), 4.10 (2H, q, J 7.25 Hz), 5.22 (1H, dd, J 1.6,17.4 Hz), 5.39 (1H, dd, J 1.4,10.9 Hz), 5.85 (1H, d, J 8.5 Hz), 6.59 (1H, dd, J 11.0,17.4 Hz) 6.61 (1H, s) and 8.80 (1H, s); MS (EI) m/z 499.

EXAMPLE 160

Mutilin 14-{N-[(1,5-Dimethylpyrazol-3-yl)-carbonyl]carbamate}

Step 1. (3R)-3-Deoxo-11-deoxy-3-methoxy-11-oxo-4-epi-mutilin 14-{N-[(1,5-dimethylpyrazol-3-yl)carbonyl] carbamate}

1,5-Dimethylpyrazole-3-carboxylic acid was converted to the acid chloride and reacted with (3R)-3-deoxo-11-deoxy-3-methoxy-11-oxo-4-epi-mutilin (0.334 g) as described for Example 157. Following purification by silica gel chromatography the title compound was obtained as a colourless foam (0.450 g); $^1$H NMR (CDCl$_3$) 0.90 (3H, d, J 6.9 Hz), 1.00 (3H, d, 16.4 Hz), 1.05–1.65 (m), 1.20 (3H, s), 1.35 (3H, s), 1.70(1H, d, J 6.5 Hz), 1.78 (1H, d, J 2.2 Hz), 1.95–2.10 (2H, m), 2.14–2.28 (1H, m), 2.30 (3H, s), 2.51 (1H, dd, J 10.1,15.3 Hz), 2.92 (1H, q, J 6.3 Hz), 3.22 (3H, s), 3.40–3.57 (1H, m), 3.81 (3H, s), 5.0 (1H, d, J 17.2 Hz), 5.29 (1H, d, J 10.7 Hz), 5.82 (1H, d, J 9.9 Hz), 6.63 (1H, s), 6.78 (1H, dd, J10.7,17.5 Hz), and 8.94 (1H, s).

Step 2. Mutilin 14-{N-[(1.5-dimethylpyrazol-3-yl)carbonyl] carbamate}

The product from step 1, (0.420 g) in 1,4-dioxan (4.0 ml) was stirred at room temperature for 4 h with Lukas reagent (1.4 ml). The solution was then diluted with ethyl acetate and neutralized with saturated sodium hydrogen carbonate solution. The organic solution was washed with saturated sodium chloride solution, dried (MgSO$_4$) and evaporated to yield the crude product. After purification by silica gel chromatography the title compound was isolated as a white solid, (0.360 g); $^1$H NMR (CDCl$_3$) 0.80 (3H, d, J 6.5 Hz), 0.90 (3H, d, J7.0 Hz), 1.19 (3H, s), 1.32–1.88 (m), 1.55 (3H, s), 2.29 (3H, s), 2.05–2.45 (5H, m), 3.39 (1H, dd, J 6.5,10.9 Hz), 3.80 (3H, s), 5.22 (1H, dd, J 11.6,17.4 Hz), 5.39 (1H, dd, J 1.4,10.9 Hz), 5.82 (1H, d, J 8.5 Hz), 6.60 (1H, dd, J 11.0,17.4 Hz) 6.62 (1H, s) and 8.79 (1H, s); MS (EI) m/z 485.

EXAMPLE 161

Mutilin 14-[N-(N-Methylnipecotyl)carbamate]

Step 1. (3R)-3-Deoxo-11-deoxy-3-methoxy-11-oxo-4-epi-mutilin 14-[N-(N-methylnipecotyl)carbamate]

(±)-Ethyl N-methylnipecotate (5.0 g) was dissolved in 5M hydrochloric acid (100 ml) and stirred at room temperature for 16 h. The solution was then evaporated at reduced pressure and the residue re-evaporated from toluene (×2). Trituration gave the hydrochloride salt of (±)-N-methylnipecoric acid as a white solid (3.91 g).

The hydrochloride salt of (±)-N-methylnipecotic acid (1.0 g) was suspended in dichloromethane (25 ml) and stirred at room temperature for 2 h with oxalyl chloride (0.58 ml) and DMF (1 drop). The solvent was then evaporated to yield the hydrochloride salt of N-methylnipecotyl chloride as a pale yellow solid.

The above acid chloride (0.596 g) was suspended in dry dichloromethane and stirred at room temperature for 4 h with (3R)-3-deoxo 11-deoxy-3-methoxy-11-oxo-4-epi-mutilin (0.334 g), silver cyanate (0.450 g) and triethylamine (0.276 ml). The suspension was then filtered through Celite, diluted with ethyl acetate and washed with water and saturated sodium chloride solution. The organic solution was dried (MgSO4), filtered and evaporated to yield the crude product. Silica gel column chromatography, eluting with a gradient of 0–5% 9:1 methanol/35% ammonia solution in dichloromethane gave the title compound as a diastereomeric mixture and as a colourless oil (0.290 g); $^1$H NMR (CDCl$_3$) 0.85 and 0.88 (2×d, all 3H, J 6.9 Hz), 1.00 (3H, d, J 6.4 Hz), 1.05–1.85 (m), 1.20 (3H, s), 1.25 (3H, s), 1.9–2.40 (6H, m), 2.32 (3H, 2×s), 2.48 (1H, m), 2.69(1H, broad res.), 2.80–2.98 (3H, broad q,), 3.22 (3H, s), 3.40–3.53 (1H, m), 4.98 (1H, d, J 17.6 Hz), 5.29 (1H, d, J 10.7 Hz), 5.62–5.72 (1H, 2×d, J 9.9 Hz) and 6.78–6.91 (1H,m); MS (EI) m/z 503.

Step 2. Mutilin 14-[N-(N-Methylnipecotyl)carbamate]

The product from step 1, (0.250 g) in 1,4-dioxan (3.0 ml) was stirred at room temperature for 4 h with conc. hydrochloric acid (2.0 ml). The solution was then diluted with ethyl acetate and neutralized with saturated sodium hydrogen carbonate solution. The organic solution was washed with saturated sodium chloride solution, dried (MgSO$_4$) and evaporated to yield the crude product. After purification by silica gel chromatography, eluting with a gradient of 0–5% 9:1 methanol/35% ammonia solution in dichloromethane, the title compound was isolated as a diastereoisomeric mixture and as a white foam, (0.205 g); $^1$H NMR (CDCl$_3$) 0.78 (3H, 2×d, J 6.7 Hz), 0.89 (3H, d, J 7.0 Hz), 1.19 (3H, s), 1.35–2.40 (m), 1.47 (3H, s), 2.30 (3H, 2×s),2.63–2.90 (2H, broad res.), 3.35 (1H, broad res.), 5.22 (1H, d, J 17.4 Hz), 5.39 (1H, dd, J 1.4,11.0 Hz), 5.60–5.72 (1H, 2×d, J 8.5 Hz), and 6.63 (1H, dd, J 11.0,17.4 Hz); MS (EI) m/z 488.

EXAMPLE 162

Mutilin 14-[N-(1-Methylpyrrolidin-3-oyl)-carbamate]

Step 1. 3-Ethoxycarbonyl-1-methylpyrrolidin-2-one

1-Methyl-2-pyrrolidinone (9.9 g) and diethyl carbonate (50 g) were dissolved in toluene and refluxed for 1 h with the proylson for the removal of water (Dean and Stark apparatus). After cooling, sodium hydride (50% dispersion in oil; 8.53 g) was carefully added and the stirred suspension was heated to reflux for 4 h under an atmosphere of argon.

After cooling, acetic acid (15 ml) was added and the suspension was filtered. The filtrate was evaporated and the residue chromatographed over silics gel to yield the desired product as a colourless oil (5.9 g); $^1$H NMR (CDCl$_3$) 1.30 (3H, t), 2.18–2.50 (2H, m), 2.88 (3H, s), 3.3–3.59 (3H, m), 4.25 (2H, t).

Step 2. 3-Ethoxycarbonyl-1-methylpyrrolidine

The product from step 1 (2.0 g) was dissolved in dry dichloromethane (MDC) and added to a solution of triethyloxonium tetrafluoroborate (2.8 g) in MDC (100 ml). The solution was stirred under argon at room temperature for 16 h., and then evaporated. The residue was dissolved in ethanol, cooled to ice-bath temperature under argon and sodium borohydride (0.889 g) was added. The resulting solution was stirred at room temperature for 16 h. Water (15 ml) was added and the solution was evaporated and re-evaporated from toluene (×2). The residue was chromatographed over silica gel, eluting with a gradient of 0–20% methanol/35% ammonia solution (9:1) in MDC, to yield the desired product as a pale yellow oil (0.450 g); MS (ES) m/z 158 (MH$^+$).

Step 3. (3R)-3-Deoxo-11-deoxy-3-methoxy-11-oxo-4-epi-mutilin 14-[N-1-methylpyrrolidin-3-oyl)carbamate]

The ethyl ester from step 2 was converted to the acid chloride by the procedure described in example 5, step 1. This acid chloride was reacted with (3R)-3-deoxo-11-deoxy-3-methoxy-11-oxo-4-epi-mutilin (0.668 g) according to the procedure of example 5 to yield the title compound as a diastereomeric mixture and as a pale yellow foam (0.350 g); MS (ES) m/z 489 (MH$^+$).

Step 4. Mutilin 14-[N-(1-Methylpyrrolidin-3-oyl) carbamate]

The product from step 3, (0.320 g) in 1,4-dioxan (4.0 ml) was stirred at room temperature for 4 h with conc. hydrochloric acid (2.0 ml). The solution was then diluted with ethyl acetate and neutralized with saturated sodium hydrogen carbonate solution. The organic solution was washed with saturated sodium chloride solution, dried (MgSO$_4$) and evaporated to yield the crude product. After purification by silica gel chromatography, eluting with a gradient of 0–5% 9:1 methanol/35% ammonia solution in dichloromethane, the title compound was isolated as a diastereoisomeric mixture and as a pale yellow foam, (0.245 g); $^1$H NMR (CDCl$_3$) inter alia 0.75 (3H, d, J 6.7 Hz), 0.89 (3H, d, J 7.0 Hz), 1.19 (3H, s), 1.48 (3H, s), 2.42 (3H, 2×s), 2.82–3.05 (2H, broad res.), 3.37 (1H, broad res.), 5.22 (1H, d), 5.38 (1H, d) 5.60–5.72 (1H, 2×d, J 8.6 Hz), and 6.50–6.65 (1H, m); MS (ES) m/z 475 (MH$^+$).

EXAMPLE 163

Mutilin 14-[N-(1-Allylpiperidin-4-oyl)carbamate]

Step 1. (3R)-3-Deoxo-11-deoxy-3-methoxy-11-oxo-4-epi-mutilin 14-[N-(1-allyipiperidin-4-oyl)carbamate]

1-Allylpiperidine-4-carboxylic acid was converted to the acid chloride hydrochloride by the procedure described in Example 161. This acid chloride was then reacted with (3R)-3-deoxo-11-deoxy-3-methoxy-11-oxo-4-epi-mutilin (0.334 g) by the procedure outlined in Example 161 to yield the title compound as a colourless foam (0.373 g) after silica gel column chromatography; MS (ES) m/z 529 (MH$^+$).

Step 2. Mutilin 14-[N-(1-Allylpiperidin-4-oyl)carbamate]

The product from Step 1, (0.340 g) in 1,4-dioxan (3.0 ml) was stirred at room temperature for 7 h with conc. hydrochloric acid (2.0 ml). The solution was then diluted with ethyl acetate and neutralized with saturated sodium hydrogen carbonate solution. The organic solution was washed with saturated sodium chloride solution, dried (MgSO$_4$) and evaporated to yield the crude product. After purification by silica gel chromatography, eluting with a gradient of 0–10% 9:1 methanol/35% ammonia solution in dichloromethane, the title compound was isolated as a white solid, (0.192 g); $^1$H NMR (CDCl$_3$) 0.75 (3H, d, J 6.5 Hz), 0.89 (3H, d, J 7.0 Hz), 1.20 (3H, s), 1.40–2.45 (m), 1.45 (3H, s), 2.90–3.10 (5H, m) 3.39 (1H, dd, J 6.6,10.4 Hz), 5.10–5.30 (3H, m), 5.37 (1H, dd, J 1.2,10.9 Hz), 5.70 (1H, d, J 8.4 Hz), 5.78–5.98 (1H, m), 6.50 (1H, dd, J 11.10,17.4 Hz) and 7.43 (1H, s); MS (ES) m/z 515 (MH$^+$).

EXAMPLE 164

Mutilin 14-[N-(1-Cyclopropylmethylpiperidin-4-oyl)carbamate]

Step 1. (3R)-3-Deoxo-11-deoxy-3-methoxy-11-oxo-4-epi-mutilin 14-[N-1-cyclopropylmethyyl piperidin-4-oyl) carbamate]

1-Cyclopropylmethylpiperidine-4-carboxylic acid was converted to the acid chloride hydrochloride by the procedure described in Example 161. This acid chloride was then reacted with (3R)-3-deoxo-11-deoxy-3-methoxy-11-oxo-4-epi-mutilin (0.334 g) by the procedure outlined in Example 161 to yield the title compound as a colouriess foam (0.450 g) after silica gel column chromatography; MS (EI) m/z 542 (M$^+$).

Step 2. Mutilin 14-[N-(1-cyclopropylmethyl piperidin-4-oyl)carbamate]

The product from step 1, (0.400 g) in 1,4-dioxan (5.0 ml) was stirred at room temperature for 7 h with conc. hydrochloric acid (2.0 ml). The solution was then diluted with ethyl acetate and neutralized with saturated sodium hydrogen carbonate solution. The organic solution was washed with saturated sodium chloride solution, dried (MgSO$_4$) and evaporated to yield the crude product. After purification by silica gel chromatography, eluting with a gradient of 0–10% 9:1 methanol/35% ammonia solution in dichloromethane, the title compound was isolated as a white solid, (0.190 g); $^1$H NMR (CDCl$_3$) 0.12 (2H,m), 0.53 (2H, m), 0.75 (3H, d, J 6.5 Hz), 0.90 (3H, d, J 7.0 Hz), 1.20 (3H, s), 1.35–2.40 (m), 1.42 (3H, s), 2.95–3.18 (3H, m), 3.39 (1H, dd, J 6.6,10.4 Hz), 5.25(1H, dd, J 1.4, 17.4 Hz), 5.38 (1H, dd, J 1.2,10.9 Hz), 5.70 (1H, d, J 8.4 Hz), 6.50 (1H, dd, J 11.10,17.4 Hz) and 7.40 (1H, s); MS (EI) m/z 515.

EXAMPLE 165

Mutilin 14-[N-(nipecotyl)carbamate]

Step 1. N-t-Butoxycarbonyl nipecotic acid (±)-Nipecotic acid was dissolved in water (25 ml) and stirred rapidly at room temperature for 16 h with a solution of t-buroxycarbonyl anhydride (3.27 g) in 1,4-dioxan (25 ml). The solution was then evaporated to small volume, adjusted to pH 2.0 by the addition of 5M hydrochloric acid solution, and the resulting precipitate was extracted with dichloromethane. The organic solution was washed with brine, dried (MgSO$_4$) and evaporated at reduced pressure. The residue was triturated with ether/hexane and the resulting white solid collected by filtration (1.10 g); MS (EI) m/z 229

Step 2. Mutilin 11-dichloroacetyl-14-[N-(N-t-butoxycarbonyl-nipecotyl)carbamate]

The product from Step 1 (0.458 g) was converted to the acid chloride by the procedure described in Example 161. This was then dissolved in dry dochloromethane (20 ml) and stirred vigorously at room temperature for 3 days with silver cyanate (0.6 g), mutilin 11-dichloroacetate (0.432 g) and tetrakis(triphenylphosphine) palladium(0) (0.002 g). The suspension was filtered through Celite and the solvent evaporated at reduced pressure. The residue was chromatographed over silics gel, eluting with ethyl acetate/hexane mixtures to provided the title compound as a white foam (0.213 g); $v_{max}$ (CH$_2$Cl$_2$) 3383, 1784, 1755, 1735, 1686 cm$^{-1}$.

Step 3. Mutilin 14-[N-(N-t-butoxycarbonyl-nipecotyl) carbamate]

The product from Step 2 was dissolved in tetrahydrofuran (2 ml) and stirred vigorously at room temperature for 1.5 h with 1M sodium hydroxide solution (0.407 ml). The reaction solution was diluted with ethyl acetate, washed with brine, dried (MgSO$_4$) and evaporated. Silica gel column chromatography proylded the title compound as a diastereoisomeric mixture and an oil (0.103 g); $v_{max}$ (CH$_2$Cl$_2$) 3540, 3419, 1783, 1732, 1697 cm$^{-1}$; MS (ES) m/z 573 ([M−H]$^-$).

Step 4. Mutilin 14-[N-(nipecotyl)carbamate]

The product from Step 3 (0.08 g) was dissolved in dichloromethane (2 ml) and stirred at room temperature for 16 h with trifluoracetic acid (0.120 ml). The solvent was then evaporated and the residue was partitioned between ethyl acetate and saturated sodium hydrogen carbonate solution. The organic solution was washed with brine. dried (MgSO$_4$) and evaporated at reduced pressure. Silica gel column chromatography, eluting with a gradient of 0–10% methanol/35% ammonia solution (9:1) in dichloromethane proylded the title compound as a diastereoisomeric mixture and as a white foam (0.035 g); $v_{max}$ (CH$_2$Cl$_2$) 1771, 1734, 1702 cm$^{-1}$; $^1$H NMR (CDCl$_3$) inter alia 0.78 (3H, 2×d, 6.9 Hz), 0.89 (3H, d, 7.02), 1.20 (3H, 2×s,), 1.48 (3H, s), 3.32–3.41 (1H, broad res.), 5.22 (1H, d, J 17.3 Hz), 5.37 (1H, d, J 11.1 Hz), and 6.60 (1H, 2×dd, J 10.9, 17.3 Hz); MS (CI) m/z 475 (MH$^+$).

EXAMPLE 166

Mutilin 14-[N-(4-amino-3-methoxybenzoyl)]-carbamate

Step 1. 3-Methoxy-4-Nitrobenzoyl Chloride

To a stirred solution of 3-methoxy-4-nitrobenzoic acid (1.21 g, 6.24 mmol) in dry dichloro-methane (6 ml) was added oxalyl chloride (1.1 ml) followed by N,N-dimethylformamide (1 drop). The mixture was stirred at room temperature under argon for 3 hours. The solvent was evaporated in vacuo. The residue was purified by chromatography on silica gel eluting with 50% ethyl acetate in hexane to yield the title compound (0.89 g, 66%); $v_{max}$ (CH$_2$Cl$_2$) 1771 cm$^{-1}$; MS (EI) m/z 215 (M$^+$). Found M+214.9984, C$_8$H$_6$NO$_4$Cl requires 214.9985.

Step 2. (3R)-3-Deoxo-11-deoxy-3-methoxy-11-oxo-4-epi-mutilin-14-[N-(3-methoxy-4-nitrobenzoyl )]-carbamate Silver cyanate (669 mg, 4.5 mmol) was suspended in dry dichloromethane (10 ml) under an atmosphere of argon. A solution of the acid chloride from Step 1 (0.89 g, 4.1 mmol) in dichloromethane (10 ml) was added and the heterogeneous mixture stirred at reflux under subdued light. After 40 minutes the reaction was allowed to cool and treated with (3R)-3-deoxo-11-deoxy-3-methoxy-11-oxo-4-epi-mutilin (668 mg, 2.0 mmol) and the reaction stirred for 17 hours. The mixture was filtered through celite. The extract was washed with saturated sodium hydrogen carbonate (×2) and brine, dried (MgSO$_4$) and the solvent evaporated in vacuo. The residue was purified by chromatography on silica gel eluting with 20, 30 and 40% ethyl acetate in hexane to yield the title compound (720 mg, 65%) $v_{max}$ (CH$_2$Cl$_2$) 3054, 2987, 1780, 1698 and 1421 cm$^{-1}$; $^1$H NMR (CDCl$_3$) inter alia 3.23 (3H,s), 3.42–3.52 (1H,m), 4.03 (3H, s), 5.03 (1H, d, J 17.4 Hz), 5.31 (1H, d, J 10.7 Hz), 5.86 (1H, d, J 9.9 Hz), 6.66 (1H, dd, J 10.7, 17.5 Hz), 7.34 (1H, dd, J 1.6, 8.3 Hz), 7.62 (1H, d, J, 1.6 Hz), 7.89 (1H, d, J 8.3 Hz), 8.07 (1H, bs); MS (CI) m/z 574.3 (MNH$_4^+$).

Step 3. (3R)-3-Deoxo-11-deoxy-3-methoxy-11-oxo-4-epi-mutilin-14-[N-(4-amino-3-methoxybenzoyl)]-carbamate (3R)-3-Deoxo-11-deoxy-3-methoxy-11-oxo-4-epi-mutilin 14-[N (3-methoxy-4-nitro- benzoyl)] carbamate (720 mg, 1.29 mmol) was suspended in ethanol (30 ml).

Addition of ethyl acetate (6 ml) with warming brought about complete dissolution. Tin(II) chloride (1.26 g, 6.65 mmol) was added and the reaction warmed to reflux whilst under an atmosphere of argon. After 4 hours the solvent was evaporated in vacuo and the residue taken up in ethyl acetate and water, an emulsion was formed and removed by filtration through Kieselguhr. The organic phase was neutralised with sodium hydrogen carbonate (×2), washed with brine and dried (MgSO$_4$). The residue was purified by chromatography on silica gel eluting with 20, 30, 40 and 60% ethyl acetate in hexane to yield the title compound (211 mg, 31%); $v_{max}$ (CH$_2$Cl$_2$) 3100, 2986, 1771, 1698, 1617 and 1479 cm$^{-1}$; $^1$H NMR (CDCl$_3$) inter alia 3.22 (3H, s), 3.42–3.50 (1H, m), 3.91 (3H, s), 4.32 (2H, s), 5.01 (1H, d, J 17.5 Hz), 5.29 (1H, d, J 10.7 Hz), 6.66 (1H, d, J 8.2 Hz), 6.75 (1H, dd, J 10.6, 17.5 Hz), 7.20 (1H, dd, J 1.9, 8.2 Hz),7.40 (1H,d, J 1.8 Hz), 7.99 (1H,bs); MS (EI) m/z 526 (M$^+$).

Step 4. Mutilin-14-[N-(4-amino-3-methoxybenzoyl)]-carbamate

The product of Step 3 (191 mg, 0.36 mmol) in dioxan (2 ml) was treated with a saturated solution of zinc chloride in conc. HCl (2 ml) and the reaction stirred at room temperature for 1 hour. The solution was poured into ethyl acetate and saturated sodium hydrogen carbonate solution. The aqueous phase was re-extracted with ethyl acetate (×2) and the combined orzanic phases were washed with brine. The organic phase was dried (MgSO$_4$) and the solvent evaporated in vacuo. The residue was purified by chromatography on silica gel eluting with 60, 70, 80, 90 and 100% ethyl acetate in hexane to yield the title compound 56 mg, 30%); $v_{max}$ (CH$_2$Cl$_2$) 3100, 2986, 1772, 1733,1617 and 1479 cm$^{-1}$; $^1$H NMR (CDCl$_3$), inter alia 3.34–3.41 (1H, m), 3.90 (3H, s), 4.29 (2H, s), 5.27 (1H, dd, J 1.4, 17.4 Hz), 5.36 (1H, dd, J 1.4, 11.0 Hz), 5.83 (1H, d, J 8.4 Hz), 6.58 (2H, dd, J 8.9, 15.3 Hz), 6.65 (1H, d, J 6.2 Hz), 7.17 (1H, dd, J 1.9 .8.2 Hz), 7.37 (1H, d, J 1.8 Hz),7.85 (1H,bs); MS (NH$_3$DCI) m/z 513 (MH$^+$).

EXAMPLE 167

Mutilin-14-[N-(4-fluorobenzoyl)]-carbamate

Step 1. (3R)-3-Deoxo-11-deoxy-3-methoxy-11-oxo-4-epi-mutiin-14-(N-(4-fluorobenzoyl)]-carbamate 4-Fluorobenzoyl chloride (0.57 ml, 4.82 mmol) was reacted with (3R)-3-deoxo-11-deoxy-3-methoxy-11-oxo-4-epi-mutilin (978 mg, 2.92 mmol) and silver cyanate (787 mg, 5.25 mmol) in dichloromethane (12 ml), as for Example 166, Step 2, to afford the title compound (979 mg, 82%); $v_{max}$ (CH$_2$Cl$_2$) 3420, 3054, 2986, 1778, 1698, 1604 and 1479 cm$^{-1}$: $^1$H NMR (CDCl$_3$) inter alia 3.23 (3H, s), 3.42–3.50 (1H, m), 5.02 (1H, d, J 17.5 Hz), 5.28 (1H, d, J 9.9 Hz), 5.85 (1H, d, J 10.0 Hz), 6.70 (1H, dd, J 10.7 ,17.5 Hz), 7.14–7.21 (2H, m), 7.84–7.89 (2H, m),8.07 (1H,bs); MS (CI) m/z 517 (MNH$_4^+$).

Step 2. Mutilin 14-[N-(4-nluorobenzoyl)]-carbamate

The product of Step 1 (959 mg, 1.92 mmol) in dioxane (12 ml) was treated with a saturated solution of zinc chloride in conc. HCl (12 ml), as for Example 166, Step 4, to afford the title compound (140 mg, 15%); $v_{max}$ (CH$_2$Cl$_2$) 3414, 3054, 2987, 1779, 1684, 1604, and 1479 cm$^{-1}$; $^1$H NMR (CDCl$_3$) inter alia 3.33–3.40 (1H, m), 5.22 (1H, dd, J 1.4 ,17.4 Hz), 5.33 (1H, dd, J 1.4, 10.9 Hz), 5.81 (1H, d, J 8.5 Hz), 6.52 (1H, dd, J 11.0, 17.3 Hz), 7.03–7.17 (2H, m), 7.80–7.88 (2H, m), 8.30 (1H, bs); MS (Electrospray) m/z 503 (MNH$_4^+$).

EXAMPLE 168

Mutilin 14-[N-(4-methylsulphonyl benzoyl)]-carbamate

Step 1. 4-Methylsulphonylbenzoyl Chloride

To a stirred solution of 4-methylsulphonyl benzoic acid (1 g. 4.99 mmol) in dry dichloromethane (10 ml) was added oxalyl chloride (0.88 ml, 9.87 mmol) followed by N,N-dimethyl formamide (2 drops). The reaction was stirred at room temperature under argon for 5 hours. The solvent was evaporated in vacuo. The product was used immediately in the next reaction; $v_{max}$ (CH$_2$Cl$_2$) 1784 cm$^{-1}$.

Step 2. (3R)-3-Deoxo-11-deoxy-3-methoxy-11-oxo-4-epi-mutilin 14-[N-(4-methyl-sulphonyl benzoyl]-carbamate The product from Step 1 in dichloromethane (12 ml) was treated with silver cyanate (787 mg, 5.25 mmol) and (3R)-3-deoxo-11-deoxy-3-methoxy-11-oxo-4-epi-mutilin (814 mg, 2.43 mmol) and the reaction stirred for 2 hours. The title compound was isolated by the same procedure as described in Example 166, Step 2, (1.19 g, 91%); $v_{max}$ (CH$_2$Cl$_2$) 3064, 2984, 1780, 1718 and 1476 cm$^{-1}$; $^1$H NMR (CDCl$_3$) inter alia 3.09 (3H, s), 3.23 (3H, s), 3.42–3.49 (1H, m), 5.03 (1H, d, J 17.4 Hz), 5.31 (1H, d, J 10.7 Hz), 5.85 (1H, d, J 9.9 Hz), 6.68 (1H, dd, J 10.7, 17.5 Hz), 7.96–8.00 (2H, m), 8.04–8.07 (2H, m), 8.12 (1H, bs); MS (Electrospray) m/z 558 (M–H$^-$).

Step 3. Mutilin 14-[N-(4-methylsulphonyl benzoyl)]-carbamate

The product of Step 2 (1.17 g, 2.14 mmol) in dioxane (13 ml) was treated with a saturated solution of zinc chloride in conc. HCl (13 ml), as for Example 166, Step 4, to afford the title compound (342 mg, 30%); $v_{max}$ (CH$_2$Cl$_2$) 3057, 2936, 1782, 1733 and 1478 cm$^{-1}$; $^1$H NMR (CDCl$_3$) inter alia 3.08 (3H, s), 3.38 (1H, dd, J 10.7, 6.6 Hz), 5.2H (1H, dd, J 17.4, 1.4 Hz), 5.38 (1H, dd, J 10.9, 1.3 Hz), 5.82 (1H, d, J 8.5 Hz), 6.53 (1H, dd, J 11.1 ,7.4 Hz), 7.94–7.97 (2H, m), 8.02–8.05 (2H, m), 8.07 (1H, s); MS (Electrospray) m/z 544 (M–H$^-$).

EXAMPLE 169

Mutilin 14-[N-(3-(2-Dimethylaminoethoxy)-4-fluorobenzoyl)]-carbamate

Step 1. 4-Fluoro-3-hydroxybenzoic acid

Sulphuric acid (concentrated, 11 ml) was stirred and heated to 90° C. 2-Fluoro-5-trifluoro-methylphenol (2.5 g, 13.88 mmol) was added portion wise during 25 minutes. The mixture was heated to 120° C. for 10 minutes. The mixture was cooled to ambient temperature and poured onto a mixture of ice and water. The precipitate was isolated, washed with water and dried, to afford the title compound (1.0 g, 47%); $v_{max}$ (CH$_2$Cl$_2$) 3420, 3054, 2987, 1636 and 1422 cm$^{-1}$; MS (EI) m/z 156 (M$^+$). Found M$^+$156.0223. C$_7$H$_5$O$_3$F requires 156.0223.

Step 2. 3-Acetoxy-4-fluorobenzoic acid

The product from Step 1 (1.0 g, 6.41 mmol) in dichloromethane (35 ml) was treated with triethylamine (1.95 ml, 12.97 mmol) and 4-dimethylaminopyridine (24.7 mg, 0.20 mmol). The reaction was cooled in an ice-bath and treated with acetic anhydride (0.62 ml, 6.57 mmol) and stirred for 2 hours at room temperature under argon. The solution was washed with HCl (5M) and water, dried (MgSO$_4$) and the solvent evaporated in vacuo to afford the title compound (1.08 g, 86%); $v_{max}$ (CH$_2$Cl$_2$) 3054, 2987, 1777, 1670 and 1422 cm$^{-1}$; MS (Electrospray) m/z 197 (M–H$^-$). Found M$^+$ 198.0326. C$_9$H$_7$O$_4$F requires 198.0328.

Step 3. 3-Acetoxy-4-fluorobenzoyl chloride

The product from Step 2 (1.06 g, 5.35 mmol) in dichloromethane (14 ml) was treated with oxalyl chloride (0.60 ml, 6.88 mmol) followed by N,N-dimethylformamide (1 drop), as for Example 168, Step 1. The product was used immediately in the next reaction $v_{max}$ (CH$_2$Cl$_2$) 1778 cm$^{-1}$.

Step 4. (3R)-3-Deoxo-11-deoxy-3-methoxy-11-oxo-4-epi-mutilin 14-[N-(3-acetoxy-4-tluorobenzoyl]-carbamate The product from Step 3 in dichloromethane (20 ml) was treated with silver cyanate (0.84 g, 5.60 mmol) and (3R)-3-deoxo-11-deoxy-3-methoxy-11-oxo-4-epi-mutilin (0.64 g, 1.92 mmol) and the reaction stirred for 3 hours. The title compound (70% pure) was isolated by the same procedure as described in Example 166, Step 2, (1.06 g, 96%); $v_{max}$ (CH$_2$Cl$_2$) 3418, 3054, 2986, 1779, 1697 and 1422 cm$^{-1}$; MS (Electrospray) m/z 556 (M–H$^+$).

Step 5. (3R)-3-Deoxo-11-deoxy-3-methoxy-11-oxo-4-epi-mutilin 14-[N-(4-fluoro-3-hydroxybenzoyl]-carbamate The product from Step 4 (1.06 g, 1.90 mmol of 70% pure material) in dioxane (15 ml) was treated with 1.0M sodium hydroxide solution (7 ml) for 3 hours at room temperature. The reaction was poured into ethyl acetate and dilute HCl. The aqueous phase was re-extracted with ethyl acetate. The organic phase was washed with brine, dried (MgSO$_4$) and the solvent removed in vacuo. The residue was purified by chromatography on silica gel eluting with 20, 30, 40 and 50% ethyl acetate in hexane to afford the title compound (420 mg, 43%); $v_{max}$ (CH$_2$Cl$_2$) 3420, 3054, 2986, 1778, 1697, and 1480 cm$^{-1}$; $^1$H NMR (CDCl$_3$) inter alia 2.52 (1H, dd, J 10.1, 15.3 Hz), 2.90 (1H, q, J 6.3 Hz), 3.23 (1H, s), 3.42–3.49 (1H, m), 5.01 (1H, d, J 17.5 Hz), 5.27 (1H, d, J 10.7 Hz), 5.85 (1H, d, J 9.9 Hz), 6.69 (1H, dd, J 10.7 and 17.5 Hz), 7.14–7.21 (1H, m), 7.33–7.39 (1H, m), 7.52–7.56 (1H, m), 8.05 (1H, bs); MS (ES) m/z 516 (MH$^+$). Found 515.2686 C$_{29}$H$_{38}$NO$_6$F requires 515.2683.

Step 6. (3R)-3-Deoxo-11-deoxy-3-methoxy-11-oxo-4-epi-mutilin 14-N-[3-(2-dimethyl-aminoethoxy)-4-fluorobenzoyl]-carbamate The product from Step 5 (400 mg, 0.78 mmol) was dissolved in acetone (6 ml) and treated with dimethylaminoethylchloride hydrochloride (113 mg, 0.78 mmol) and potassium carbonate (213 mg). The reaction was heated to reflux for 12 hours under argon. The reaction was diluted with ethyl acetate and washed with brine and water. The organic phase was dried (MgSO$_4$) and the solvent removed in vacuo. The residue was purifed by chromatography on silica gel eluting with 25 and 50% ethanol in ethyl acetate to afford the title compound (150 mg, 33%); $v_{max}$ (CH$_2$Cl$_2$) 3054, 2986, 1777, 1698 and 1480 cm$^{-1}$; $^1$H NMR (CDCl$_3$) 2.38 (6H, s), 2.55 (1H, dd, J 10.1, 15.2 Hz), 2.81 (2H, t, J 5.7 Hz), 2.91 (1H, dd, J 6.5, 12.9 Hz), 3.23 (3H, s), 3.43–3.50 (1H, m), 4.21 (2H, t, J 5.7 Hz), 5.03 (1H, d, J 17.4 Hz), 5.31 (1H, d, J 10.7 Hz), 6.72 (1H, dd, J 10.7 and 17.5 Hz), 7.12–7.20 (1H, m), 8.02 (1H, bs).

Step 7. Mutilin 14-N-[3-(2-dimethylaminoethoxy)-4-nuorobenzoyl]-carbamate

The product from Step 6 (80 mg, 0.14 mmol) in dioxane (1 ml) was treated with conc. HCl (1 ml) and the reaction stirred at room temperature for 4 hours. The title compound was isolated by the same procedure as described in Example 166, Step 4, (65 mg, 76%); $v_{max}$(CH$_2$Cl$_2$) 3054, 2988, 1777, 1732, 1609 and 1422 cm$^{-1}$. $^1$H NMR (CDCl$_3$) inter alia 2.45 (6H, s), 2.91 (2H, t, J 5.5 Hz) 3.37 (1H, d, J 6.4 Hz), 4.28 (2H, t, J 5.5 Hz), 5.23 (1H, dd, J 1.3, 17.4 Hz), 5.36 (1H, dd, J 1.3, 11.1 Hz), 5.83 (1H, d, J 8.4 Hz), 6.55 (1H, dd, J 11.0, 17.3 Hz), 7.10–7.19 (1H, m), 7.33–7.39 (1H, m), 7.55–7.62 (1H, m), 8.33 (1H, bs); MS (S) m/z 573 (M+H$^+$), 571 (M–H$^-$).

EXAMPLE 170

Mutilin 14-{N-[4-(2-dimethylaminoethyloxy)-benzoyl]}-carbamate hydrochloride

Step 1 (3R)-3-Deoxo-11-deoxy-3-methoxy-11-oxo-4-epi-mutilin 14-{N-[4-(2-dimethyl-aminoethyloxy)benzoyl]}-carbamate A solution of (3R)-3-deoxo-1-deoxy-3-methoxy-11-oxo-4-epi-mutilin 14-[N-(4-hydroxy-benzoyl)]-carbamate (1 g, 2 mmole) in acetone (20 ml) was treated with powdered K$_2$CO$_3$ (560 mg) and 2-dimethylaminoethylchloride hydrochloride (290 mg), and stirred at reflux under argon for 11 hours. The mixture was diluted with EtOAc, washed with water, dried and evaporated. Chromatography on silica, eluting with 2:1 EtOAc/EtOH gave the title compound as a yellow foam (0.51 g, 45%); $v_{max}$ (CHCl$_3$) 3436, 1775, 1697, 1606, 1579, 1512, 1488, 1168 cm$^{-1}$; $^1$H NMR δ(CDCl$_3$) 0.87 (3H, d, J 6.7 Hz), 0.98 (3H, d, J 6.3 Hz), 1.0–1.6 (12H, m), 1.6–1.75 (2H, m), 1.85–2.05 (2H, m), 2.1–2.2 (1H, m), 2.32 (6H, s), 2.4–2.55 (1H, m), 2.73 (2H, t, J 5.5 Hz), 2.87 (1H, q, J 6.3 Hz), 3.18 (3H, s), 3.35–3.5 (1H, m), 4.08 (2H, t, J 5.5 Hz), 4.95 (1H, d, J 17.5 Hz), 5.22 (1H, d, J 10.7 Hz), 5.81 (1H, d, J 9.8 Hz), 6.67 (1H, dd, J 17.5 and 10.7 Hz), 6.94 (2H, d, J 8.8 Hz), 7.81 (2H, d, J 8.8 Hz); MS (ammonia CI) m/z 569 (MH$^+$, 10%), 352 (20%), 317 (70%), 303 (50%), 235 (100%), 209 (70%); (negative ion eiectrosprany) m/z 567 (M–H$^-$, 100%).

Step 2 Mutilin 14-{N-[4-(2-dimethylaminoethyloxy)-benzoyl]}-carbamate

The product from Step 1 (0.5 g) in dioxan (6 ml) was ice-cooled, treated with a saturated solution of ZnCl$_2$ in conc. HCl (2 ml) and stirred at room temp. for 5 hours. The mixture was diluted with EtOAc, washed with excess aqueous NaHCO$_3$ and water, dried and evaporated. Chromatography on silica, eluting with 3:1 and then 1:1 EtOAc/EtOH, gave the title compound as a gum (230 mg, 47%); $v_{max}$ (CHCl$_3$) 3565, 3442, 1777, 1731, 1709, 1606, 1579, 1513, 1469 cm$^{-1}$; $^1$H NMR δ(CDCl$_3$) 0.79 (3H, d, J 6.4 Hz), 0.87 (3H, d, J 6.9 Hz), 1.0–1.2 (4H, m), 1.3–1.8 (11H, m), 2.0–2.3 (5H, m), 2.36 (6H, s), 2.78 (2H, t, J 5.5 Hz), 3.36 (1H, d, J 6.3 Hz), 4.11 (2H, t, J 5.5 Hz), 5.20 (1H, dd, J 17.5 and 1.3 Hz), 5.31 (1H, dd, J 11 and 1.1 Hz), 5.80 (1H, d, J 8.3 Hz), 6.52 (1H, dd, J 17.5 and 11 Hz), 6.95 (2H, d, J 8.9 Hz), 7.79 (2H, d, J 8.9 Hz), 8.40 (1H, s); MS (EI) m/z 554 (M$^+$, 5%), 163 (100%); (NH$_3$DCI) m/z 555 (MH$^+$, 30%), 235 (100%).

Step 3 Mutilin 14-{N-[4-(2-dimethylaminoethyloxy)benzoyl]}-carbamate hydrochloride The product from Step 2 (225 mg) in EtOAc (5 ml) was treated with 4M HCl in dioxan (0.25 ml). The solvents were evaporated to leave the product as a white solid (193 mg). $v_{max}$ (CHCl$_3$) 3676, 3434, 2287 (br), 1778, 1733, 1654, 1607, 1468 cm$^{-1}$; $^1$H NMR δ ((CD$_3$)$_2$SO) 0.70 (3H, d, J 5.9 Hz), 0.83 (3H, d, J 7.7 Hz), 1.0–1.2 (4H:, m), 1.2–1.8 (10H, m), 2.0–2.3 (4H, m), 2.42 (1H, s), 2.83 (6H, s), 3.4–3.6 (3H, m), 4.43 (2H, t, J 5 Hz), 4.55 (1H, d, J 5.9 Hz, disappears on D$_2$O exchange), 5.0–5.2 (2H, m), 5.60 (1H, d, J 7.8 Hz), 6.26 (1H, dd, J 17.5 and 11.1 Hz), 7.10 (2H, d, J 8.9 Hz), 7.88 (2H, d, J 8.9 Hz), 10.36 (1H, br s, disappears on D$_2$O exchange), 10.63 (1H, s, disappears on D$_2$O exchange).

EXAMPLE 171

Mutilin 14-{N-[4-(glucosyloxy)-benzoyl]}-carbamate

Step 1. Mutilin 14-{N-[4-(tetra-O-acetyl-glucosyloxy)-benzoyl]}-carbamate

A solution of acetobromo-alpha-D-glucose (411 mg, 1 mmol) in acetone (2 ml) was added to a solution of mutilin 14-[N-(4-hydroxy-benzoyl)]-carbamate(483 mg, 1 mmol) and 1N sodium hydroxide (1 ml) in water (2 ml) and acetone (5 ml). After three hours at room temeperature a further portion of 1N sodium hydroxide (1 ml) was added followed by acetobromo-alpha-D-glucose (411 mg) in acetone (2 ml). The mixture was left overnight at room temperature and then diluted with water and extracted with ethyl acetate. The extract was washed with brine, dried (MgSO$_4$) and evaporated to a foam which was chromatographed on silica gel, using 20% acetone-toluene to give the product as a white foam (140 mg): Rf 0.2; $v_{max}$ (CHCl$_3$) 3439 w, 1757 br, 1721 (shoulder) cm–1.; $^1$H NMR (d$_6$ acetone) inter alia 8.6 (1H, br s, NH), 7.80–7.82 (2H, arom), 7.02–7.04 (2H, arom), 6.57 (1H, dd, J 17.5, 11), 5.81 (1H, d, J 8, H-14), 5.35 (1H, dd, 11, 1.5), 5.32 (1H, dd, J 9, 9, gluc H-3), 5.28 (1H, dd, J 9,9, gluc H-2), 5.23 (1H, dd, J 17.5, 1.5), 5.21 (1H, d, J 7.4, gluc H-1), 5.16 (1H, dd, J 9,9, gluc H-4), 4.28 (1H dd J 12.3, 5.5, gluc H-6), 4.17 (1H, dd, J 12.3, 2.5, gluc H-6), 3.94 (1H, ddd, J 7.9, 5.5, 2.5, gluc H-5), 3.40 (1H, dd, J 10.4, 6.5); $^{13}$C NMR inter alia 169.2, 169.4, 170.1 and 170.4 (4×C=O of acetate), 98.2 (CH of glucoside); MS (+ve ion electrospray) m/z 814 (MH$^+$), 831 (MNH$_4$$^+$), 836 (MNa$^+$).

Step 2. Mutilin 14-{N-[4-(glucosyloxy)-benzoyl]}-carbamate

The product of Step 1 (117 mg, 0.14 mmol) was partly dissolved in methanol (4 ml) and triethylamine (0.02 ml) was added. The mixture was stirred at room temperature for a total of 48 h during which time further portions of triethyalmine (0.02 ml×2) were added while monitoring the reaction by tlc. The mixture was evaporated to dryness and chromatographed on silica gel, using 20% methanol-chloroform giving the title compound as a white solid (55 mg, 61%): Rf 0.33; $^1$H NMR (d$_6$ acetone) inter alia 8.00(1H, br s, NH), ca7.9 (2H, arom), ca7.15 (2H, arom), 6.46 (1H, dd, J 17.6, 11), 5.77 (1H, d, J 8, H-14), 5.25 (1H, dd, J 17.6, 2), 5.18 (1H, dd, J 11, 2), 4.60 (1H, d J 3.5, exch D$_2$O), 4.35 (1H, d, 13.5, exch D$_2$O), 4.27 (1H, d, J 3.5 exch D$_2$O), 3.87 (1H, dd, J 11.8, 1.4 with D$_2$O); MS (–ve ion electrospray) m/z 644 (100%, M–H$^-$).

EXAMPLE 172

Mutilin 14-[N-(2-azido-phenyl-acetyl)]-carbamate

Step 1. (3R)-3-Deoxo-11-deoxy-3-methoxy-11-oxo-4-epi-mutilin 14-[N-(2-azido-phenyl-acetyl)]-carbamate A solution of (3R)3-deoxo-11-deoxy-3-methoxy-11-oxo-4-epi-mutilin (667 mg, 2 mmol) in dichloromethane (25 ml) was added to a stirred mixture of D(–)-alpha-azido-phenylacetyl chloride (5 mmol) and siver cyanate (750 mgs, 5 mmol) in dichloromethane (10 ml). The mixture was stirred overnight at room temperature filtered and evaporated to dryness. The crude product was chromatographed on silica gel, eluting with 5% acetone-toluene to give the title compound as a white solid (841 mg, 80%), Rf 0.32; $v_{max}$ (CHCl$_3$) 3389, 2119, 1787, 1756, 1719, 1697 cm$^{-1}$; $^1$H NMR (CDCl$_3$) inter alia 8.0 (1H, br s, exch D$_2$O), 7.42 (5H, arom), 6.49 (1H, dd, J ca 18, 10.7), 5.70 (1H, d, J 10), 5.52 (1H, brs, PhCH-CO), 5.26 (1H, d, J 10.7); MS (–ve ion electrospray) m/z 535 (M–H$^-$).

Step 2. Mutilin 14-[N-(2-azido-phenyl-acetyl)]-carbamate

The product of Step 1 (536 mg, 1 mmol) was dissolved in dioxan (15 ml) and a saturated solution of zinc chloride in conc hydrochloric acid (4 ml) was added with cooling in bath of cold water. The clear yellow solution was stirred at room temperature for 3.5 hour. The mixture was diluted with cold aq. sodium bicarbonate and extracted with ethyl acetate. The extract was washed with water and with brine and dried (MgSO$_4$). Evaporation gave a crude product which was purified by chromatography on silica gel eluting with 5% acetone-toluene giving the title compound as a white foam (413 mg, 79%); Rf 0.05; $v_{max}$ (CHCl$_3$) 3565, 3388, 2112, 1789, 1756 (shoulder), 1725 cm$^{-1}$; $^1$H NMR (CDCl$_3$) inter alia 7.84 (1H, br s), 7.40 (5H, arom), 6.38 (1H, dd, J 17, 11), 5.67 (1H, d, J 8.5), 5.54 (1H, br s, PhCH-CO), 5.23 (1H, d, J 11), 5.11 (1H, d, J 17); 3.33 (1H, dd, J 10.5, 6.5); MS (+ve ion electrospray) m/z 540 (MNH$_4$$^+$), MS (–ve ion electrospray) m/z 521 (100%, M–H$^-$).

EXAMPLE 173

19,20-Dihydro-mutilin 14-[N-(alpha-amino-phenylacetyl)]-carbamate hydrochloride

Mutilin 14-[N-(2-azido-phenyl-acetyl)]-carbamate (240 mg, 0.46 mmol) (Example 172) was dissolved in dioxan (5 ml) and water (1 ml) and 4M HCl in dioxan (0.25 ml) was added. The solution was shaken with 10%Pd-C (100 mg) in an atmosphere of hydrogen for 45 minutes. The catalyst was removed by filtration and washed with aqueous dioxan. The filtrate was evaporated to an oil and azeotroped with ethanol and with chloroform. The resulting crude solid was recrystallised from ethanol-ether to give the title compound as an off-white solid (123 mg, 50%), mp 175–180° C.: $v_{max}$ (CHCl$_3$) ca 2600–3200, 1757, 1733, 1703 cm$^{-1}$; $^1$H NMR (d$_4$ methanol) inter alia 7.49 (5H, arom), 5.72 (1H, br, PhCH-CO), 5.55 (1H, d, J 8), 3.41(1H, d, J 6); $^{13}$C NMR (CDCl$_3$-d$_4$ methanol) inter alia 7.7, 10.9, 14.5, 16.0, 20.4, 24.7, 26.0, 26.7, 30.2, 34.4 (CH and CH$_2$), 36.5, 40.5, 40.7, 41.9,45.5, 57.0, 58.4, 71.5, 75.9, 128.5, 129.2, 130.0, 131.4, 150.5, 169, 218.0; MS (NH$_3$ DCI) m/z 499 (100%, MH$^+$); MS(glycerol FAB) Found m/z 499.3170 (MH$^+$) C$_{29}$H$_{43}$N$_2$O$_5$ requires 499.3172.

EXAMPLE 174

Mutilin 14-[N-(cyclohexyl-acetyl)]-carbamate

Step 1. (3R)-3-Deoxo-11-deoxy-3-methoxy-11-oxo-4-epi-mutilin 14-[N-(cyclohexyl-acetyl)]-carbamate A solution cyclohexyl-acetyl isocyanate (2.5 mmol) in dichloromethane (10 ml) was added to one of (3R)-3-deoxo-11-deoxy-3-methoxy-11-oxo-4-epi-mutilin (334 mg, 1 mmol) in dichloromethane (3 ml) at room temerature. The solution was stirred overnight at room temperature and evaporated to dryness. The crude product was chromatographed on silica gel, eluting with ethyl acetate 1:2 to give the title compound as a white foam (252 mg, 50%), Rf 0.42; $v_{max}$ (CHCl$_3$) 3395, 1782 w, 1749, 1697 cm$^{-1}$.; $^1$H NMR (CDCl$_3$) inter alia 7.47 (1H, br s, exch D$_2$O), 6.64 (1H, dd, J 17.5, 10.5), 5.74 (1H, d, J 10), 5.33 (1H, d, J 10.5), 5.03 (1H, d, J 17.5), 3.4–3.5 (1H, m); MS (NH$_3$ DCI)) m/z 519 (8%, MNH$_4^+$).

Step 2. Mutilin 14-[N-(cyciohexyl-acetyl)]-carbamate

The product of Step 1 (400 mg, 0.8 mmol) was dissolved in dioxan (4 ml) and a saturated solution of zinc chloride in conc hydrochloric acid (2 ml) was added. The solution was stirred at room temperature for 2 hour and then diluted with cold aq. sodium bicarbonate and extracted with ethyl acetate. The extract was washed with aq. sodium bicarbonate and with brine and dried (MgSO$_4$). Evaporation gave a crude product which was purified by chromatography on silica gel eluting with ethyl acetate 1:2 giving the title compound as a white solid (152 mg, 39%); mp 198–200° C.; $v_{max}$ (CHCl$_3$) 3397, 2928, 1735, 1712 cm$^{-1}$; $^1$H NMR (CDCl$_3$) inter alia 7.29 (1H, br s), 6.49 (1H, dd, J 17.3, 11), 5.70 (1H, d, J 7.5), 5.38 (1H, dd, J 11, 1.4), 5.23 (1H, d, J 17.3, 1.4); 3.36 (1H, dd, J 10.5, 6.5), 2.62 (2H, d, J 6.6); MS (–ve ion electrospray) m/z 486 (50%, M–H$^-$).

EXAMPLE 175

Mutilin 14-[N-(cinnamoyl)]-carbamate

Step 1. (3R)-3-Deoxo-11-deoxy-3-methoxy-11-oxo-4-epi-mutilin 14-[N-(cinnamoyl)]-carbamate A solution cinnamoyl isocyanate (2 mmol) in dichloromethane (5 ml) was added to one of (3R)-3-deoxo-11-deoxy-3-methoxy-1-oxo-4-epi-mutilin (501 mg, 1.5 mmol) in dichloromethane (5 ml) at room temerature. The solution was stirred for 1 hour and a further portion of cinnamoyl isocyanate (1 mmol) in dichloromethane (2.5 ml) was added. The mixture was stirred at room temperature for 2 days and evaporated to dryness. The crude product was chromatographed on silica gel, eluting with ethyl acaetate 1:4 to give the title compound as a white solid (710 mg, 93%), Rf 0.38; $v_{max}$ (CHCl$_3$) 3400, 1776 w, 1747, 1690, 1621 cm$^{-1}$.: $^1$H NMR (CDCl$_3$) interalia 7.89 (1H, d, J 16), 7.59–7.65 (2H, m), 7.58 (1H, d, J 16), 7.50 (1H, br s, exch D$_2$O), 7.4–7.5 (3 H, m), 6.68 (1H, dd, J 17.5, 10.5), 5.78 (1H, d, J 10), 5.36 (1H, d, J 10.5), 5.05 (1H, d, J 17.5), 3.4–3.5 (1H, m), 3.23 (3H, s); MS (NH$_3$ DCI).) m/z 508 (MH$^+$), 525 (MNH$_4^+$).

Step 2. Mutilin 14-[N-(cinnamoyl)]-carbomate

The product of Step 1 (507 mg, 1 mmol) was dissolved in dioxan (4 ml) and a saturated solution of zinc chloride in conc hydrochloric acid (2 ml) was added. The solution was stirred at room temperature overnight and then diluted with cold aq. sodium bicarbonate and extracted with ethyl acetate. The extract was washed with water and with brine and dried (MgSO$_4$). Evaporation gave a crude product which was purified by chromatography on silica gel eluting with ethyl acetate 1:2 giving the title compound as a white solid (316 mg, 64%); mp 148–151° C.; $v_{max}$ (CHCl$_3$) 3400, 1735, 1682, 1622 cm$^{-1}$; MS (NH$_3$ DCI)) m/z 494 (10%, MH$^+$), 511 (12%, MNH$_4^+$).

EXAMPLE 176

19,20-Dihydro-mutilin 14-(1-Methylpiperidin-4-oyl)-carbamate

Mutilin 14-(1-methylpiperidin-4-oyl)-carbamate (100 mg) as a solution in THF (5 ml) with 10% palladium/carbon catalyst was hydrogenated for 1 hour at room temperature. The catalyst was filtered off through celite and the solution concentrated to give the title compound as a colourless solid, (100 mg, quant.); $v_{max}$ (CH$_2$Cl$_2$) 3630(w), 3390(w), 1732, 1710 1470 and 1406 cm$^{-1}$; $^1$H NMR (CDCl$_3$) inter alia 1.40 (3H, s), 1.43 (3H, s), 2.89 (2H, d J 11.4 Hz), 3.07 (1H, m), 3.41 (1H, d, J 6.0 Hz), 5.55 (1H, d, J 8.03 Hz) and 7.38 (1H, s); MS(EI) m/z 490 (M$^+$) (Found: M$^+$, 490.341; C$_{28}$H$_{46}$N$_2$O$_5$ requires 490.341).

EXAMPLE 177

19,20-Dihydro-mutilin 14-(1-Methylpiperidin-4-oyl)-carbamate hydrochloride 19,20-Dihydro-mutilin 14-(1-methylpiperidin-4-oyl)-carbamate (348 mg) in ethyl acetate at room temperature was vigorously stirred and treated with 1M hydrochloric acid in ether in a dropwise fashion until no further precipitation was observed. The title compound was filtered off and dried in vacuo over 12 hours, and was thus obtained as a white solid (302 mg, 81%); $^1$H NMR (D$_2$O) inter alia 0.68 (6H, m), 0.86 (3H, d, J 7.2 Hz), 2.85 (3H,s), 3.04 (2H, d, J 11.0), 3.55 (3H, m) and 5.56 (1H, d J 7.8 Hz).

EXAMPLE 178

19,20-Dihydromutilin 14-{N-[(3S,4R)-1-azabicyclo[2.2.1]hept-3-ylcarbonyl]}-carbamate A solution of mutilin 14-{N-[(3S,4R)-1-azabicyclo[2.2.1]hept-3-ylcarbonyl]}-carbamate (95 mg, 0.20 mmol) in 1:1 ethanol:tetrahydrofuran (10 ml) was hydrogenated for 12 hours over 10% palladium on carbon (90 mg). The solution was filtered through celite and the solvent evaporated in vacuo to yield the title compound (85 mg, 87%); $v_{max}$ (KBr) 3421, 2957, 1772, 1733, 1702 and 1464 cm$^{-1}$; $^1$H NMR (d$_6$-DMSO) inter alia 0.68 (3H, d, J 7.1 Hz), 0.82 (3H, d, J 6.8 Hz), 4.46 (1H, d, J 5.9 Hz), 5.46 (1H, d, J 17.6 Hz), 10 53 (1H, bs); MS (EI) m/z 488 (M$^+$). Found: M$^+$, 488.3256; C$_{28}$H$_{44}$N$_2$O$_5$ requires 488.3250.

EXAMPLE 179

19,20-Dihydromutilin 14-[N-(quinuclidine-4-carbonyl)]-carbamate

A solution of mutilin 14-[N-(quinuclidine-4-carbonyl)]-carbamate (100 mg, 0.20 mmol) in 2:1 tetrahydrofuran:ethanol (30 ml) was hydrogenated for 1 hour over 10% palladium on carbon (10 mg). The solution was filtered through celite and the solvent evaporated in vacuo to yield the title compound as a white solid (90 mg, 90%); $v_{max}$ $(CH_2Cl_2)$ 2960, 1782, 1733, 1716 and 1479 cm$^{-1}$: $^1$H NMR (CDCl$_3$) inter alia 0.69 (3H, d, J 6.6 Hz), 3.42 (1H, d, J 5.9 Hz), 5.61 (1H, d, J 8.2 Hz), 7.37 (1H, bs); MS (EI) m/z 502 (M$^+$). Found: M$^+$, 502.3411; C$_{29}$H$_{46}$N$_2$O$_5$ requires 502.3407.

EXAMPLE 180

19,20-Dihydro-mutilin 14-[N-(3-(2-Dimethylaminoethoxy)-4-fluorobenzoyl)]-carbamate Mutilin 14-[N-(3-(2-dimethylaminoethoxy)4-fluorobenzoyl)]-carbamate (0.200 g) was dissolved in ethanol (30 ml) and shaken at ambient temperature and atmospheric pressure with hydrogen in the presence of 10% palladium on charcoal catalyst for 2 hours. The supension was filtered through Celite and the filtrate evaporated to yield the title compound as a white foam (0.201 g); $^1$H NMR inter alia (CDCl$_3$) 0.75–0.85 (6H, m), 0.90–1.05 (6H, m), 1.51 (3H, s), 2.38 (6H, s), 2.79 (2H, t, J 5.61 Hz), 3.41 (1H, d, J 5.95 Hz), 4.20 (2H, t, J 5.64 Hz), 5.70 (1H, d, J 8.03 Hz), 7.11 (1H, dd, J 8.43 and 10.35 Hz), 7.28–7.38 (1H, m), 7.55 (1H, dd, J 2.0 and 7.9 Hz), 8.0 (1h, broad s); MS (ES) m/z 575 (MH$^+$).

EXAMPLE 181

Mutilin 14-[N-(Quinuclidin-3-oyl)carbamate]
Step 1. (3R)-3-Deoxo-11-deoxy-3-methoxy-11-oxo-4-epi-mutilin 14-[N-(quinuclidin-3-oyl)carbamate]

Quinuclidine-3-carboxylic acid was converted to the acid chloride hydrochloride by the procedure described in Example 161. This acid chloride was then reacted with (3R)-3-deoxo-11-deoxy-3-methoxy-11-oxo-4-epi-mutilin (1.002 g) by the procedure outlined in Example 161 to yield the title compound as a colourless foam (1.116 g) after silica gel column chromatography; MS (ES) m/z 515 (MH$^+$).
Step 2. Mutilin 14-[N-(Quinuclidin-3-oyl)carbamate]

The product from Step 1, (1.13 g) in 1,4-dioxan (12 ml) was stirred at room temperature for 7 h with conc. hydrochloric acid (5 ml). The solution was then diluted with ethyl acetate and neutralized with saturated sodium hydrogen carbonate solution. The organic solution was washed with saturated sodium chloride solution, dried (MgSO$_4$) and evaporated to yield the crude product. After purification by silica gel chromatography, eluting with a gradient of 0–20% 9:1 methanol/35% ammonia solution in dichloromethane, the title compound was isolated as a white solid, (0.340 g). This solid, which was a mixture of two diastereoisomers, was digested in hot ethyl acteate and the resulting white solid was collected by filtration to yield one pure diastereoisomer of the title compound (0.140 g); $^1$H NMR inter alia (CDCl$_3$) 0.75 (3H, d, J 6.5 Hz), 0.90 (3H, d, J 7.0 Hz), 1.20 (3H, s), 1.40 (3H, s), 2.70–3.10 (5H, m), 3.20–3.42 (3H, m), 5.15–5.40 (2H, ddd), 5.70 (1H, d, J 8.3 Hz), 6.50 (1H, dd, J 10.95, 17.4 Hz) and 7.40 (1H, s); MS (ES) m/z 501 (MH$^+$). The mother liquors contained predominantly the other diastercoisomer of the title compound (0.200 g); $^1$H NMR inter alia (CDCl$_3$) 0.75 (3H, d, J 6.5 Hz), 0.90 (3H, d, J 7.0 Hz), 1.20 (3H, s), 1.41 (3H, s), 2.12–2.4 (3H, m), 2.70–3.10 (5H, m), 3.24–3.42 (3H, m), 5.15–5.45 (2H, m), 5.69 (1H, d, J 8.3 Hz), 6.50 (1H, dd, J 11.0, 17.35 Hz) and 7.40 (1H, s); MS (ES) m/z 501 (MH$^+$).

EXAMPLE 182

Mutilin 14-{N-[(3S,4R)-1-azabicyclo[2.2.1]hept-3-ylcarbonyl]}-carbamate hydrochloride A solution of mutilin 14-{N-[(3S,4R)-1-azabicyclo[2.2.1]hept-3-ylcarbonyl]}-carbamate (1.0 g; 2.06 mmol) in acetone (100 ml) was treated with 1M HCl in diethyl ether (4.2 ml; 4.20 mmol). The solution was stirred for 1 hour at room temperature and then concentrated in vacuo. The residue was triturated with diethyl ether to yield the title compound as a white solid (1.02 g, 95%); $v_{max}$ (KBr) 3421, 2924, 1772, 1734, 1704 and 1465 cm$^{-1}$; $^1$H NMR (D$_2$O) inter alia 0.62 (3H, d, J 6.0 Hz), 0.90 (3H, d, J 6.9 Hz), 5.22 (2H, dd, J 16.7, 11.1 Hz), 5.61 (1H, d, J 8.1 Hz), 6.35 (1H, dd, J 17.5, 11.1 Hz).

EXAMPLE 183

Mutilin 14-[N-(1-azabicyclo[3.2.1]octan-5-oyl)] carbamate
Step 1. (3R)-3-Deoxo-11-deoxy-3-methoxy-11-oxo-4-epi-mutilin 14- [N-(1-azabicyclo[3.2.1]octan-5-oyl)]-carbamate Triethylamine (0.58 ml, 4.2 mmol) was added to a stirred mixture of racemic 1-azabicyclo[3.2.1]octane-5-carbonyl chloride hydrochloride (4 mmol), (3R)-3-deoxo-11-deoxy-3-methoxy-11-oxo-4-epi-mutilin (668 mg, 2 mmol) and silver cyanate (600 mg) in dichloromethane (25 ml). The mixture was stirred overnight at room temperature, filtered and the filtrate evaporated to dryness. The crude product was purified by chromatography on silica gel, eluting with 35% ammonia solution:methanol:dichloromethane 1:9:90 to give the title compound as a white solid (480 mg), Rf 0.1; $^1$H NMR (CDCl$_3$) inter alia 7.4 (1H, br s), 5.79 (1H, d, J 10), 3.21 (3H, s), 2.75–3.0 (6H, m); MS (+ve ion electrospray) m/z 515 (30%, MNH$_4^+$), m/z 556 (100%, M+H+MeCN$^+$).
Step 2. Mutilin 14-[N-(1-azabicyclo[3.2.1]octan-5-oyl)]-carbamate The product of Step 1 (480 mg, 0.93 mmol) was dissolved in dioxan (2.5 ml) and conc hydrochloric acid (2.5 ml) was added slowly with cooling in an ice bath. The clear solution was stirred at room temperature for 4 hours and then diluted with water and basified by addition of sodium carbonate. The mixture was extracted with ethyl acetate and washed with brine. Drying (MgSO$_4$) and evaporation gave a crude product which was purified by chromatography on silica gel eluting with 35% ammonia solution:methanol:dichloromethane 1:9:90, giving two diastereoisomers of the title compound as a white solid (274 mg, 58%); Rf 0.08; $v_{max}$ (CHCl$_3$) 2962,1772, 1736 m, 1628 cm$^{-1}$; $^1$H NMR (CDCl$_3$) inter alia 7.58 (1H, br s), 6.51 (1H, dd, J 17, 11), 5.75 (1H, d, J 8.4), 5.34 (1H, dd, J 11, 1.25), 5.19 (1H, d, J 17, 1.25), 3.36 (1H, br), 3.08–3.2 (1H,m), 2.7–3.05 (5H, m): MS (+ve ion electrospray) m/z 501 (100%. MH$^+$), MS (–ve ion electrospray) m/z 499 (100%, M–H$^-$).

EXAMPLE 184

Mutilin 14-[N-(1-azabicyclo[2.2.2]octan-2-oyl)] carbamate
Step 1. (3R)-3-Deoxo-11-deoxy-3-methoxy-11-oxo-4-epi-mutilin 14-[N-(1-azabicyclo[2.2.2]octan-2-oyl )]-carbamate Triethylamine (0.2 ml, 1.5 mmol) was added to a stirred mixture of racemic 1-azabicyclo[2.2.2]octane-2-carbonyl chloride hydrochloride (ca 3 mmol), (3R)-3-deoxo-11-deoxy-3-methoxy-11-oxo-4-epi-mutilin (501 mg, 1.5 mmol) and silver cyanate (225 mg) in dichloromethane (10 ml). The mixture was stirred overnight at room temperature, filtered and the filtrate diluted with dichloromethane and washed with aq sodium bicarbonate and with brine. Drying (MgSO$_4$) and evaporation gave a crude product which was purified by chromatography on silica gel, eluting with ethyl acetate: n-hexane 1:1. The title compound was obtained as a colourless gum (220 mg), Rf 0.12.
Step 2. Mutilin 14-[N-(1-azabicyclo[2.2.2]octan-2-oyl)]-carbamate The product of Step 1 (200 mg) was dissolved in dioxan (2 ml) and conc hydrochloric acid (2 ml) was added slowly with cooling in an ice bath. The clear solution was stirred at room temperature for 3 hours and then diluted with water and basified by addition of sodium bicarbonate. The mixture was extracted with ethyl acetate and washed with brine. Drying (MgSO$_4$) and evaporation gave a crude product which was purified by chromatography on silica gel eluting with 5% methanol in chloroform, giving two diastereoisomers of the title compound as a white foam (135 mg, 69%); Rf 0.08; $v_{max}$ (CHCl$_3$) 3309, 2946, 1780, 1735 m, 1713 cm$^{-1}$; MS (+ve ion electrospray) m/z 501 (22%, MH$^+$), MS (−ve ion electrospray) m/z 499 (100%, M−H$^−$).

What is claimed is:

1. A compound selected from the group consisting of Mutilin 14-N-phenylcarbamate), Mutilin 14-(N-methylcarbamate), Mutilin 14-(N-iso-propylcarbamate), Mutilin 14-(N-phenylsulphonylcarbamate), Mutilin 14-(N-4-methoxyphenylcarbamate), Mutilin 14-carbamate, Mutilin 14-N-benzylcarbamate), Mutilin 14-N-(Bensylaminosulfonyl)carbamate], Mutilin 14-[N-(2,6-Dichloropyridin-4-yl)carbamate], Mutilin-14-(N,N-Dimethylcarbamate), 14-O-(Indolinylcarbonyl) mutilin, Mutilin 14-[N-(2-Hydroxyethyl)carbamate], Mutilin 14(-Methyl-N-benzylcarbamate), 14-O-(Morpholinocarbonyl)mutilin, Mutilin 14(N-methyl-N-phenylcarbaTnate), Mutilin 14-[N-(3-dimethylaminopropyl)carbamate], Mutilin 14-(N-hydroxycarbamate), Mutilin 14-(N-methoxycarbamate), Mutilin 14-(N-dimethylarninocarbamate), Mutilin 14-[N-(methanesulphonylamino)carbamate], Mutilin 14-(N-methanesulphonylcarbamate), Mutilin 14-(N-benzoylaminocarbamate), Mutilin 14-(N-benzoylcarbamate), Mutilin 14-[N-(2-phenylethyl) carbamate], Mutilin 14-[N-(1-(R)-phenyl-2-hydroxy) ethylcarbamate], Mutilin 14-[N-2-(methoxycarbonyl) ethylcarbamate], Mutilin 14-[N-2-carboxyethylcarbamate], Mutilin 14-[N-(hydroxyiminobenzyl)carbamate], Mutilin 14-[N-(4-methoxybenzoyl)carbamate], Mutilin 14-[N-(4-nitrobenzoyl)carbamate], Mutilin 14-[N-(3-nitrobenzoyl)carbamate], Mutilin 14-[N-(4-aminobenzoyl)carbamate], Mutilin 14-[N-(3-aminobenzoyl)carbamate], Mutilin 14-[N-(2-hydroxybenzoyl)carbamate], Mutilin 14-[N-(4-Acetoxybenzoyl)carbamate], Mutilin 14-[N-(4-hydroxybenzoyl)carbamate], Mutilin 14-[N-(3-methoxybenzoyl)carbamate], Mutilin 14-[N-(2-methoxybenzoyl)carbamate], Mutilin 14-[N-(phenylacetyl)carbamate], Mutilin 14-[N-(4-carboxybenzoyl)carbamate], Mutilin 14-(N-phenoxycarbamate), Mutilin 14-[N-(4-trifluoromethylbenzoyl)carbarmate], Mutilin 14-[N-(3-trifluoromethylbenzoyl)carbamate], Mutilin 14-[N-(2-trifluoromethylbenzoyl)carbamate], Mutilin 14-[N-iso-nicotinoylcarbamate], Mutilin 14[N-nicotinoylcarbamate], Mutilin 14-[N-2-furoylcarbainate), Mutilin 14-[N-acetylcarbamate], Mutilin 14-[N-(4-chlorobenzenesulphonyl)]-carbamate, Mutilin 14-[N-(4-fluorobenzenesulphonyl)]-carbamate, Mutilin 14-[N-(4-n-propylbenzenesulphonyl)]-carbamate, Mutilin 14-[N-(4-hydroxybenzenesulphonyl)]-carbamate, Mutilin 14-[N-(3,4-dimethoxybenzoyl)carbamate], Mutilin 14-[N-(3,4-methylenedioxybenzoyl)carbamate], Mutilin 14-(N-p-methoxysulphonylcarbamate), Mutilin 14-[N-(4-hydroxybenzoyl)carbamate], Mutilin 14-[N-(4-hydroxymethylbenzoyl)]-carbamate, Mutilin 14-(N-(4-methanesulfonamidobenzoyl)]-carbamate, Mutilin 14-[N-(4-Aminosulphonylphenyl)]-carbamate, Mutilin 14-{N-[4-([2R]-2,3-dihydroxypropyloxy)benzoyl]}-carbarmate, Mutilin 14-(N-Chloroacetyl)-carbamate, 19,20-Dihydromutilin 14-[N-(4-hydroxybenzoyl)]-carbamate, Mutilin 14-[N-(3-Amino-1,2,4-triazolylthioacetyl)]-carbamate, Mutilin 14-[N-(2-N,N-Diethylaminoethylthio-acetyl)]carbamate, Mutilin 14-[N-(4-nitrobenzenesulphonyl)]-carbamate, Mutilin 14-[N-(4-cyanobenzenesulphonyl)]-carbamate, Mutilin 14-[N-(4-aminobenzenesulphonyl)]-carbamate, Mutilin 14-[N-(6-Ethoxybenzothiazolyl-2-sulphonyl)]-carbamate, Mutilin 14-[N-(2,4-Dimnethylthiazolyl-5-sulphonyl)]-carbamate, Mutilin 14-[N-(Thiophene-2-sulphonyl)]-carbamate, Mutilin 14-[N-(5-Acetamido-1,3,4-thiadiazolyl-2-sulphonyl)]-carbamate, Mutilin 14-[N-(3-amino-4-methoxybenzoyl)]-carbamate, Mutilin 14-[N-(3-methanesulphonamido-4-methoxybenzoyl)]-carbamate, Mutilin 14-[N-(isoxaxol-5-oyl)]-carbamate, Mutilin 14-[N-(methoxyacetyl)]-carbamate, Mutilin 14-[N-(6-methoxynicotinoyl)]-carbamate, Mutilin 14-[N-(pyrazin-2-oyl)]-carbamate, Mutilin 14-(N-thiophen-2-oyl)-carbamnate, Mutilin 14-[(S)-Tetrahydrofuran-2-oyl]-carbamate, Mutilin 14-[(R)-Tetrahydrofuran-2-oyl]carbamate, Mutilin 14-[N-(2,4-Difluorobenzoyl)]-carbamate, Mutilin 14-[N-(3,4-Difluorobenzoyl)]-carbamate, Mutilin 14-[N-(1-tert-butyloxycarbonyl-azetidin-3-oyl)]-carbamate, Mutilin 14-(N-azetidin-3-oyl)-carbamate, Mutilin 14-[N-(1-ethyl-piperidin-4-oyl)]-carbamate, Mutilin 14-{N-[1-(1-methyl-ethyl)-piperidin-4-oyl]}-carbamate, Mutilin 14-{N-[1-(2-methoxy-ethyl)-piperidin-4-oyl]}-carbamate, Mutilin 14-[N-(1-propyl-piperidin-4-oyl)] 3-carbamate, Mutilin 14-[N-(quinuclidin-4-oyl)] carbamate, Mutilin 14-[N-(quinuclidin-4-oyl)]-carbamate hydrochloride, Mutilin 14-{N-(1-azabicyclo[2.2.1]heptan-4-oyl)}-carbamate, Mutilin 14-[N-(N,N-dimnethylcarbamoyl)]-carbamate, Mutilin 14-[N-(1-methyl (6H)-6-oxopyridine-3-carbonyl)]-carbamate, Mutilin 14-[N-(6-chloronicotinoyl)]-carbamate, Mutilin 14-[N-(2-methoxyisonicotinoyl)]-carbamate, Mutilin 14-[N-(morpholine-4-ylcarbonyl)]-carbamate, Mutilin 14-[N-(thiomorpholine-4-ylcarbonyl)]-carbamate, Mutilin 14-[N-(thiomorpholine-4-ylcarbonyl-1,1-dioxide)]-carbamate, Mutilin 14-[N-(1-methylpiperazin-4-ylcarbonyl)]-carbamate, Mutilin 14-[N-(4-{4-(2-morpholinoethyloxy)}-benzoyl)]-carbamate, Mutilin 14-[N-(3-(2-dimethylaminoethoxy)-benzoyl)]-carbamate, Mutilin 14-[N-(4-(3-dimethylaminopropyl)-benzoyl)]-carbamate, Mutilin 14-[N-(4-[2-pyrrolidin-1-yl-ethoxy])-benzoyl)]-carbamate, Mutilin 14[N-(4-[3-(4-methylpiperazin-1-yl)-propyloxy]-benzoyl)]-carbamate, Mutilin 14-[N-(3-fluoro-4-hydroxybenzoyl)]-carbamate, Mutilin 14-[N-(4-[2-dimethylaminoethoxy]-3-fluorobenzoyl)]carbamate, Mutilin 14-[N-(4-[2-dimethylaminoethoxy]-3-methoxybenzoyl)]-carbamate, Mutilin 14-{N-[(3S, 4R)-1-azabicyclo[2.2.1]hept-3-ylcarbonyl]}-carbamate, Mutilin 14-(piperidin-4-oyl)-carbamate, Mutilin 14-(2,3-dibydroimidazol[2,1-b]thiazol-6-oyl)-carbamate, Mutilin 14-(2,3-dihydroimidazol[2,1-b]

thiazol-5-oyl)-carbamate, Mutilin 14-(1-Methylpiperidin-4-oyl)-carbamate, Mutilin 14-(1-Methylpiperidin-4-oyl)-carbamate Hydrochloride salt, Mutilin 14-(2-Chloropropionyl)-carbamate, Mutilin 14-(2-diethylaminopropionyl)-carbamate, Mutilin 14-(Acryloyl)-carbamate, Mutilin 14-(1-Benzylpiperidin-4oyl)-carbamate, Mutilin 14-[1-(4-Methoxybenzyl)piperidin-4-oyl]-carbamate, Mutilin 14[1-(4-Methoxybenzyl)piperidin-4-oyl]-carbamate Hydrochloride salt, Mutilin 14-[1-(4-Fluorobenzyl)piperidin-4-oyl]carbamate, Mutilin 14-[1-(pyridin-2-ylmethyl)piperidin-4-oyl]-carbamate, Mutilin 14-{1-[(2-methylthiazol-4-yl)methyl]-piperidin-4-oyl}-carbamate, Mutilin 14-(N-3-pyridylacetyl)-carbamate, Mutilin 14-(N-2-pyridylmethyl)-carbamate, (E)-Mutilin 14-[N-3-(1-methyl-1,2,3-triazol-4-yl)acryloyl]-carbamate, Mutilin 14-N-{[(2-(N,N-Diethylamino)-ethylthio]-acetyl}-carbamate Hydrochloride, Mutilin 14-N-(Formyloxyacetyl)carbamate, Mutilin 14-N-(Hydroxyacetyl)-carbamate, Mutilin 14-N-(Iodoacetyl)-carbamate, Mutilin 14-N-(Azidoacetyl)-carbamate, Mutilin 14-N-[2-(3-Hydroxypyrid-2-ylthio)-acetyl]-carbamate, Mutilin 14-N-[2-(4-Methylpyrimidin-2-ylthio)-acetyl]-carbamate, Mutilin 14-N-[2-(1-Oxopyrid-2-ylthio)-acetyl]-carbamate, Mutilin 14-N-(Ethylthio-acetyl)-carbamate, Mutilin 14-N-(Ethylsulfinyl-acetyl)-carbamate, Mutilin 14-N-(Ethylsulfonyl-acetyl)-carbamate, Mutilin 14-N-[tert-Butyloxycarbonylmethylthio-acetyl]-carbamate, Mutilin 14-N-[2-(Ethyloxycarbonyl)ethylthio-acetyl]-carbamate, Mutilin 14-N-[(5-Methyl-1,3,4-thiadiazol-2-ylthio)-acetyl]-carbamate, Mutilin 14-N-[(1-Methyltetrazol-5-ylthio)-acetyl]-carbamate, Mutilin 14-N-[(1-Phenyl-tetrazol-5-ylthio)-acetyl]-carbamate, Mutilin 14-N-[(1,3,4-Thiadiazol-2-ylthio)-acetyl]-carbamate, Mutilin 14-N-[(5-Aminocarbonyl-1,3,4-thiadiazol-2-ylthio)-acetyl]-carbamate, Mutilin 14-N-[(5-Aminocarbonyl-1,3,4-oxadiazol-2-ylthio)-acetyl]-carbamate, Mutilin 14N-[1-(2-Dimethylaminoethyl)-tetrazol-5-ylthio)-acetyl}-carbamate, Mutilin 14-N-[(1,2,3-Triazol-5-ylthio)-acetyl]-carbamate, Mutilin 14-N-{[1-(Methoxycarbonylmethyl)-tetrazol-5-ylthio]-acetyl}-carbamate, Mutilin 14-N-{[3-(Methoxycarbonyl)-pyrid-2-ylthio]-acetyl}-carbamate, Mutilin 14-N-[(2-Furylmethylthio)-acetyl]-carbamate, Mutilin 14-N-[(2,3-Dihydroxypropylthio)-acetyl]-carbamate, Mutilin 14-N-[(Pyrid-2-ylthio)-acetyl]-carbamate, Mutilin 14-N-[(Cyanothio)-acetyl]-carbamate, Mutilin 14-N-[N-Acetylglycyl]carbamate, Mutilin 14-N-(N,N-Diethylglycyl)carbamate, Mutilin 14{N-[(1-Methyl-1,2,3-triazol-4-yl)-carbonyl]-carbamate}, Mutilin 14-{N-[(1,2,3-thiadiazol-4-yl)-carbonyl]carbamate}, Mutilin 14-{N-[(1-ethyl-5-methylpyrazol-3-yl)-carbonyl]carbamate}, Mutilin 14-{N-[(1,5-Dimethylpyrazol-3-yl)-carbonyl]carbamate}, Mutilin 14-[N-(N-Methylnipecotyl)carbamate], Mutilin 14-[N-(1-Methylpyrrolidin-3-oyl)-carbamate], Mutilin 14-[N-(1-Allylpiperidin-4-oyl)carbamate], Mutilin 14-[N-(1-Cyclopropylmethylpiperidin-4-oyl)carbamate], Mutilin 14-(N-(nipecotyl)carbamate], Mutilin 14-[N-(4-amino-3-methoxybenzoyl)]-carbamate, Mutilin-14-[N-(4-fluorobenzoyl)]-carbamate, Mutilin 14-[N-(4-methylsulphonyl benzoyl)]-carbamate, Mutilin 14-[N-(3-(2-Dimethylaminoethoxy)4-fluorobenzoyl)]-carbamate, Mutilin 14-{N-[4-(2-dimethylaminoethyloxy)-benzoyl]}-carbamate hydrochloride, Mutilin 14-{N-[4-(glucosyloxy)-benzoyl]}-carbamate, Mutilin 14-[N-(2-azido-phenyl-acetyl)]-carbamate, 19,20-Dihydro-mutilin 14-[N-(alpha-amino-phenylacetyl)]-carbamate hydrochloride, Mutilin 14-[N-(cyclohexyl-acetyl)]-carbamate, Mutilin 14-[N-(cinnamoyl)]-carbamate, 19,20-Dihydro-mutilin 14-(1-Methylpiperidin-4-oyl)-carbamate, 19,20-Dihydro-mutilin 14-(1-Methylpiperidin-4-oyl)-carbamate hydrochloride, 19,20-Dihydromutilin 14-{N-(3S,4R)-1-azabicyclo[2.2.1]hept-3-ylcarbonyl]}-carbamate, 19,20-Dihydromutilin 14-[N-(quinuclidine-4-carbonyl)]-carbamate,19,20-Dihydro-mutilin 14-[N-(3-(2-Dimethylaminoethoxy)-4-fluorobenzoyl)]-carbamate, Mutilin 14-[N-(Quinuclidin-3-oyl)carbamate], Mutilin 14-{N-[(3S,4R)-1-azabicyclo[2.2.1]hept-3-ylcarbonyl]}-carbamate hydrochloride, Mutilin 14-[N-(1-azabicyclo[3.2.1]octan-5-oyl)]carbamate, and Mutilin 14-[N-(1-azabicyclo[2.2.2]octan-2-oyl)]carbamate.

2. A pharmaceutical composition comprising a compound selected from the group consisting of:

Mutilin 14-(N-phenylcarbamate), Mutilin 14-(N-methylcarbamate),

Mutilin 14-(N-iso-propylcarbamate), Mutilin 1-N-phenylsulphonylcarbamate),

Mutilin 14-(N-4-methoxybenylcarbamate), Mutilin 14-carbamate,

Mutilin 14-(N-benzylcarbamate), Mutilin 14-[N-(Bensylaminosulfonyl)carbamate], Mutilin 14-[N-(2,6Dichloropyridin-4-yl)carbamate], Mutilin-14-(N,N-Dimethylcarbamate), 14-O-(Indolinylcarbonyl)mutilin, Mutilin 14-[N-(2-Hydroxyethyl)carbamate], Mutilin 14-(N-Methyl-N-benzylcarbamate), 14-O-(Morpholinocarbonyl)mutilin, Mutilin 14-(N-methyl-N-phenylcarbamate), Mutilin 14-[N-(3-dimethylaminopropyl)carbamate], Mutilin 14-(N-hydroxycarbamate), Mutilin 14-(N-methoxycarbamate), Mutilin 14-(N-dimethylaminocarbamate), Mutilin 14-[N-(methanesulphonylamino)carbamate], Mutilin 14-(N-methanesulphonylcarbamate), Mutilin 14-(N-benzoylaminocarbamate), Mutilin 14-(N-benzoylcarbamate), Antibacterial Activity, 14-[N-(2-phenylethyl)carbamate], Mutilin 14-[N-(1-(R)-phenyl-2-hydroxy)ethylcarbamate], Mutilin 14-[N-2-(methoxycarbonyl)ethylcarbamate], Mutilin 14-[N-2-carboxyethylcarbamate], Mutilin 14-[N-(hydroxyiminobenzyl)carbamate], Mutilin 14-[N-(4methoxybenzoyl)carbamate], Mutilin 14-[N-(4-nitrobenzoyl)carbamate], Mutilin 14-[N-(3-nitrobenzoyl)carbamate], Mutilin 14-[N-(4-aminobenzoyl)carbamate], Mutilin 14-[N-(3-aminobenzoyl)carbamate], Mutilin 14-[N-(2-hydroxybenzoyl)carbamate], Mutilin 14-[N-(4-Acetoxybenzoyl)carbamate], Mutilin 14-[N-(4-hydroxybenzoyl)carbamate], Mutilin 14-[N-(3-methoxybenzoyl)carbamate], Mutilin 14[N-(2-methoxybenzoyl)carbamate], Mutilin 14-[N-(phenylacetyl)carbamate], Mutilin 14-[N-(4-carboxybenzoyl)carbamate], Mutilin 14-(N-phenoxycarbamate), Mutilin 14-[N-(4- trifluoromethylbenzoyl)carbamate], Mutilin 14-[N-(3-trifluoromethylbenzoyl)carbamate], Mutilin 14-[N-(2-trifluoromethylbenzoyl)carbamate], Mutilin 14-[N-isonicotinoylcarbamate], Mutilin 14-[N-nicotinoylcarbamate], Mutilin 14-[N-2-furoylcarbamate], Mutilin 14-[N-aceylcarbamate], Mutilin 14-[N-(4-chlorobenzenesulphonyl)]-carbamate, Mutilin 14-[N-(4-fluorobenzenesulphonyl)]-carbamate, Mutilin 14-[N-(4-n-propylbenzenesulphonyl)]-carbamate, Mutilin 14-[N-(4-hydroxybenzenesulphonyl)]-carbamate, Mutilin 14-[N-(3,4-dimethoxybenzoyl)carbamate], Mutilin 14-[N-(3,4-methylenedioxybenzoyl)carbamate], Mutilin 14-(N-p-methoxysulphonylcarbamate), Mutilin 14-[N-(4-hydroxybenzoyl)carbamate], Mutilin 14-[N-(4-hydroxymethylbenzoyl)]-carbamate, Mutilin 14-[N-(4-methanesulfonamidobenzoyl)]-carbamate, Mutilin 14-[N-(4-Aminosulphonylphenyl)]-carbamate, Mutilin 14-{N-[4-([2R]-2,3-dihydroxy-propyloxy)benzoyl]}-carbamate, Mutilin 14-(N-Chloroacetyl)-carbamate, 19,20-Dihydromutilin 14-[N-(4-hydroxybenzoyl)]-carbamate, Mutilin 14-[N-(3-Amino-1,2,4-triazolylthioacetyl)]-carbamate, Mutilin 14-[N-(2-N,N-Diethylaminoethylthio-acetyl)]-carbamate, Mutilin 14-[N-(4-nitrobenzenesulphonyl)]-carbamate, Mutilin 14-[N-(4-cyanobenzenesulphonyl)]-carbamate, Mutilin 14-[N-(4-aminobenzenesulphonyl)]-carbamate, Mutilin 14-[N-(6-Ethoxybenzothiazolyl-2-sulphonyl)]-carbamate, Mutilin 14-[N-(2,4-Dimethylthiazolyl-5-sulphonyl)]-carbamate, Mutilin 14-[N-(Thiophene-2-sulphonyl)]-carbamate, Mutilin 14-[N-(5-Acetamido 1,3,4-thiadiazolyl-2-sulphonyl)]-carbamate, Mutilin 14-[N-(3-amino-4-methoxybenzoyl)]-carbamate, Mutilin 14-[N-(3-methanesulphonamido4-methoxybenzoyl)]-carbamate, Mutilin 14-[N-(isoxaxol-5-oyl)]-carbamate, Mutilin 14-[N-(methoxyacetyl)]-carbamate, Mutilin 14-[N-(6-methoxynicotinoyl)]-carbamate, Mutilin 14[N-(pyrazin-2-oyl)]-carbamate, Mutilin 14-(N-thiophen-2-oyl)-carbamate, Mutilin 14-[(S)-Tetrahydrofuran-2-oyl]-carbamate, Mutilin 14-[(R)-Tetrahydrofuran-2-oyl]carbamate, Mutilin 14-[N-(2,4-Difluorobenzoyl)]-carbamate, Mutilin 14-[N-(3,4-Difluorobenzoyl)]carbamate, Mutilin 14-[N-(1-tert-butyloxycarbonyl-azetidin-3-oyl)]-carbamate, Mutilin 14-(N-azetidin-3-oyl)-carbamate, Mutilin 14-[N-(1-ethyl-piperidin-4-oyl)]-carbamate, Mutilin 14-{N-[1-(1-methyl-ethyl)-piperidin-4-oyl]}-carbamate, Mutilin 14-{N-[1-(2-methoxy-ethyl)-piperidin-4-oyl]}-carbamate, Mutilin 14-[N-(1-propyl-piperidin-4-oyl)]-carbamate, Mutilin 14-[N-(quinuclidin-4-oyl)]-carbamate, Mutilin 14-[N-(quinuclidin-4-oyl)]-carbamate hydrochloride, Mutilin 14-{N-(1-azabicyclo[2.2.1]heptan-4-oyl)}-carbamate, Mutilin 14-[N-(N,N-dimethylcarbamoyl)]-carbamate, Mutilin 14-[N-(1-methyl (6H)-6-oxopyridine-3-carbonyl)]-carbamate, Mutilin 14-[N-(6-chloronicotinoyl)]-carbamate, Mutilin 14-[N-(2-methoxyisonicotinoyl)]-carbamate, Mutilin 14-[N-(morpholine-4-ylcarbonyl)]-carbamate, Mutilin 14-[N-(thiomorpholine-4-ylcarbonyl)]-carbamate, Mutilin 14-[N-(thiomorpholine-4-ylcarbonyl-1,1-dioxide)]-carbamate, Mutilin 14-[N-(1-methylpiperazin-4-ylcarbonyl)]-carbamate, Mutilin 14-[N-(4-{4-(2-morpholinoethyloxy)}-benzoyl)]-carbamate, Mutilin 14-[N-(3-(2-dimethylaminoethoxy)-benzoyl)]-carbamate, Mutilin 14-[N-(4-(3-dimethylaminopropyl)-benzoyl)]carbamate, Mutilin 14-[N-(4-[2-pyrrolidin-1-yl-ethoxy])-benzoyl)]-carbamate, Mutilin 14-[N-(4-[3-(4-methylpiperazin-1-yl)-propyloxy]-benzoyl)]-carbamate, Mutilin 14-[N-(3-fluoro-4-hydroxybenzoyl)]-carbamate, Mutilin 14-[N-(4-[2-dimethylaminoethoxy]-3-fluorobenzoyl)]-carbamate, Mutilin 14-[N-(4-[2-dimethylaminoethoxy]-3-methoxybenzoyl)]-carbamate, Mutilin 14-{N-[(3S,4R)-1-azabicyclo[2.2.1]hept-3-ylcarbonyl]}-carbamate, Mutilin 14-(piperidin-4-oyl)-carbamate, Mutilin 14-(2,3-dihydroimidazol[2,1-b]thiazol-6-oyl)-carbamate, Mutilin 14-(2,3-dihydroimidazol[2,1-b]thiazol-5-oyl)-carbamate, Mutilin 14-(1-Methylpiperidin-4-oyl)-carbamate, Mutilin 14-(1-Methylpiperidin-4-oyl)-carbamate Hydrochloride salt, Mutilin 14-(2-Chloropropionyl)-carbamate, Mutilin 14-(2-diethylaminopropionyl)-carbamate, Mutilin 14-(Acryloyl)carbamate, Mutilin 14-(1-Benzylpiperidin-4-oyl)-carbamate, Mutilin 14-[(-4-Methoxybenzyl)piperidin-4-oyl]-carbamate, Mutilin 14-[1-(4-Methoxybenzyl)piperidin-4-oyl]-carbamnate Hydrochloride salt, Mutilin 14-[1-(4-Fluorobenzyl)piperidin-4-oyl]-carbamate, Mutilin 14-[1-(pyridin-2-ylmethyl)piperidin-4-oyl]-carbamate, Mutilin 14-{1-[(2-methylthiazol-4-yl)methyl]-piperidin-4-oyl}-carbamate, Mutilin 14-(N-3-pyridylacetyl)-carbamate, Mutilin 14-(N-2-pyridylmethyl)-carbamate, (E)-Mutilin 14-[N-3-(1-methyl-1,2,3-trazol4-yl)acryloyl]-carbamate, Mutilin 14-N-{[2-(N,N-Diethylamino)-ethylthio]-acetyl}-carbamate Hydrochloride, Mutilin 14-N-(Formyloxy-acetyl)-carbamate, Mutilin 14-N-(Hydroxyacetyl)-carbamate, Mutilin 14-N-(Iodoacetyl)-carbamate, Mutilin 14-N-(Azidoacetyl)-carbamate, Mutilin 14-N-[2-(3-Hydroxypyrid-2-ylthio)-acetyl]-carbamate, Mutilin 14-N-[2-(4-Methylpyrimdin-2-ylthio)-acctyl]-carbamate, Mutilin 14-N-[2-(1-Oxopyrid-2-ylthio)-acetyl]-carbamate, Mutilin 14-N-(Ethylthio-acetyl)-carbamate, Mutilin 14-N-(Ethylsulfinyl-acetyl)-carbamate, Mutilin 14-N-(Ethylsulfonyl-acetyl)-carbamate, Mutilin 14-N-[tert-Butyloxycarbonylmethylthio-acetyl]-carbamate, Mutilin 14-N-[2-(Ethyloxycarbonyl)ethylthio-acetyl]-carbamate, Mutilin 14-N-[(5-Methyl-1,3,4-thiadiazol-2-ylthio)-acetyl]-carbamate, Mutilin 14-N-[(1-Methyltetrazol-5-ylthio)-acetyl]-carbamate, Mutilin 14-N-[(1-Phenyl-tetrazol-5-ylthio)-acetyl]-carbamate, Mutilin 14-N-[(1,3,4-Thiadiazol-2-ylthio)-acetyl]-carbamate, Mutilin 14-N-[(5-Aminocarbonyl-1,3,4-thiadiazol-2-ylthio)-acetyl]-carbamate, Mutilin 14-N-[(5-Aminocarbonyl-1,3,4-oxadiazol-2-ylthio)-acetyl]-carbamate, Mutilin 14-N-[1-(2-Dimethylaminoethyl)-tetrazol-5-ylthio]-acetyl}-carbamate, Mutilin 14-N-[(1,2,3-Triazol-5-yltho)-acetyl]-carbamate, Mutilin 14-N-{[1-(Methoxycarbonylmethyl)-tetrazol-5-ylthio]-acetyl}-carbamate, Mutilin 14-N-{[3-(Methoxycarbonyl)-pyride-2-ylthio]-acetyl}-carbamate, Mutilin 14-N-[(2-Furylmethylthio)-acetyl]-carbamate, Mutilin 14-N-[(2,3-Dihydroxypropylthio)-acetyl]-carbamate, Mutilin 14-N-[(Pyrid-2-ylthio)-acetyl]-carbamate, Mutilin 14-N-[(Cyanothio)-acetyl]-carbamate, Mutilin 14-N-[N-Acetylglycyl]carbamate, Mutilin 14-N-(N,N-Diethylglycyl)carbarate, Mutilin 14-{N-[(1-Methyl-1,2,3-triazol-4-yl)-carbonyl]-carbamate}, Mutilin 14-{N-[(1,2,3-thiadiazol-4-yl)-carbonyl]carbamate}, Mutilin 14-{N-[(1-ethyl-5-methylpyrazol-3-yl)-carbonyl]carbamate}, Mutilin 14-{N-[(1,5-Dimethylpyrazol-3-yl)-carbonyl]carbamate}, Mutilin 14-[N-(N-Methylnipecotyl)carbamate], Matilin 14-[N-(1-Methylpyrrolidin-3-oyl)-carbamate], Mutilin 14-[N-(1-Allylpiperidin-4-oyl)carbamate], Mutilin 14-[N-(1-Cyclopropylmethylpiperidin-4-oyl)carbamate], Mutilin 14-[N-(nipecotyl)carbamate], Mutilin 14-[N-(4-amino-3-methoxybenzoyl)]-carbamate, Mutilin-14-[N-(4-fluorobenzoyl)]-carbamate, Mutilin 14-[N-(4-methylsulphonylbenzol)]-carbamate, Mutilin 14-[N-(3-(2-Dimethylaminoethoxy)-4-fluorobenzoyl)]-carbamate, Mutilin 14-{N-[4-(2-dimethylaminoethyloxy)-benzoyl]}-carbamate hydrochloride, Mutilin 14-{N-[4-(glucosyloxy)-benzoyl]}-carbamate, Mutilin 14-[N-(2-azido-phenyl-acetyl)]-carbamate, 19,20-Dihydro-mutilin 14-[N-(alpha-amino-phenylacetyl)]-carbamate hydrochloride, Mutilin 14-[N-(cyclohexyl-acetyl)]-carbamate, Mutilin 14-[N-(cinnamoyl)]-carbamate, 19,20-Dihydro-mutilin 14-(1-Methylpiperidin-4-oyl)-carbamate, 19,20-Dihydro-mutilin 14-(1-Methylpiperidin-4-oyl)-carbamate hydrochloride, 19,20-Dihydromutilin 14-{N-[(3S,4R)-1-azabicyclo[2.2.1]hept-3-ylcarbonyl]}-carbamate, 19,20-Dihydromutilin 14-[N-(quinuclidine-4-carbonyl)]-carbamate, 19,20-Dihydro-mutilin 14-[N-(3-(2-Dimethylaminoethoxy)4-fluorobenzoyl)]-carbamate, Mutilin 14-[N-(Quinuclidin-3-oyl)carbamate], Mutilin 14-{N-[(3S,4R)-1-azabicyclo[2.2.1]hept-3-ylcarbonyl]}-carbamate hydrochloride, Mutilin 14-[N-(1-azabicyclo[3.2.1]octan-5-oyl)]carbamate, and Mutilin 14-[N-(1-azabicyclo(2.2.2)octan-2-oyl)]carbamate;

together with a pharmaceutically acceptable carrier or excipient.

3. A method of treating microbial infections in animals, especially in humans and in domesticated mammals, which comprises administering an antimicrobially effective amount of a compound according to claim 1, or a composition according to claim 2, to a patient in need thereof.

4. A method of using a compound according to claim 1, in the preparation of a medicament composition for use in the treatment of microbial infections.

* * * * *